(12) United States Patent
Sulsky et al.

(10) Patent No.: US 6,649,622 B2
(45) Date of Patent: Nov. 18, 2003

(54) TETRAHYDROPYRIMIDONE INHIBITORS OF FATTY ACID BINDING PROTEIN AND METHOD

(75) Inventors: Richard Sulsky, West Trenton, NJ (US); Jeffrey A. Robl, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/771,310

(22) Filed: Jan. 26, 2001

(65) Prior Publication Data

US 2002/0091078 A1 Jul. 11, 2002

Related U.S. Application Data

(60) Provisional application No. 60/178,598, filed on Jan. 28, 2000.

(51) Int. Cl.[7] ............... C07D 239/22; A61K 31/513; A61P 3/10
(52) U.S. Cl. .......... 514/274; 544/231; 544/243; 544/315; 544/316; 544/318
(58) Field of Search ............. 514/274; 544/315, 544/316, 318, 231, 243

(56) References Cited

U.S. PATENT DOCUMENTS 3,951,976 A * 4/1976 Krenzer .............. 544/310

FOREIGN PATENT DOCUMENTS

| DE | 3627246 A1 | * | 2/1988 |
| DE | 3627257 A1 | * | 2/1998 |
| JP | 06118653 A2 | * | 4/1994 |
| WO | WO96/38421 | | 12/1996 |
| WO | WO 00/15229 | | 3/2000 |
| WO | WO 00/15230 | | 3/2000 |

OTHER PUBLICATIONS

Gieldanowski, Jerzy; Pelczarska, Alicja, Diss. Pharm. Pharmacol., 23(4), 325–34 (English) 1971; CA 1972, vol. 76, abstract 121453.*
Knabe, Joachim; Wunn, Wolfgang, Arch. Pharm. (Weinheim, Ger.), 312(11), 973–4 (German) 1979; CA 1980, vol. 92, abstract 76446.*
Kowalczyk–Bronisz, Stefania H., Arch. Immunol. Ther. Exp., 32(2), 295–305 (English) 1984; CA 1985, vol. 102, abstract 55820..*
Grillot, Anne–Laure; Hart, David J., Tetrahedron, 51(42), 11377–92 (English) 1995.*

* cited by examiner

Primary Examiner—Mukund J. Shah
Assistant Examiner—Thomas McKenzie
(74) Attorney, Agent, or Firm—Maureen O'Brien; Sammy G. Duncan, Jr.

(57) ABSTRACT aP2 inhibiting compounds are provided having the formula

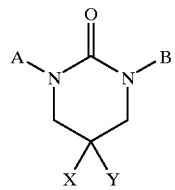

wherein A, B, X, and Y are as described herein.

A method is also provided for treating diabetes and related diseases, especially Type II diabetes, employing such aP2 inhibitor or a combination of such aP2 inhibitor and another antidiabetic agent such as metformin, glyburide, troglitazone and/or insulin.

11 Claims, No Drawings

TETRAHYDROPYRIMIDONE INHIBITORS OF FATTY ACID BINDING PROTEIN AND METHOD

This application claims priority to U.S. Provisional application Ser. No. 60/178,598 filed Jan. 28, 2000 the entirety of which is incorporated herein by reference.

FIELD OF THE INVENTION

The present invention relates to tetrahydropyrimidones which are inhibitors of fatty acid binding protein (aP2) and to a method for treating diabetes, especially Type II diabetes, as well as hyperglycemia, hyperinsulinemia, obesity, Syndrome X, diabetic complications, atherosclerosis and related diseases, and other chronic inflammatory and autoimmune/inflammatory diseases, employing such tetrahydropyrimidones alone alone or in combination with one or more types of therapeutic agents. In addition, the compounds of the present invention act as inhibitors of aldose reductase and thus are useful in the treatment of diabetic complications such as diabetic retinopathy, diabetic neuropathy and diabetic nephropathy.

BACKGROUND OF THE INVENTION

Fatty acid binding proteins (FABPs) are small cytoplasmic proteins that bind to fatty acids such as oleic acids which are important metabolic fuels and cellular regulators. Dysregulation of fatty acid metabolism in adipose tissue is a prominent feature of insulin resistance and the transition from obesity to non-insulin dependent diabetes mellitus (NIDDM or Type II diabetes).

aP2 (adipocyte fatty binding protein), an abundant 14.6 KDa cytosolic protein in adipocytes, and one of a family of homologous intracellular fatty acid binding proteins (FABPs), is involved in the regulation of fatty acid trafficking in adipocytes and mediates fatty acid fluxes in adipose tissue. G. S. Hotamisligil et al, "Uncoupling of Obesity from Insulin Resistance Through a Targeted Mutation in aP2, the Adipocyte Fatty Acid Binding Protein", Science, Vol. 274, Nov. 22, 1996, pp. 1377–1379, report that aP2-deficient mice placed on a high fat diet for several weeks developed dietary obesity, but, unlike control-mice on a similar diet, did not develop insulin resistance or diabetes. Hotamisligil et al conclude "aP2 is central to the pathway that links obesity to insulin resistance" (Abstract, page 1377).

DIALOG ALERT DBDR928 dated Jan. 2, 1997, Pharmaprojects No. 5149 (Knight-Ridder Information) discloses that a major drug company "is using virtual screening techniques to identify potential new antidiabetic compounds." It is reported that "the company is screening using aP2, a protein related to adipocyte fatty acid binding protein."

U.S. application Ser. No. 09/391,053, filed Sep. 7, 1999 and U.S. application Ser. No. 09/519,079 filed Mar. 6, 2000 disclose methods for treating diabetes employing an aP2 inhibitor.

DESCRIPTION OF THE INVENTION

In accordance with the present invention, tetrahydropyrimidone compounds are provided which have the structure of formula I

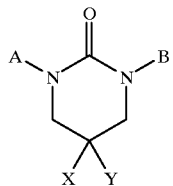

including pharmaceutically acceptable salts thereof, prodrug esters thereof, and all stereoisomers thereof, wherein A and B are the same or different and are independently
—J,
—$(CR^3R^4)_n$—J,
—$R^5(CR^3R^4)_p$—J,
—$(CR^3R^4)_m R^5(CR^6R^7)_p$—J,
—$(CR^3R^4)_n(CR^6R^7)_p$—J,
—S(O)J where J is other than hydrogen,
—$S(O_2)$J where J is other than hydrogen, and
—$NH(CR^3R^4)_n$—J;

J is independently $R^1$ or $R^2$;

$R^1$ and $R^2$ are independently hydrogen, alkyl, substituted alkyl, cycloalkyl, substituted cycloalkyl, alkenyl, substituted alkenyl, cycloalkenyl, substituted cycloalkenyl, aryl, substituted aryl, heteroaryl, substituted heteroaryl, aralkyl, substituted aralkyl, heteroaralkyl, substituted heteroaralkyl, cycloheteroalkyl and substituted cycloheteroalkyl;

$R^3$ and $R^4$ are the same or different and are independently H, alkyl, cycloalkyl, alkenyl, cycloalkenyl, alkynyl, alkoxycarbonyl, alkylcarbonyl, aminocarbonyl, alkylaminocarbonyl, arylaminocarbonyl, arylcarbonyl, aryl and heteroaryl, halo, hydroxy, alkoxy and aryloxy;

or $R^3$ and $R^4$ together with the atom to which they are bonded may form a 3 to 9-membered saturated or unsaturated ring.

$R^5$ is a bond, O, $NR^8$, S, SO, $SO_2$, CO or CONH;

$R^6$ and $R^7$ are the same or different and are independently H, alkyl, cycloalkyl, aryl, hydroxy, amino, halo, alkoxy, aryloxy, alkylthio, arylthio, alkylamino, dialkylamino, arylamino, diarylamino, alkoxycarbonyl, alkylaminocarbonyl or alkylcarbonylamino;

$R^8$ is H, aryl, arylcarbonyl, alkylaminocarbonyl, arylaminocarbonyl, alkoxycarbonyl, aryloxycarbonyl, alkyl or alkylcarbonyl;

$R^9$ is H, alkyl, substituted alkyl, cycloalkyl, substituted cycloalkyl, cycloheteroalkyl, substituted cycloheteroalkyl, aryl, substituted aryl, aralkyl, substituted aralkyl, heteroaryl, substituted heteroaryl, heteroarylalkyl, substituted heteroarylalkyl or a prodrug ester thereof;

$R^{10}$ is H, alkyl, substituted alkyl, cycloalkyl, substituted cycloalkyl, cycloheteroalkyl, substituted cycloheteroalkyl, aryl, substituted aryl, aralkyl, substituted aralkyl, heteroaryl, substituted heteroaryl, heteroarylalkyl, substituted heteroarylalkyl or a prodrug ester thereof;

$R^{11}$ is hydrogen, alkyl, substituted alkyl, cycloalkyl, substituted cycloalkyl, alkenyl, substituted alkenyl, cycloalkenyl, substituted cycloalkenyl, aryl, substituted aryl, heteroaryl, substituted heteroaryl, aralkyl, substituted aralkyl, heteroaralkyl, substituted heteroaralkyl, cycloheteroalkyl and substituted cycloheteroalkyl;

$R^{12}$ and $R^{13}$ are the same or different and are independently H, alkyl, substituted alkyl, cycloalkyl, substituted cycloalkyl, cycloheteroalkyl, substituted cycloheteroalkyl, aryl, substituted aryl, aralkyl, substituted aralkyl, heteroaryl, substituted heteroaryl, heteroarylalkyl, substituted heteroarylalkyl or a pro drug ester thereof;

or $R^{12}$ and $R^{13}$ together with the nitrogen atom to which they are bonded together form an optionally substituted cycloheteroalkyl ring;

X is selected from —Z, —$(CR^3R^4)_n$—Z, —O—$(CR^3R^4)_p$—Z, —S—$(CR^3R^4)_p$—Z, —NHC(=O)Z, —CH=CHZ, -(cycloalkylene)-Z, or —$N(R^8)(CR^3R^4)_n$—Z;

Y is H, alkyl, aryl, aralkyl, alkoxy, aryloxy, alkylthio, arylthio, hydroxy, —$(CR^3R^4)_n$—$CO_2R^9$, —$(CR^3R^4)_n$—$CONR^{12}R^{13}$, —$NR^3R^4$, aralkoxy, or heteroarylalkyl, provided that Y is other than hydroxy or $NH_2$ when X is —O$(CR^3R^4)_p$—Z, —S$(CR^3R^4)_p$—Z, —NHC(=O)Z, or —$N(R^8)(CR^3R^4)_n$—Z;

or X and Y, taken together with the atom to which they are joined, provide a group of the formula

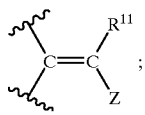

Z is $CO_2R^9$, $SO_3H$, $PO_3R^9R^{10}$, CONHOH, $CONR^{12}R^{13}$, $(CR^3R^4)_mOH$, or tetrazole of the formula

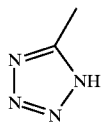

or its tautomer;

n is an integer selected from 0 to 5;
m is an integer selected from 1 to 5; and
p is an integer selected from 0 to 4.

In addition, the present invention provides for novel intermediates useful in the synthesis of compounds of formula I. Such intermediates have the structure of formula II

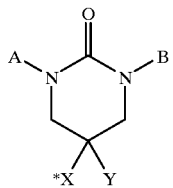

where A and B are as defined above,

X* is W, —$(CR^3R^4)_n$—W, —O$(CR^3R^4)_n$—W, —S$(CR^3R^4)_n$—W, —NHC(=O)W, —CH=CHW, -(cycloalkylene)-W, or —$N(R^8)(CR^3R^4)_n$—W;

Y is H, alkyl, alkenyl, aryl, aralkyl, heteroarylalkyl, alkoxy, aryloxy, aralkoxy, alkylthio, arylthio, hydroxy, or $NR^3R^4$ provided that Y is other than hydroxy or $NH_2$ when X is —O$(CR^3R^4)_p$—W, —S$(CR^3R^4)_p$—W, —NHC(=O)W, or —$N(R^8)(CR^3R^4)_n$—W;

W is cyano, halogen, hydroxy, alkenyl, C(O)Cl, or C(O)H.

or X* and Y, taken together with the atom to which they are joined, provide a group of the formula

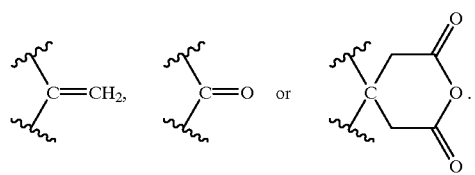

In addition, in accordance with the present invention, a method is provided for treating diabetes, especially Type II diabetes, and related diseases such as insulin resistance, hyperglycemia, hyperinsulinemia, elevated blood levels of fatty acids or glycerol, obesity, hypertriglyceridemia, atherosclerosis, inflammation, diabetic retinopathy, diabetic neuropathy and diabetic nephropathy wherein a therapeutically effective amount of a compound of structure I is administered to a human patient in need of treatment.

In addition, in accordance with the present invention, a method is provided for treating diabetes and related diseases as defined above and hereinafter, wherein a therapeutically effective amount of a combination of a compound of structure I and another type antidiabetic agent is administered to a human patient in need of treatment.

In the above method of the invention, the compound of structure I will be employed in a weight ratio to another antidiabetic agent (depending upon its mode of operation) within the range from about 0.01:1 to about 100:1, preferably from about 0.5:1 to about 10:1.

Examples of X moieties include (but are not limited to)

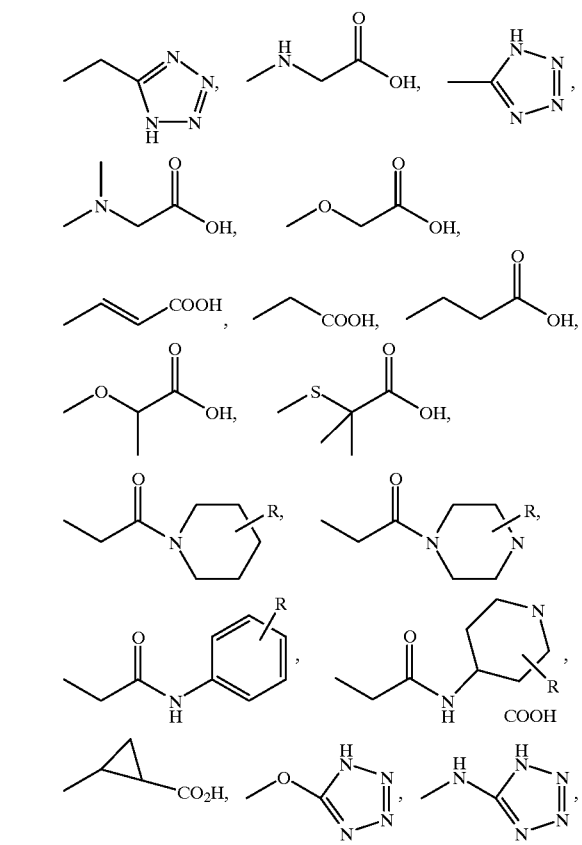

-continued

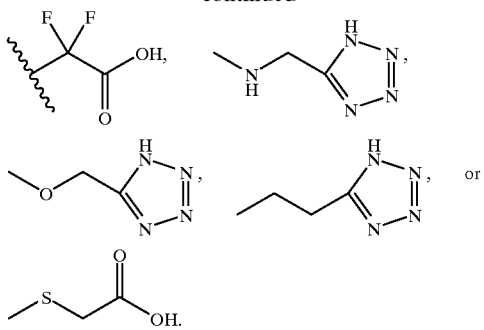

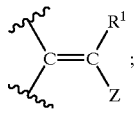

Preferred compounds of formula I include compounds where

A is $(CR^3R^4)_n$—$R^1$ where n is 0 to 5, and $R^3$ and $R^4$ are the same or different and are selected from hydrogen, alkyl and substituted alkyl;

$R^1$ is substituted alkyl, aryl, substituted aryl, heteroaryl, substituted heteroaryl, alkyl or cycloalkyl;

B is $R^2$ or $(CR^3R^4)_n$—$R^2$ where n is 1 and $R^3$ and $R^4$ are the same or different and a selected from hydrogen, alkyl and substituted alkyl;

$R^2$ is aryl, substituted aryl, cycloalkylalkyl, heteroaryl or substituted heteroaryl;

Y is hydrogen, OH, —$(CR^3R^4)_n$—$CONR^{12}R^{13}$, or —$(CR^3R^4)_n$—$CO_2R^9$;

X is $(CR^3R^4)_n$—Z where n is 0 or 1 and $R^3$ and $R^4$ are the same or different and are selected from hydrogen, hydroxy, alkyl and substituted alkyl;

or X and Y, taken together with the atom to which they are joined, provide a group of the formula and Z is $CO_2R^9$, $CONR^{12}R^{13}$, $PO_3H_2$, $CONHOH$, or tetrazole.

More preferred compounds of formula I include compounds where

A is $R^1$;

$R^1$ is aryl (especially where aryl is phenyl), substituted aryl (especially where substituted with one or more halogen, alkoxy or aryloxy) or substituted alkyl (especially where substituted with one or more alkoxy or aryloxy);

B is $(CR^3R^4)_n$—$R^2$ where n is 1 and $R^3$ and $R^4$ are hydrogen $R^2$ is aryl (especially where aryl is phenyl or napthyl), or substituted aryl (especially substituted with one or more halogen, alkyl, substituted alkyl alkoxy; arylalkoxy, or cyano);

Y is hydrogen, OH, —$(CR^3R^4)_n$—$CONR^{12}R^{13}$, or —$(CR^3R^4)_n$—$CO_2R^9$ (especially where n is 1 and $R^3$, $R^4$ and $R^9$ are each hydrogen);

X is —$(CR^3R^4)_n$—Z where n is 0 or 1 and $R^3$ and $R^4$ are hydrogen; and

Z is $CO_2H$, $CONR^{12}R^{13}$, or tetrazole.

Most preferred compounds of formula I include compounds where

A is $R^1$;

$R^1$ is substituted alkyl (especially where substituted with one or more aryloxy), substituted aryl (especially where aryl is phenyl and the substituents are selected from halogens);

B is $(CR^3R^4)_n$—$R^2$ where n is 1 and $R^3$ and $R^4$ are hydrogen $R^2$ is aryl (especially where aryl is phenyl or napthyl), or substituted aryl (especially where the substituents are selected from halogen, and alkoxy);

Y is hydrogen, —$(CR^3R^4)_n$—$CONR^{12}R^{13}$, or —$(CR^3R^4)_n$—$CO_2R^9$ where n is 1 and $R^3$, $R^4$ and $R^9$ are each hydrogen;

X is —$(CR^3R^4)_n$—Z where n is 1 and $R^3$ and $R^4$ are hydrogen; and

Z is $CO_2H$ or $CONR^{12}R^{13}$ (especially where $R^{12}$ and $R^{13}$ are independently hydrogen, optionally substituted aryl or optionally substituted cycloheteroalkyl).

DETAILED DESCRIPTION OF THE INVENTION

Compounds of the invention of general structure I may be synthesized as illustrated in the schemes set forth below.

Scheme 1

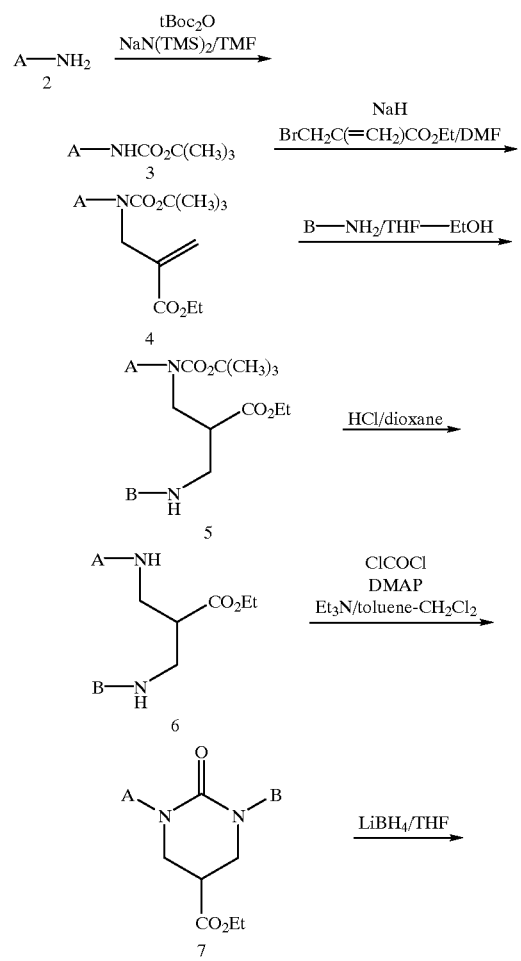

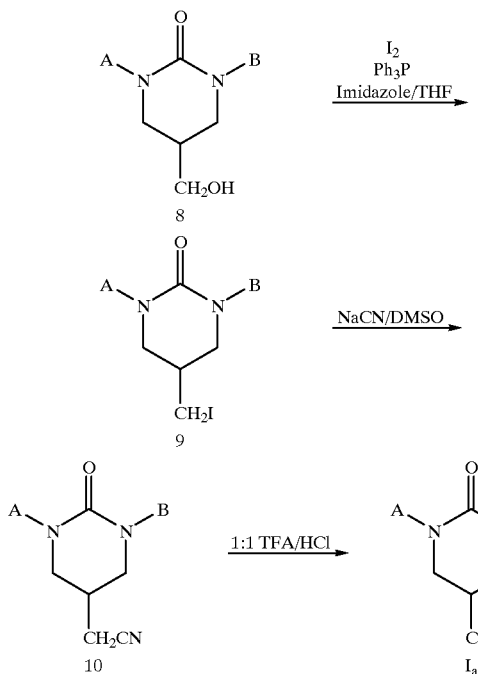

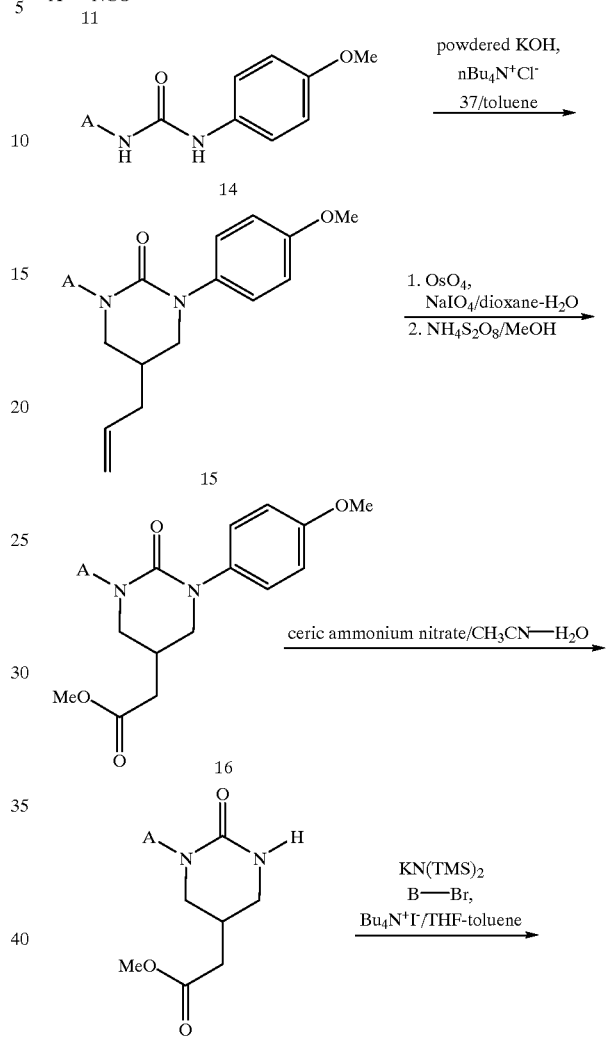

Amine 2 is converted to carbamate 3 followed by alkylation with 3-bromomethacrylate to provide 4. Congugate addition of 4 with the desired amine provides 5. Removal of the Boc protecting group from 5, with 4 N HCl/dioxane, provides 6. Cyclization of 6, with phosgene and triethylamine, provides cyclic urea 7. Reduction of 7 with lithium borohydride provides alcohol 8 which is transformed into iodide 9 and then nitrile 10. Hydrolysis of 10 provides compound I$_a$.

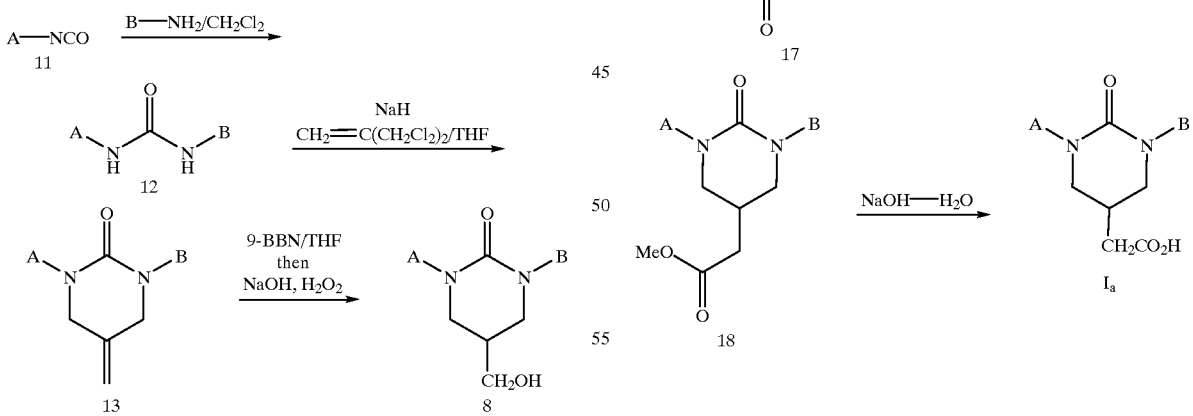

Alternatively, alchohol 80 can be synthesized from isocyanate 11 by treatment with an appropriate amine to form urea 12, which upon reaction with 2-chloromethyl-1-chloro-2-propene and two equivalents of sodium hydride provides cyclic urea intermediate 13. Hydroboration of 13 provides alchohol 8.

Alternatively I$_a$ can be formed from isocyanate 11 by treatment with para-anisole to provide urea 14. Phase-transfer catalyzed alkylation of 14 with the known bis-mesylate 37 (see scheme 4) provides cyclic urea 15. Cleavage of 15 and subsequent oxidation/methanolysis provides ester 16. Removal of the methoxyphenyl protecting group by known methods (e.g., ceric ammonium nitrate) provides 17. Reaction of 17 with an appropriate bromide provides 18 which upon saponification provides I$_a$.

Scheme 4

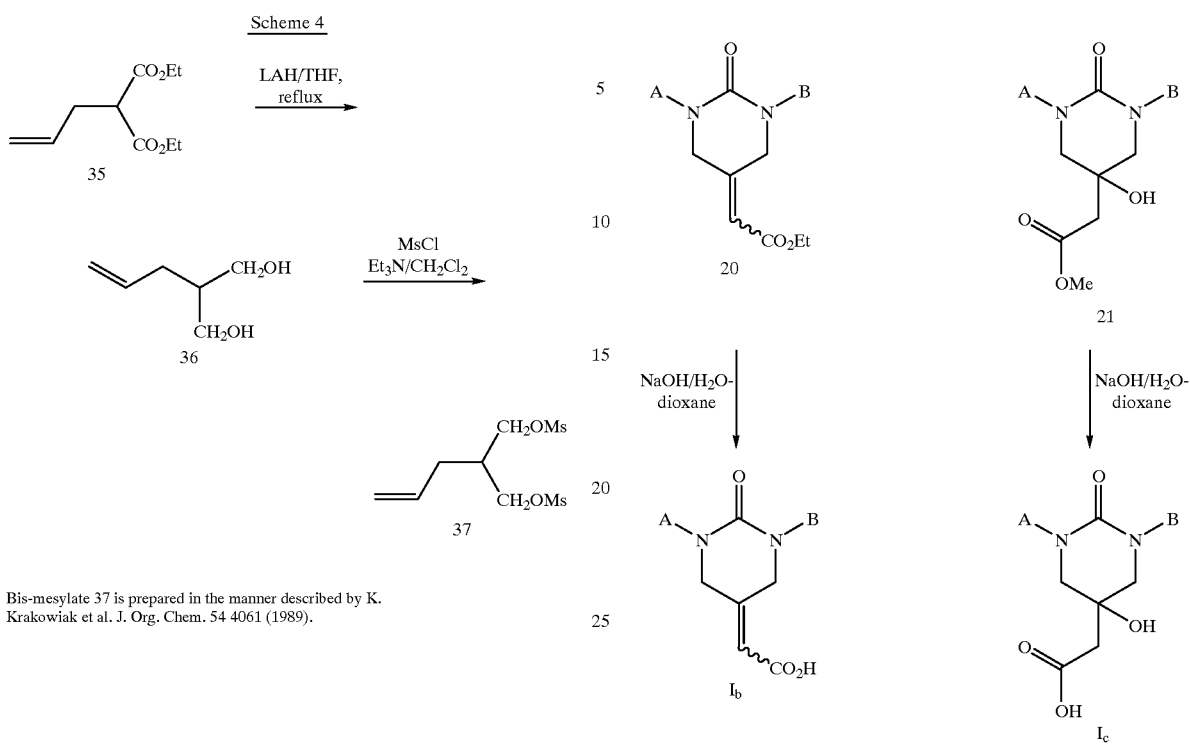

Bis-mesylate 37 is prepared in the manner described by K. Krakowiak et al. J. Org. Chem. 54 4061 (1989).

Additional compounds within formula I can be generated from compounds disclosed in schemes 1 through 3 through conversion of the substituent groups to other functionality by the usual methods of chemical synthesis, as illustrated in the following schemes 5 through 16, and the following examples. In generating such additional compounds one skilled in the art will recognize that it may be necessary to protect reactive functionality such as hydroxy, amino, thio or carboxy groups, where these are desired in the final product, to avoid their unwanted participation in reactions. The introduction and removal of protecting groups are well known to those skilled in the art (for example see Green, T. W., "Protective Groups in Organic Synthesis", John Wiley and Sons 1991).

Scheme 5

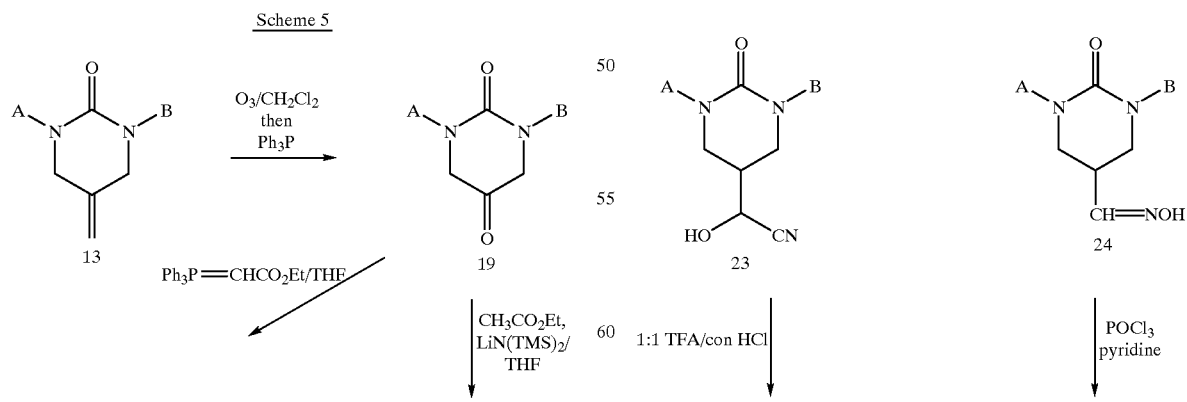

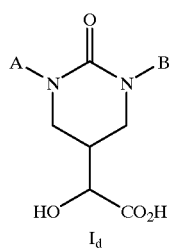
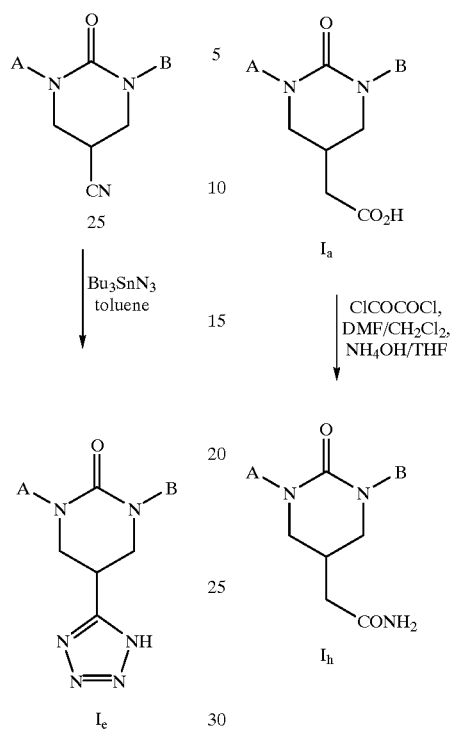
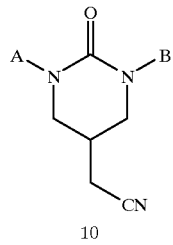
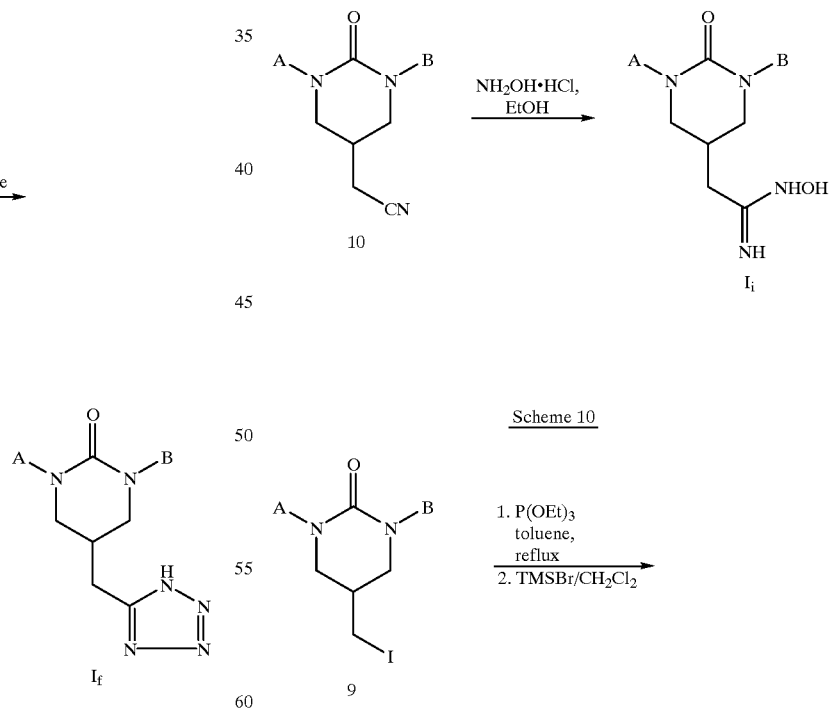

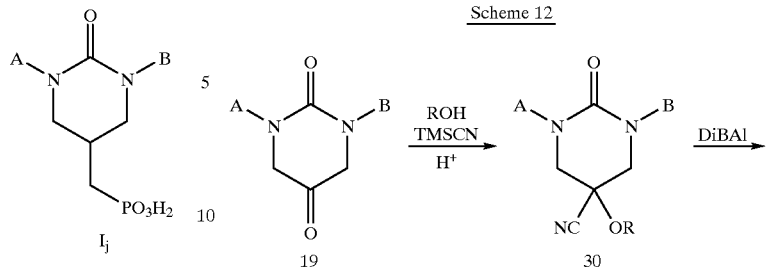
Scheme 11
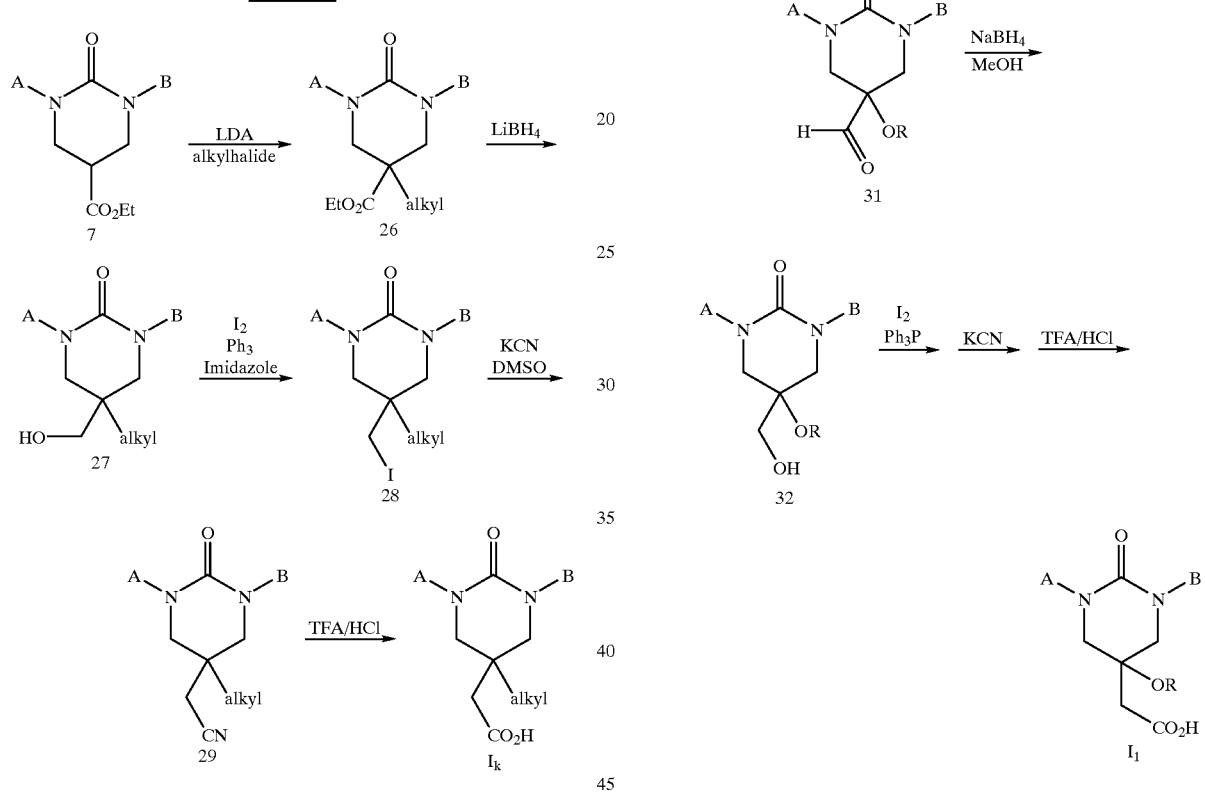
Scheme 12
Scheme 13
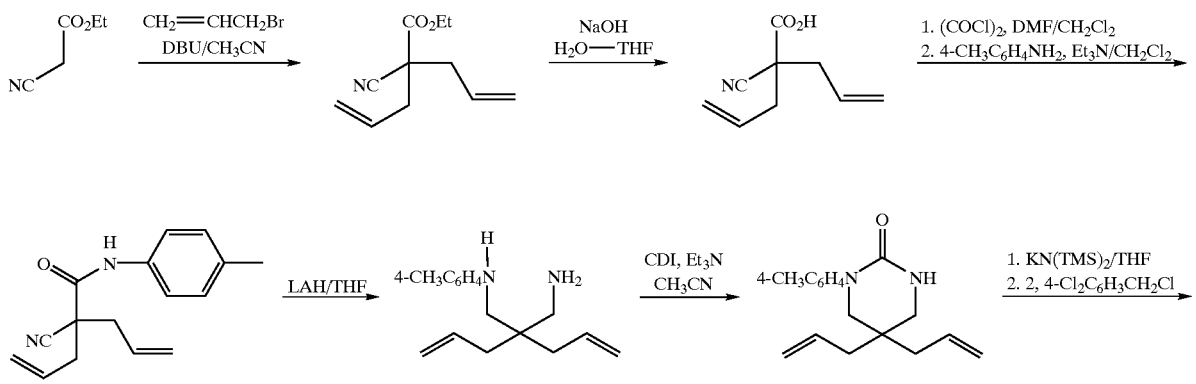

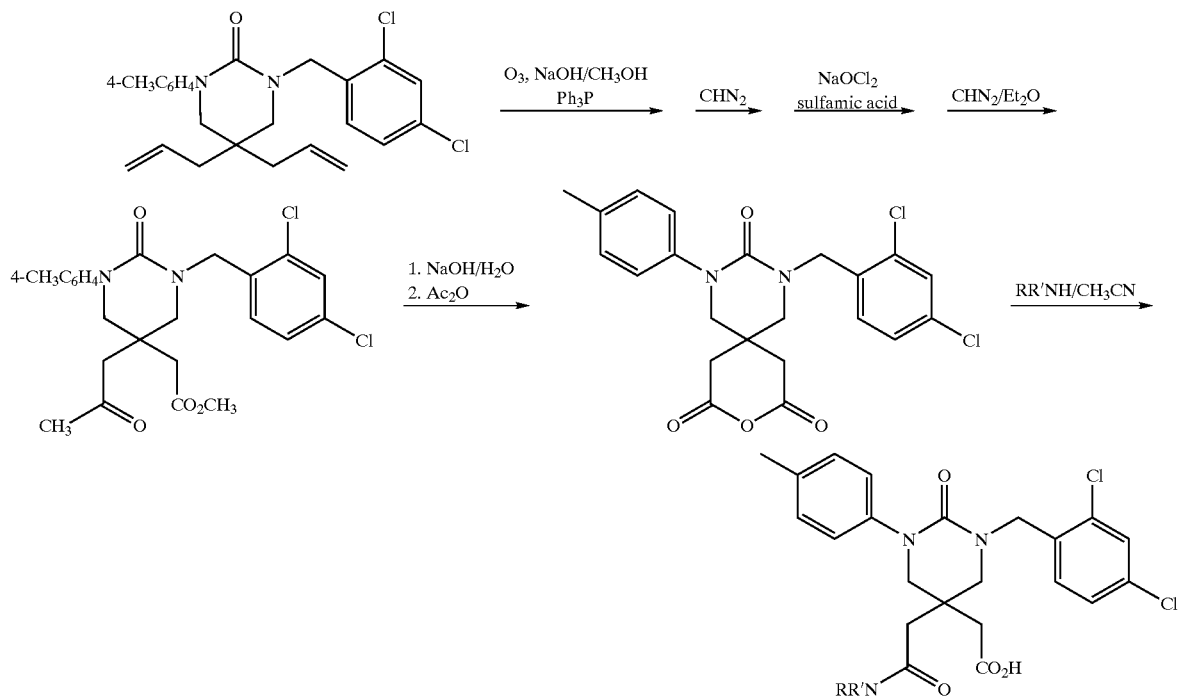
Scheme 14
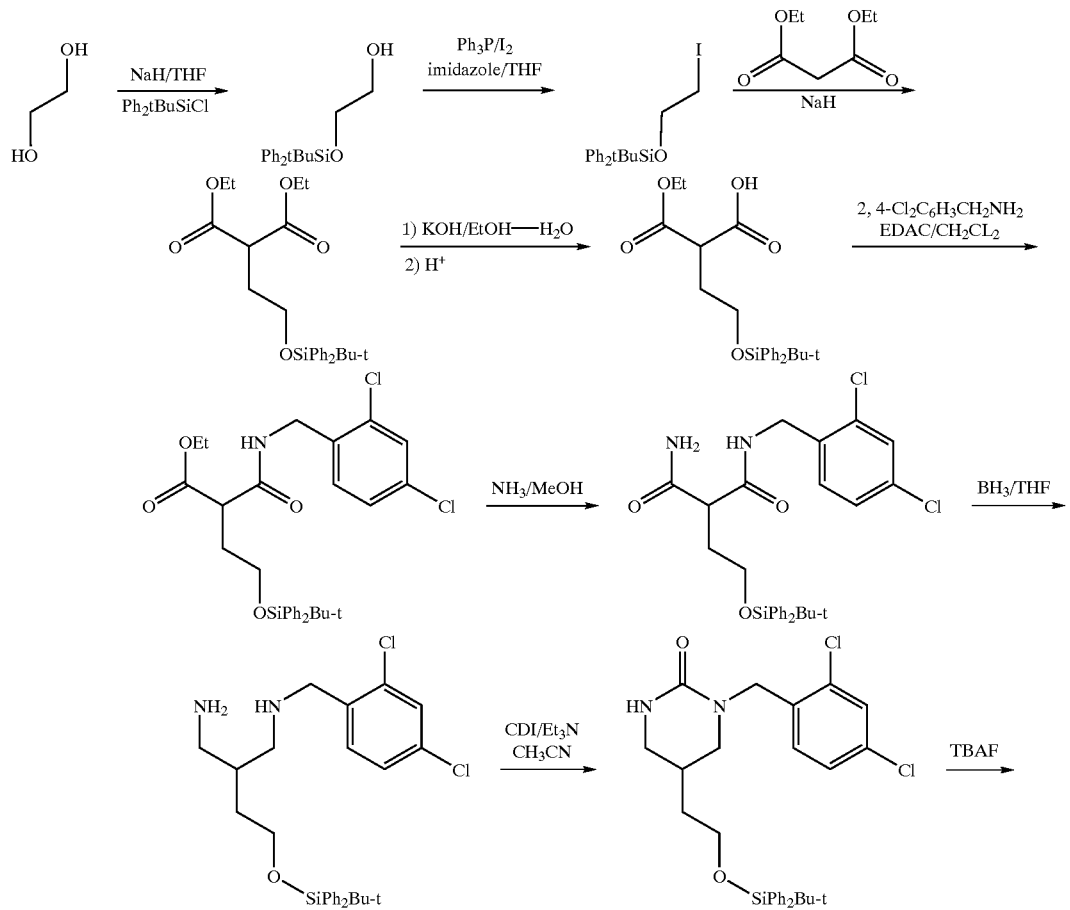

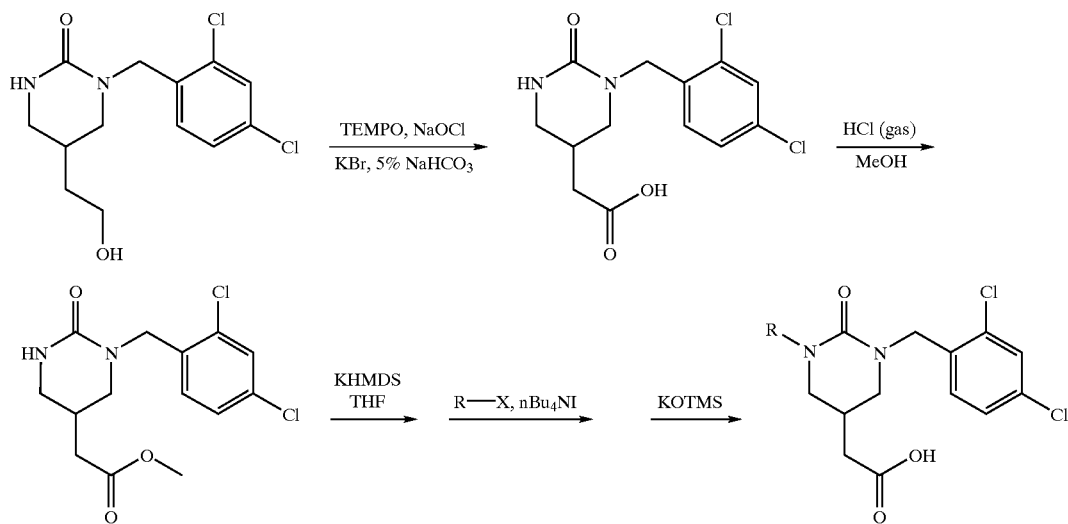
Scheme 15
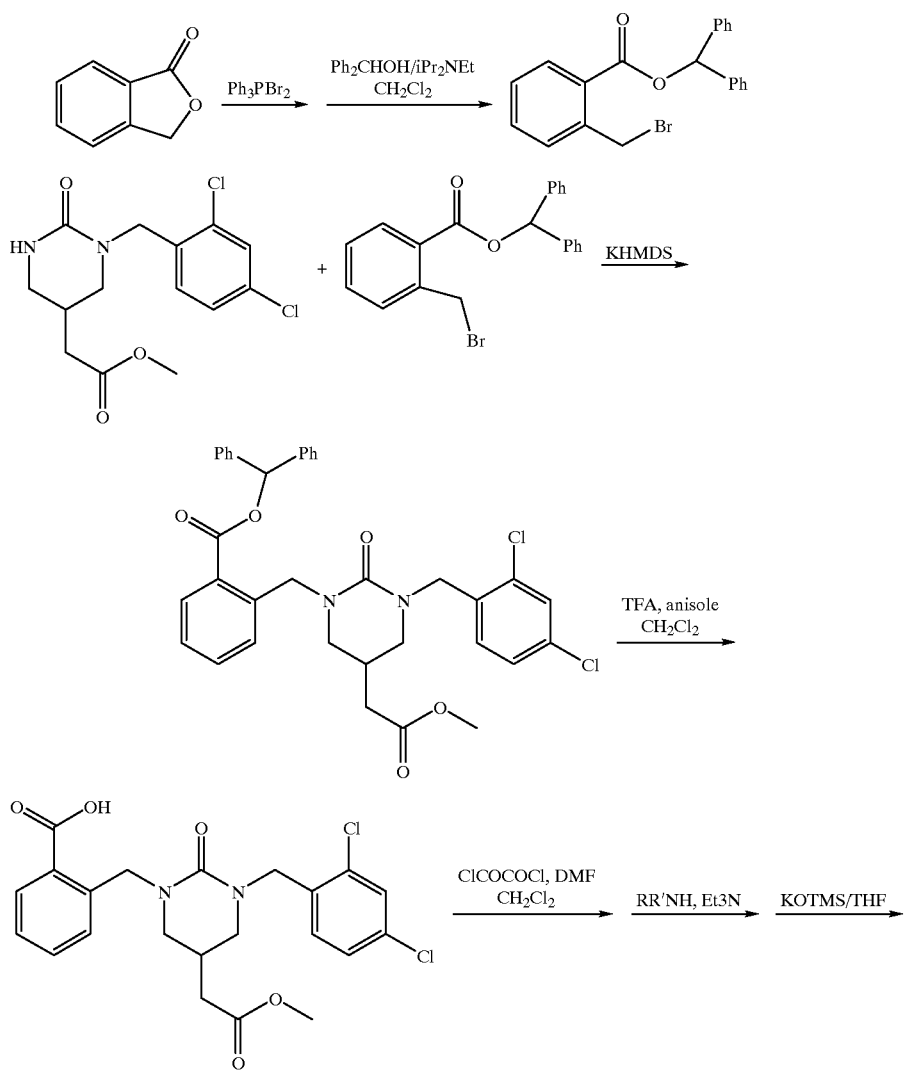

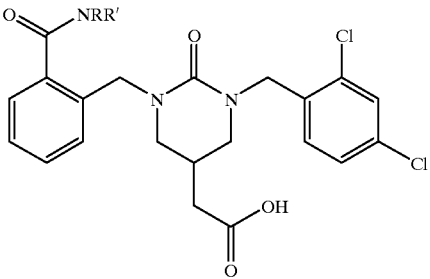

Scheme 16

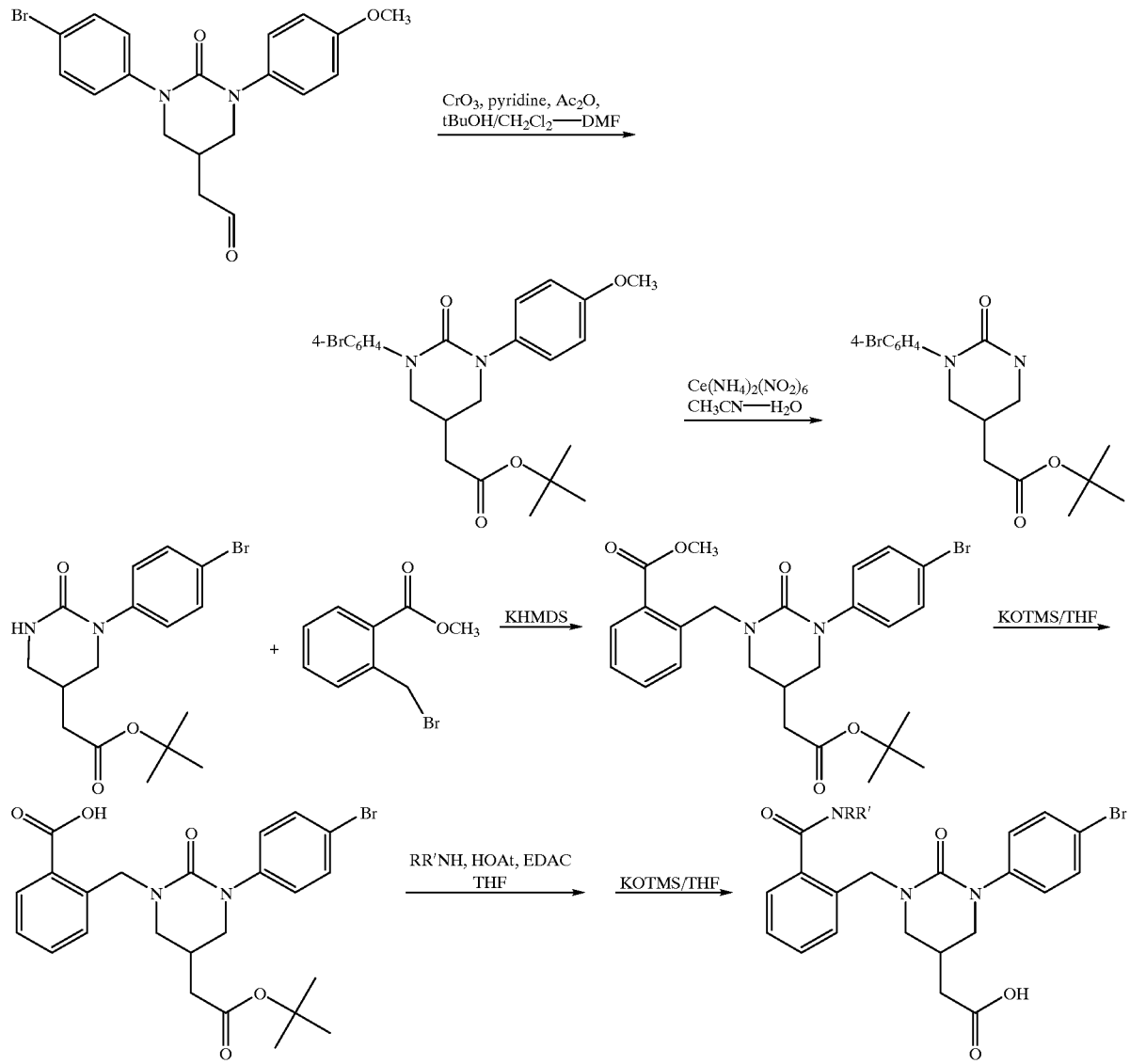

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkoxy, (alkoxy)alkoxy, alkoxyalkyl, (hydroxy)alkoxyalkyl, (alkoxy)

alkoxyalkyl, aryl, aryloxy, (aryl)aryl or diaryl, (aryl) alkoxyaryl, diaryl, arylalkyl, (aryl)alkoxy, (aryl) alkoxyalkyl, (aryloxy)aralkyl, alkenyl, cycloalkyl, cycloalkylalkyl, cycloalkylalkyloxy, amino, substituted amino, alkylamino, hydroxy, hydroxyalkyl, hydroxycarbonyl, alkylcarbonyl, alkoxycarbonyl, arylcarbonyl, acyl, cycloheteroalkyl, (cycloheteroalkyl) alkyl, heteroaryl, heteroaryloxy, heteroarylalkyl, heteroarylalkoxy, aryloxyalkyl, aryloxyaryl, (amino) carbonyl, (substituted amino)carbonyl, alkanoylamino, arylcarbonylamino, nitro, cyano, thiol, haloalkyl, trihaloalkyl and/or alkylthio (where the alkyl radical is optionally substituted), arylthio (where the aryl radical is optionally substituted), sulfonylaryl and/or any of the $R^1$ groups. Where particular substituted alkyl groups are identified herein they are named by adding the term "alkyl" at the end of the name of the substituent radical (e.g., aralkyl, heteroaralkyl etc.).

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, or joined by spiro union to other cycloalkyl rings or heterocycloalkyl rings. Cycloalkyl rings include cyclopropyl, cyclobutyl, cyclopentyl, cyclohexyl, cycloheptyl, cyclooctyl, cyclodecyl and cyclododecyl, cyclohexenyl,

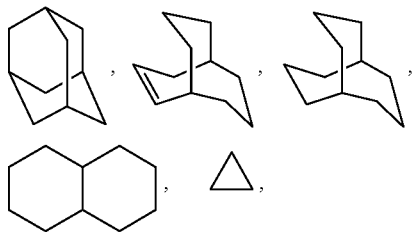

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the $R^1$ groups.

The term "cycloalkenyl" as employed herein alone or as part of another group refers to cyclic hydrocarbons containing 3 to 12 carbons, preferably 5 to 10 carbons and 1 or more double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

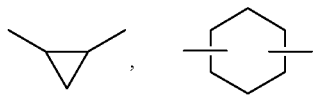

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituent groups.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_x$ or $(CH_2)_y$ (where, y is 1 to 8, preferably 1 to 5, and x is 1 to 5, preferably 1 to 3, which includes alkylene, alkenylene or alkynylene groups) as defined herein, may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino or alkylcarbonyloxy.

Examples of $(CH_2)_x$ or $(CH_2)_y$, alkylene, alkenylene and alkynylene include

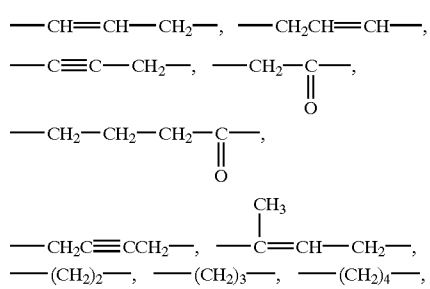

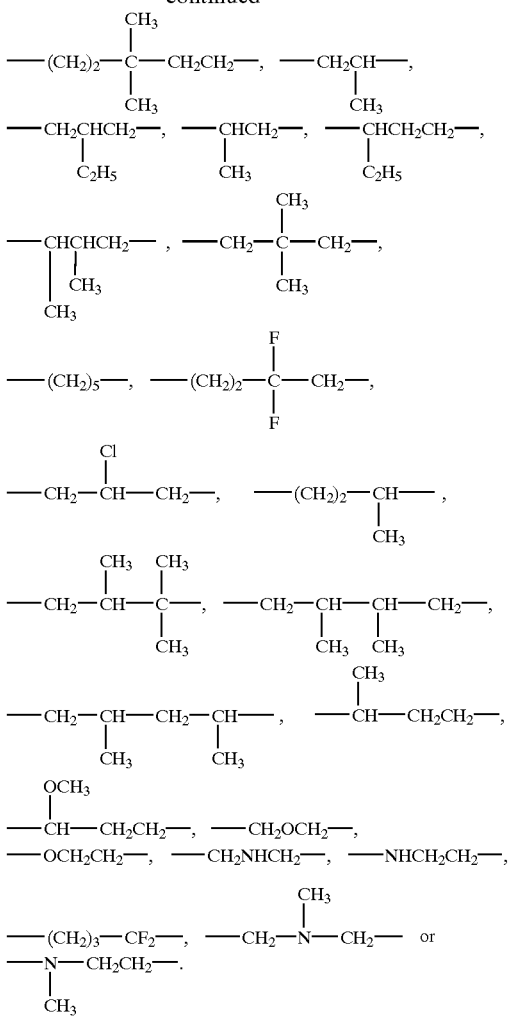

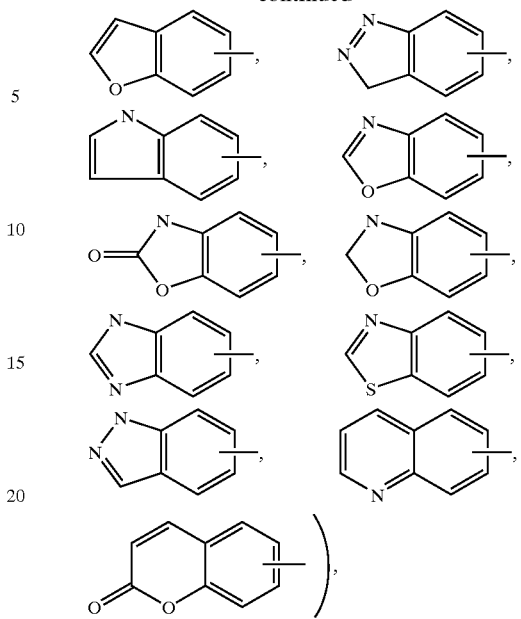

The term "halogen" or "halo" as used herein alone or as part of another group refers to chlorine, bromine, fluorine, and iodine as well as $CF_3$, with chlorine, bromine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the terms "aryl" or "ar" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

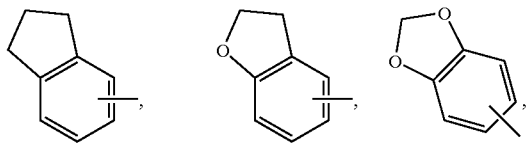

and may be optionally substituted through available carbon atoms with 1, 2, or 3 groups selected from hydrogen, halo, haloalkyl, alkyl, substituted alkyl, alkoxy, haloalkoxy, alkenyl, trifluoromethyl, trifluoromethoxy, alkynyl, cycloalkyl, (cycloalkyl)alkyl, cycloheteroalkyl, cycloheteroalkylalkyl, aryl, substituted aryl, heteroaryl, substituted heteroaryl, (aryl)alkyl, aryloxy, (aryloxy)alkyl, (aryl)alkoxy, arylthio, arylazo, heteroarylalkyl, heteroarylalkenyl, heteroarylheteroaryl, heteroaryloxy, hydroxy, nitro, cyano, amino, substituted amino, thiol, alkylthio, arylthio, heteroarylthio, arylthioalkyl, alkoxyarylthio, alkylcarbonyl, arylcarbonyl, aminocarbonyl, (substituted amino)carbonyl, (alkyl)aminocarbonyl, (substituted alkyl)aminocarbonyl, (aryl)aminocarbonyl, (substituted aryl)aminocarbonyl, alkoxycarbonyl, (amino) alkoxycarbonyl, (substituted amino)alkoxycarbonyl, alkylcarbonyloxy, arylcarbonyloxy, alkylcarbonylamino, arylcarbonylamino, arylsulfinyl, arylsulfinylalkyl, arylsulfonylamino or arylsulfonylaminocarbonyl, sulfonylaryl, (alkyl)sulfonylaryl, sulfonylarylalkyl, (alkyl) sulfonylaralalkyl, and/or any of the $R^1$ groups.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl (optionally substituted), aryl (optionally substituted), arylalkyl (optionally substituted), arylalkyl (optionally substituted), heteroaryl (optionally substituted), heteroarylalkyl (optionally substituted), cycloheteroalkyl (optionally substituted), (cycloheteroalkyl)alkyl (optionally substituted), cycloalkyl (optionally substituted), cycloalkylalkyl (optionally substituted), haloalkyl (optionally substituted), hydroxyalkyl (optionally substituted), alkoxyalkyl (optionally substituted) or thioalkyl (optionally substituted). In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1- piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, substituted alkyl, alkoxy, alkylthio, halo, trifluoromethyl, hydroxy, aryl or substituted aryl.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl group

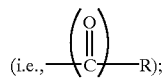

examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like. Such groups may also be identified by adding the term "carbonyl" at the end of the name of the organic radical R bonded to the acyl group (e.g., alkylaminocarbonyl, alkoxycarbonyl, etc).

Unless otherwise indicated, the term "cycloheteroalkyl" as used herein alone or as part of another group refers to a 5-, 6- or 7-membered saturated or partially unsaturated ring which includes 1 or more hetero atoms such as nitrogen, oxygen and/or sulfur, linked through a carbon atom or a heteroatom, where possible, optionally via the linker $(CH_2)_x$, such as

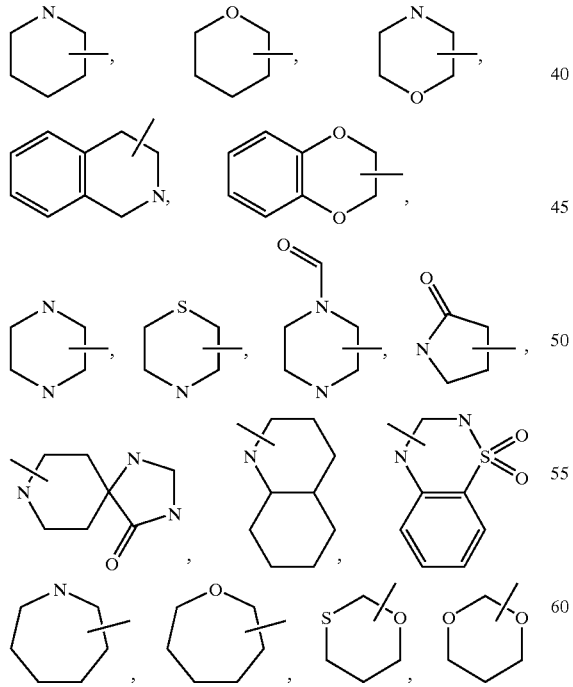

and the like. The above groups may include 1 to 4 substituents such as alkyl, substituted alkyl, halo, oxo, aryl, substituted aryl, aralkyl, substituted aralkyl and/or any of the $R^1$ groups. In addition, any of the cycloheteroalkyl rings can be fused to a cycloalkyl, aryl, heteroaryl or cycloheteroalkyl ring. In addition, any of the cycloheteroalkyl rings can be joined by spiro union to cycloalkyl rings or other heterocycloalkyl rings.

Unless otherwise indicated, the term "heteroaryl" as used herein alone or as part of another group refers to monocyclic and bicyclic aromatic rings containing from 5 to 10 atoms, which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), where the nitrogen and sulfur heteroatoms may optionally be oxidized and the nitrogen heteroatoms may optionally be quaternized. The heteroaryl group may optionally include 1 to 4 substituents such as halo, haloalkyl, alkyl, substituted alkyl, alkoxy, haloalkoxy, alkenyl, trifluoromethyl, trifluoromethoxy, alkynyl, cycloalkyl, cycloalkyl-alkyl, cycloheteroalkyl, cycloheteroalkylalkyl, aryl, substituted aryl, heteroaryl, substituted heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonylaminocarbonyl, sulfonylaryl, sulfonylarylalkyl, and/or any of the $R^1$ groups. Examples of heteroaryl groups include the following:

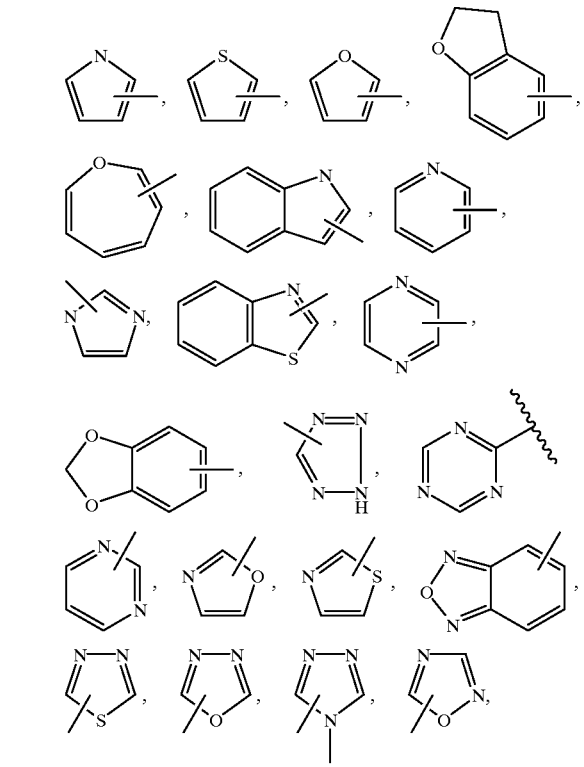

-continued

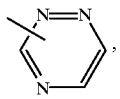

and the like.

The term "cycloheteroalkylalkyl" as used herein alone or as part of another group refers to cycloheteroalkyl groups as defined above linked through a C atom or heteroatom to a $(CH_2)_x$ chain.

The term "heteroarylalkyl" or "heteroarylalkenyl" as used herein alone or as part of another group refers to a heteroaryl group as defined above linked through a C atom or heteroatom to a —$(CH_2)_x$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for carboxylic acids such as similar carboxylic acid esters such as methyl, ethyl benzyl and the like. Other examples include the following groups: (1-alkanoyloxy)alkyl such as,

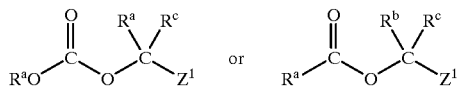

wherein $R^a$, $R^b$ and $R^c$ are H, alkyl, aryl or aryl-alkyl; however $R^aO$ cannot be HO, and where $Z^1$ is

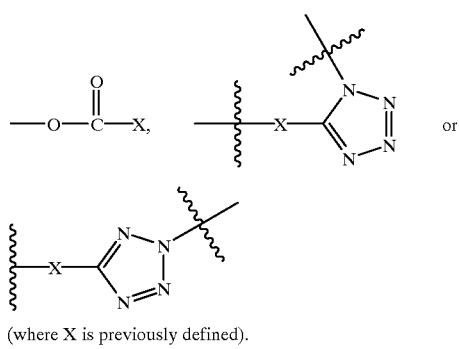

(where X is previously defined).

Examples of such prodrug esters include

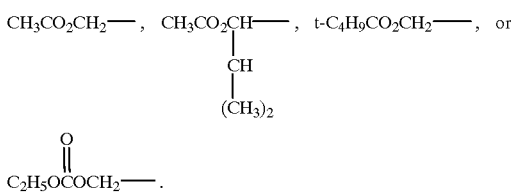

Other examples of suitable prodrug esters include

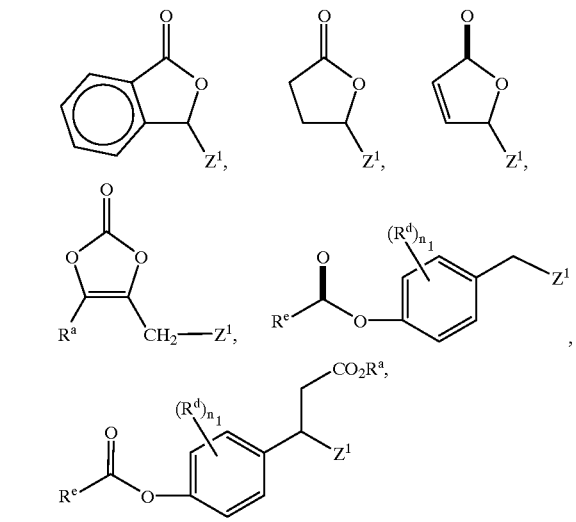

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains a both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

To the extent that compounds of the formula I, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. When diastereomeric or enantiomeric products are prepared, they can be separated by conventional methods for example, chromatographic or fractional crystallization.

Where desired, the compounds of structure I may be used in combination with one or more other types of therapeutic agents which may be administered orally in the same dosage form, in a separate oral dosage form or by injection.

The other type of therapeutic agent which may be optionally employed in combination with the aP2 inhibitor of formula I may be 1, 2, 3 or more antidiabetic agents or antihyperglycemic agents including insulin secretagogues or insulin sensitizers, or other antidiabetic agents preferably having a mechanism of action different from aP2 inhibition and may include biguanides, sulfonyl ureas, glucosidase inhibitors, glycogen phosphorylase inhibitors, PPAR γ agonists, such as thiazolidinediones, SGLT2 inhibitors, PPAR α/γ dual agonists, dipeptidyl peptidase IV (DP4) inhibitors, and/or meglitinides, as well as insulin, and/or glucagon-like peptide-1 (GLP-1).

It is believed that the use of the compounds of structure I in combination with another antidiabetic agent produces antihyperglycemic results greater than that possible from each of these medicaments alone and greater than the combined additive anti-hyperglycemic effects produced by these medicaments.

The other antidiabetic agent may be an oral antihyperglycemic agent preferably a biguanide such as metformin or phenformin or salts thereof, preferably metformin HCl.

Where the other antidiabetic agent is a biguanide, the compounds of structure I will be employed in a weight ratio to biguanide within the range from about 0.01:1 to about 100:1, preferably from about 0.1:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.5:1 to about 50:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.1:1 to about 10:1.

The sulfonyl urea and insulin sensitizer in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylen) and LY-315902 (Lilly), which may be administered via injection, intranasal, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. provisional application No. 60/155,400, filed Sep. 22, 1999, the disclosure of which is incorporated herein by reference, employing dosages as set out therein, which compounds designated as preferred are preferred for use herein.

The other antidiabetic agent may be an SGLT2 inhibitor such as disclosed in U.S. provisional application No. 60/158,773, filed Oct. 12, 1999, employing dosages as set out herein. Preferred are the compounds designated as preferred in the above application.

The other antidiabetic agent may be a DP4 inhibitor such as disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The aP2 inhibitor of formula I will be employed in a weight ratio to the meglitinide, PPAR γ agonist, PPAR α/γ dual agonist, SGLT2 inhibitor or DP4 inhibitor within the range from about 0.01:1 to about 100:1, preferably from about 0.2:1 to about 10:1.

The compounds of structure I may also be employed in combination with one or more hypolipidemic agent, lipid-lowering agent or other lipid agent. The hypolipidemic agent, lipid-lowering agent or other lipid agent which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, bile acid sequestrants, nicotinic acid and derivatives thereof, and/or cholesterol ester transfer protein inhibitors such as CP-529414 (Pfizer).

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

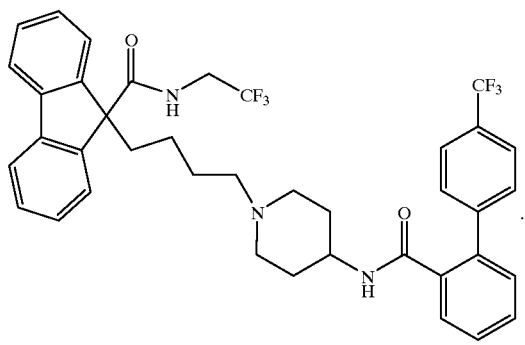

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, atavastatin (Nissan/Sankyo's nisvastatin (NK-104)) disclosed in U.S. Pat. No. 5,011,930, Shionogi-Astra/Zeneca rosuvastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl)

phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, C1–1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

Preferred hypolipidemic agents are pravastatin, lovastatin, simvastatin, atorvastatin, fluvastatin, cerivastatin, atavastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties, Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The other type of therapeutic agent which may be optionally employed with the aP2 inhibitor of formula I may be 1, 2, 3 or more of an anti-obesity agent including a beta 3 adrenergic agonist, a lipase inhibitor, a serotonin (and dopamine) reuptake inhibitor, a thyroid receptor beta drug and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor beta compound which may be optionally employed in combination with a compound of formula I may be a thyroid receptor ligand as disclosed in WO97/21993 (U. Cal SF), WO99/00353 (KaroBio) and GB98/284425 (KaroBio), with compounds of the KaroBio applications being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The other type of therapeutic agent which may be optionally employed with the aP2 inhibitor of formula I may be 1, 2, 3 or more of an antihypertensive agent including an ACE inhibitor, a vasopeptidase inhibitor, an angiotensin II antagonist, a calcium channel blocker, a potassium channel opener, an alpha-blocker, a beta blocker, a centrally acting alpha agonist, and/or a diuretic.

The ACE inhibitor which may be optionally employed in combination with a compound of formula I may be lisinopril, enalapril, quinapril, benazepril, fosinopril, fentiapril, ramipril, captopril, enalaprilat, moexipril, tranolapril, perindopril, ceranopril, zofenopril or cetapril.

Preferred ACE inhibitors are captopril, as well as fosinopril, enalapril, lisinopril, quinapril, benazepril, fentiapril, ramipril, and moexipril.

The vasopeptidase inhibitor (also known as NEP/ACE inhibitors) which may be optionally employed with the aP2 inhibitor of formula I may be omapatrilat (most preferred) and [S-(R*,R*)]-hexahydro-6-[(2-mercapto-1-oxo-3-phenylpropyl)amino]-2,2-dimethyl-7-oxo-1H-azepine-1-acetic acid (BMS 189,921 also preferred), as well as those disclosed in U.S. Pat. Nos. 5,362,727, 5,366,973, 5,225,401, 4,722,810, 5,223,516, 4,749,688. U.S. Pat. Nos. 5,504,080, 5,552,397, 5,612,359, 5,525,723, European Patent Application 0599,444, 0481,522, 0599,444, 0595,610, European Patent Application 0534363.A2, 534,396 and 534,492, and European Patent Application 0629627.A2.

Preferred are those NEP/ACE inhibitors which are designated as preferred in the above patents/applications which U.S. patents/applications are incorporated herein by reference.

The angiotensin II receptor antagonist (also referred to herein as angiotensin II antagonist or AII antagonist) which may be optionally employed in combination with a compound of formula I may be irbesartan, losartan, valsartan, candesartan, telmisartan, tasosartan and/or eprosartan, with irbesartan or losartan being preferred.

The calcium channel blocker (also referred to as a calcium antagonist) which may be optionally employed in combination with a compound of formula I may be amlodipine, diltiazem, nifedipine, verapamil, feldodipine, nisoldipine, isradipine and/or nicardipine, with amlodipine, diltiazem, verapamil and nifedipine being preferred.

The alpha-blocker which may be optionally employed in combination with a compound of formula I may be terazosin, doxazosin or prazosin, all of which are preferred.

The beta-blocker which may be optionally employed in combination with a compound of formula I may be nadolol, atenolol, propranolol, metoprolol, carvediol or sotalol, with atenolol and nadolol being preferred.

The potassium channel opener which may be optionally employed in combination with a compound of formula I may be minoxidil.

The centrally acting cc agonist antihypertensive agent which may be optionally employed in combination with a compound of formula I may be clonidine or guanfacine, with clonidine being preferred.

The diuretic which may be optionally employed in connection with a compound of formula I may be hydrochlorothiazide, torasemide, furosemide, spironolactone and/or indapamide, with hydrochlorothiazide and furosemide being preferred.

The antiplatelet agent (also known as platelet aggregation inhibitor) which may be optionally employed in combination with a compound of formula I may be aspirin, clopidogrel, ticlopidine, dipyridamole, abciximab, tirofiban, eptifibatide, anagrelide and/or ifetroban, with aspirin and clopidogrel being preferred.

The anti-infective agent which may be optionally employed in combination with a compound of formula I may be an anti-infective that is effective against chlamydial infections, such as azithromycin, gatifloxacin, ciprofloxacin, levofloxacin and trovafloxacin, with azithromycin and gatifloxacin being preferred.

The various antihypertensive agents and antiplatelet agents and anti-infective agents described above may be employed in the same dosage form with the compound of formula I or in different dosage forms, in dosages and regimens as generally known in the art or in the PDR.

In carrying our the method of the invention, a pharmaceutical composition will be employed containing the compounds of structure I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 20 and 2,000 mg per day, which can be administered in a single dose or in the form of individual doses from 1–4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

aP2 inhibitor activity of the compounds of the invention may be determined by use of an in vitro assay system which measures the potentiation of inhibition of aP2 by displacement of a fluorescent substrate from aP2 by the inhibitor. Inhibition constants (Ki values) for the aP2 inhibitors of the invention may be determined by the method described below:

Production of purified recombinant human aP2 protein. Recombinant human aP2 protein is produced by standard recombinant DNA technology. In the typical case, aP2 is produced by heterologous expression in E. coli strain BL21 (D53) transformed with pETlla vector containing the full length human aP2 cDNA (Baxa, C. A., Sha, R. S., Buelt, M. K., Smith, A. J., Matarese, V., Chinander, L. L., Boundy, K. L., and Bernlohr, D. A. (1989). Human adipocyte lipid-binding protein: purification of the protein and cloning of its complementary DNA. Biochemistry 28: 8683–8690 and Xu, Z., Buelt, M. K., Banaszak, L. J., and Bernlohr, D. A. (1991). Expression, purification and crystallization of the adipocyte lipid binding protein. J. Biol. Chem. 266:14367–14370). Purification of aP2 from E. coli is conducted as described by Xu, yielding essentially homogeneous aP2 protein with molecular weight ~14600 daltons and free of endogenous fatty acids. The purified aP2 is capable of binding up to one mole of free fatty acid per mole protein. The binding and structural properties of recombinant aP2 protein were previously shown to be identical to aP2 protein isolated from adipose tissue.

In vitro assay of aP2 inhibitors. Inhibitors of aP2 are evaluated in a homogeneous fluorescent-based competition assay using recombinant aP2 protein and 1,8-anilinonaphthalene-sulfonic acid (1,8-ANS) as assay substrate. This competition assay was adapted from generalized procedures described previously (Kane, C. D. and Bernlohr, D. A. (1996). A simple assay for intracellular lipid-binding proteins using displacement of 1-anilino-8-sulfonic acid. (1996) Anal. Biochem. 233:197–204 and Kurian E., Kirk, W. R. and Prendergast, F. G. (1996) Affinity of fatty acid for r-rat intestinal fatty acid binding protein. Biochemistry, 35, 3865–3874). The method relies on the increase in fluorescence quantum yield of 1,8-ANS upon binding to the fatty acid binding site of aP2. The assay is run using appropriate concentrations of inhibitor, 1,8-ANS, and aP2 protein, in order to calculate the inhibitor binding constant (Ki) for compounds being evaluated. The Ki calculation was based on the procedure previously described for calculation of dissociation constants described by Kurian. Lower Ki values indicate higher affinities of compounds binding to aP2.

In the assay as conducted for the inhibitors described herein, a series of aliquots of aP2 (5 $\mu$M) in solution in 10 mM potassium phosphate buffer (pH 7.0) are mixed with an equimolar concentration of test compound, followed by the addition of a series of increasing concentrations of 1,8-ANS (from 0 to 5 $\mu$M). The assay typically is conducted in 96-well plate format with reagents added using robotic instrumentation (Packard Multiprobe 104). The fluorescence value for each test is determined using a Cytofluor-4000 multi-well fluorescence plate reader (Perceptive Biosystems) using excitation wavelength 360 nm and emission wavelength 460 nm, or using other suitable spectrofluorometer. In preparation for the assay, test compounds are initially prepared at 10 mM in dimethylsulfoxide. All subsequent dilutions and assay additions are made in 10 mM potassium phosphate buffer, pH 7.0.

X-ray crystallography of the inhibitor-aP2 complex can be performed by one skilled in the art using contemporary biophysical methodologies and commercial instrumentation. Such crystallographic data can be used to conclusively determine if a compound used in the present invention has embodied the structural requirement necessary for inhibition of aP2. An example of such an X-ray crystallographic determination is presented below:

Crystals of aP2 complexed with the inhibitors were typically grown by the hanging drop method. aP2, at 8.3 mg/ml, was pre-equilibrated with 1–5 mM of the inhibitor in 0.1 M Tris-HCl pH 8.0, 1% w/v DMSO for four hours. 2 $\mu$l drops containing equilibrated protein and reservoir solution at a 1:1 ratio were suspended on plastic cover slips and equilibrated against a 1 ml reservoir containing 2.6–3.0M ammonium sulfate in 0.1 M Tris-HCl pH 8.0. Crystals typically appeared in 2–3 days and reached maximum size within 2 weeks. Data was typically collected on a single flash-frozen crystal (Oxford Cryosystems) using a Rigaku rotating anode and an R-axis II image plate detector of a Bruker multiwire area detector. Diffraction from aP2 crystals was excellent. Diffraction was consistently observed to better than 2.0 Å resolution often to beyond 1.5 Å resolution. Data was processed either with DENZO/SCALEPACK (R-axis II data), or Xengen (Bruker data). XPLOR was used for structure refinement and model building was done using the molecular modeling package CHAIN. After a single round of refinement, examination of the $F_o$-$F_c$ map typically allowed facile building of the inhibitor into aP2 binding cavity. Iterative fitting and refinement were continued until improvement was no longer seen in the electron density map or R-free.

The following Examples illustrate embodiments of the present invention, and are not intended to limit the scope of the claims. Abbreviations employed herein are defined below. Compounds of the Examples are identified by the example and step in which they are prepared (for example, "1A" denotes the title compounds of step A of Example 1), or by the example only where the compound is the title compound of the example (for example "4" denotes the title compound of Example 4).

9-BBN=9-borabicyclo[3.3.1]nonane
Calc=calculated
DiBAl=diisobutylaluminum hydride
DMAP=Dimethylaminopyridine
DMF=dimethylformamide
DMSO=dimethylsulfoxide
Et=ethyl
Fnd=found
h=hours
LC/MS=liquid chromatography/mass spectrometry
LDA=lithium diisopropylamide
Me=methyl
Ms=mesyl=methanesulfonyl OAc=acetate
Ph=phenyl
TFA=trifluoroacetic acid
THF=tetrahydrofuran
TMS=trimethylsilyl

EXAMPLE 1

1-(4-Bromophenyl)-3-[(2,4-dichlorophenyl)methyl]tetrahydro-5-(hydroxymethyl)-2(1H)-pyrimidinone

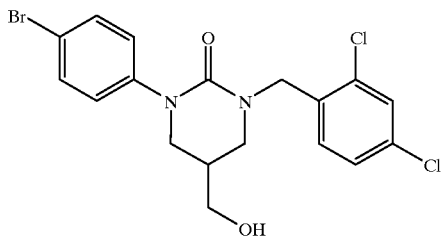

A.

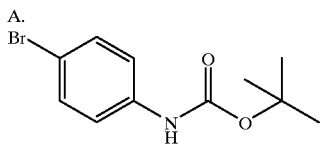

To a solution of 4-bromoaniline (1.72 g, 10.0 mmol) in THF (10 mL) at room temperature under nitrogen, was added a solution of sodium hexamethyldisilazide (22.0 mL, 1 M in THF, 22 mmol) over 10 min. A dark brown viscous solution formed. After 30 min, di-t-butyldicarbonate (2.4 g, 11 mmol) was added in one portion. The reaction was stirred for 4 h, quenched with 10% citric acid solution and extracted twice with $CH_2Cl_2$. The extracts were combined, dried ($Na_2SO_4$) and evaporated under reduced pressure to provide a red-brown semi-solid. Purification by flash chromatography on silica gel (5×20 cm column, 42:58 $CH_2Cl_2$/hexanes) gave 1A as a white solid, 1.73 g, (64% yield), mp 110–112° C. LC/MS gave the correct molecular ion [(M+H)$^+$=272] for the desired compound.

B.

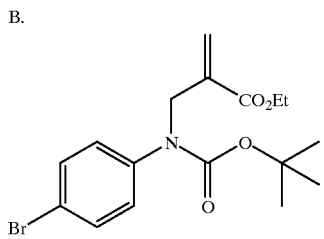

To a solution of 1A (1.58 g, 5.80 mmol) in DMF (3 mL) at room temperature under argon was added sodium hydride (240 mg, 60% mineral oil dispersion, 6.0 mmol) portionwise over 5 min. After 20 min more, the resulting light yellow solution was treated with ethyl 2-(bromomethyl) propenoate (1.0 mL, 7.25 mmol). A precipitate formed at once. After 10 min, the reaction was quenched with saturated $NH_4Cl$ solution and extracted twice with ether. The extracts were combined, dried ($Na_2SO_4$) and evaporated. Purification by flash chromatography on silica gel (5×20 cm column, 3:1 $CH_2Cl_2$/hexanes) gave 1B as a colorless oil, 1.90 g, (85% yield). LC/MS gave the correct molecular ion [(M+H)$^+$=384] for the desired compound.

C.

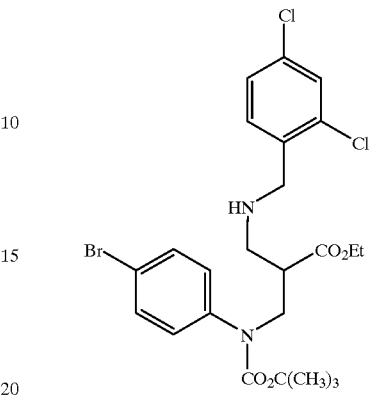

To a stirred solution of 1B (1.259 g, 3.28 mmol) in THF/EtOH (1:1, 8 mL) was added 2,4-dichlorobenzylamine (2.0 mL, 14.8 mmol) at 45° C. under argon. After 42 h, the reaction mixture was evaporated and the residue purified by flash chromatography on silica gel (5×20 cm column, 6:19 EtOAc/hexanes) to give the title compound as a colorless oil, 1.72 g, (94% yield). LC/MS gave the correct molecular ion [(M+H)$^+$=559] for the desired compound.

D.

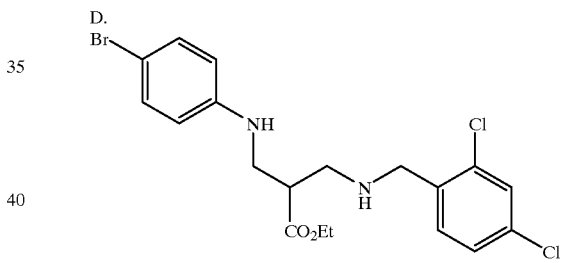

A solution of 1C (364 mg, 0.65 mmol) in 4 N HCl/dioxane (3 mL) was stirred at room temperature under argon for 4 h. The solution was evaporated and the residue partitioned between saturated $NaHCO_3$ solution and EtOAc. The organic extract was dried ($Na_2SO_4$) and evaporated to give 1D as a colorless oil, 299 mg, (100% yield). LC/MS gave the correct molecular ion [(M+H)$^+$=459] for the desired compound. The material was used without purification in the next reaction.

E.

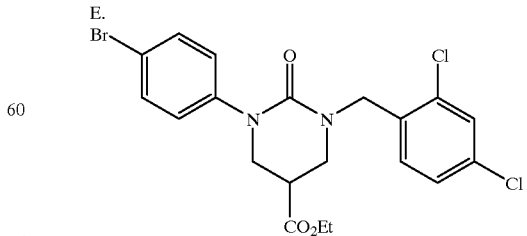

To a solution of 1D (299 mg, 0.65 mmol), triethylamine (212 μL, 1.52 mmol) and DMAP (7 mg, 0.06 mmol) in CH$_2$Cl$_2$ (3 mL) at 0° C. under argon was added phosgene solution (355 μL, 1.98 $\underline{M}$ in toluene, 0.70 mmol). The reaction mixture was stirred and warmed to room temperature. After 24 h, the reaction was quenched with saturated NaHCO$_3$ solution and extracted three times with EtOAc. The organic extracts were combined, dried, evaporated and purified by flash chromatography on silica gel ( 5×15 cm column, 1:9:10 Et$_2$O/hexanes/CH$_2$Cl$_2$) to give 1E as a white solid, 145 mg, (46% yield), mp 130–132° C. LC/MS gave the correct molecular ion [(M+H)$^+$=485] for the desired compound.

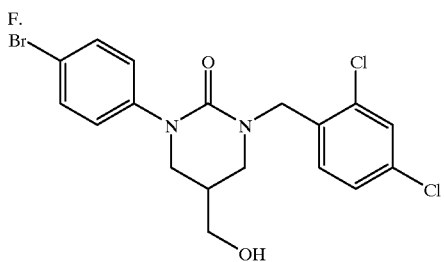

F.

To a solution of 1E (305 mg, 0.63 mmol) in CH$_2$Cl$_2$ (5 mL) at room temperature under argon, was added diisobutylaluminum solution (1.4 mL, 1 $\underline{M}$ in hexanes, 1.4 mmol). After 20 h, the reaction was treated with potassium sodium tartrate (10 mL, 1 $\underline{M}$) solution and stirred 1 h. The reaction mixture was extracted three times with dichloromethane. The organic extracts were combined, dried (MgSO$_4$) and evaporated. The residue was purified by flash chromatography on silica gel (5×15 cm column, 11:9 EtOAc/hexanes ) to give the title compound 1 as a colorless oil, 200 mg, (71% yield). LC/MS gave the correct molecular ion [(M+H)$^+$=443] for the desired compound.

EXAMPLE 2

Alternative Method 1-(4-Bromophenyl)-3-[(2,4-dichlorophenyl)methyl]tetrahydro-5-(hydroxymethyl)-2(1 H)-pyrimidinone

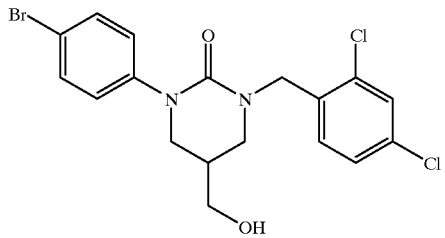

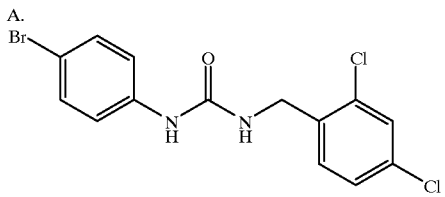

A.

To a stirred solution of 4-bromophenylisocyanate (4.95 g, 25.0 mmol) in CH$_2$Cl$_2$ (50 mL) at room temperature under N$_2$ was added a solution of 2,4-dichlorophenylmethylamine (3.36 mL, 25.0 mmol) in CH$_2$Cl$_2$ (10 mL) over 5 min. The reaction warmed autogenously as a white precipitate formed. After 2 h, the reaction was filtered, and the collected solids were washed with hexanes and dried in vacuo (60° C.) to give 2A as a white solid, 9.23 g (99% yield), mp 220–223° C. LC/MS gave the correct molecular ion [(M+H)$^+$=373] for the desired compound.

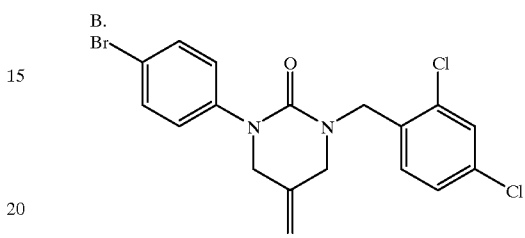

B.

To a stirred slurry of 2A (6.75 g, 18.0 mmol) in DMF (50 mL) at room temperature under N$_2$ was added NaH (60% oil dispersion, 1.48 g, 37.0 mmol) over 15 min. The slurry was heated to 50° C. and stirred for 30 min. To the resulting mixture was added 3-chloromethyl-3-chloro-1-propene (2.26 mL, 19.5 mmol) in one portion. A light yellow precipitate formed. After 2 h, the reaction mixture was cooled to room temperature, quenched with 5% potassium hydrogen sulfate solution and extracted twice with ether. The organic extracts were combined, washed twice with water, once with brine, dried (MgSO$_4$) and evaporated. Purification by flash chromatography on silica gel (12.5×30 cm column, CH$_2$Cl$_2$) provided 2B as a white solid, 6.10 g (80% yield), mp 122–124° C. LC/MS gave the correct molecular ion [(M+H)$^+$=425] for the desired compound.

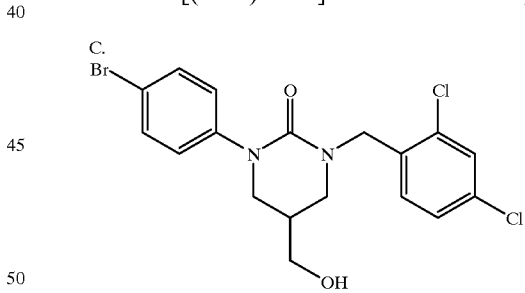

C.

To a solution of 2B (2.13 g, 5.00 mmol) in THF (5 mL) at room temperature under argon, was added 9-BBN solution (11 mL, 0.5 $\underline{M}$ in THF, 5.5 mmol). The reaction mixture was heated to reflux. After 14 h, the reaction was cooled to room temperature and treated with aqueous sodium hydroxide solution (2 mL, 3 $\underline{M}$) and then, cautiously, 30% hydrogen peroxide (2 mL) at a rate to keep the temperature below 40° C. After cooling to room temperature, the reaction was diluted with water and extracted twice with EtOAc. The organic extracts were combined, dried (MgSO$_4$) and evaporated. Recrystallization from EtOAc/hexanes gave the title compound 2 as a white solid, 2.03 g, (91% yield), mp 127–129° C. LC/MS gave the correct molecular ion [(M+H)$^+$=443] for the desired compound.

EXAMPLE 3

1-(4-Bromophenyl)-3-[(2,4-dichlorophenyl)methyl]
hexahydro-2-oxo-5-pyrimidineacetic acid

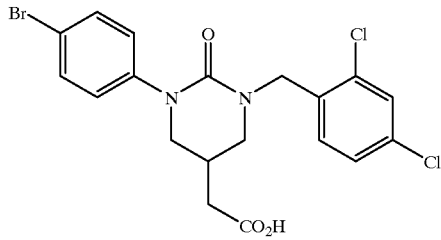

A.

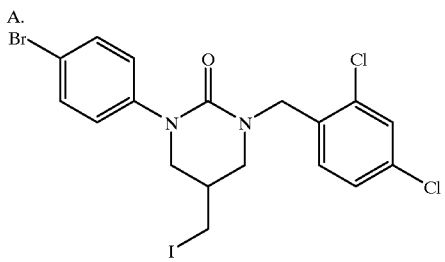

To a stirred solution of the title compound of Example 2 (204.5 mg, 0.460 mmol), imidazole (70 mg, 1.03 mmol) and triphenylphosphine (121 mg, 0.461 mmol) in THF (2 mL) at room temperature under $N_2$ was added a solution of iodine (117 mg, 0.461 mmol) in THF (1 mL) over 5 min. After 10 min, the light purple solution was quenched with 5% $NaHSO_3$ solution and extracted twice with ether (5 mL). The extracts were combined, dried ($MgSO_4$) and evaporated. Purification by flash chromatography on silica gel (5×7 cm column, $CH_2Cl_2$) gave 3A as a colorless oil, 190 mg (75% yield). LC/MS gave the correct molecular ion [(M+H)$^+$=553] for the desired compound.

B.

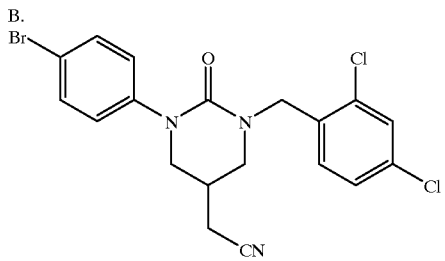

A stirred solution of 3A (190 mg, 0.35 mmol) and potassium cyanide (80 mg, 1.2 mmol) in DMSO (2 mL) was heated at 50° C. under $N_2$ for 8 h. The reaction mixture was cooled, added to water (20 mL) and extracted three times with ether (5 mL). The extracts were combined, washed with water and brine, dried ($MgSO_4$) and evaporated. Purification by flash chromatography on silica gel (2.5×15 cm column, 1:49 ether/$CH_2Cl_2$) gave 3B as a colorless oil, 131 mg (84% yield). LC/MS gave the correct molecular ion [(M+H)$^+$=452] for the desired compound.

C.

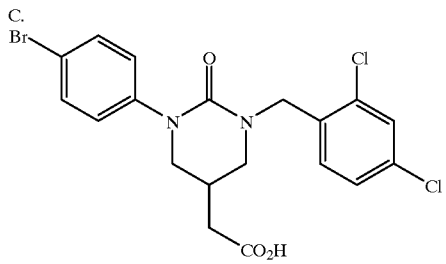

A stirred solution of 3B (578 mg, 1.28 mmol) in ethanol (5 mL) and concentrated HCl (5 mL) was heated at reflux under $N_2$ for 24 h. The reaction mixture was cooled, added to water (20 mL) and extracted twice with $CH_2Cl_2$ (20 mL). The extracts were combined, washed with water, dried ($MgSO_4$) and evaporated. The residuum was dissolved in THF (5 mL) and stirred with sodium hydroxide solution (1 M, 5 mL) for 1 h. The reaction mixture was diluted with water (10 mL) and extracted twice with ether (10 mL). The aqueous phase was treated with dilute hydrochloric acid (1 M, 5.5 mL) and extracted twice with $CH_2Cl_2$. The extracts were combined, dried ($MgSO_4$) and evaporated. Recrystallization (EtOAc/hexanes) provided the title compound 3 as a white solid, 499 mg (83% yield), mp 183–185° C. LC/MS gave the correct molecular ion [(M+H)$^+$=471] for the desired compound.

Elemental analysis for $C_{19}H_{17}N_2O_3BrCl_2$ Calc.% C, 48.33; H, 3.63; N, 5.93; Br, 16.92; Cl, 15.01. Fnd. C, 48.05; H, 3.56; N, 5.77; Br, 17.08; Cl, 15.15.

EXAMPLE 4

1-(4-Bromophenyl)-3-[(2,4-dichlorophenyl)methyl]
hexahydro-2-oxo-5-pyrimidineacetamide

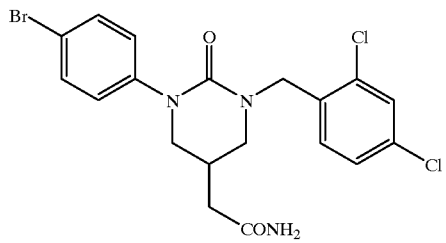

To a solution of the compound of Example 3 (23 mg, 0.049 mmol) in $CH_2Cl_2$ (1 mL) at room temperature under $N_2$ was added oxalyl chloride solution (2 M in $CH_2Cl_2$, 0.2 mL, 0.4 mmol) and then DMF (10 µL). After 2 h, the solution was evaporated. To the resulting oil was added $CH_2Cl_2$ (2 mL) and ammonium hydroxide (concentrated solution, 1 mL). After 1 h, the reaction was evaporated. Purification by flash chromatography on silica gel (2.5×7 cm column, 1:49 $CH_3OH$/EtOAc) and recrystallization (THF/hexanes) gave the title compound 4 as a white solid, 20 mg (87% yield), mp 167–169° C. LC/MS gave the correct molecular ion [(M+H)$^+$=470] for the desired compound.

EXAMPLE 5

1-(4-Bromophenyl)-3-[[2,4-dichloro-3-(phenylmethyl)phenyl]methyl]hexahydro-2-oxo-5-pyrimidineacetic acid

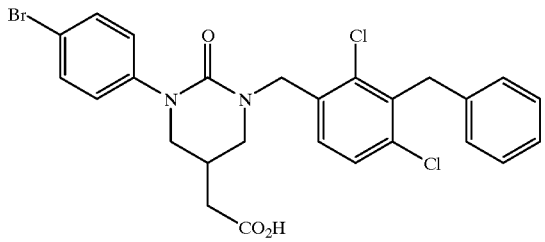

A.

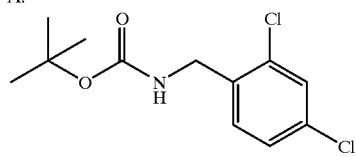

To a solution of 2,4-dichlorobenzylamine (1.76 g, 10.0 mmol) in CH$_2$Cl$_2$ (20 mL) at room temperature under N$_2$ was added di-t-butyldicarbonate (2.18 g, 10.0 mmol). After 30 min, the solution was evaporated. Purification by flash chromatography on silica gel (5×15 cm column, CH$_2$Cl$_2$) gave 5A as a colorless oil, 2.06 g (75% yield). LC/MS gave the correct molecular ion [(M+H)$^+$=276] for the desired compound.

B.

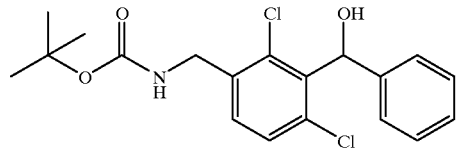

To a solution of 5A (748 mg, 2.71 mmol) in THF (5.5 mL) at −75° C. under N$_2$ was added n-BuLi solution (2.5 M in hexanes, 2.50 mL, 6.2 mmol) over 15 min. After 30 min, the deep orange solution was treated with a solution of benzaldehyde (0.33 mL, 3.2 mmol) in THF (1 mL) over 5 min. The resulting thick gelatinous reaction mixture was allowed to warm to room temperature as a solution formed. After 1 h, the reaction was quenched with 10% citric acid and extracted twice with EtOAc. The organic extracts were combined, dried (MgSO$_4$) and evaporated. Purification by flash chromatography on silica gel (5×15 cm column, 1:39 EtOAc/CH$_2$Cl$_2$) gave 5B as an amorphous white solid, 410 mg (40% yield). LC/MS gave the correct molecular ion [(M+H)$^+$=382] for the desired compound.

C.

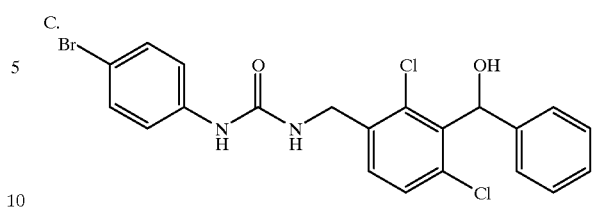

5B (286 mg, 0.75 mmol) was treated with HCl/dioxane (4 N, 5 mL) at room temperature under N$_2$ for 4 h. The solution was evaporated, the residue dissolved in CH$_2$Cl$_2$ (10 mL) and stirred rapidly with saturated NaHCO$_3$ solution. The organic phase was separated, dried (Na$_2$SO$_4$) and evaporated. The residue was dissolved in CH$_2$Cl$_2$ (5 mL) and treated with 4-bromophenylisocyanate (140 mg, 0.7 mmol). After 10 min, the reaction mixture was evaporated. Purification by flash chromatography on silica gel (2.5×20 cm column, 1:7 EtOAc/CH$_2$Cl$_2$) gave 5C as an amorphous white solid, 235 mg (70% yield). LC/S gave the correct molecular ion [(M+H)$^+$=479] for the desired compound.

D.

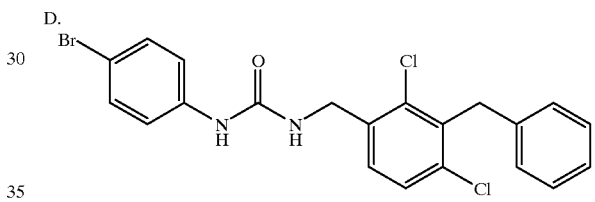

To a stirred solution of 5C (152 mg, 0.317 mmol) in TFA (2 mL) at room temperature under N$_2$ was added triethylsilane (160 μL, 1.0 mmol). After 1 h, the resulting slurry was treated with saturated NaHCO$_3$ solution and the resulting solids filtered, washing with water and dried in vacuo to give 5D as a white solid, 145 mg (98% yield). LC/MS gave the correct molecular ion [(M+H)$^+$=463] for the desired compound.

E.

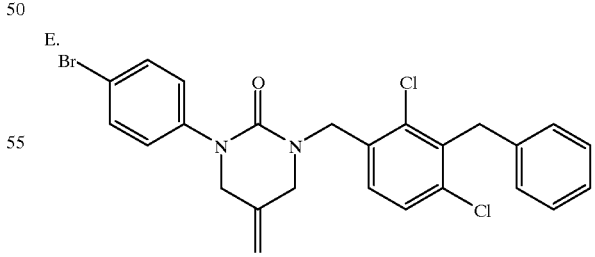

By using the method of Example 2 Part B, but with 5D (1.00 g, 2.15 mmol), 5E was obtained as a white amorphous solid, 830 mg (75% yield). LC/MS gave the correct molecular ion [(M+H)$^+$=515] for the desired compound.

F.

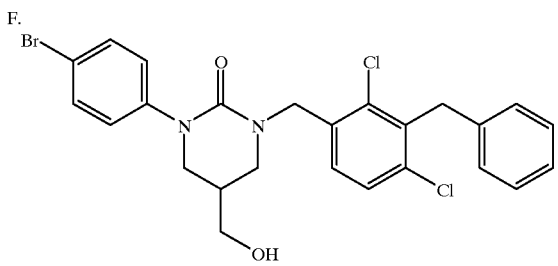

By using the method of Example 2 Part C, but with 5E (690 mg, 1.34 mmol), 5F was obtained as a white amorphous solid, 465 mg (65% yield). LC/MS gave the correct molecular ion [(M+H)+=533] for the desired compound.

G.

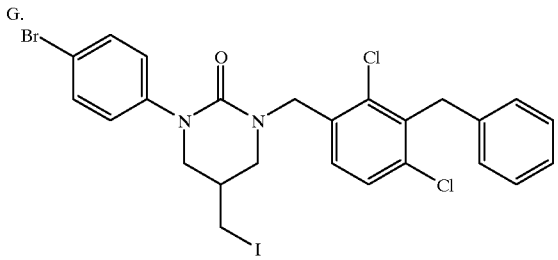

By using the method of Example 3 Part A, but with 5F (445 mg, 0.83 mmol), 5G was obtained as a white amorphous solid, 475 mg (89% yield). LC/MS gave the correct molecular ion [(M+H)+=643] for the desired compound.

H.

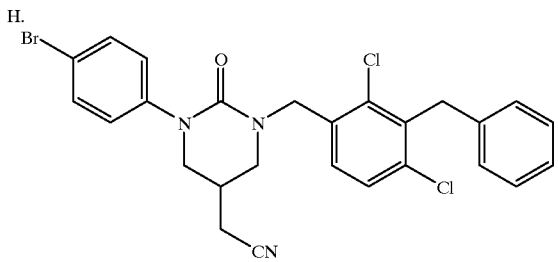

By using the method of Example 3 Part B, but with 5G (460 mg, 0.714 mmol), 5H was obtained as a white amorphous solid, 310 mg (80% yield). LC/MS gave the correct molecular ion [(M+H)+=542] for the desired compound.

I.

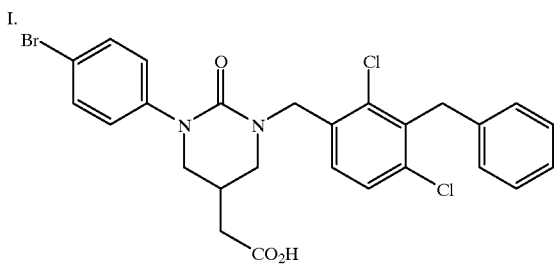

By using the method of Example 3 Part C, but with 5H (300 mg, 0.55 mmol), the title compound 5 was obtained as a white solid, 235 mg (76% yield), mp 174–176° C. LC/MS gave the correct molecular ion [(M+H)+=561] for the desired compound.

EXAMPLE 6

[[1-(4-Bromophenyl)-3-[(2,4-dichlorophenyl)methyl]hexahydro-2-oxo-5-pyrimidinyl]methyl] phosphonic acid

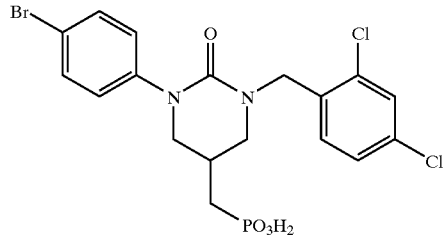

A.

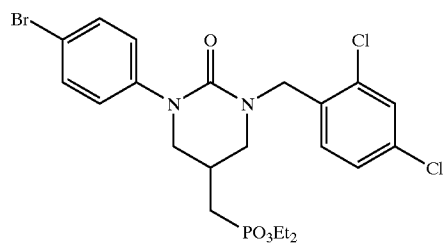

A solution of 3A (346 mg, 0.624 mmol) in freshly distilled triethylphosphite (4 mL) was heated at reflux under $N_2$ for 24 h. The reaction mixture was then distilled at 100° C. at 0.5 Torr to remove volatile materials. Purification of the residuum by flash chromatography on silica gel (2.5×15 cm column, EtOAc) gave 6A as a colorless oil, 275 mg (67% yield). LC/MS gave the correct molecular ion [(M+H)+=563] for the desired compound.

B.

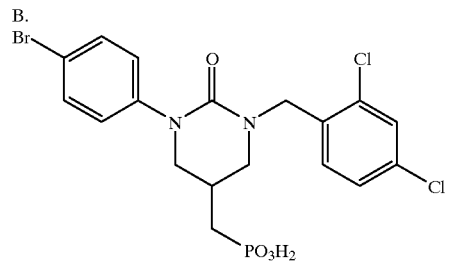

To a solution of 6A (315 mg, 0.481 mmol) in $CH_2Cl_2$ (5 mL) was added bromotrimethylsilane (0.20 mL, 1.5 mmol) at room temperature under $N_2$. After 24 h, the reaction mixture was evaporated and the residuum dissolved in EtOAc. The organic solution was washed three times with hydrochloric acid (3 M), dried ($MgSO_4$) and partially evaporated. Hexanes were added to the concentrated solution and the resulting white solid isolated and dried in vacuo to give the title compound 6, 225 mg (92% yield), mp>220° C. LC/MS gave the correct molecular ion [(M+H)+=507] for the desired compound.

Elemental analysis as $C_{18}H_{19}N_2O_4BrCl_2P$+0.25 $H_2O$+ 0.33 EtOAc Calc.% C, 42.76; H, 4.11; N, 5.16; Br, 14.72; Cl, 13.06. Fnd. C, 42.90; H, 3.73; N, 5.26; Br, 14.54; Cl, 12.73.

EXAMPLE 7

1-[(2,4-Dichlorophenyl)methyl]hexahydro-2-oxo-3-(2-phenoxyphenyl)-5-pyrimidineacetic acid

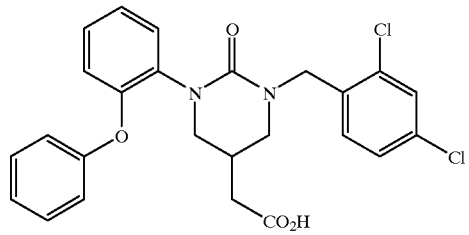

A.

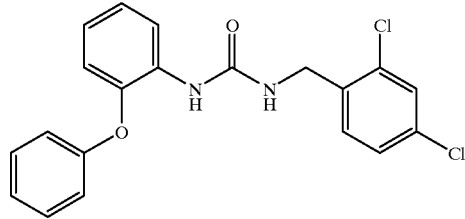

To a stirred solution of 2-phenoxybenzoic acid (2.14 g, 10.0 mmol) in $CH_2Cl_2$ (10 mL) at room temperature was added a solution of oxalyl chloride (2 M in $CH_2Cl_2$, 7 mL, 14 mmol) and then DMF (100 μL). The solution was stirred 1 h and then evaporated. The resulting oil was dissolved in acetone (10 mL) and, at room temperature with rapid stirring, treated with a solution of sodium azide (2.5 g, 38 mmol) in water (10 mL). After 20 min, the mixture was poured into ice water (50 mL) and extracted three times with toluene (20 mL portions). The organic extracts were combined, dried ($MgSO_4$) and heated to reflux, using a Dean-Stark trap to remove water. After 1 h, the resulting solution was cooled and treated with 2,4-dichlorobenzylamine (1.40 mL, 10.0 mmol). After 20 min, the slurry was evaporated and the residual solid suspended in $CH_2Cl_2$. Filtration gave 7A as a white solid, 3.23 g (86% yield). LC/MS gave the correct molecular ion $[(M+H)^+=387]$ for the desired compound.

B.

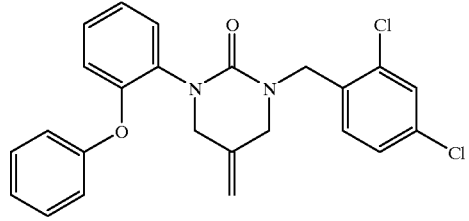

By using the method of Example 2 Part B, but with 7A (2.71 g, 7.00 mmol), 7B was obtained as a white amorphous solid, 979 mg (32% yield). LC/MS gave the correct molecular ion $[(M+H)^+=439]$ for the desired compound.

C.

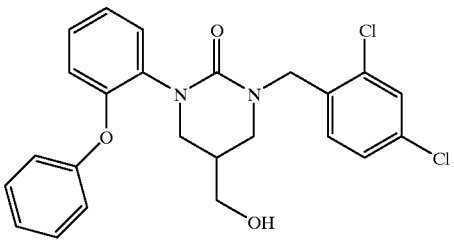

By using the method of Example 2 Part C, but with 7B (974 mg, 2.22 mmol), 7C was obtained as a white amorphous solid, 598 mg (59% yield). LC/MS gave the correct molecular ion $[(M+H)^+=533]$ for the desired compound.

D.

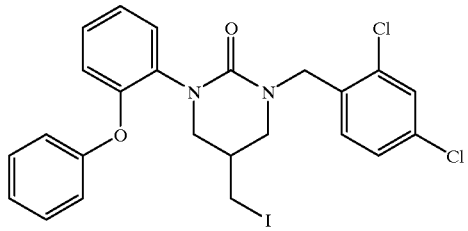

By using the method of Example 3 Part A, but with 7C (590 mg, 1.29 mmol), 7D was obtained as a white amorphous solid, 640 mg (87% yield). LC/MS gave the correct molecular ion $[(M+H)^+=567]$ for the desired compound.

E.

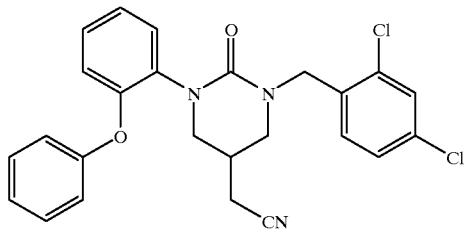

By using the method of Example 3 Part B, but with 7D (625 mg, 1.10 mmol), 7E was obtained as a white amorphous solid, 446 mg (87% yield). LC/MS gave the correct molecular ion $[(M+H)^+=467]$ for the desired compound.

F.

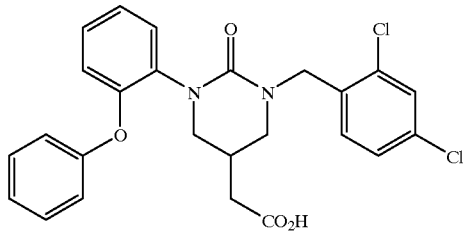

By using the method of Example 3 Part C, but with 7E (167 mg, 0.358 mmol), the title compound 7 was obtained as a light yellow amorphous solid, 161 mg (92% yield). LC/MS gave the correct molecular ion $[(M+H)^+=485]$ for the desired compound.

Elemental analysis as $C_{25}H_{22}N_2O_4Cl_2+1 H_2O$ Calc.% C, 59.65; H, 4.81; N, 5.57; Cl, 14.09. Fnd. C, 59.71; H, 4.49; N, 5.33; Cl, 14.04.

EXAMPLE 8

1-(4-Bromophenyl)-3-[(4-chlorophenyl)methyl]hexahydro-2-oxo-5-pyrimidineacetic acid

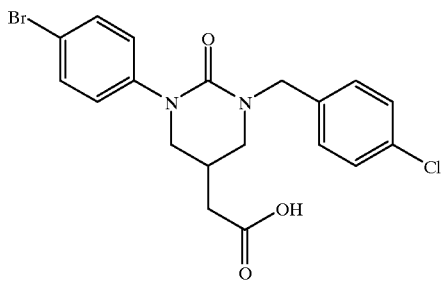

A.

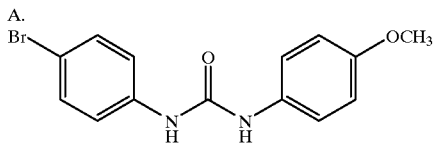

To a stirred solution of 4-bromophenyl isocyanate (49.50 g, 250 mmol) in $CH_2Cl_2$ (250 mL) at room temperature was added a solution of 4-methoxyaniline (30.79 g, 250 mmol) in $CH_2Cl_2$ (250 mL) dropwise. After addition, the reaction mixture was stirred at room temperature for 30 minutes as a precipitate formed. The precipitate was filtered and washed with $CH_2Cl_2$ (500 mL×2) to give 8A as a white solid, 77.01 g, (96% yield). LC/MS gave the correct molecular ion [(M+H)⁺=321] for the desired compound.

B.

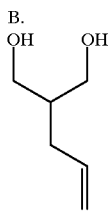

To a stirred solution of lithium aluminum hydride (1 M in THF, 270 mL, 270 mmol) under nitrogen at room temperature was added a solution of diethyl allylmalonate (49.0 g, 245 mmol) in THF (30 mL) dropwise over 40 min. The temperature was not allowed to rise above 50° C. The reaction mixture was stirred at room temperature for 5 h and quenched with saturated sodium chloride (500 mL) at 0° C. and stirred for 30 min. The slurry was filtered through Celite. The filtrate was extracted three times with EtOAc (300 mL), the organic extracts were combined, dried ($Na_2SO_4$) and evaporated to give 8B as a colorless oil, 24.0 g. (85% yield).

C.

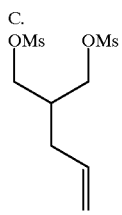

To a stirred solution of 8B (23.70 g, 174 mmol) in $CH_2Cl_2$ (360 mL) under nitrogen at 0° C. was added triethylamine (53.4 mL, 343 mmol), and then methanesulfonyl chloride (28.3 mL, 364 mmol) dropwise. The temperature was not allowed to rise above 10° C. After addition, the reaction mixture was stirred at 0° C. for 2 h and diluted with $CH_2Cl_2$ (400 mL). The reaction mixture was washed with 10% citric acid solution (400 mL), water (400 mL) and brine (400 mL), dried ($Na_2SO_4$) and evaporated to give 8C as a yellow oil, 52.02 g, (93% yield).

D.

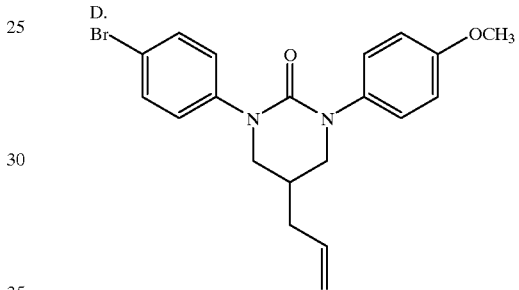

To a stirred slurry of 8A (33.02 g, 103.4 mmol), NaOH (20.68 g, 517 mmol) and tetrabutylammonium iodide (600 mg) in toluene (300 mL) under nitrogen at room temperature was added a solution of 8C (32.85 g, 108.6 mmol) in toluene (50 mL). The reaction mixture was heated at reflux for 5 h. A clear solution was formed from the original slurry. After the reaction mixture was cooled to room temperature, $CH_2Cl_2$ (600 mL) was added. The reaction mixture was washed with aqueous 5% $KHSO_4$ (600 mL), $H_2O$ (600 mL), saturated $NaHCO_3$ solution and brine (600 mL), dried ($Na_2SO_4$) and evaporated. Purification by flash chromatography on silica gel (3:47 $Et_2O/CH_2Cl_2$) gave 8D as a yellow oil, 20 g, (48% yield). LC/MS gave the correct molecular ion [(M+H)⁺=401] for the desired compound.

E.

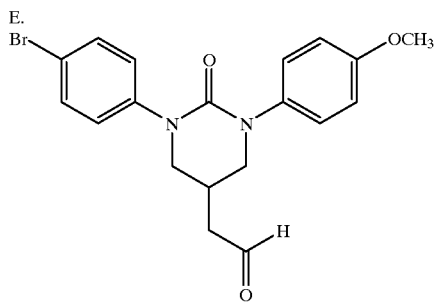

To a stirred cloudy suspension of 8D (13.6 g, 31.2 mmol) in MeOH (400 mL) and H₂O (200 mL), was added a solution of OsO₄ (2.5% in tert-butyl alcohol, 3.1 mL). The reaction mixture was stirred under nitrogen at room temperature for 45 min. Sodium periodate (20.02 g, 93.6 mmol) was added over 30 min and the reaction mixture was then stirred for 5 h. Water (400 mL) was added to the reaction mixture and then extracted three times with CH₂Cl₂ (300 mL). The organic extracts were combined, washed twice with H₂O (300 mL), once with brine (300 mL); dried (MgSO₄) and evaporated. Purification by flash chromatography on silica gel (7:93 Et₂O/CH₂Cl₂) gave 8E as a white solid, 8.0 g, (65% yield). LC/MS gave the correct molecular ion [(M+H)⁺=403] for the desired compound.

F.
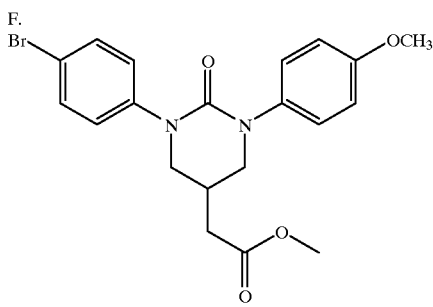

Ammonium persulfate (4.78 g, 20.96 mmol) was added portionwise to cold concentrated H₂SO₄ (6.2 mL, 116 mmol) under nitrogen at a rate such that the temperature was not allowed to rise above 15° C. The resulting solution was added dropwise to a stirred suspension of 8E (3.25 g, 8.06 mmol) in MeOH (25 mL) at 0° C. The reaction mixture was stirred at 0° C. for 2 h and stored at 5° C. overnight and then diluted with H₂O (100 mL) and extracted three times with CH₂Cl₂ (100 mL). The extracts were combined, washed with saturated aqueous NaHCO₃ (100 mL), H₂O (100 mL) and brine (100 mL), dried (Na₂SO₄) and evaporated. Purification by flash chromatography on silica gel (1:9 Et₂O/CH₂Cl₂) gave 8F as a white solid, 3.2 g, (92% yield). LC/MS gave the correct molecular ion [(M+H)⁺=433] for the desired compound.

G.
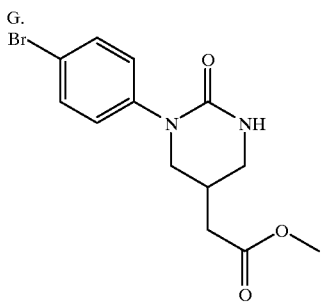

To a stirred solution of ammonium cerium (IV) nitrate ((23.63 g, 43.10 mmol) in H₂O (60 mL) at −10° C. was added a solution of 8F (6.225 g, 14.37 mmol) in CH₃CN (100 mL) over 30 min. The reaction mixture was stirred at −10° C. for 5 min and quenched with 10% aqueous sodium acetate (500 mL). The reaction mixture was extracted three times with EtOAc (200 mL) and twice with CH₂Cl₂ (150 mL). The extracts were combined, washed with 10% NaHSO₃ (300 mL), H₂O (300 mL) and brine (300 mL), dried (Na₂SO₄) and evaporated. Purification by flash chromatography on silica gel (100% EtOAc) gave 8G as a white solid, 2.58 g, (55% yield). LC/MS gave the correct molecular ion [(M+H)⁺=327] for the desired compound.

H.
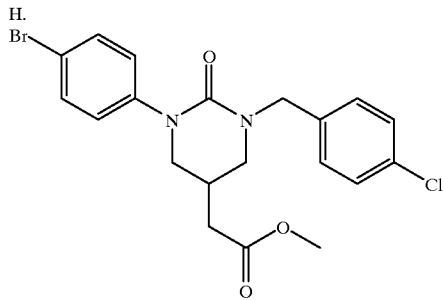

To a stirred solution of 8G (98.4 mg, 0.3 mmol) in DMF (1.5 mL) under nitrogen at room temperature was added NaH (60% oil dispersion 12.1 mg, 0.303 mmol) in one portion. The reaction mixture was stirred at room temperature for 5 min and a solution of 4-chlorobenzyl chloride (53.2 mg, 0.33 mmol) in DMF (0.5 mL) was then added. The reaction mixture was stirred at room temperature overnight. The reaction mixture was diluted with H₂O (5 mL) and extracted three times with EtOAc (10 mL). The extracts were combined, washed once each with H₂O, saturated NaHCO₃ solution and brine, and then dried (Na₂SO₄) and evaporated. Purification by flash chromatography (1:19 Et₂O/CH₂Cl₂) gave 8H as a white solid, 33.4 mg, (24% yield). LC/MS gave the correct molecular ion [(M+H)⁺=451] for the desired compound.

I.
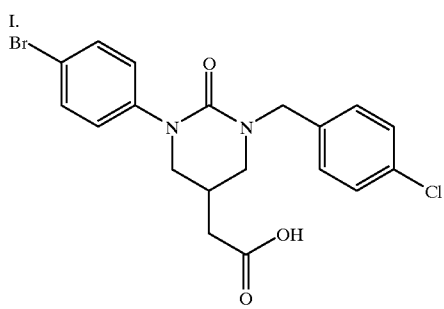

To a stirred solution of 8H (79.4 mg, 0.176 mmol) in MeOH (1.5 mL) at room temperature was added aqueous NaOH solution (5 M, 1.5 mL). The reaction mixture was stirred at room temperature overnight and concentrated to about 1.5 mL. The residue was diluted with H₂O (4 mL) and acidified by adding HCl (1 M) dropwise to pH 2. The reaction mixture was extracted three times with CH₂Cl₂ (10 mL). The extracts were combined, washed with H₂O and brine, and then dried (Na₂SO₄) and evaporated to give the title compound as a white foam, 40.0 mg, 52% yield. LC/MS gave the correct molecular ion [(M+H)⁺=437] for the desired compound.

EXAMPLE 9

1-(4-Bromophenyl)-3-[(2,4-dichlorophenyl)methyl] hexahydro-2-oxo-5-pyrimidineacetic hydroxamic acid

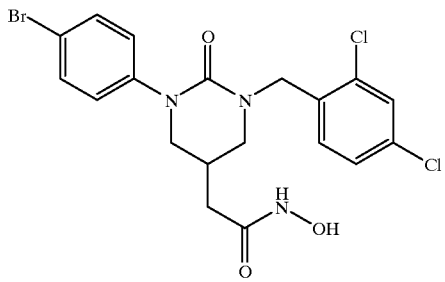

A.

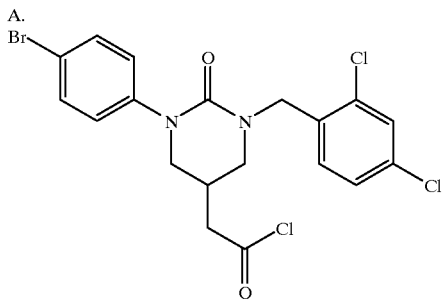

To a stirred solution of compound 3C (194 mg, 0.2 mmol) in $CH_2Cl_2$ (8 mL) under nitrogen at room temperature was added a solution of oxalyl chloride (2 M in $CH_2Cl_2$, 0.5 mL, 1 mmol) and DMF (1 drop). The reaction mixture was stirred for 1 h and evaporated. The residue was dissolved in $CH_2Cl_2$ (5 mL) and evaporated three times. The residue was dried in vacuo for 1 h to give 9A as a colorless oil.

B.

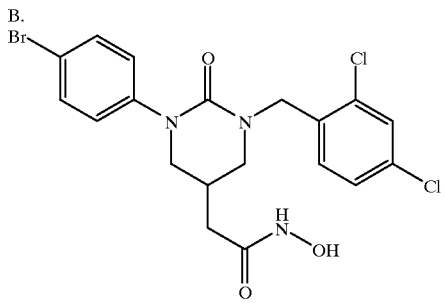

To a stirred slurry of hydroxylamine hydrochloride (35 mg, 0.5 mmol) and $Et_3N$ (0.14 mL, 1.0 mmol) in $CH_2Cl_2$ (5 mL) under nitrogen at room temperature was added a solution of 9A (98.2 mg, 0.2 mmol) in $CH_2Cl_2$ (5 mL) dropwise. The reaction mixture was stirred at room temperature overnight and then evaporated. Purification by preparative HPLC gave the title compound 9 as a pink solid, 15.0 mg, (15% yield). LC/MS gave the correct molecular ion $[(M+H)^+=486]$ for the desired compound.

EXAMPLE 10

1-(4-Bromophenyl)-3-[(2,4-dichlorophenyl)methyl] tetrahydro-5-(2-hydroxyethyl)-2(1H)-pyrimidinone

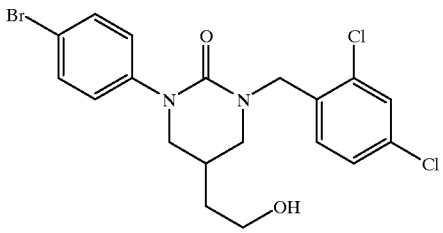

A.

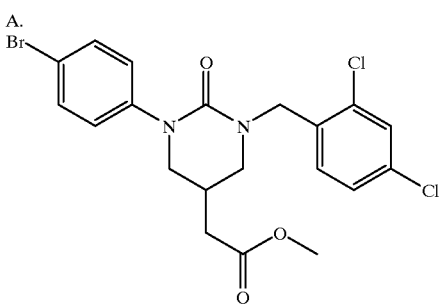

To a stirred solution of compound 3C (90 mg, 0.19 mmol) in $CH_2Cl_2$ (10 mL) under nitrogen at room temperature was added a solution of oxalyl chloride (2 M in $CH_2Cl_2$, 0.4 mL, 0.8 mmol) and DMF (1 drop). The reaction mixture was stirred at room temperature for 1 h and concentrated in vacuum. The residue was dissolved in $CH_2Cl_2$ (5 mL) and evaporated three times. The residue was dried in vacuo for 1 h and MeOH (10 mL) was added to the residue. The reaction mixture was stirred at room temperature for 1 h and concentrated in vacuum to give 10A as an oil, 87.5 mg, (95% yield). LC/MS gave the correct molecular ion $[(M+H)^+=485]$ for the desired compound.

B.

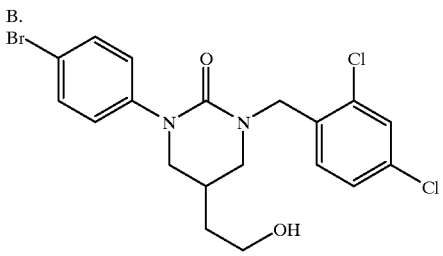

To a stirred solution of 10A (87 mg, 0.18 mmol) in $CH_2Cl_2$ (8 mL) under nitrogen at $-78°$ C. was added a solution of diisobutylaluminum hydride (1 M in $CH_2Cl_2$, 0.4 mL, 0.4 mmol) dropwise. The reaction mixture was stirred at $-78°$ C. for 30 min, and then slowly warmed to room temperature and stirred at room temperature overnight. The reaction mixture was quenched with 5% $KHSO_4$ and stirred at room temperature for 1 h. The reaction mixture was extracted three times with CH₂Cl₂ (10 mL). The extracts were combined, washed with H₂O (10 mL) and brine (10 mL), dried (Na₂SO₄) and evaporated. Purification by flash chromatography on silica gel (1:50 MeOH/CH₂Cl₂) gave the title compound 10 as a white solid, 23 mg, (28% yield). LC/MS gave the correct molecular ion [(M+H)⁺=457] for the desired compound.

EXAMPLE 11

1-(4-Bromophenyl)-3-[(2-chlorophenyl)methyl] hexahydro-2-oxo-5-pyrimidineacetic acid

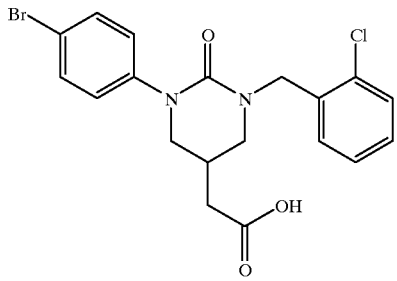
A.

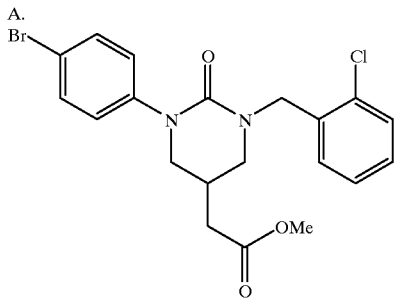
B.

By using the method of Example 8 Part H, but with 2-chlorobenzyl chloride, 11A was prepared as an oil, 230 mg, 70% yield.

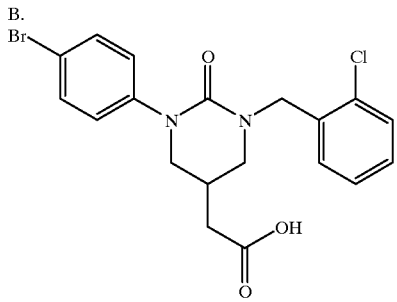

By using the method of Example 8 Part I, but with 11A (157 mg, 0.37 mmol), the title compound 11 was prepared as a colorless foam, 140 mg (90% yield). LC/MS gave the correct molecular ion [(M+H)⁺=437] for the desired compound.

EXAMPLE 12

1-(4-Bromophenyl)-3-[(4-fluorophenyl)methyl] hexahydro-2-oxo-5-pyrimidineacetic acid

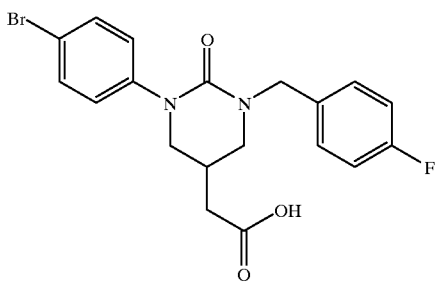

To a stirred suspension of compound 8C (102.3 mg, 0.31 mmol) in THF (8 mL) under nitrogen at room temperature was added a solution of potassium bis(trimethylsily)amide (0.5 M in toluene, 0.66 mL, 0.33 mmol). After 5 min, a solution of 4-fluorobenzylchloride (50 mg, 0.34 mmol) in THF (0.5 mL) was added, followed by tetrabutylammonium iodide (115.6 mg, 0.31 mmol). The reaction mixture was stirred under nitrogen at room temperature for 1 h and quenched with 5% aqueous Na₂SO₃. To the reaction was added NaOH (1 N, 1.5 mL) and the mixture was stirred at room temperature overnight. The reaction mixture was acidified to pH 2 by adding HCl (1M) dropwise at 0° C. and then extracted with CH₂Cl₂ (20 mL). The extract was evaporated. Purification by CUQAX13M6-HY ion exchange resin gave the title compound 12 as a foam, 57.5 mg, 36.5% yield. LC/MS gave the correct molecular ion [(M+H)⁺=421] for the desired compound.

EXAMPLE 13

1-(4-Bromophenyl)-3-[(2-fluorophenyl)methyl] hexahydro-2-oxo-5-pyrimidineacetic acid

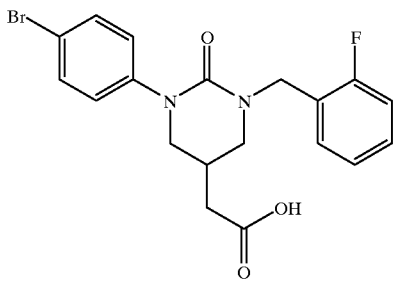

To a mechanically agitated suspension of compound 8G (51.0 mg, 0.16 mmol) and tetrabutylammonium iodide (57.6 mg, 0.16 mmol) in THF (1 mL) under nitrogen at room temperature was added a solution of potassium bis (trimethylsily)amide (0.5 M in toluene, 0.36 mL, 0.18 mmol). After 5 min, a solution of 2-fluorobenzylchloride (27.1 mg, 0.19 mmol) in THF (0.5 mL) was added. The reaction mixture was agitated under nitrogen at room temperature for 1.5 h and then added to a solution of potassium trimethylsilanolate (40 mg, 0.31 mmol) in THF (0.4 mL). After 16 h, the reaction mixture was quenched with 2% trifluoroacetic acid in MeOH (2 mL) and evaporated. CH₂Cl₂ (4 mL) was added and a precipitate formed. The precipitate was filtered and the filtrate was evaporated.

Purification of the filtrate residue by CUQAX13M6-HY ion exchange chromatography gave the title compound 13 as a foam, 30.0 mg, 46% yield. LC/MS gave the correct molecular ion [(M+H)$^+$=421] for the desired compound.

EXAMPLES 14–51

The title compounds were prepared as part of a solution phase library run using the following procedure.

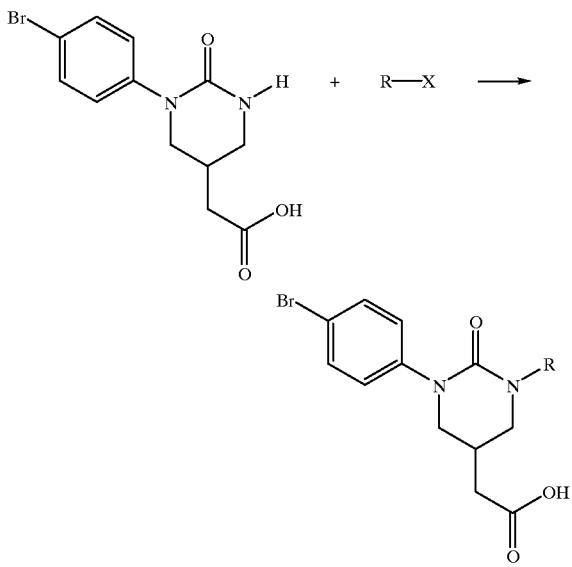

To a suspension of Example 8 part G compound (80.0 mg, 0.24 mmol) and tetrabutylammonium iodide (90.3 mg, 0.24 mmol) in THF (1.5 mL) under nitrogen at room temperature was added a solution of potassium bis(trimethylsilyl)amide (0.5 M in toluene, 0.56 mL, 0.28 mmol). After 5 min, a solution of RX (0.29 mmol) in THF (0.6 mL) was added. The reaction mixture was shaken in a nitrogen atmosphere at room temperature for 1.5 h. To the reaction mixture was added a solution of potassium trimethylsilanolate (63 mg, 0.49 mmol) in THF (0.6 mL) and the mixture was agitated at room temperature overnight. 2% CF$_3$COOH in MeOH (3.4 mL) was added and the reaction mixture was agitated at room temperature for 30 min. The reaction mixture was filtered and the filtrate was evaporated. CH$_2$Cl$_2$ (4 mL) was added and filtered through Celite. The filtrate was evaporated and the resulting crude product was purified by the procedure outlined below.

1) The CUQAX13M6-HY cartridge was conditioned with MeOH (10 mL×2) and 1:1 MeOH/CH$_2$Cl$_2$ (10 mL);
2) The crude product was dissolved in CH$_2$Cl$_2$ (2 mL) and loaded onto a CUQAX13M6-HY cartridge;
3) The cartridge was washed with CH$_2$Cl$_2$ (10 mL), CH$_2$Cl$_2$/MeOH (50 MeOH, 10 mL) and MeOH (10 mL)
4) The product was eluted with a solution of 2% CF$_3$COOH in MeOH.

The final fraction containing product was concentrated and purified by preparative HPLC to afford the title compound. Mass spectrometric and HPLC data collected for all compounds Following the above procedure, the following compounds of the invention were prepared:

| Ex. | X—R | Structure | Name | (M + H) positive ions |
|---|---|---|---|---|
| 14 | [2-(bromomethyl)biphenyl structure] | [structure] | 1-([1,1'-Biphenyl]-2-ylmethyl)-3-(4-bromophenyl)hexahydro-2-oxo-5-pyrimidineacetic acid | 479 |
| 15 | [3-chloro-2-fluorobenzyl bromide structure] | [structure] | 1-(4-Bromophenyl)-3-[(3-chloro-2-fluorophenyl)-methyl]hexahydro-2-oxo-5-pyrimidineacetic acid | 455 |
| 16 | [2,3-dichlorobenzyl chloride structure] | [structure] | 1-(4-Bromophenyl)-3-[(2,3-dichlorophenyl)methyl]hexahydro-2-oxo-5-pyrimidineacetic acid | 472 |

-continued
| Ex. | X—R | Structure | Name | (M + H) positive ions |
|---|---|---|---|---|
| 17 | 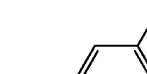 | 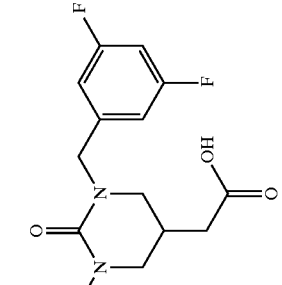 | 1-(4-Bromophenyl)-3-[(2,4-difluorophenyl)-methyl]hexahydro-2-oxo-5-pyrimidineacetic acid | 439 |
| 18 | 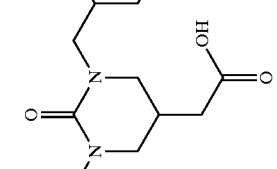 | 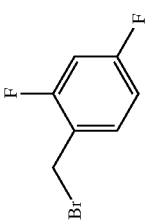 | 1-(4-Bromophenyl)-3-[(3,5-difluorophenyl)-methyl]hexahydro-2-oxo-5-pyrimidineacetic acid | 439 |
| 19 | 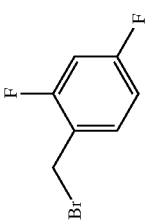 | 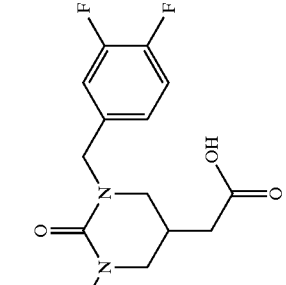 | 1-(4-Bromophenyl)-3-[(3,4-difluorophenyl)-methyl]hexahydro-2-oxo-5-pyrimidineacetic acid | 439 |

-continued

| Ex. | X—R | Structure | Name | (M + H) positive ions |
|---|---|---|---|---|
| 20 | (2-(phenylsulfonylmethyl)benzyl bromide) | 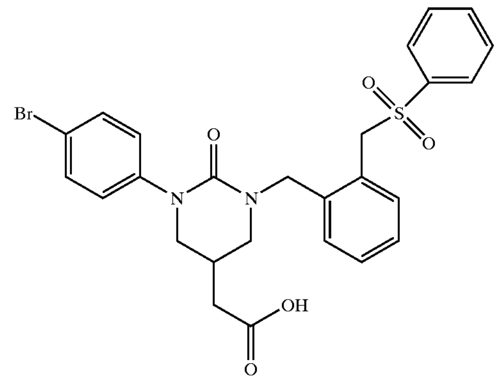 | 1-(4-Bromophenyl)-hexahydro-2-oxo-3-[[2-[phenylsulfonyl)methyl]phenyl]methyl]-5-pyrimidineacetic acid | 557 |
| 21 | (6-chloro-1,3-benzodioxol-5-yl)methyl chloride | 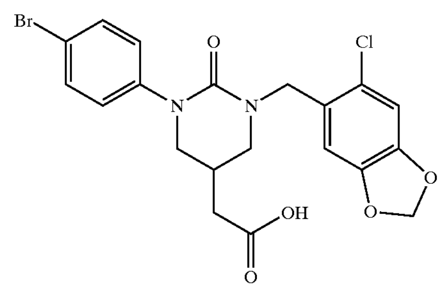 | 1-(4-Bromophenyl)-3-[(6-chloro-1,3-benzodioxol-5-yl)methyl]hexahydro-2-oxo-5-pyrimidineacetic acid | 481 |
| 22 | (2-naphthalenyl)methyl bromide | 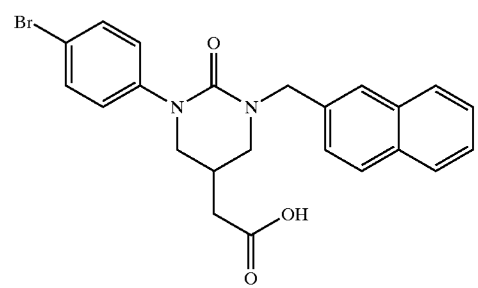 | 1-(4-Bromophenyl)-hexahydro-3-(2-naphthalenylmethyl)-2-oxo-5-pyrimidineacetic acid | 453 |

-continued
| Ex. | X—R | Structure | Name | (M + H) positive ions |
|---|---|---|---|---|
| 23 | 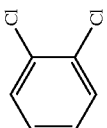 | 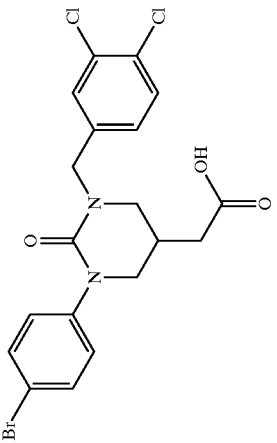 | 1-(4-Bromophenyl)-3-[(3,4-dichlorophenyl)-methyl]hexahydro-2-oxo-5-pyrimidineacetic acid | 472 |
| 24 | 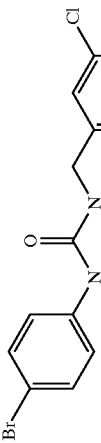 | 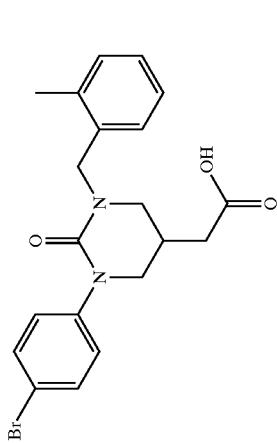 | 1-(4-Bromophenyl)-3-[(2-methylphenyl)methyl]hexahydro-2-oxo-5-pyrimidineacetic acid | 417 |
| 25 | 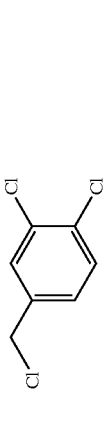 | 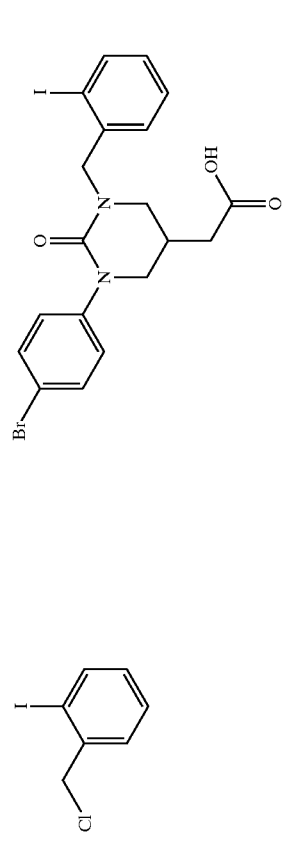 | 1-(4-Bromophenyl)-hexahydro-3-[(2-iodophenyl)methyl]-2-oxo-5-pyrimidineacetic acid | 529 |

-continued
| Ex. | X—R | Structure | Name | (M + H) positive ions |
|---|---|---|---|---|
| 26 | 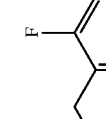 | 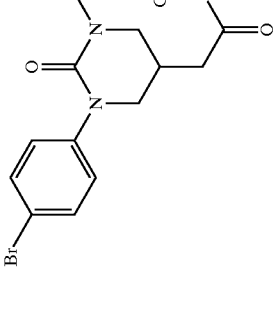 | 1-(4-Bromophenyl)-3-[(2-chloro-6-fluorophenyl)-methyl]hexahydro-2-oxo-5-pyrimidineacetic acid | 455 |
| 27 | 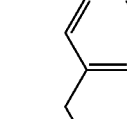 | 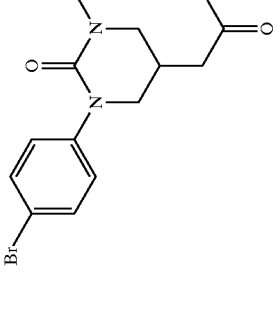 | 1-(4-Bromophenyl)-3-[(3-chlorophenyl)methyl]hexahydro-2-oxo-5-pyrimidineacetic acid | 437 |
| 28 | 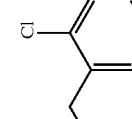 | 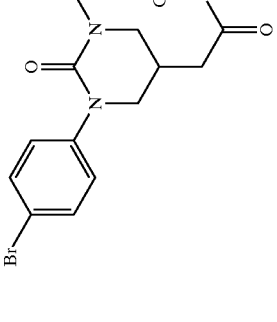 | 1-(4-Bromophenyl)-3-[(2,6-dichlorophenyl)methyl]hexahydro-2-oxo-5-pyrimidineacetic acid | 472 |

| Ex. | X—R | Structure | Name | (M + H) positive ions |
|---|---|---|---|---|
| 29 | 4-(trifluoromethyl)benzyl bromide | 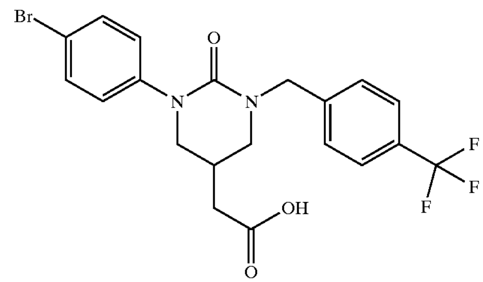 | 1-(4-Bromophenyl)-hexahydro-2-oxo-3-[[4-(trifluoromethyl)phenyl]methyl]-5-pyrimidineacetic acid | 471 |
| 30 | 2,6-difluorobenzyl bromide | 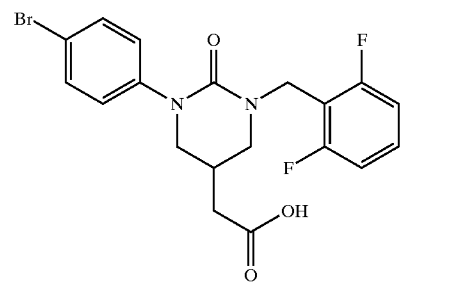 | 1-(4-Bromophenyl)-3-[(2,6-difluorophenyl)methyl]hexahydro-2-oxo-5-pyrimidineacetic acid | 439 |
| 31 | 4-methylbenzyl chloride | 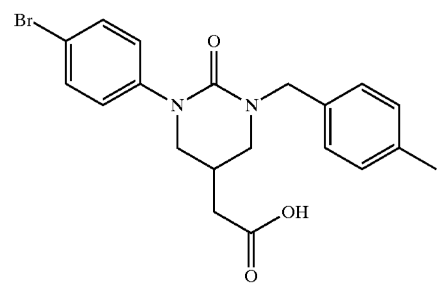 | 1-(4-Bromophenyl)-hexahydro-3-[(4-methylphenyl)methyl]-2-oxo-5-pyrimidineacetic acid | 417 |

| Ex. | X—R | Structure | Name | (M + H) positive ions |
|---|---|---|---|---|
| 32 | 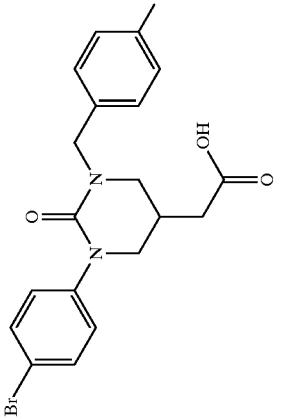 | 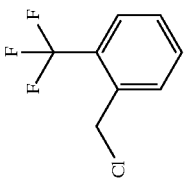 | 1-(4-Bromophenyl)-hexahydro-2-oxo-3-[[2-(trifluoromethyl)phenyl]methyl]-5-pyrimidineacetic acid | 471 |
| 33 | 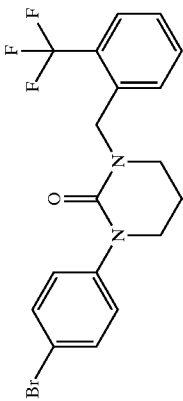 | 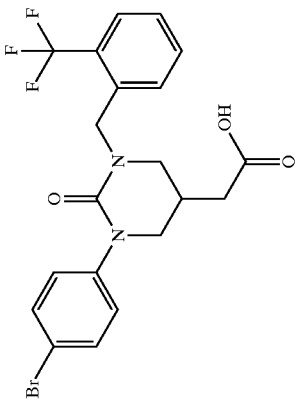 | 1-(4-Bromophenyl)-3-[(2-bromophenyl)methyl]hexahydro-2-oxo-5-pyrimidineacetic acid | 481 |
| 34 | 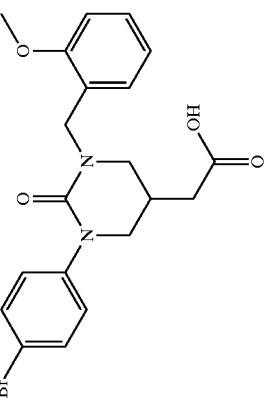 | 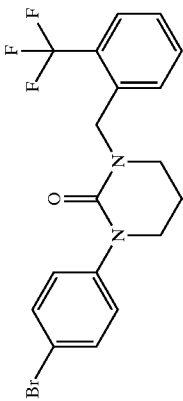 | 1-(4-Bromophenyl)-hexahydro-3-[(2-methoxyphenyl)methyl]-2-oxo-5-pyrimidineacetic acid | 433 |

-continued
| Ex. | X—R | Structure | Name | (M + H) positive ions |
|---|---|---|---|---|
| 35 | 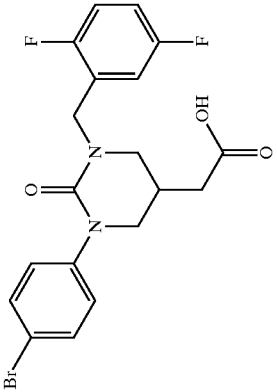 | 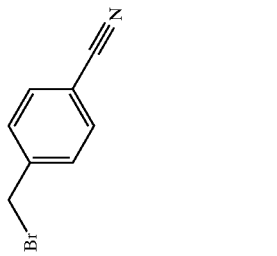 | 1-(4-Bromophenyl)-3-[(2,5-difluorophenyl)methyl]hexahydro-2-oxo-5-pyrimidineacetic acid | 439 |
| 36 | 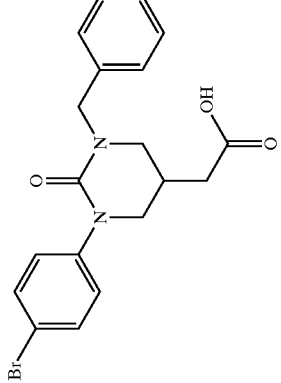 | 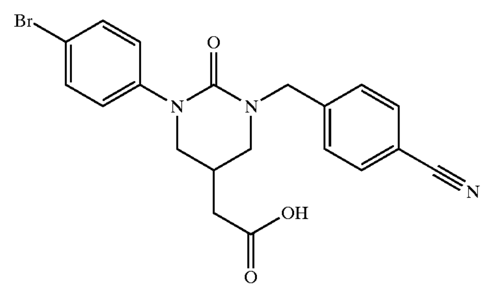 | 1-(4-Bromophenyl)-3-[(4-cyanophenyl)methyl]hexahydro-2-oxo-5-pyrimidineacetic acid | 428 |
| 37 | 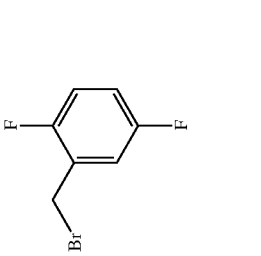 | 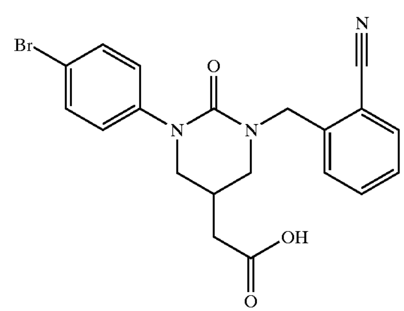 | 1-(4-Bromophenyl)-3-[(2-cyanophenyl)methyl]hexahydro-2-oxo-5-pyrimidineacetic acid | 428 |

| Ex. | X—R | Structure | Name | (M + H) positive ions |
|---|---|---|---|---|
| 38 | 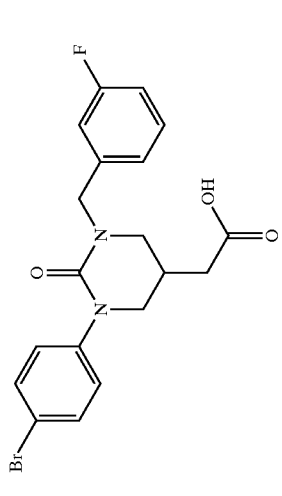 | 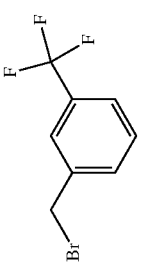 | 1-(4-Bromophenyl)-hexahydro-2-oxo-3-[[3-(trifluoromethyl)phenyl]methyl]-5-pyrimidineacetic acid | 471 |
| 39 | 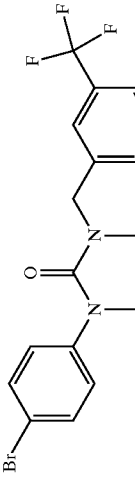 | 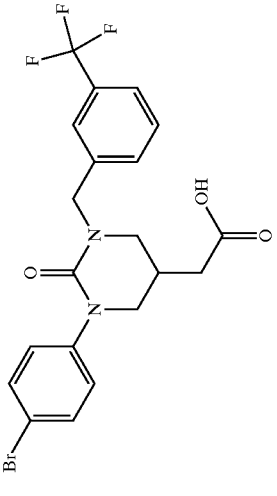 | 1-(4-Bromophenyl)-3-[(3-fluorophenyl)methyl]hexahydro-2-oxo-5-pyrimidineacetic acid | 421 |
| 40 | 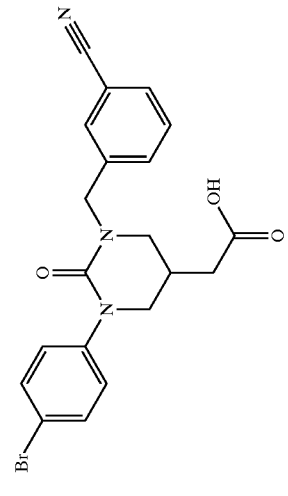 | 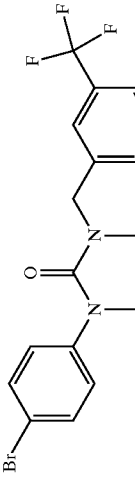 | 1-(4-Bromophenyl)-3-[(3-cyanophenyl)methyl]hexahydro-2-oxo-5-pyrimidineacetic acid | 428 |

| Ex. | X—R | Structure | Name | (M + H) positive ions |
|---|---|---|---|---|
| 41 | 2-fluoro-5-(trifluoromethyl)benzyl bromide | 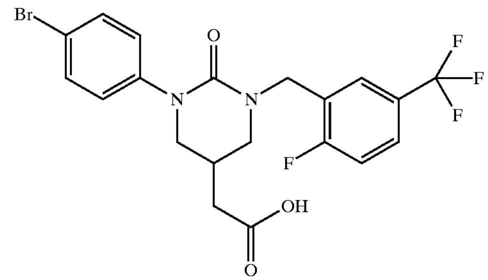 | 1-(4-Bromophenyl)-3-[[2-fluoro-5-(trifluoromethyl)phenyl]methyl]hexahydro-2-oxo-5-pyrimidineacetic acid | 489 |
| 42 | 4-fluoro-2-(trifluoromethyl)benzyl bromide | 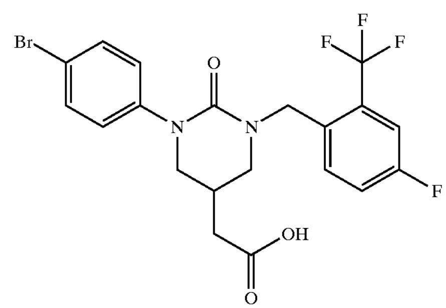 | 1-(4-Bromophenyl)-3-[[4-fluoro-2-(trifluoromethyl)phenyl]methyl]hexahydro-2-oxo-5-pyrimidineacetic acid | 489 |
| 43 | 4-fluoro-3-(trifluoromethyl)benzyl bromide | 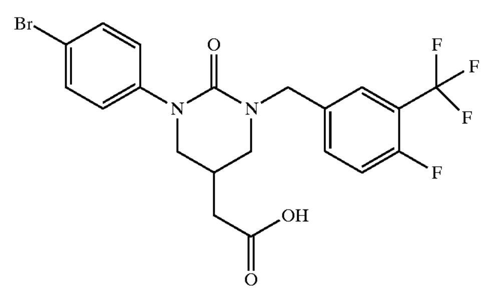 | 1-(4-Bromophenyl)-3-[[4-fluoro-3-(trifluoromethyl)phenyl]methyl]hexahydro-2-oxo-5-pyrimidineacetic acid | 489 |

-continued

| Ex. | X—R | Structure | Name | (M + H) positive ions |
|---|---|---|---|---|
| 44 | 4-(benzyloxy)benzyl chloride | [structure with 4-(benzyloxy)benzyl group] | 1-(4-Bromophenyl)-hexahydro-2-oxo-3-[[4-(phenylmethoxy)phenyl]methyl]-5-pyrimidineacetic acid | 509 |
| 45 | 2,5-dimethylbenzyl chloride | [structure with 2,5-dimethylbenzyl group] | 1-(4-Bromophenyl)-3-[(2,5-dimethylphenyl)methyl]hexahydro-2-oxo-5-pyrimidineacetic acid | 431 |
| 46 | 2,5-dichlorobenzyl chloride | [structure with 2,5-dichlorobenzyl group] | 1-(4-Bromophenyl)-3-[(2,5-dichlorophenyl)methyl]hexahydro-2-oxo-5-pyrimidineacetic acid | 472 |

| Ex. | X—R | Structure | Name | (M + H) positive ions |
|---|---|---|---|---|
| 47 | 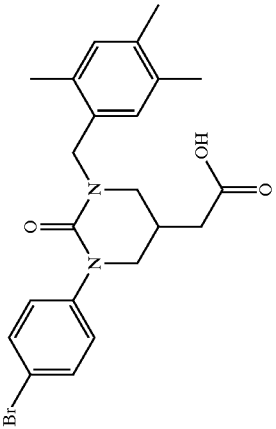 | 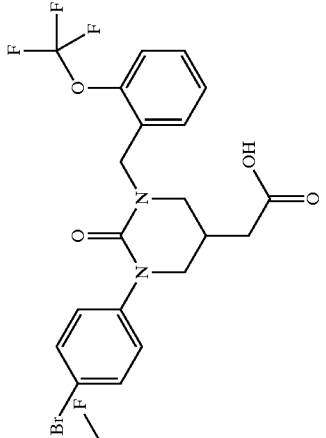 | 1-(4-Bromophenyl)-hexahydro-2-oxo-3-[(2,4,5-trimethylphenyl)methyl]-5-pyrimidineacetic acid | 445 |
| 48 | 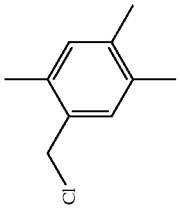 | 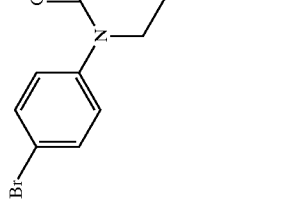 | 1-(4-Bromophenyl)-hexahydro-2-oxo-3-[[2-(trifluoromethoxy)phenyl]methyl]-5-pyrimidineacetic acid | 487 |
| 49 | 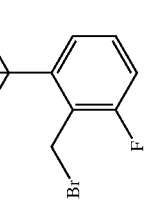 | 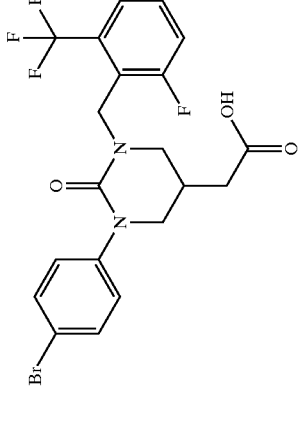 | 1-(4-Bromophenyl)-3-[[2-fluoro-6-(trifluoromethyl)phenyl]methyl]hexahydro-2-oxo-5-pyrimidineacetic acid | 489 |

| Ex. | X—R | Structure | Name | (M + H) positive ions |
|---|---|---|---|---|
| 50 | 4-methoxybenzyl chloride | 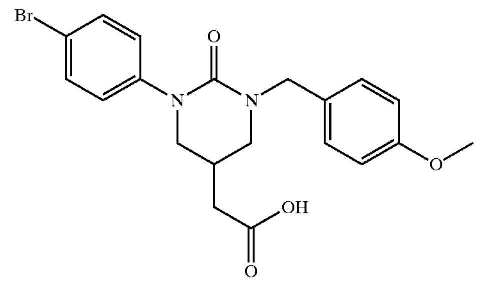 | 1-(4-Bromophenyl)-hexahydro-3-[(4-methoxyphenyl)methyl]-2-oxo-5-pyrimidineacetic acid | 433 |
| 51 | 2-chloro-4-fluorobenzyl bromide | 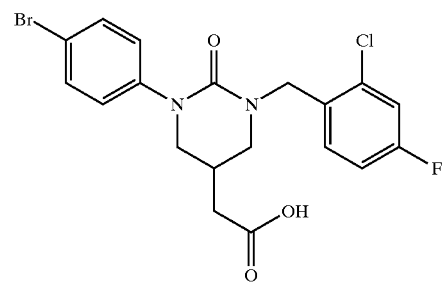 | 1-(4-Bromophenyl)-3-[(2-chloro-4-fluorophenyl)methyl]hexahydro-2-oxo-5-pyrimidineacetic acid | 455 |

EXAMPLE 52

1-(4-Bromophenyl)-3-[[2,4-dichloro-6-(phenylmethoxy)phenyl]methyl]hexahydro-2-oxo-5-pyrimidineacetic acid

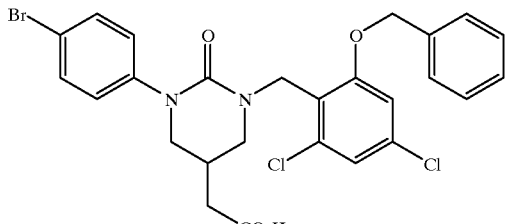

A.

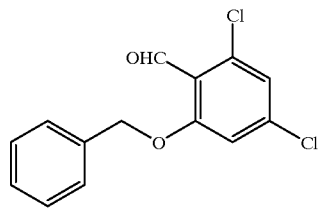

To a solution of 2,4-dichloro-6-hydroxy benzaldehyde (1.87 g, 10.0 mmol) in DMF (10 mL) at room temperature under $N_2$ was added sodium hydride (60% oil dispersion, 440 mg, 11 mmol). After 20 min, benzyl bromide (1.40 mL, 12 mmol) was added to the yellow solution. The reaction mixture was heated to 50° C. for 16 h, then cooled to room temperature and then quenched with 5% $KHSO_4$ solution. The resulting solids were collected, washed with water and dissolved in $CH_2Cl_2$. The solution was dried ($MgSO_4$) and partially evaporated. Addition of hexanes and filtration gave 52A as a white solid, 2.10 g (75% yield). LC/MS gave the correct molecular ion [(M+H)$^+$=281] for the desired compound.

B.

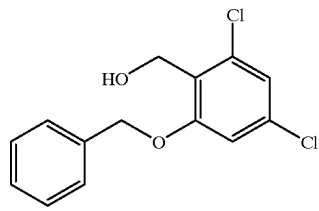

To a solution of 52A (562 mg, 2.00 mmol) in THF (5 mL) at 0° C. under $N_2$ was added lithium borohydride solution (2 $\underline{M}$ in THF, 0.3 mL, 2.4 meq) over 1 min. After 15 min, the solution was warmed to room temperature. After an additional 30 min, the reaction was quenched with saturated $NaHCO_3$ solution and extracted once with ether and once with $CH_2Cl_2$. The organic extracts were combined, dried ($MgSO_4$) and evaporated to give 52B as a colorless oil, 548 mg (97% yield). LC/MS gave the correct molecular ion [(M+Na)$^+$=305] for the desired compound.

C.

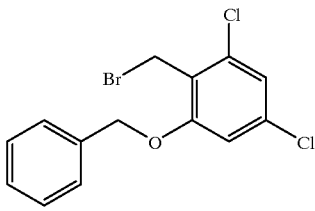

To a stirred solution of 52B (546 mg, 1.92 mmol) in $CH_2Cl_2$ (5 mL) at room temperature was added a solution of $PBr_3$ (1 $\underline{M}$ in $CH_2Cl_2$, 1.05 mL, 3.15 meq) over 20 min. After 14 h, the reaction mixture was quenched with saturated $NaHCO_3$ solution and extracted twice with $CH_2Cl_2$. The organic extracts were combined, dried ($Na_2SO_4/K_2CO_3$) and evaporated to give 52C as an amorphous white solid, 654 mg (98% yield).

D.

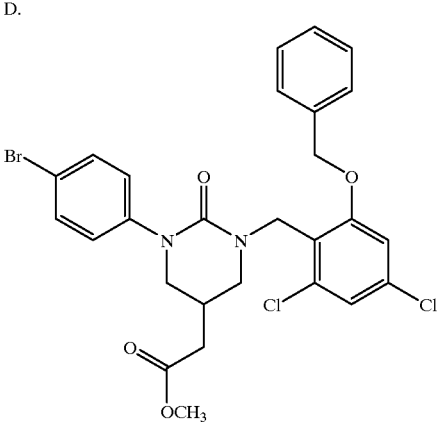

To a stirred solution of compound 8G (196 mg, 0.60 mmol) in THF (4 mL) at room temperature under $N_2$ was added potassium hexamethyldisilazide solution (0.5 $\underline{M}$ in toluene, 1.3 mL, 0.65 mmol). After 30 min, the resulting solution was treated with 52C (228 mg, 0.66 mmol) and tetrabutylammonium iodide (244 mg, 0.66 mmol). The reaction mixture was stirred 14 h, quenched with 5% $KHSO_4$ solution and extracted twice with EtOAc. The extracts were combined, dried ($MgSO_4$) and evaporated. Purification by flash chromatography gave 52D as a white amorphous solid, 120 mg (34% yield). LC/MS gave the correct molecular ion [(M+H)$^+$=591] for the desired compound.

E.

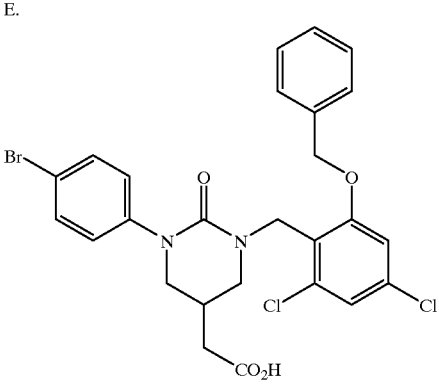

By using the method of Example 8 Part I, but with 52D (110 mg, 0.19 mmol), the title compound 52 was prepared as a white solid, 98 mg (89% yield). LC/MS gave the correct molecular ion [(M+H)$^+$=577] for the desired compound.

Elemental analysis for $C_{26}H_{23}N_2O_4BrCl_2+0.32\ H_2O$. Calc.% C, 53.47; H, 4.08; N, 4.80. Fnd. C, 53.47; H, 4.13; N, 4.61.

EXAMPLE 53

1-(4-Bromophenyl)-3-[(2,4-dichlorophenyl)methyl]hexahydro-α-hydroxy-2-oxo-5-pyrimidineacetic acid

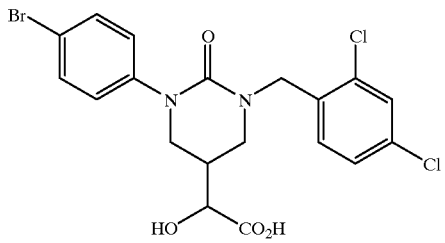

A.

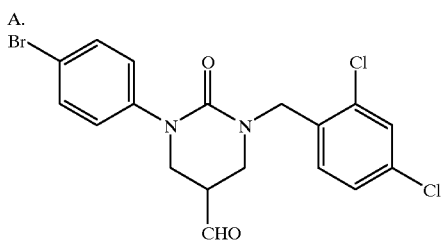

To a solution of pyridine (1.94 mL, 24 mmol) in $CH_2Cl_2$ (30 mL) at 5° C. under $N_2$ was added chromium trioxide (1.20 g, 12 mmol). The resulting red-orange solution was warmed to room temperature over 20 min and then a solution of compound 2C (896 mg, 2.02 mmol) in 5:1 $CH_2Cl_2$/DMF (6 mL) was added as a steady stream. After 15 min, the supernatant solution was decanted from gummy solids. The solids were washed three times with ether. The organic extracts were combined and evaporated. The residuum was dissolved in ether and washed once with 5% $NaHSO_3$ solution. The organic phase was dried ($MgSO_4$) and evaporated. Purification by flash chromatography on silica gel (5×12 cm column, 3:97 ether/$CH_2Cl_2$) gave 53A as a white solid, 397 mg (44% yield), mp 138.5–140.5° C. LC/MS gave the correct molecular ion [(M+H)$^+$=441] for the desired compound.

B.

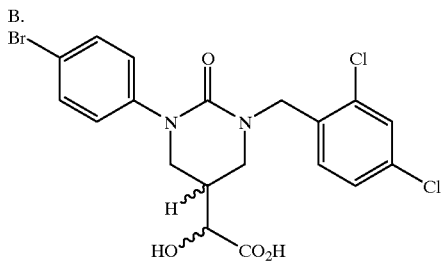

To a solution of 53A (221 mg, 0.5 mmol) in $CH_2Cl_2$ (1 mL) under $N_2$ at room temperature was added trimethylsilylcyanide (67 μL, 0.5 mmol) and zinc iodide (1 mg, 0.003 mmol). After 16 h, the reaction mixture was quenched with water and extracted twice with $CH_2Cl_2$. The extracts were combined, dried ($MgSO_4$) and evaporated. The amorphous white residue was dissolved in 1:1 concentrated HCl/TFA (2 mL) and heated to 110° C. for 8 h. The reaction mixture was cooled and diluted with water. The resulting gummy solids were filtered, air-dried and recrystallized from EtOAc/hexanes to give the title compound 53 (a mixture of diastereomers) as an amorphous white solid, 93 mg (38% yield). LC/MS gave the correct molecular ion [(M+H)$^+$=487] for the desired compound.

EXAMPLE 54

1-(4-Bromophenyl)-3-[(2,4-dichlorophenyl)methyl]hexahydro-5-hydroxy-2-oxo-5-pyrimidineacetic acid

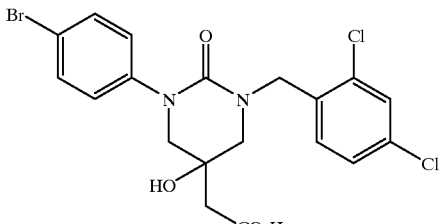

A.

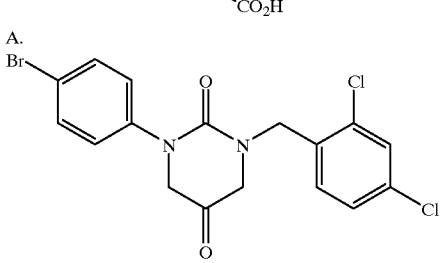

To a stirred solution of compound 2B (1.20 g, 2.82 mmol) in $CH_2Cl_2$ (100 mL) at −78° C. was bubbled 2% ozone/oxygen from a commercial ozonizer. After 10 min, a bright blue solution had formed. Excess ozone was purged with a nitrogen stream, the nearly colorless solution was then treated with triphenylphosphine (1.0 g, 3.8 mmol) and the mixture warmed to room temperature. After 1 h, the solution was evaporated. Purification of the residual solids by flash chromatography on silica gel (5×20 cm column, 1:399 ether/$CH_2Cl_2$) gave 54A as a white solid, 895 mg (74% yield), mp 128–130° C. LC/MS gave the correct molecular ion [(M+H)$^+$=427] for the desired compound.

B.

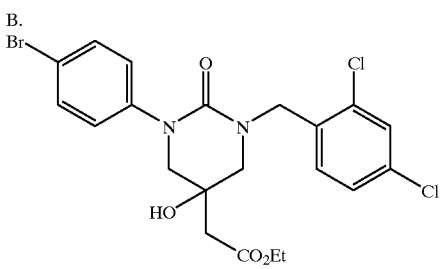

To a solution of lithium hexamethyldisilazide (1 $\underline{M}$ in THF, 1.03 mL, 1.03 mmol) in THF (1 mL) at −78° C. under $N_2$ was added EtOAc (100 μL, 1.0 mmol) over 5 min. After 15 min, a solution of 54A (425 mg, 1.0 mmol) in THF (2 mL) was added over 10 min. After an additional 10 min, hydrochloric acid (3 $\underline{N}$, 0.35 mL) was added rapidly and the reaction mixture was warmed to room temperature. The resulting yellow solution was partitioned between EtOAc and brine. The organic extract was dried (MgSO$_4$) and evaporated. Purification by flash chromatography on silica gel (5×15 cm column, 9:91 ether/CH$_2$Cl$_2$) gave 54B as a colorless oil, 326 mg (64% yield). LC/MS gave the correct molecular ion [(M+H)$^+$=515] for the desired compound.

C.

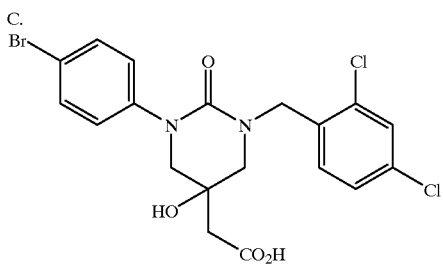

To a solution of 54B (320 mg, 0.62 mmol) in THF (2 mL) was added sodium hydroxide solution (1 M, 1 mL, 1 mmol) at room temperature under N$_2$. After 18 h, the reaction was quenched with 10% citric acid solution and partially evaporated to remove THF. The resulting precipitate was filtered, washed with water and dried in vacuo to give the title compound 54 as a white solid, 290 mg (96% yield), mp 206–207° C. LC/MS gave the correct molecular ion [(M+H)$^+$=487] for the desired compound.

Elemental analysis for C$_{19}$H$_{17}$N$_2$O$_4$BrCl$_2$. Calc.% C, 46.75; H, 3.51; N, 5.74; Br, 16.37; Cl, 14.53. Fnd. C, 46.76; H, 3.59; N, 5.61; Br, 16.44; Cl, 14.28.

EXAMPLE 55

1-(4-Bromophenyl)-3-[(2,4-dichlorophenyl)methyl] hexahydro-2-oxo-5-pyrimidinecarboxylic acid

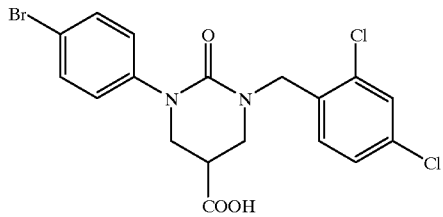

To a stirred solution of compound 2C (100 mg, 0.22 mmol), in acetone (2 mL) at room temperature under N$_2$ was added a solution of Jones reagent until an orange color persisted (120 μL, 0.32 mmol). After 10 min, the light orange solution was quenched with 2-propanol and diluted with equal volumes of ethyl acetate and water. The layers were equilibrated, the organic fraction dried (MgSO$_4$) and evaporated. Purification by trituration with hot hexanes followed by trituration with cold chloroform gave the title compound 55 as a white solid, 50 mg (49% yield), mp 229–232 C. LC/MS gave the correct molecular ion [(M+H)$^+$=457] for the desired compound.

Elemental analysis for C$_{18}$H$_{15}$N$_2$O$_3$Cl$_2$Br+0.6 CHCl$_3$: Calc. C, 42.17; H, 2.97; N, 5.29. Fnd: C, 42.43; H, 2.97; N, 5.29.

EXAMPLE 56

1-(4-Bromophenyl)-3-[(2,4-dichlorophenyl)methyl] tetrahydro-5-(1H-tetrazol-5-yl)-2(1H)-pyrimidinone

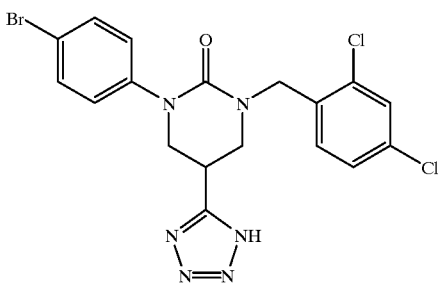

A.

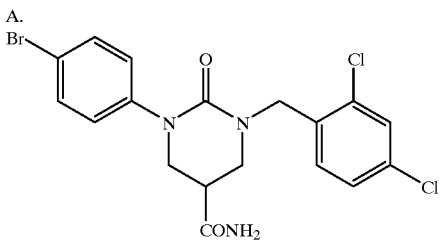

To a stirred solution of compound 55A (650 mg, 1.41 mmol) in CH$_2$Cl$_2$ (5 mL) at room temperature was added oxalyl chloride solution (2 M in CH$_2$Cl$_2$, 1.0 mL, 2 mmol) and DMF (50 μL). After 1 h, the reaction mixture was evaporated and the residuum was dissolved in THF (5 mL). The solution was cooled to 0° C. under N$_2$ and treated with an ammonia solution (0.5 M in dioxane, 6 mL, 3 mmol) over 10 min. After 1 h, the reaction was quenched with saturated NaHCO$_3$ solution and extracted twice with EtOAc. The organic extracts were combined, dried (MgSO$_4$) and evaporated to give 56A as a tan solid, 412 mg (64% yield). LC/MS gave the correct molecular ion [(M+H)$^+$=456] for the desired compound.

B.

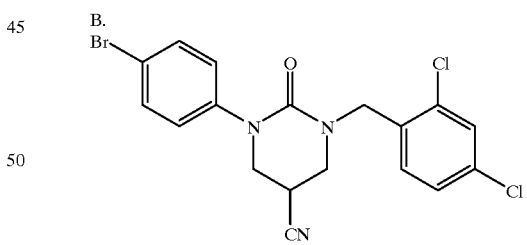

To a stirred solution of 56A (397 mg, 0.868 mmol) in THF (5 mL) at room temperature under N$_2$ was added pyridine (145 μL, 1.74 mmol) and trifluoroacetic anhydride (180 μL, 1.28 mmol). The reaction mixture was refluxed for 20 h, then cooled, quenched with hydrochloric acid (1 M, 10 mL) and extracted twice with EtOAc. The organic extracts were combined, dried (MgSO$_4$) and evaporated. Purification by flash chromatography on silica gel (2.5×15 cm column, 2:123 ether/CH$_2$Cl$_2$) gave 56B as a white amorphous solid, 310 mg (81% yield). LC/MS gave the correct molecular ion [(M+H)$^+$=438] for the desired compound.

C.

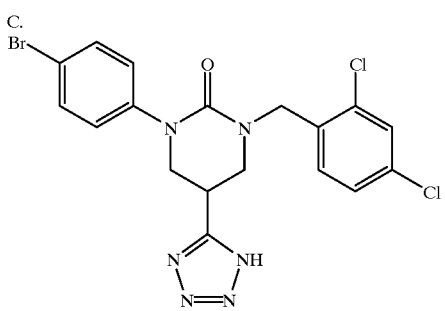

To a stirred solution of 56B (100 mg, 0.23 mmol) in toluene (2 mL) at room temperature under $N_2$ was added azidotrimethyltin (70 mg, 0.34 mmol). The reaction mixture was refluxed for 20 h, then cooled, quenched with methanol and evaporated. Purification by flash chromatography on silica gel (2.5×15 cm column, 1:19:182 HOAc/MeOH/$CH_2Cl_2$) gave the title compound 56 as a white solid, 79 mg (71% yield), mp 207–209° C. LC/MS gave the correct molecular ion [(M+H)$^+$=481] for the desired compound.

EXAMPLE 57

1-(4-Bromophenyl)-3-[(2,4-dichlorophenyl)methyl]tetrahydro-5-(1H-tetrazol-5-ylmethyl)-2(1H)-pyrimidinone

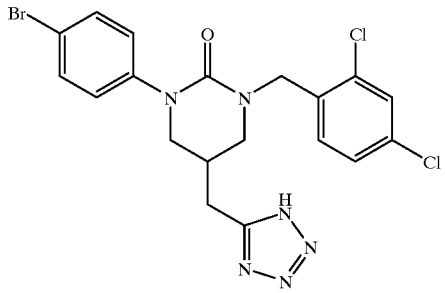

To a stirred solution of compound 3B (245 mg, 0.543 mmol) in toluene (2 mL) at room temperature under $N_2$ was added azidotrimethyltin (180 mg, 0.87 mmol). The reaction mixture was refluxed for 48 h, then cooled, quenched with methanol and evaporated. Purification by flash chromatography on silica gel (2.5×15 cm column, 1:13:186 HOAc/MeOH/$CH_2Cl_2$) gave the title compound 57 as a white solid, 114 mg (42% yield), mp 155–157° C. LC/MS gave the correct molecular ion [(M+H)$^+$=495] for the desired compound.

EXAMPLE 58

(Z)-2-[1-(4-Bromophenyl)-3-[(2,4-dichlorophenyl)methyl]hexahydro-2-oxo-5-pyrimidinylidene]acetic acid and (E)-2-[1-(4-Bromophenyl)-3-[(2,4-dichlorophenyl)methyl]hexahydro-2-oxo-5-pyrimidinylidene]acetic acid

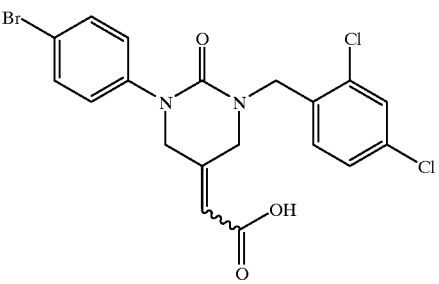

A.

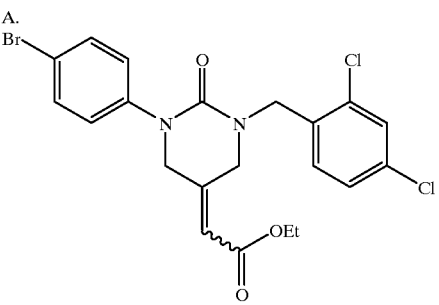

To a stirred solution of compound 54A (310 mg, 0.724 mmol) in THF (2 mL) at room temperature under $N_2$ was added ethyl (triphenylphosphoranylidene) acetate (280 mg, 0.80 mmol). After 40 h, the reaction mixture was evaporated. Purification of the residuum by flash chromatography on silica gel (2.5×15 cm column, 1:49 ether/$CH_2Cl_2$) gave 58A as a colorless oil, 2:3 ratio of cis/trans isomers, 277 mg (77% yield), mp 155–157° C. LC/MS gave the correct molecular ion [(M+H)$^+$=497] for the desired compound.

B.

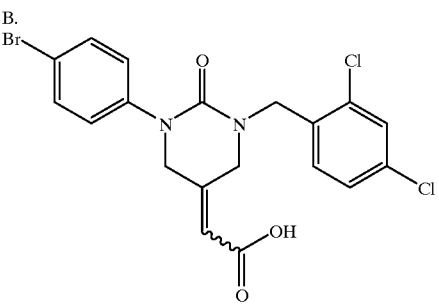

To a stirred solution of 58A (270 mg, 0.54 mmol) in THF (2 mL) at room temperature under $N_2$ was added sodium hydroxide solution (1 M, 1 mmol). After 14 h, the reaction mixture was diluted with water (5 mL) and extracted twice with ether. The aqueous phase was brought to pH 2 with hydrochloric acid (1 M). The resulting solid was filtered, washed with water and dried in vacuo to give the title compound 58 as an amorphous white solid, 2:3 ratio of cis/trans isomers, 260 mg (100% yield). LC/MS gave the correct molecular ion [(M+H)$^+$=469] for the desired compound.

EXAMPLE 59

1-[(2,4-Dichlorophenyl)methyl]hexahydro-3-(4-methylphenyl)-2-oxo-5,5-pyrimidinediacetic acid

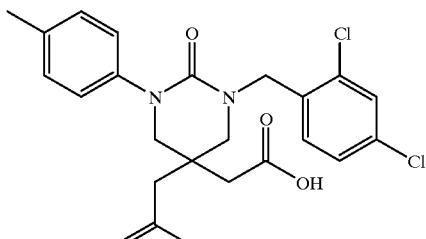

A.

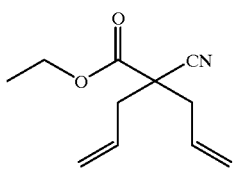

To a stirred solution of ethyl cyanoacetate (5.65 g, 50 mmol) in $CH_3CN$ (50 mL) at $-5°$ C. under argon was added a solution of 1,8-diazabicyclo[5.4.0]undec-7-ene (DBU, 15.1 mL, 103 mmol) in $CH_3CN$(15 mL) dropwise over 20 min. After addition was complete, allyl bromide (9.0 mL, 105 mmol) was added immediately and the reaction was stirred for 30 min and then refluxed for 1 h. After cooling to room temperature, the reaction mixture was evaporated and the residue partitioned between 3 $\underline{N}$ HCl (30 mL) and EtOAc (100 mL). The organic extract was dried ($MgSO_4$) and evaporated. Purification by flash chromatography on silica gel (2:1 $CH_2Cl_2$/hexanes as elutant) provided 59A as a colorless oil, 7.96 g (82%). LC/MS gave the correct molecular ion [(M+Na)$^+$=216] for the desired compound.

B.

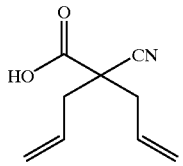

To a stirred solution of 59A (7.89 g, 40.8 mmol) in THF (40 mL) at room temperature under argon was added sodium hydroxide solution (1 $\underline{M}$, 42 mL, 42 mmol). After 14 h, the solution was treated with potassium hydrogen sulfate (7.5 g, 70 mmol) and evaporated to near dryness. The residue was agitated with $CH_2Cl_2$ (100 mL) and the solution was filtered through $MgSO_4$. Evaporation gave 59B as a crystalline white solid, 6.75 g (100%), mp 42–44° C.

C.

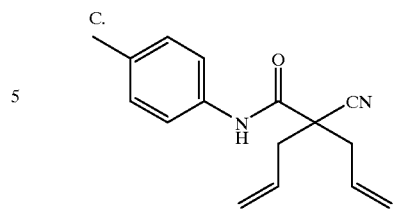

To a stirred solution of 59B (888 mg, 5.37 mmol) in $CH_2Cl_2$ (100 mL) at room temperature under argon was added oxalyl chloride in dichloromethane (2 $\underline{M}$, 3.8 mL, 7.6 mmol) and DMF (100 µL). After 3 h, the reaction mixture was evaporated and the residue redissolved in $CH_2Cl_2$ (10 mL). The resulting cloudy solution was added to a room temperature solution of p-toluidine (590 mg, 5.51 mmol) and triethylamine (1.5 mL, 11 mmol) in $CH_2Cl_2$ (10 mL). After 3 h, the solution was diluted with additional $CH_2Cl_2$ and washed with 5% $KHSO_4$ solution. The organic solution was dried ($MgSO_4$) and evaporated. Purification by flash chromatography on silica gel ($CH_2Cl_2$ as elutant) provided 59C as a white crystalline solid, 1.21 g (89% yield), mp 69–71° C. LC/MS gave the correct molecular ion [(M+H)$^+$=255] for the desired compound.

D.

To a stirred solution of lithium aluminumhydride (1 $\underline{M}$ in THF, 80 mL, 80 mmol) at room temperature was added, portionwise over 5 min, 59C (8.95 g, 35.2 mmol). A clear solution formed as gas evolved. After 10 min, a white opaque suspension formed, which was heated to reflux. After 15 h, the reaction was cooled to room temperature, treated dropwise with sodium hydroxide solution (1 $\underline{M}$, 3.5 mL, 3.5 mmol) and stirred for 1 h. The resulting bulky solid was slurried in THF (100 mL) and the mixture was heated to reflux for 1 h. After cooling, the solids were filtered, washing with THF. The filtrate was evaporated and then re-evaporated from toluene to give 59D as a colorless oil, 8.22 g, (96% yield). LC/MS gave the correct molecular ion [(M+H)$^+$=245] for the desired compound.

E.

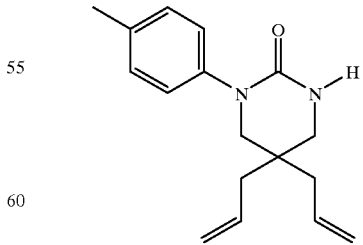

To a stirred solution of 59D (880 mg, 3.60 mmol) and triethylamine (0.56 mL, 4.0 mmol) in $CH_3CN$ (25 mL) at 5° C. under nitrogen was added a solution of carbonyl diimidazole (CDI, 292 mg, 1.8 mmol) in $CH_3CN$ (10 mL) over 20 min. After 1 h, solid CDI (292 mg, 1.8 mmol) was added and, at 1 h intervals, additional CDI was added (150 mg, 150 mg and 100 mg). After the last addition, the reaction mixture was warmed to room temperature and stirred for 14 h. After evaporation, the residue was partitioned between 5% potassium hydrogen sulfate solution and EtOAc (200 mL). The organic extract was dried (MgSO$_4$) and evaporated. Purification by flash chromatography on silica gel (3:97 CH$_3$OH/EtOAc) gave 59E as a white solid, 515 mg, (53% yield), mp 143–144° C. LC/MS gave the correct molecular ion [(M+H)$^+$=271] for the desired compound.

F.

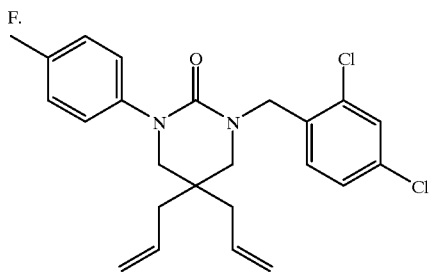

To a stirred solution of 59E (500 mg, 1.85 mmol) in THF (10 mL) at room temperature under nitrogen was added a solution of potassium hexamethyldisilazane (0.5 M in toluene, 4.0 mL, 2.0 mmol) over 1 min. After 30 min, 2,4-dichlorobenzyl chloride (305 μL, 2.2 mmol) was added, followed by solid tetrabutylammonium iodide (810 mg, 2.2 mmol). After 14 h, the reaction was quenched (5% KHSO$_4$) and extracted twice with EtOAc. The extracts were combined, washed with 10% NaHSO$_3$, dried (MgSO$_4$) and evaporated. Purification by flash chromatography on silica gel (2:1 hexanes/EtOAc) gave 59F as a colorless oil, 785 mg, (99% yield). LC/MS gave the correct molecular ion [(M+H)$^+$=430] for the desired compound.

G.

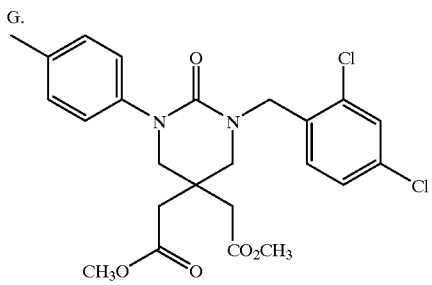

To a solution of sodium hydroxide in methanol (2.5 M, 55 mL, 138 mmol) at room temperature was added a solution of 59F (5.86 g, 13.6 mmol) in CH$_2$Cl$_2$ (215 mL). The reaction flask was protected with a Drierite-filled tube and cooled to −74° C. The reaction mixture was treated with a ~2–3% O$_3$/O$_2$ mixture for 4 h (ozone addition was stopped when LC/MS of an aliquot showed <5% of 59F remaining in the reaction mixture). The reaction was purged with nitrogen and then allowed to warm to room temperature overnight. The resulting solution was treated with hydrochloric acid (3 M, 46 mL, 138 mmol) and extracted twice with CH$_2$Cl$_2$. The combined extracts were evaporated, redissolved in CH$_2$Cl$_2$, dried (MgSO$_4$) and re-evaporated. The white foam product (6.42 g) was dissolved in CH$_2$Cl$_2$ (~40 mL) and treated with excess diazomethane in Et$_2$O. The excess diazomethane was dispersed with a nitrogen stream and the reaction mixture dried (MgSO$_4$) and evaporated. The resulting oil was again dissolved in CH$_2$Cl$_2$ (~30 mL) and stirred at room temperature with triphenylphosphine (3.57 g, 13.6 mmol) for 30 min. Purification by flash chromatography on silica gel (CH$_2$Cl$_2$ followed by 1:19 Et$_2$O/CH$_2$Cl$_2$) gave a colorless oil (4.10 g), a mixture of aldehyde and methyl ester.

The oil was dissolved in THF (20 mL) and treated with sulfamic acid (1.10 g, 1.1 mmol) and H$_2$O (15 mL). After stirring 10 min, sodium chlorite (80%, 1.28 g) in H$_2$O (5 mL) was added at room temperature. After 45 min, the reaction mixture was extracted twice with EtOAc. The extracts were combined, dried (MgSO$_4$) and evaporated to give a light yellow foam (4.42 g). The foam was dissolved in CH$_2$Cl$_2$ and treated as above with ethereal diazomethane. Purification of the product by flash chromatography on silica gel (3:47 Et$_2$O/CH$_2$Cl$_2$) gave 59G as a colorless solid, 3.58 g, (57% yield). LC/MS gave the correct molecular ion [(M+H)$^+$=494] for the desired compound.

H.

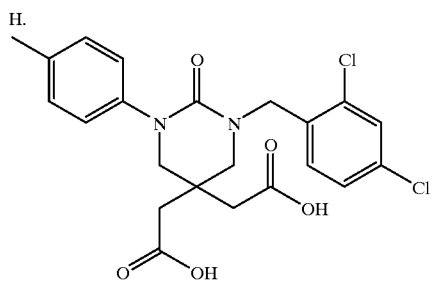

To a stirred solution of 59G (3.80 g, 7.70 mmol) in THF (20 mL) under nitrogen at room temperature was added sodium hydroxide solution (1 M, 20 mL, 20 mmol). The reaction mixture was heated at 50° C. for 4 h, cooled and partially evaporated to remove organic solvent. The aqueous remainder was acidified with hydrochloric acid (3 M, 7 mL, 21 mmol). The resulting solids were collected, washed with water and air-dried to give 59H as a white solid, 3.24 g, (90% yield), mp 156–158° C. LC/MS gave the correct molecular ion [(M+H)$^+$=465] for the desired compound.

EXAMPLE 60

1-(4-Bromophenyl)-3-[(4-chlorophenyl)methyl]hexahydro-2-oxo-5,5-pyrimidinediacetic acid anhydride

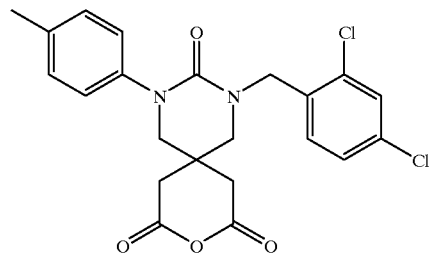

A stirred solution of 59H (3.20 g, 6.9 mmol) was refluxed in acetic anhydride (15 mL) for 6 h under argon. After cooling to room temperature, the reaction mixture was evaporated and the residue distilled trap-to-trap (110° C. @ 1 mm Hg) to remove the last traces of acetic acid or anhydride. The residue provided 60 as a colorless glass, 3.16 g (100%,~93% pure by NMR). LC/MS gave the correct molecular ion [(M+CH$_3$OH)$^+$=478] for the desired compound.

EXAMPLES 61–146

The title compounds were prepared as part of a solution phase library run using the following procedure.

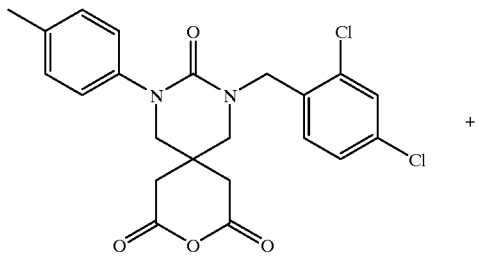

+

RR'NH ⟶

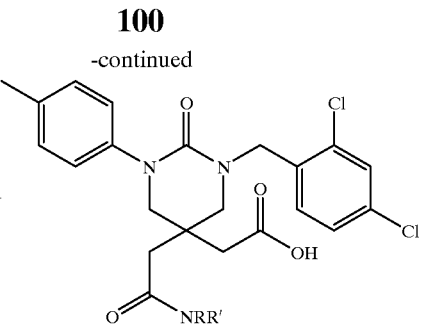

To a solution of 60 compound (22 mg, 0.05 mmol) in CH₃CN (0.5 mL) under nitrogen at room temperature was added a solution of RR'NH (0.15 mmol) in CH₃CN (0.5 mL). The reaction mixture was shaken in a nitrogen atmosphere at room temperature for 24 h. Each reaction was then diluted with water to a volume of 2.0 mL and purified by preparative HPLC to afford the title compound. Mass spectrometric and HPLC data were collected for all compounds.

Following the above procedure, the following compounds of the invention were prepared:

| Ex. | Structure | Name | (M + H) positive ion |
|---|---|---|---|
| 61 | 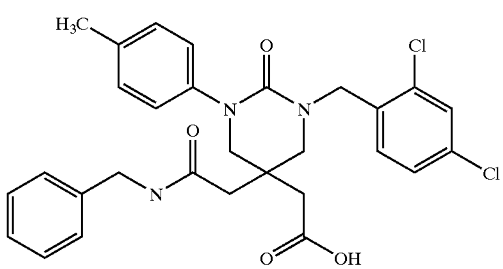 | 1-[(2,4-Dichlorophenyl)-methyl]hexahydro-3-(4-methylphenyl)-2-oxo-5-[2-oxo-2-[(phenyl-methyl)-amino]ethyl]-5-pyrimidineacetic acid | 554 |
| 62 | 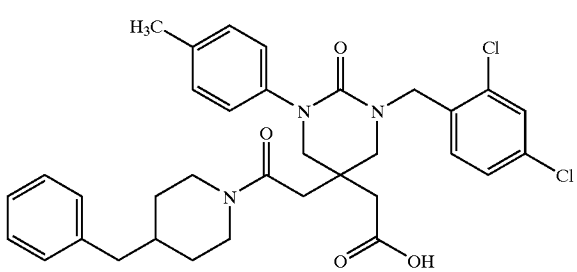 | 1-[(2,4-Dichlorophenyl)-methyl]hexahydro-3-(4-methylphenyl)-2-oxo-5-[2-oxo-2-[4-(phenyl-methyl)-1-piperidinyl]-ethyl]-5-pyrimidineacetic acid | 622 |
| 63 | 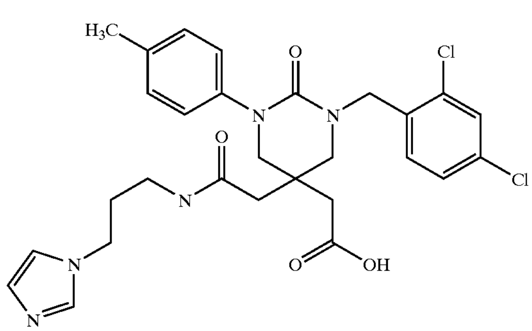 | 1-[(2,4-Dichlorophenyl)-methyl]hexahydro-3-(4-methylphenyl)-2-oxo-5-[2-[[3-(1H-imidazol-1-yl)propyl]-amino]-2-oxoethyl]-5-pyrimidineacetic acid | 572 |

| Ex. | Structure | Name | (M + H) positive ion |
|---|---|---|---|
| 64 | 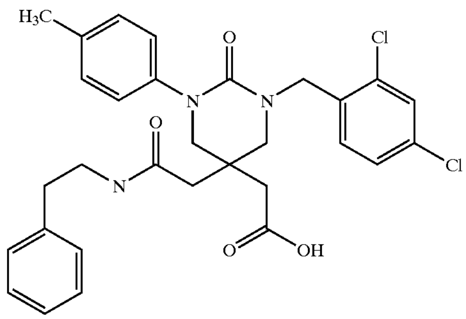 | 1-[(2,4-Dichlorophenyl)-methyl]hexahydro-3-(4-methylphenyl)-2-oxo-5-[2-oxo-2-[(2-phenyl-ethyl)-amino]ethyl]-5-pyrimi-dineacetic acid | 568 |
| 65 | 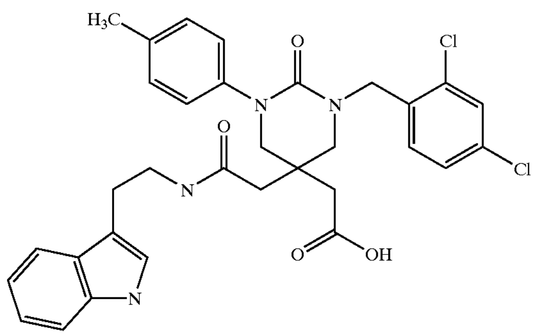 | 1-[(2,4-Dichlorophenyl)-methyl]hexahydro-3-(4-methylphenyl)-2-oxo-5-[2-[[2-(1H-indol-3-yl)ethyl]-amino]-2-oxoethyl]-5-pyrimidineacetic acid | 607 |
| 66 | 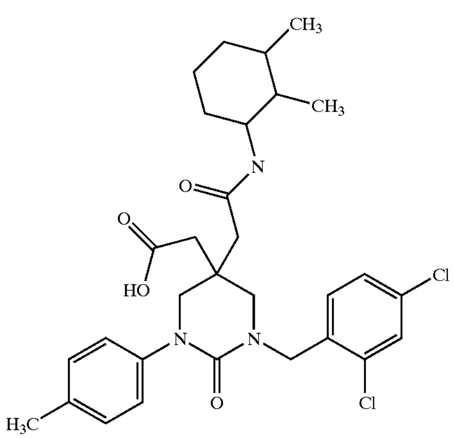 | 1-[(2,4-Dichlorophenyl)-methyl]-5-[2-[(2,3-dimethyl-cyclohexyl)-amino]-2-oxo-ethyl]hexahydro-3-(4-methyl-phenyl)-2-oxo-5-pyrimi-dineacetic acid | 574 |
| 67 | 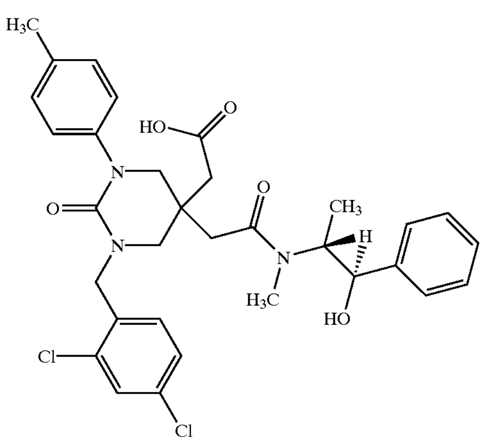 | 1-[(2,4-Dichlorophenyl)-methyl]hexahydro-3-(4-methylphenyl)-2-oxo-5-[2-[[(1R,2R)-2-hydroxy-1-methyl-2-phenylethyl]-methylamino]-2-oxoethyl]-5-pyrimidineacetic acid | 612 |

-continued

| Ex. | Structure | Name | (M + H) positive ion |
|---|---|---|---|
| 68 | 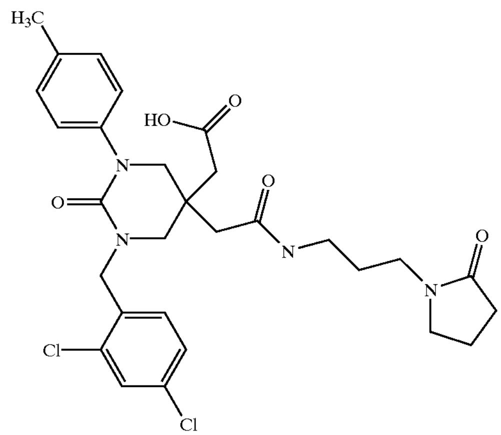 | 1-[(2,4-Dichlorophenyl)-methyl]hexahydro-3-(4-methylphenyl)-2-oxo-5-[2-oxo-2-[[3-(2-oxo-1-pyrrolidinyl)propyl]amino]ethyl]-5-pyrimidineacetic acid | 589 |
| 69 | 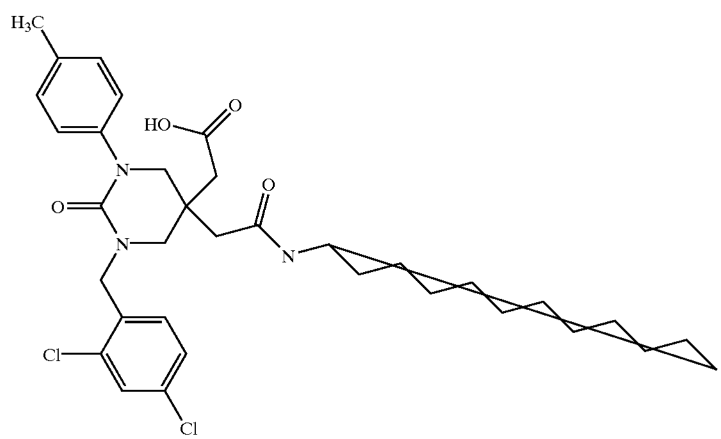 | 5-[2-(Cyclododecylamino)-2-oxoethyl]-1-[(2,4-dichloro-phenyl)methyl]-hexahydro-3-(4-methylphenyl)-2-oxo-5-pyrimidineacetic acid | 630 |
| 70 | 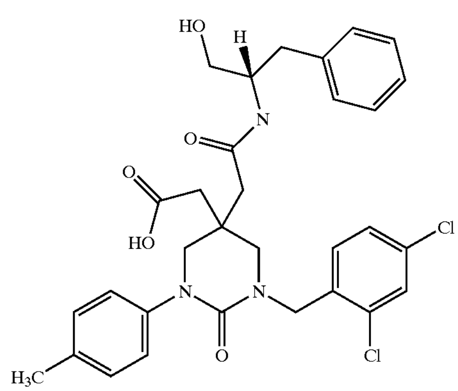 | 1-[(2,4-Dichlorophenyl)-methyl]hexahydro-5-[2-[[(1S)-2-hydroxy-1-(phenylmethyl-)ethyl]-amino]-2-oxoethyl]-3-(4-methylphenyl)-2-oxo-5-pyrimidineacetic acid | 598 |

-continued

| Ex. | Structure | Name | (M + H) positive ion |
|---|---|---|---|
| 71 | 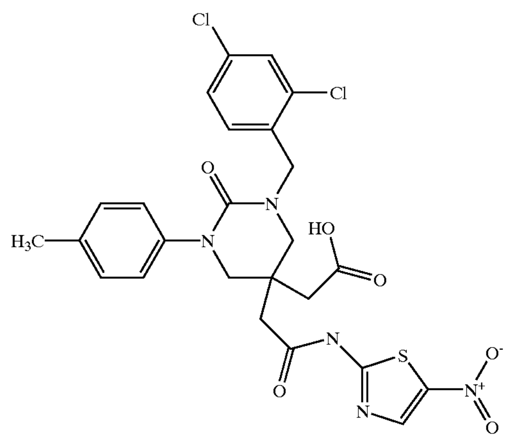 | 1-[(2,4-Dichlorophenyl)-methyl]hexahydro-3-(4-methylphenyl)-5-[2-[(5-nitro-2-thiazolyl)amino]-2-oxo-ethyl]-2-oxo-5-pyrimidine-acetic acid | 592 |
| 72 | 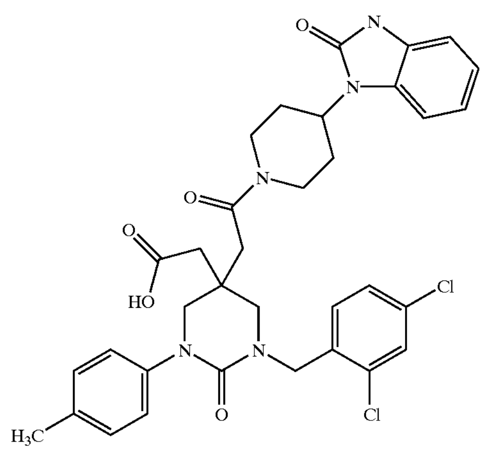 | 1-[(2,4-Dichlorophenyl)-methyl]-5-[2-[4-(2,3-dihydro-2-oxo-1H-benzimidazol-1-yl)-1-piperidinyl]-2-oxoethyl]-hexahydro-3-(4-methyl-phenyl)-2-oxo-5-pyrimidine-acetic acid | 664 |
| 73 | 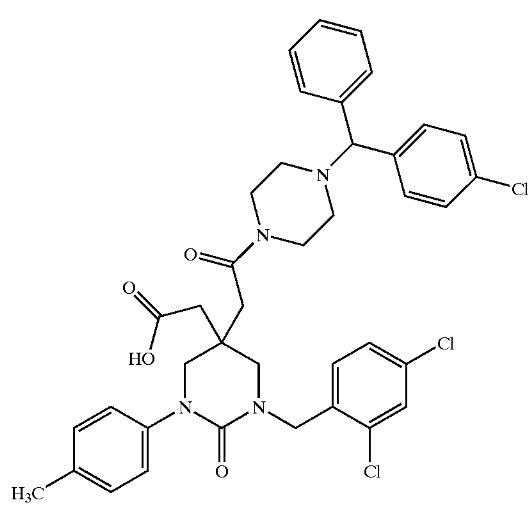 | 5-[2-[4-[(4-Chloro-phenyl)-phenylmethyl]-1-piperazinyl]-2-oxo-ethyl]-1-[(2,4-dichloro-phenyl)methyl]-hexa-hydro-3-(4-methyl-phenyl)-2-oxo-5-pyrimidineacetic acid | 734 |

| Ex. | Structure | Name | (M + H) positive ion |
|---|---|---|---|
| 74 | 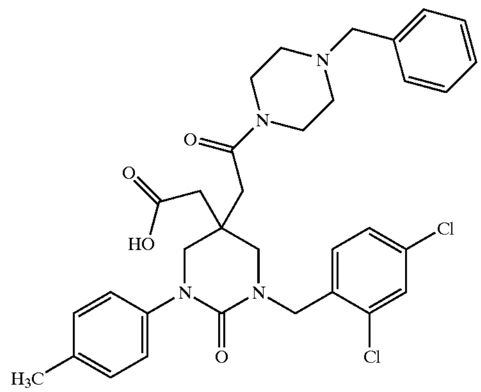 | 1-[(2,4-Dichlorophenyl)-methyl]hexahydro-3-(4-methylphenyl)-2-oxo-5-[2-[4-(phenylmethyl)-1-piperazinyl]-2-oxoethyl]-5-pyrimidine-acetic acid | 623 |
| 75 | 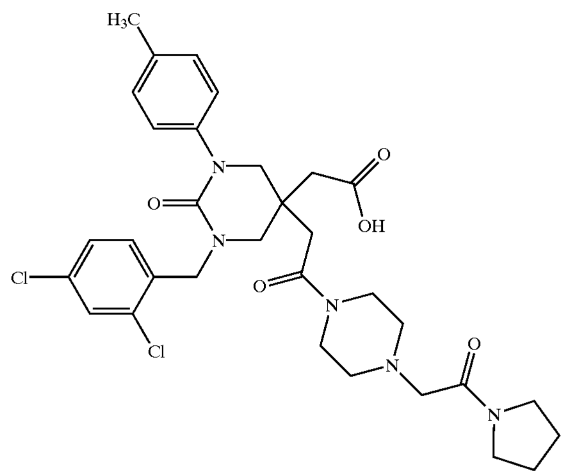 | 1-[(2,4-Dichlorophenyl)-methyl]hexahydro-3-(4-methylphenyl)-2-oxo-5-[2-oxo-2-[4-[2-oxo-2-(1-pyrrolidinyl)ethyl]-1-piperazinyl]ethyl]-5-pyrimidineacetic acid | 644 |
| 76 | 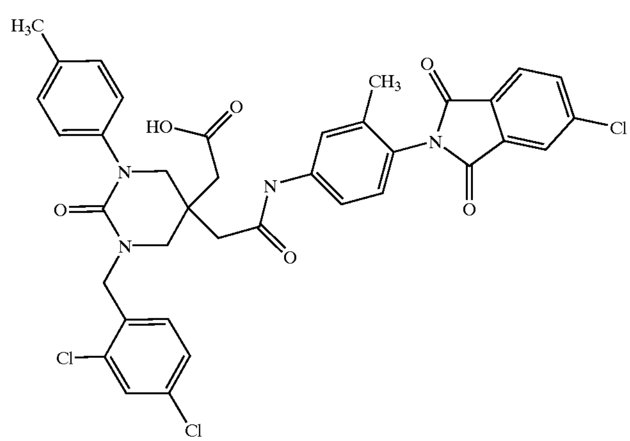 | 5-[2-[[4-(5-Chloro-1,3-dihydro-1,3-dioxo-2H-isoindol-2-yl)-3-methyl-phenyl]amino]-2-oxoethyl]-1-[(2,4-dichloro-phenyl)methyl]-hexahydro-3-(4-methyl-phenyl)-2-oxo-5-pyrimi-dineacetic acid | 734 |

| Ex. | Structure | Name | (M + H) positive ion |
|---|---|---|---|
| 77 | 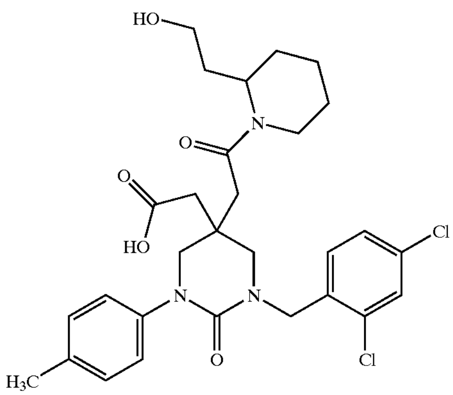 | 1-[(2,4-Dichlorophenyl)-methyl]hexahydro-5-[2-[2-(2-hydroxyethyl)-1-piperidinyl]-2-oxoethyl]-3-(4-methylphenyl)-2-oxo-5-pyrimidineacetic acid | 576 |
| 78 | 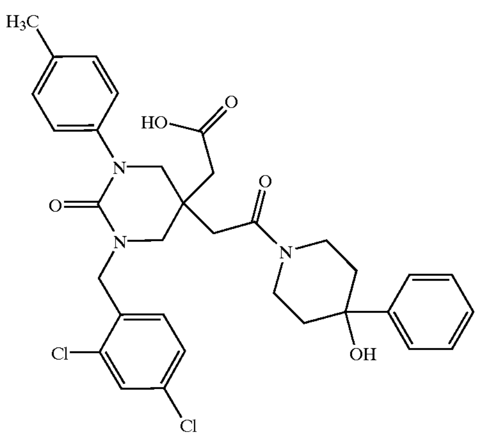 | 1-[(2,4-Dichlorophenyl)-methyl]hexahydro-5-[2-(4-hydroxy-4-phenyl-1-piperidinyl)-2-oxoethyl]-3-(4-methylphenyl)-2-oxo-5-pyrimidineacetic acid | 624 |
| 79 | 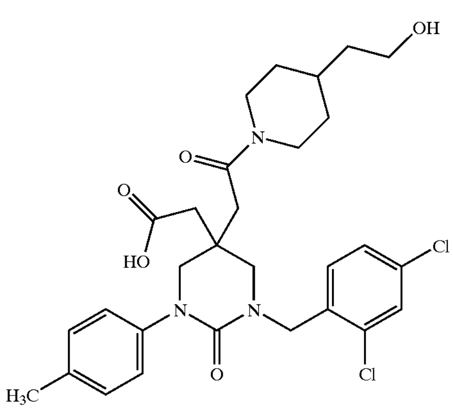 | 1-[(2,4-Dichlorophenyl)-methyl]hexahydro-5-[2-[4-(2-hydroxyethyl)-1-piperidinyl]-2-oxoethyl]-3-(4-methylphenyl)-2-oxo-5-pyrimidineacetic acid | 576 |

-continued

| Ex. | Structure | Name | (M + H) positive ion |
|---|---|---|---|
| 80 | 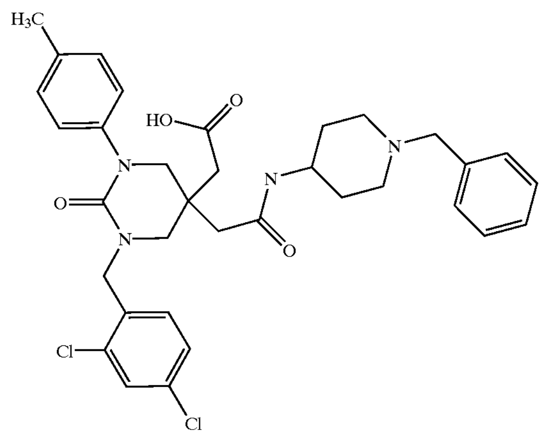 | 1-[(2,4-Dichlorophenyl)-methyl]hexahydro-3-(4-methylphenyl)-2-oxo-5-[2-[1-(phenylmethyl)-4-piperidinyl]-2-oxoethyl]-5-pyrimidine-acetic acid | 637 |
| 81 | 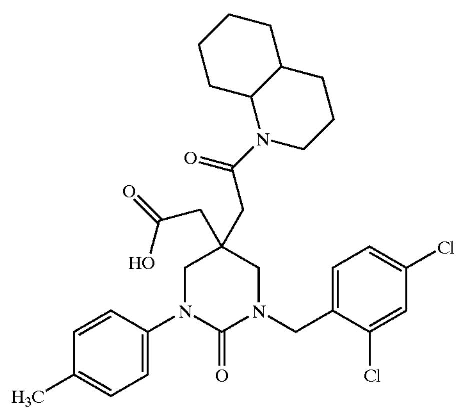 | 1-[(2,4-Dichlorophenyl)-methyl]hexahydro-3-(4-methylphenyl)-5-[2-(octa-hydro-1(2H)-quinolinyl)-2-oxoethyl]-2-oxo-5-pyrimidineacetic acid | 586 |
| 82 | 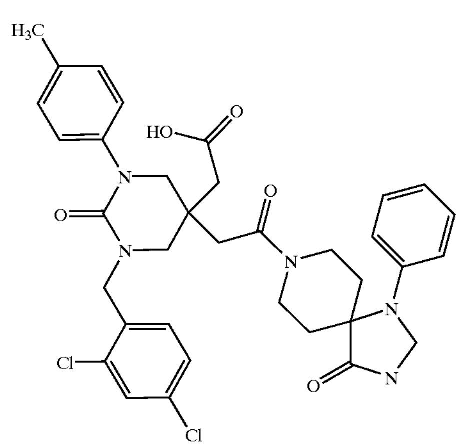 | 1-[(2,4-Dichlorophenyl)-methyl]hexahydro-3-(4-methylphenyl)-2-oxo-5-[2-oxo-2-(4-oxo-1-phenyl-1,3,8-triazaspiro-[4.5]decan-8-yl)ethyl]-5-pyrimidineacetic acid | 678 |

-continued

| Ex. | Structure | Name | (M + H) positive ion |
|---|---|---|---|
| 83 | 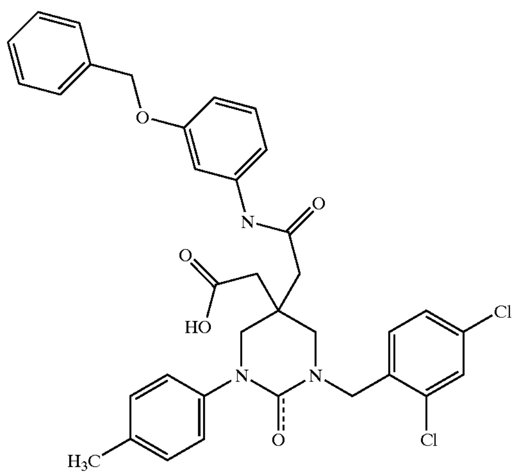 | 1-[(2,4-Dichlorophenyl)-methyl]hexahydro-3-(4-methylphenyl)-2-oxo-5-[2-oxo-2-[[3-(phenyl-meth-oxy)-phenyl]amino]-ethyl]-5-pyrimidineacetic acid | 646 |
| 84 | 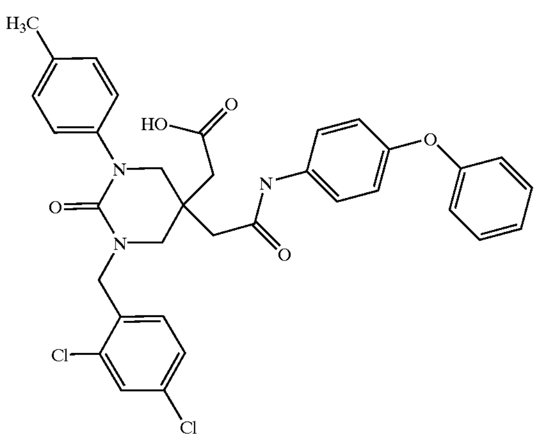 | 1-[(2,4-Dichlorophenyl)-methyl]hexahydro-3-(4-methylphenyl)-2-oxo-5-[2-oxo-2-[(4-phenoxy-phenyl)-amino]ethyl]-5-pyrimidine-acetic acid | 632 |
| 85 | 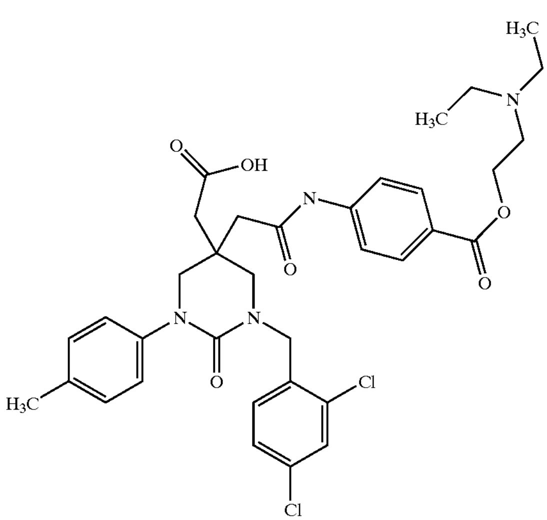 | 1-[(2,4-Dichlorophenyl)-methyl]-5-[2-[[4-[[2-(diethyl-amino)ethoxy]-carbonyl]phenyl]amino]-2-oxoethyl]-hexahydro-3-(4-methyl-phenyl)-2-oxo-5-pyrimidine-acetic acid | 683 |

-continued

| Ex. | Structure | Name | (M + H) positive ion |
|---|---|---|---|
| 86 | 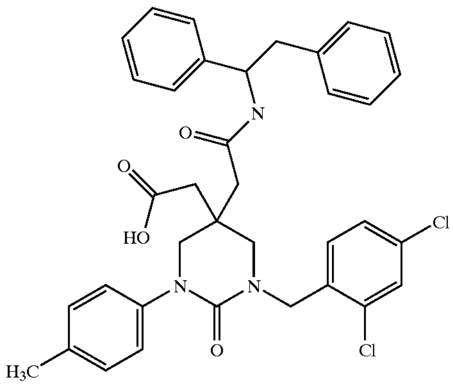 | 1-[(2,4-Dichlorophenyl)-methyl]-5-[2-[(1,2-diphenylethyl)amino]-2-oxoethyl]hexahydro-3-(4-methylphenyl)-2-oxo-5-pyrimidineacetic acid | 644 |
| 87 | 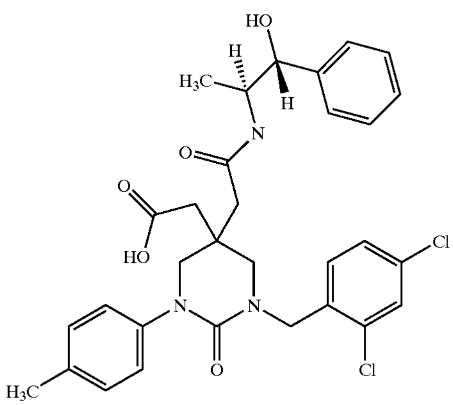 | 1-[(2,4-Dichlorophenyl)-methyl]hexahydro-5-[2-[[(1S,2R)-2-hydroxy-1-methyl-2-phenylethyl]-amino]-2-oxoethyl]-3-(4-methyl-phenyl)-2-oxo-5-pyrimidin-eacetic acid | 598 |
| 88 | 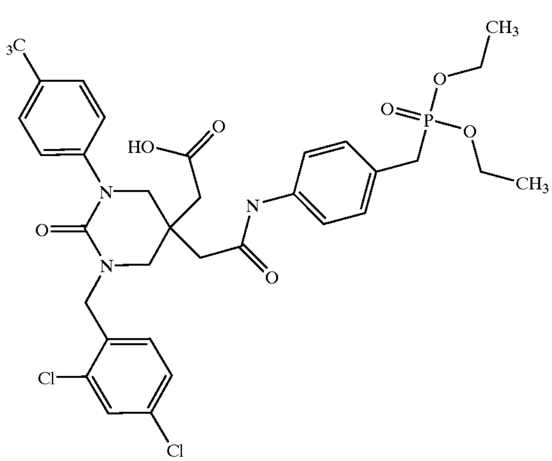 | 1-[(2,4-Dichlorophenyl)-methyl]-5-[2-[[4-[(diethoxy-phosphinyl)-methyl]phenyl]-amino]-2-oxoethyl]hexa-hydro-3-(4-methylphenyl)-2-oxo-5-pyrimidineacetic acid | 690 |

-continued

| Ex. | Structure | Name | (M + H) positive ion |
|---|---|---|---|
| 89 | 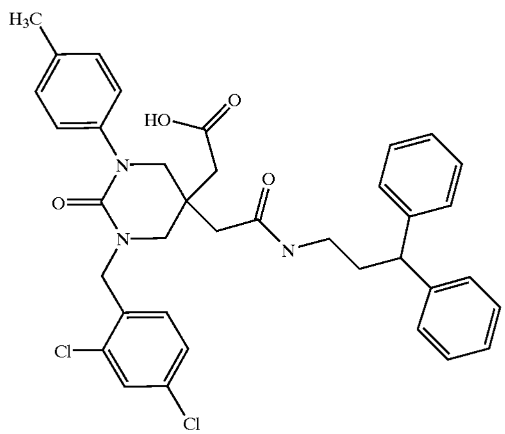 | 1-[(2,4-Dichlorophenyl)-methyl]-5-[2-[(3,3-diphenyl-propyl)amino]-2-oxoethyl]-hexahydro-3-(4-methyl-phenyl)-2-oxo-5-pyrimidine-acetic acid | 658 |
| 90 | 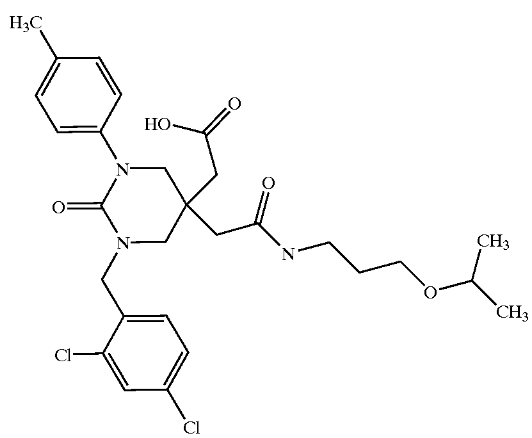 | 1-[(2,4-Dichlorophenyl)-methyl]hexahydro-5-[2-[[3-(1-methylethoxy)-propyl]amino]-2-oxoethyl]-3-(4-methyl-phenyl)-2-oxo-5-pyrimidine-acetic acid | 564 |
| 91 | 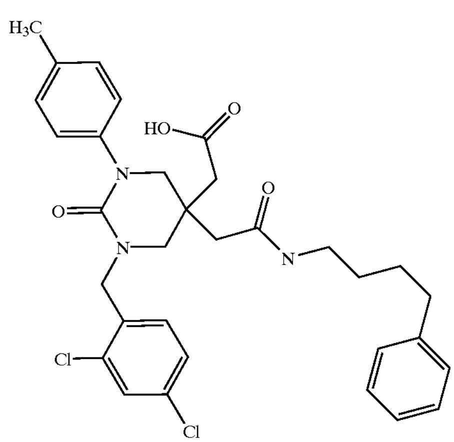 | 1-[(2,4-Dichlorophenyl)-methyl]hexahydro-3-(4-methylphenyl)-2-oxo-5-[2-oxo-2-[(4-phenyl-butyl)-amino]ethyl]-5-pyrimidine-acetic acid | 596 |

-continued

| Ex. | Structure | Name | (M + H) positive ion |
|---|---|---|---|
| 92 | 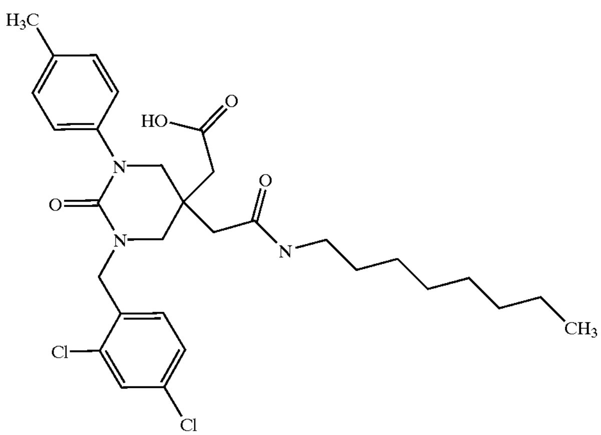 | 1-[(2,4-Dichlorophenyl)-methyl]hexahydro-3-(4-methylphenyl)-5-[2-(octyl-amino)-2-oxoethyl]-2-oxo-5-pyrimidineacetic acid | 576 |
| 93 | 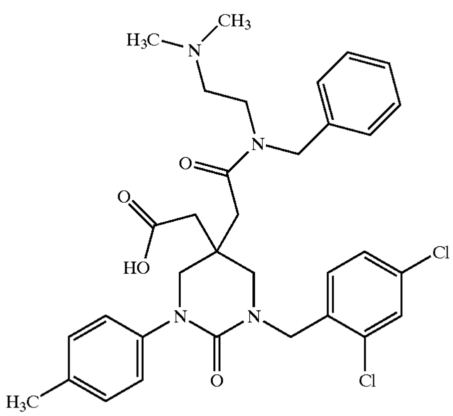 | 1-[(2,4-Dichlorophenyl)-methyl]-5-[2-[[2-(dimethyl-amino)ethyl]-(phenyl-methyl)amino]-2-oxoethyl]hexahydro-3-(4-methylphenyl)-2-oxo-5-pyrimidineacetic acid | 625 |
| 94 | 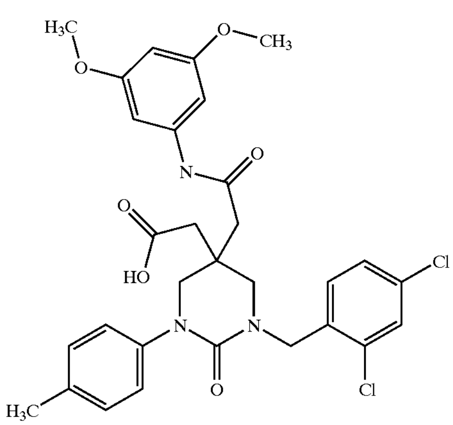 | 1-[(2,4-Dichlorophenyl)-methyl]-5-[2-[(3,5-di-methoxyphenyl)amino]-2-oxoethyl]-hexahydro-3-(4-methylphenyl)-2-oxo-5-pyrimidineacetic acid | 600 |

-continued

| Ex. | Structure | Name | (M + H) positive ion |
|---|---|---|---|
| 95 | 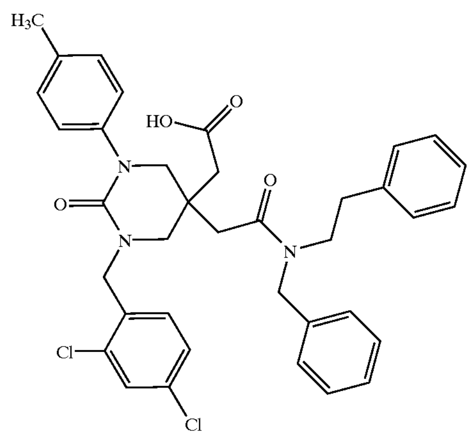 | 1-[(2,4-Dichlorophenyl)-methyl]hexahydro-3-(4-methylphenyl)-2-oxo-5-[2-oxo-2-[(2-phenyl-ethyl)-(phenylmethyl)-amino]ethyl]-5-pyrimidineacetic acid | 658 |
| 96 | 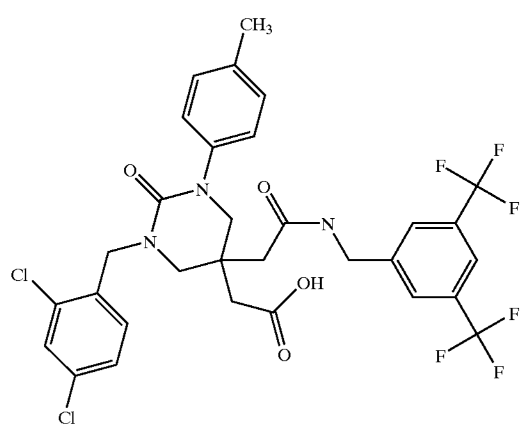 | 5-[2-[[[3,5-Bis(trifluoro-methyl)phenyl]methyl]amino]-2-oxoethyl]-1-[(2,4-dichloro-phenyl)methyl]-hexahydro-3-(4-methyl-phenyl)-2-oxo-5-pyrimidineacetic acid | 690 |
| 97 | 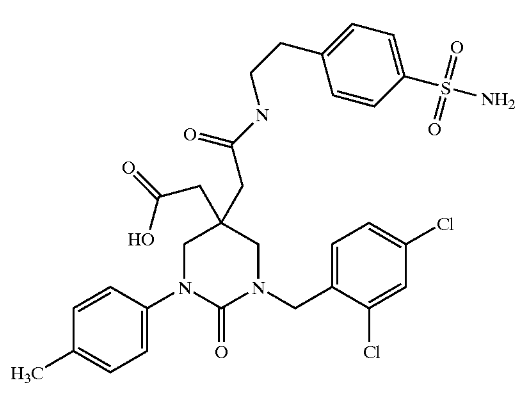 | 5-[2-[[2-[4-(Amino-sulfonyl)-phenyl]ethyl]-amino]-2-oxoethyl]-1-[(2,4-dichloro-phenyl)-methyl]hexahydro-3-(4-methylphenyl)-2-oxo-5-pyrimidineacetic acid | 647 |

-continued

| Ex. | Structure | Name | (M + H) positive ion |
|---|---|---|---|
| 98 | 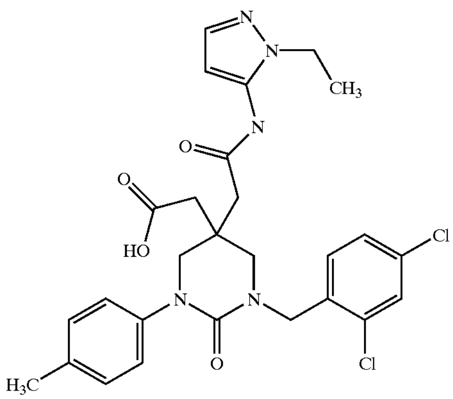 | 1-[(2,4-Dichlorophenyl)-methyl]-5-[2-[(1-ethyl-1H-pyrazol-5-yl)amino]-2-oxoethyl]hexahydro-3-(4-methylphenyl)-2-oxo-5-pyrimidineacetic acid | 558 |
| 99 | 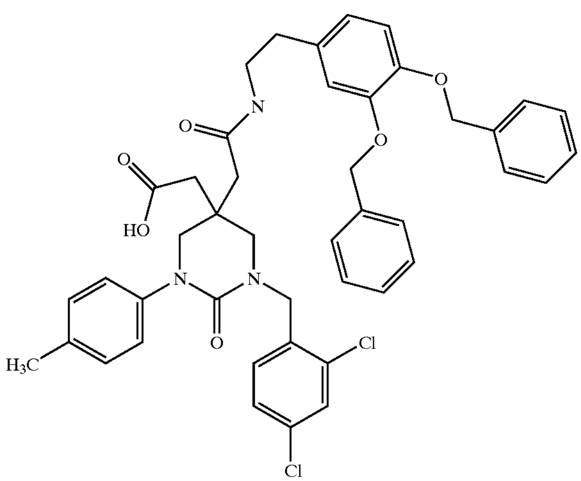 | 5-[2-[[2-[3,4-Bis(phenyl-methoxy)phenyl]ethyl]-amino]-2-oxoethyl]-1-[(2,4-dichloro-phenyl)methyl]hexahydro-3-(4-methylphenyl)-2-oxo-5-pyrimidineacetic acid | 780 |
| 100 | 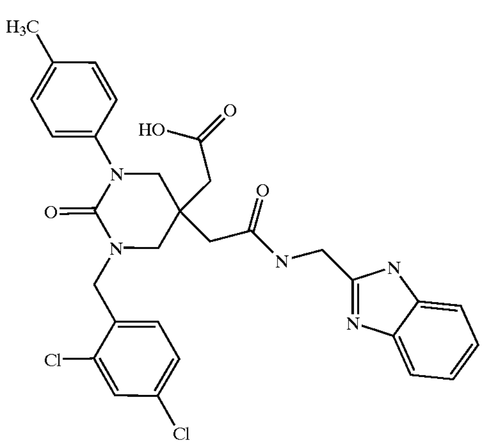 | 5-[2-[(1H-Benzimidazol-2-ylmethyl)amino]-2-oxoethyl]-1-[(2,4-dichlorophenyl)-methyl]hexahydro-3-(4-methylphenyl)-2-oxo-5-pyrimidineacetic acid | 594 |

-continued

| Ex. | Structure | Name | (M + H) positive ion |
|---|---|---|---|
| 101 | 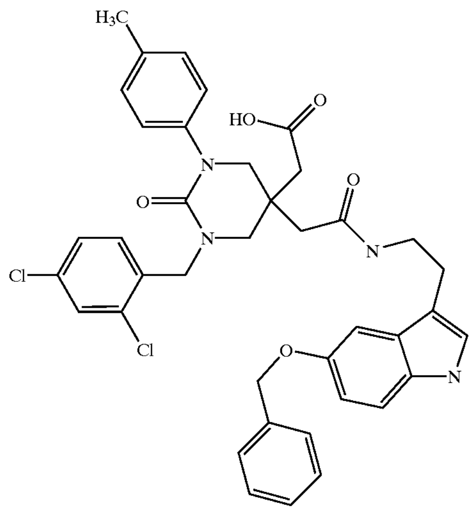 | 1-[(2,4-Dichlorophenyl)-methyl]hexahydro-3-(4-methylphenyl)-2-oxo-5-[2-oxo-2-[[2-[5-(phenylmethoxy)-1H-indol-3-yl]ethyl]-amino]ethyl]-5-pyrimidine-acetic acid | 713 |
| 102 | 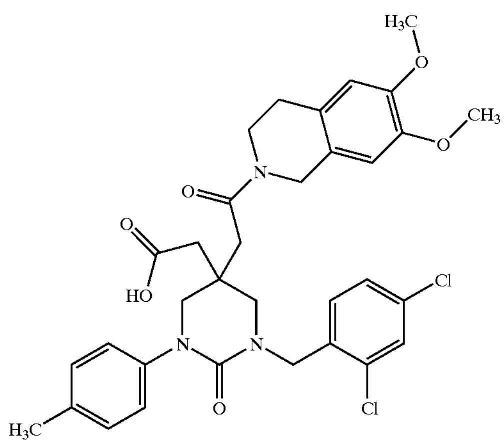 | 1-[(2,4-Dichlorophenyl) methyl]-5-[2-(3,4-dihydro-6,7-dimethoxy-2(1H)-isoquino-linyl)-2-oxoethyl]hexahydro-3-(4-methylphenyl)-2-oxo-5-pyrimidineacetic acid | 640 |
| 103 | 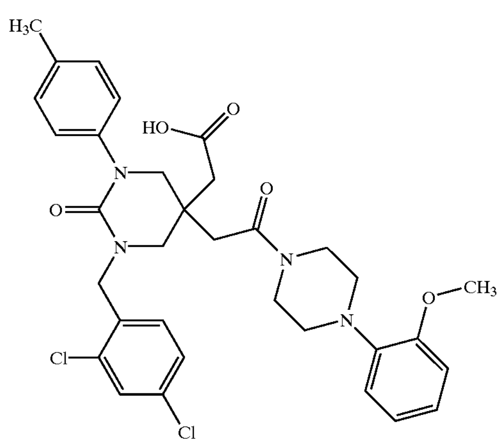 | 1-[(2,4-Dichlorophenyl)-methyl]hexahydro-5-[2-[4-(2-methoxyphenyl)-1-pipera-zinyl]-2-oxoethyl]-3-(4-methylphenyl)-2-oxo-5-pyrimidineacetic acid | 639 |

-continued

| Ex. | Structure | Name | (M + H) positive ion |
|---|---|---|---|
| 104 | 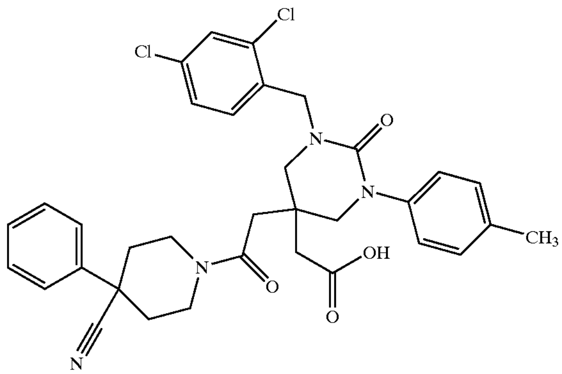 | 5-[2-(4-Cyano-4-phenyl-1-piperidinyl)-2-oxoethyl]-1-[(2,4-dichloro-phenyl)-methyl]hexahydro-3-(4-methylphenyl)-2-oxo-5-pyrimidineacetic acid | 633 |
| 105 | 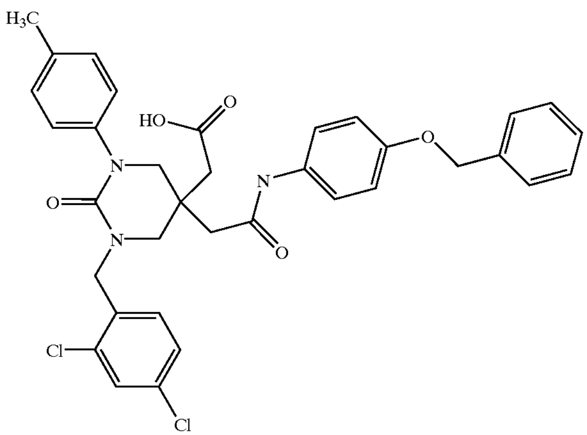 | 1-[(2,4-Dichlorophenyl)-methyl]hexahydro-3-(4-methylphenyl)-2-oxo-5-[2-oxo-2-[[4-(phenyl-methoxy)-phenyl]-amino]ethyl]-5-pyrimidineacetic acid | 646 |
| 106 | 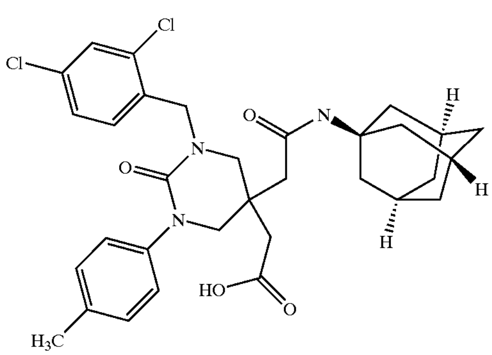 | 1-[(2,4-Dichlorophenyl)-methyl]hexahydro-3-(4-methylphenyl)-2-oxo-5-[2-(tricyclo-[3.3.1.13,7]-dec-1-ylamino)-2-oxoethyl]-5-pyrimidineacetic acid | 598 |

-continued

| Ex. | Structure | Name | (M + H) positive ion |
|---|---|---|---|
| 107 | 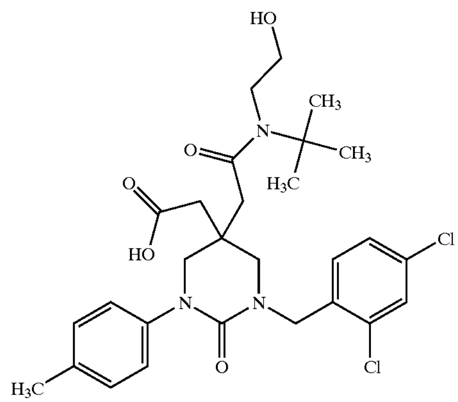 | 1-[(2,4-Dichlorophenyl)-methyl]-5-[2-[(1,1-dimethyl-ethyl)(2-hydroxyethyl)amino]-2-oxoethyl]hexahydro-3-(4-methylphenyl)-2-oxo-5-pyrimidineacetic acid | 564 |
| 108 | 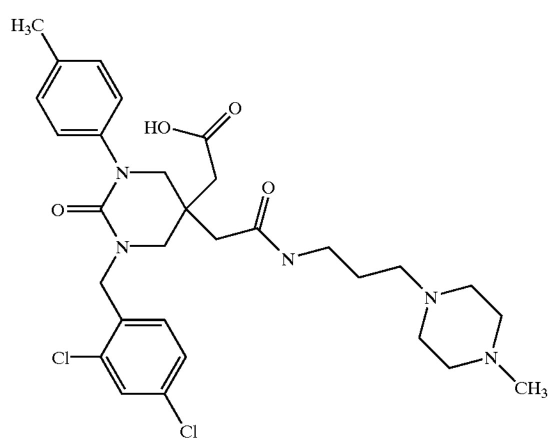 | 1-[(2,4-Dichlorophenyl)-methyl]hexahydro-3-(4-methylphenyl)-5-[2-[[3-(4-methyl-1-piperazinyl)-propyl]amino]-2-oxoethyl]-2-oxo-5-pyrimidineacetic acid | 604 |
| 109 | 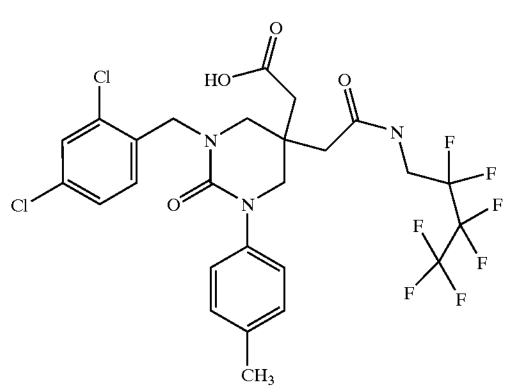 | 1-[(2,4-Dichlorophenyl)-methyl]-5-[2-[(2,2,3,3,4,4,4-heptafluorobutyl)amino]-2-oxoethyl]hexahydro-3-(4-methylphenyl)-2-oxo-5-pyrimidineacetic acid | 646 |

-continued

| Ex. | Structure | Name | (M + H) positive ion |
|---|---|---|---|
| 110 | 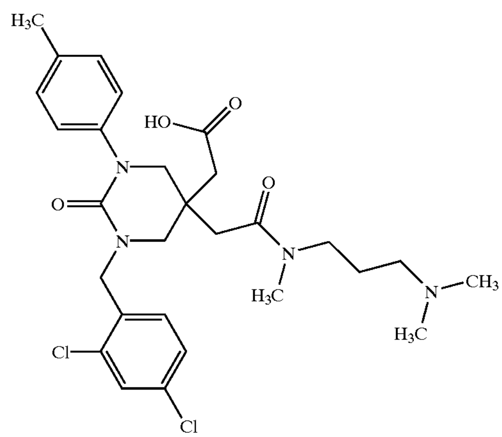 | 1-[(2,4-Dichlorophenyl)-methyl]-5-[2-[[3-(dimethyl-amino)propyl]-methylamino]-2-oxoethyl]hexahydro-3-(4-methylphenyl)-2-oxo-5-pyrimidineacetic acid | 563 |
| 111 | 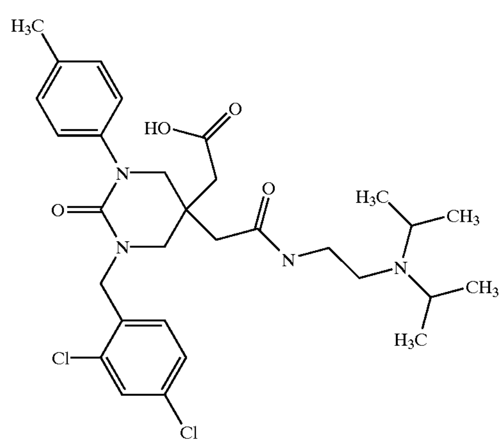 | 5[2-[[2-[Bis(1-methylethyl)-amino]-ethyl]amino]-2-oxoethyl]-1-[(2,4-dichloro-phenyl)-methyl]hexahydro-3-(4-methylphenyl)-2-oxo-5-pyrimidineacetic acid | 591 |
| 112 | 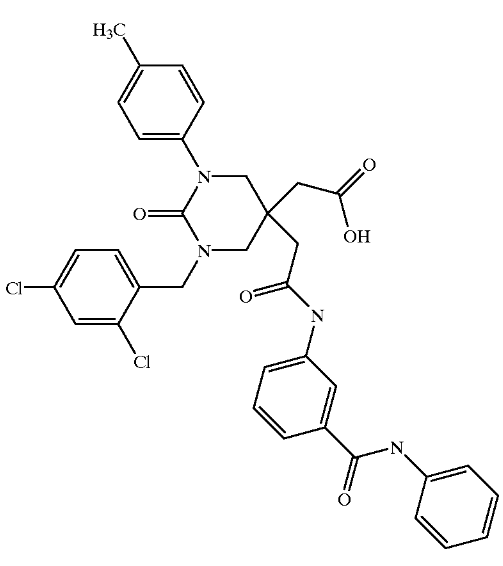 | 1-[(2,4-Dichlorophenyl)-methyl]hexahydro-3-(4-methylphenyl)-2-oxo-5-[2-[[3-[(phenylamino)-carbonyl]-phenyl]amino]-2-oxoethyl]-5-pyrimidineacetic acid | 659 |

-continued

| Ex. | Structure | Name | (M + H) positive ion |
|---|---|---|---|
| 113 | 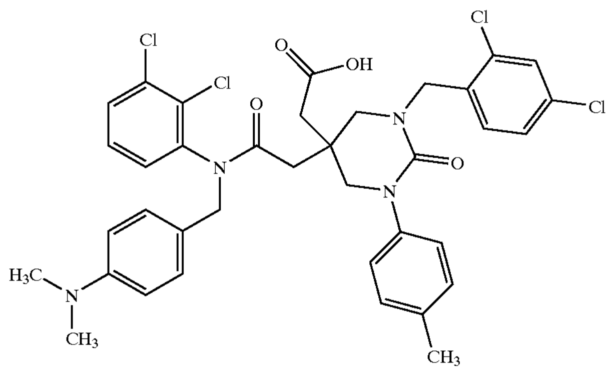 | 5-[2-[(2,3-Dichlorophenyl)[[4-(dimethylamino)phenyl]-methyl]-amino]-2-oxoethyl]-1-[(2,4-dichlorophenyl)-methyl]hexahydro-3-(4-methylphenyl)-2-oxo-5-pyrimidineacetic acid | 742 |
| 114 | 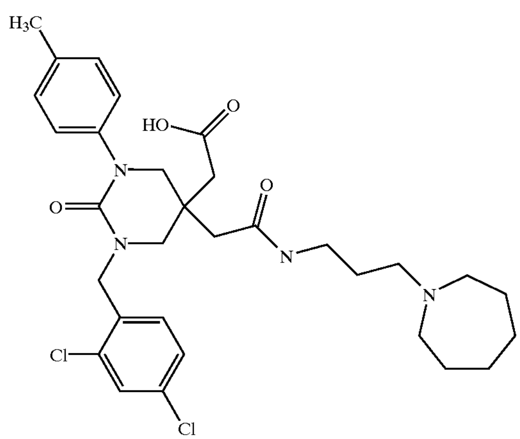 | 1-[(2,4-Dichlorophenyl)-methyl]hexahydro-5-[2-[[3-(hexahydro-1H-azepin-1-yl)propyl]-amino]-2-oxoethyl]-3-(4-methylphenyl)-2-oxo-5-pyrimidineacetic acid | 603 |
| 115 | 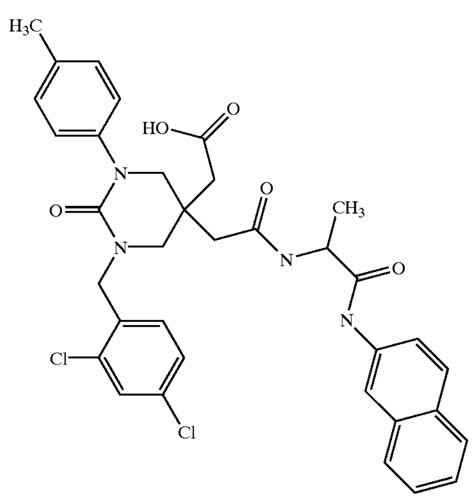 | 1-[(2,4-Dichlorophenyl)-methyl]hexahydro-5-[2-[[1-methyl-2-(2-naphthalenyl-amino)-2-oxoethyl]amino]-2-oxoethyl]-3-(4-methylphenyl)-2-oxo-5-pyrimidineacetic acid. | 661 |

-continued

| Ex. | Structure | Name | (M + H) positive ion |
|---|---|---|---|
| 116 | 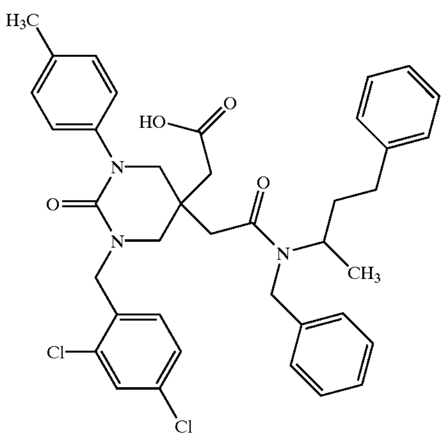 | 1-[(2,4-Dichlorophenyl)-methyl]hexahydro-3-(4-methylphenyl)-5-[2-[[(1-methyl-3-phenylpropyl)-(phenylmethyl)amino]-2-oxoethyl]-2-oxo-5-pyrimidineacetic acid | 686 |
| 117 | 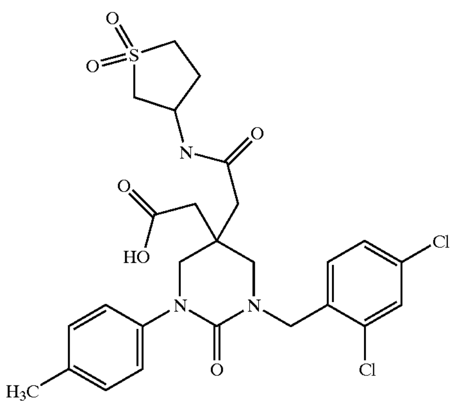 | 1-[(2,4-Dichlorophenyl)-methyl]-5-[2-[[(1,1-dioxido-3-thienyl)amino]-2-oxoethyl]-hexahydro-3-(4-methyl-phenyl)-2-oxo-5-pyrimi-dineacetic acid | 582 |
| 118 | 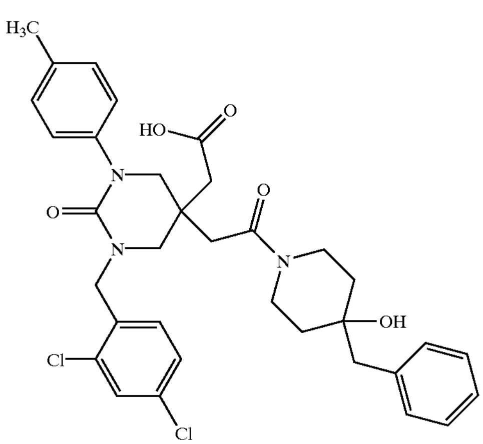 | 1-[(2,4-Dichlorophenyl)-methyl]hexahydro-5-[2-[4-hydroxy-4-(phenylmethyl)-1-piperidinyl]-2-oxoethyl]-3-(4-methylphenyl)-2-oxo-5-pyrimidineacetic acid | 638 |

| Ex. | Structure | Name | (M + H) positive ion |
|---|---|---|---|
| 119 | 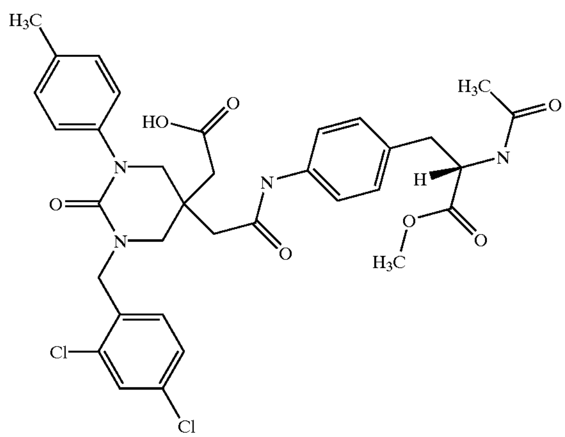 | 5-[2-[[4-[(2S)-2-(Acetylamino)-3-methoxy-3-oxopropyl]phenyl]amino]-2-oxoethyl]-1-[(2,4-dichlorophenyl)methyl]-hexahydro-3-(4-methylphenyl)-2-oxo-5-pyrimidineacetic acid | 683 |
| 120 | 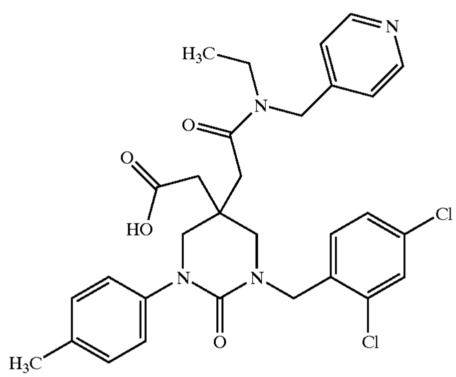 | 1-[(2,4-Dichlorophenyl)-methyl]-5-[2-[ethyl(4-pyridinylmethyl)amino]-2-oxoethyl]hexahydro-3-(4-methylphenyl)-2-oxo-5-pyrimidineacetic acid | 583 |
| 121 | 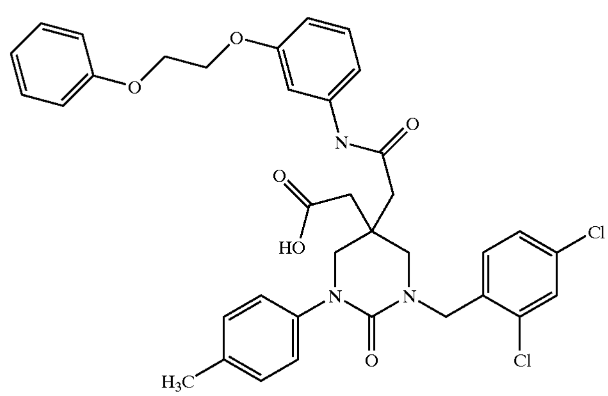 | 1-[(2,4-Dichlorophenyl)-methyl]hexahydro-3-(4-methylphenyl)-2-oxo-5-[2-oxo-2-[[3-(2-phenyoxy-ethoxy)phenyl]amino]-ethyl]-5-pyrimidineactic acid | 676 |

| Ex. | Structure | Name | (M + H) positive ion |
|---|---|---|---|
| 122 | 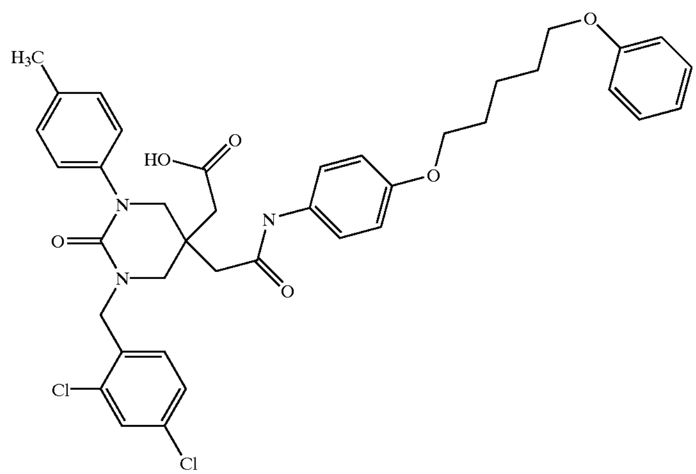 | 1-[(2,4-Dichlorophenyl)-methyl]hexahydro-3-(4-methylphenyl)-2-oxo-5-[2-oxo-2-[[4-[(5-phenoxy-pentyl)oxy]phenyl]amino]-ethyl]-5-pyrimidineacetic acid | 718 |
| 123 | 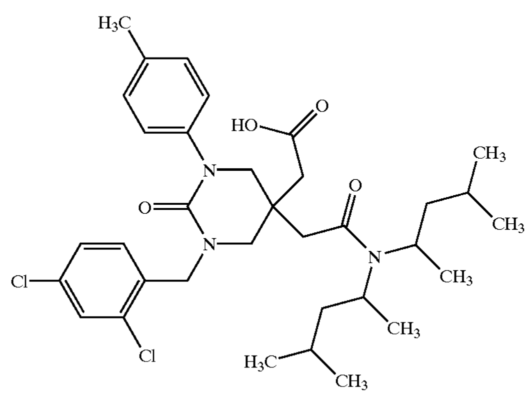 | 5-[2-[Bis(1,3-dimethylbutyl)amino]-2-oxoethyl]-1-[(2,4-dichlorophenyl)methyl]-hexahydro-3-(4-methylphenyl)-2-oxo-5-pyrimidineacetic acid | 632 |
| 124 | 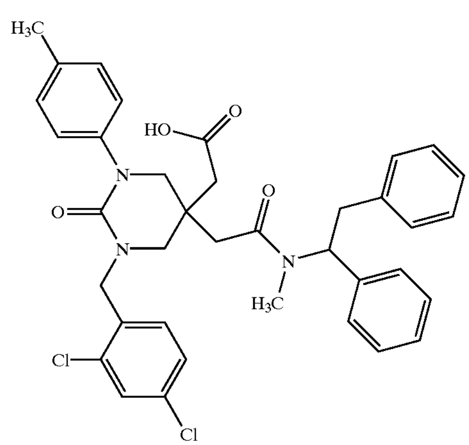 | 1-[(2,4-Dichlorophenyl)-methyl]-5-[2-[(1,2-diphenylethyl)methylamino]-2-oxoethyl]hexa-hydro-3-(4-methyl-phenyl)-2-oxo-5-pyrimidineacetic acid | 658 |

-continued

| Ex. | Structure | Name | (M + H) positive ion |
|---|---|---|---|
| 125 | 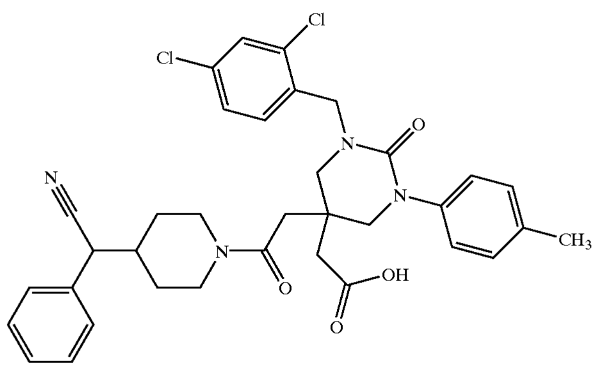 | 5-[2-[4-(Cyanophenyl-methyl)-1-piperidinyl]-2-oxoethyl]-1-[(2,4-dichlorophenyl)-methyl]hexahydro-3-(4-methylphenyl)-2-oxo-5-pyrimidineacetic acid | 647 |
| 126 | 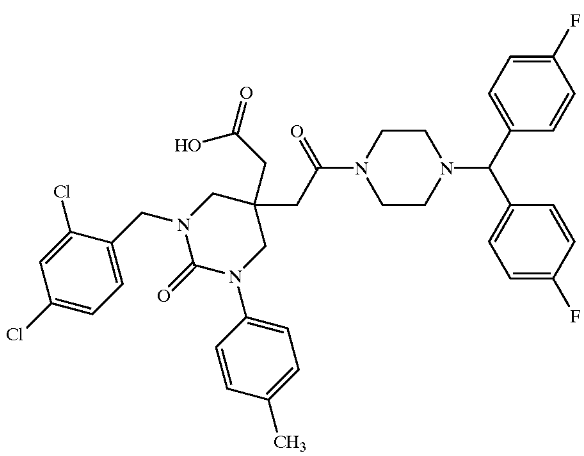 | 5-[2-[4-[Bis(4-fluoro-phenyl)-methyl]-1-piperazinyl]-2-oxoethyl]-1-[(2,4-dichloro-phenyl)-methyl]hexahydro-3-(4-methylphenyl)-2-oxo-5-pyrimidineacetic acid | 735 |
| 127 | 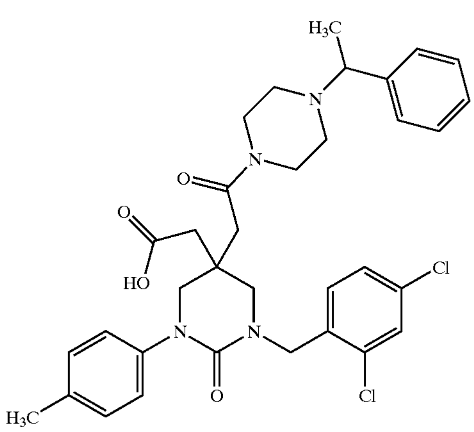 | 1-[(2,4-Dichlorophenyl)-methyl]hexahydro-3-(4-methylphenyl)-2-oxo-5-[2-oxo-2-[4-(1-phenylethyl)-1-piperazinyl]ethyl]-5-pyrimidineacetic acid | 637 |

-continued

| Ex. | Structure | Name | (M + H) positive ion |
|---|---|---|---|
| 128 | 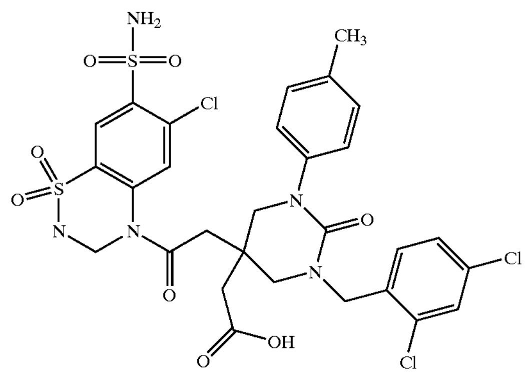 | 5-[2-[7-(Aminosulfonyl)-6-chloro-2,3-dihydro-1,1-dioxido-4H-1,2,4-benzothiadiazin-4-yl]-2-oxoethyl]-1-[(2,4-dichrolophenyl methyl] hexahydro-3-(4-methylphenyl)-2-oxo-5-pyrimidineacetic acid | 745 |
| 129 | 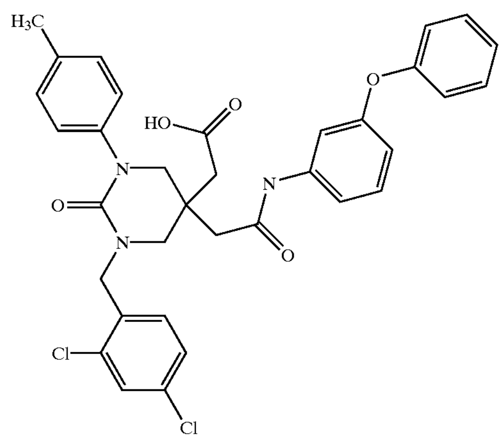 | 1-[(2,4-Dichlorophenyl)-methyl]hexahydro-3-(4-methylphenyl)-2-oxo-5-[2-oxo-2-[(3-phenoxy-phenyl)-amino]ethyl]-5-pyrimi-dineacetic acid | 632 |
| 130 | 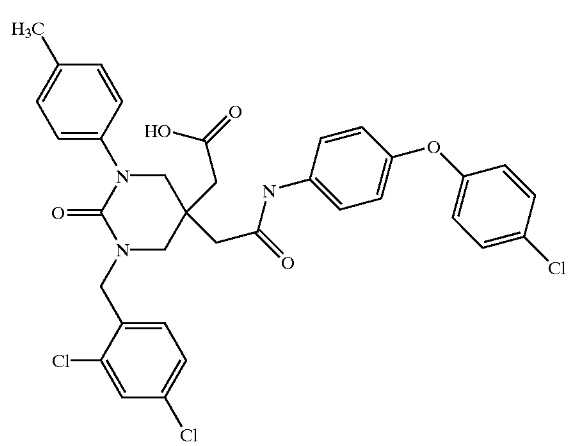 | 5-[2-[[4-(4-Chloro-phenoxy)-phenyl]-amino]-2-oxoethyl]-1-[(2,4-dichlorophenyl)-methyl]-hexahydro-3-(4-methyl-phenyl)-2-oxo-5-pyrimidine-acetic acid | 667 |

-continued

| Ex. | Structure | Name | (M + H) positive ion |
|---|---|---|---|
| 131 | 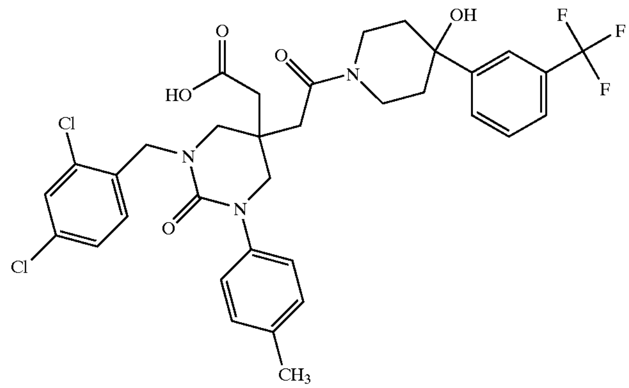 | 1-[(2,4-Dichlorophenyl)-methyl]hexahydro-5-[2-[4-hydroxy-4-[3-(trifluoro-methyl)phenyl]-1-piperidinyl]-2-oxoethyl]-3-(4-methyl-phenyl)-2-oxo-5-pyrimi-dineacetic acid | 692 |
| 132 | 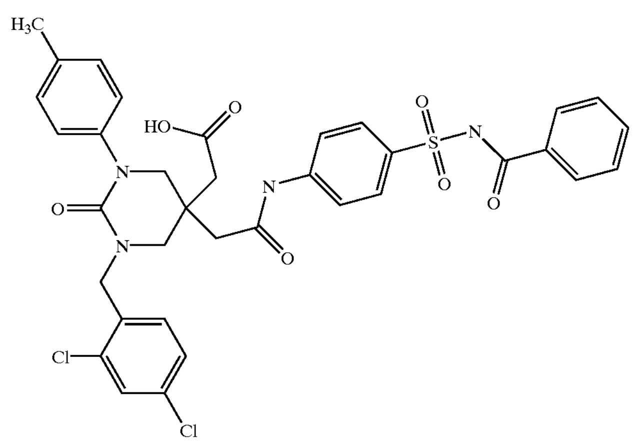 | 5-[2-[[4-[(Benzoyl-amino)-sulfonyl]phenyl]-amino]-2-oxoethyl]-1-[(2,4-dichloro-phenyl)-methyl]hexahydro-3-(4-methylphenyl)-2-oxo-5-pyrimidineacetic acid | 723 |
| 133 | 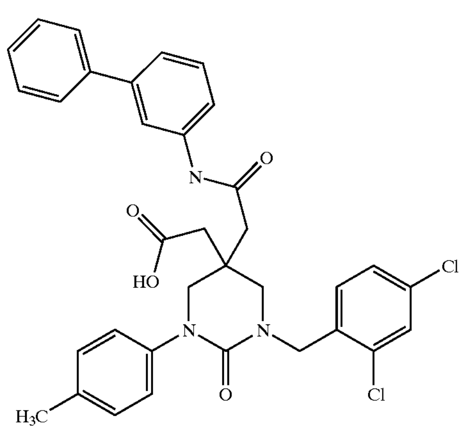 | 5-[2-([1,1'-Biphenyl]-3-ylamino)-2-oxoethyl]-1-[(2,4-dichlorophenyl)-methyl]hexahydro-3-(4-methylphenyl)-2-oxo-5-pyrimidineacetic acid | 616 |

-continued

| Ex. | Structure | Name | (M + H) positive ion |
|---|---|---|---|
| 134 | 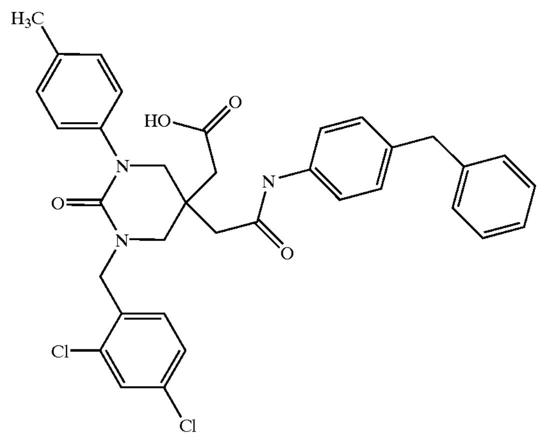 | 1-[(2,4-Dichlorophenyl)-methyl]hexahydro-3-(4-methylphenyl)-2-oxo-5-[2-oxo-2-[[4-(phenyl-methyl)-phenyl]amino]-ethyl]-5-pyrimidineacetic acid | 630 |
| 135 | 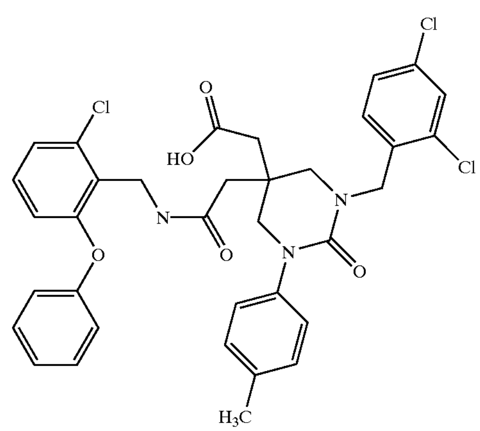 | 5-[2-[[(2-Chloro-6-phenoxyphenyl)methyl]-amino]-2-oxoethyl]-1-[(2,4-dichlorophenyl)-methyl]hexahydro-3-(4-methylphenyl)-2-oxo-5-pyrimidineacetic acid | 681 |
| 136 | 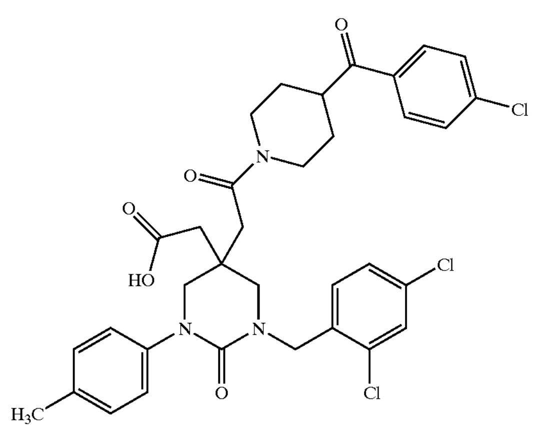 | 5[2-[4-(4-Chlorobenzoyl)-1-piperidinyl]-2-oxoethyl]-1-[(2,4-dichlorophenyl)-methyl]-hexahydro-3-(4-methyl-phenyl)-2-oxo-5-pyrimidine-acetic acid | 671 |

| Ex. | Structure | Name | (M + H) positive ion |
|---|---|---|---|
| 137 | 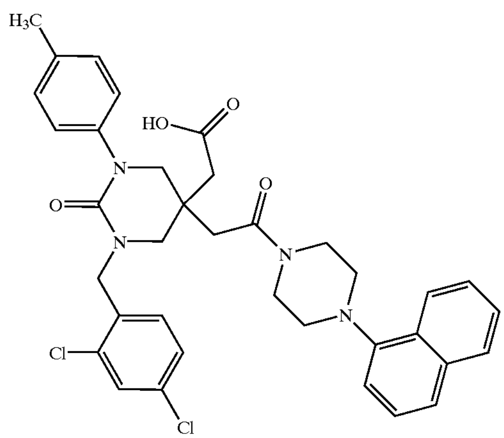 | 1-[(2,4-Dichlorophenyl)-methyl]hexahydro-3-(4-methylphenyl)-5-[2-[4-(1-naphthalenyl)-1-piperazinyl]-2-oxoethyl]-2-oxo-5-pyrimidineacetic acid | 659 |
| 138 | 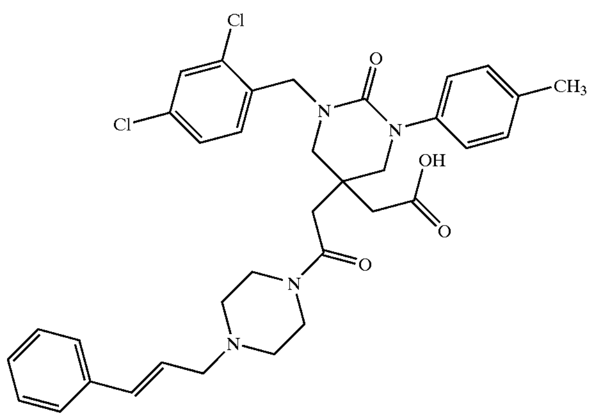 | 1-[(2,4-Dichlorophenyl)-methyl]hexahydro-3-(4-methylphenyl)-2-oxo-5-[2-oxo-2-[4-(3-phenyl-2-propenyl)-1-piperazinyl]ethyl]-5-pyrimidineacetic acid | 649 |
| 139 | 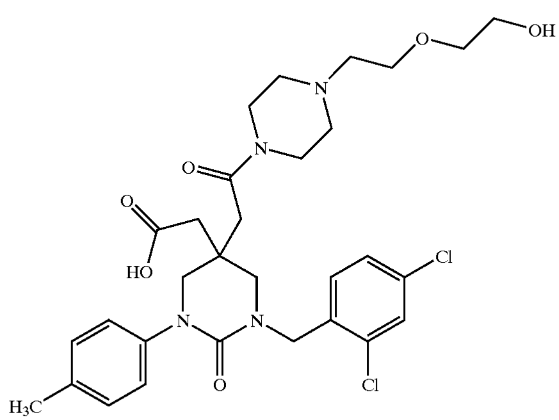 | 1-[(2,4-Dichlorophenyl)-methyl]hexahydro-5-[2-[4-[2-(2-hydroxyethoxy)ethyl]-1-piperazinyl]-2-oxoethyl]-3-(4-methylphenyl)-2-oxo-5-pyrimidineacetic acid | 621 |

-continued

| Ex. | Structure | Name | (M + H) positive ion |
|---|---|---|---|
| 140 | 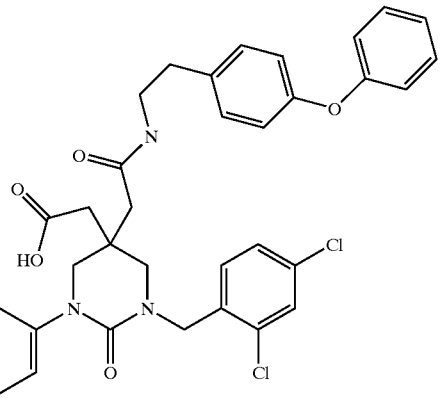 | 1-[(2,4-Dichlorophenyl)-methyl]hexahydro-3-(4-methylphenyl)-2-oxo-5-[2-oxo-2-[[2-(4-phenoxyphenyl)-ethyl]amino]ethyl]-5-pyrimidineacetic acid | 660 |
| 141 | 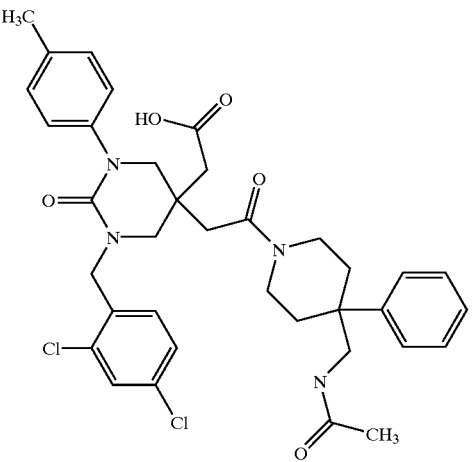 | 5-[2-[4-[(Acetylamino)-methyl]-4-phenyl-1-piperidinyl]-2-oxoethyl]-1-[(2,4-dichlorophenyl)-methyl]hexahydro-3-(4-methylphenyl)-2-oxo-5-pyrimidineacetic acid | 679 |
| 142 | 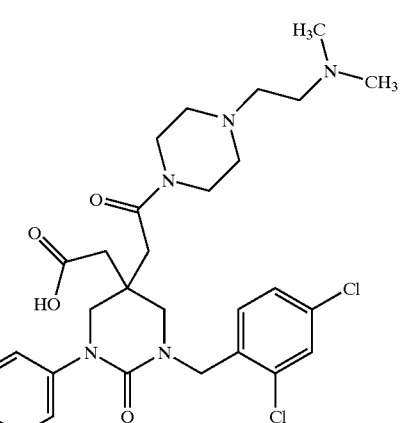 | 1-[(2,4-Dichlorophenyl)-methyl]-5-[2-[4-[2-(dimethylamino)ethyl]-1-piperazinyl]-2-oxoethyl]hexa-hydro-3-(4-methylphenyl)-2-oxo-5-pyrimidineacetic acid | 604 |

-continued

| Ex. | Structure | Name | (M + H) positive ion |
|-----|-----------|------|----------------------|
| 143 | 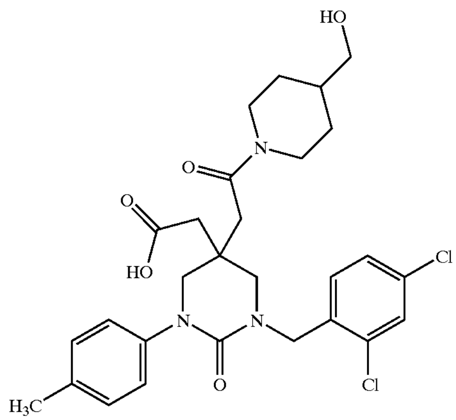 | 1-[(2,4-Dichlorophenyl)-methyl]hexahydro-5-[2-[4-(hydroxymethyl)-1-piperidinyl]-2-oxoethyl]-3-(4-methylphenyl)-2-oxo-5-pyrimidineacetic acid | 562 |
| 144 | 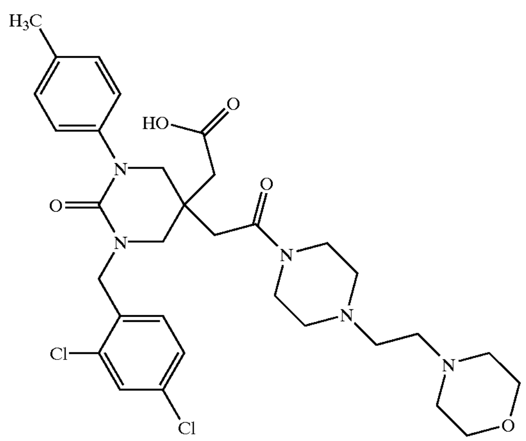 | 1-[(2,4-Dichlorophenyl)-methyl]hexahydro-3-(4-methylphenyl)-5-[2-[4-[2-(4-morpholinyl)ethyl]-1-piperazinyl]-2-oxoethyl]-2-oxo-5-pyrimidineacetic acid | 646 |
| 145 | 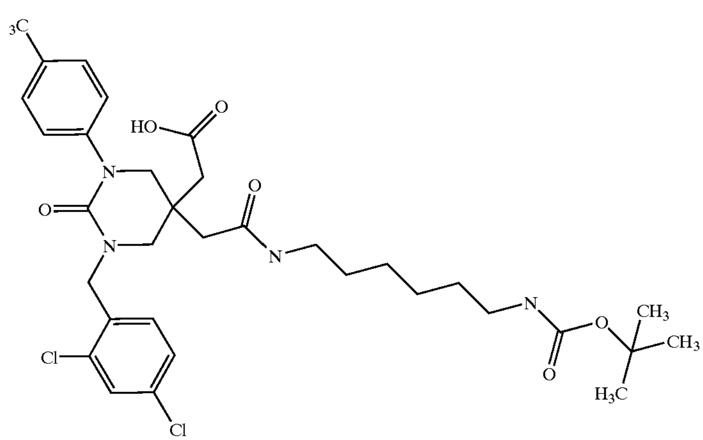 | 1-[(2,4-Dichlorophenyl)-methyl]-5-[2-[[6-[[(1,1-dimethylethoxy)carbonyl]-amino]hexyl]amino]-2-oxoethyl]hexahydro-3-(4-methylphenyl)-2-oxo-5-pyrimidineacetic acid | 663 |

| Ex. | Structure | Name | (M + H) positive ion |
|---|---|---|---|
| 146 | 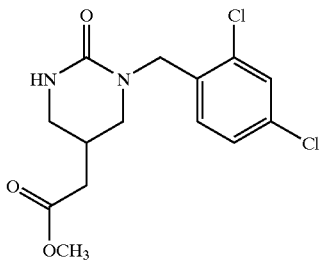 | 1-[(2,4-Dichlorophenyl)-methyl]-5-[2-[ethyl(4-phenoxyphenyl)amino]-2-oxoethyl]hexahydro-3-(4-methylphenyl)-2-oxo-5-pyrimidineacetic acid | 660 |

EXAMPLE 147

3-[(2,4-dichlorophenyl)methyl]hexahydro-2-oxo-5-pyrimidineacetic acid

A.

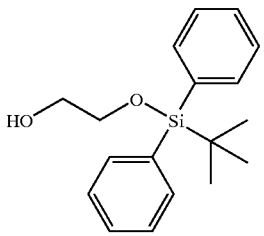

To a stirred solution of ethylene glycol (22.4 mL, 0.4 mol) in THF (200 mL) at 0° C. under argon was added sodium hydroxide (60% oil dispersion, 8.0 g, 0.2 mol) in portions over 30 min. The reaction mixture was warmed to room temperature and stirred overnight. To the resulting slurry was added a solution of t-butylchlorodiphenylsilane (52.0 mL, 0.2 mol) in THF (15 mL) in one portion. The reaction temperature rose to 35° C. before subsiding to room temperature. After 1 h, the reaction mixture was diluted with water (200 mL) and extracted three times with hexane (100 mL portions). The organic extracts were combined, washed with saturated sodium hydrogen carbonate solution, water, brine and then dried (MgSO$_4$) and evaporated. Purification by flash chromatography on silica gel (hexane, 1:2 CH$_2$Cl$_2$/hexanes and then 2:1 CH$_2$Cl$_2$/hexanes as elutants) provided 147A as a colorless oil, 48 g (80%).

B.

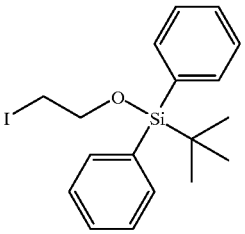

To a stirred solution of 147A (47.8 g, 159 mmol), imidazole (26 g, 382 mmol) and triphenyl phosphine (45.9 g, 175 mmol) in THF (220 mL) at 5° C. under argon was added a solution of iodine (44.4 g, 175 mmol) in THF (200 mL) at such a rate as to keep the reaction temperature below 15° C. After complete addition, the reaction mixture was warmed to room temperature and stirred overnight. The reaction was quenched with 5% sodium bisulfite solution and extracted twice with Et$_2$O (150 mL portions). The extracts were combined, washed with water and brine and dried (MgSO$_4$). Evaporation, followed by trituration of the residue in hexanes, filtration and re-evaporation of the filtrate gave 147B as a white solid, 57.5 g (88%), mp 43–44° C.

C.

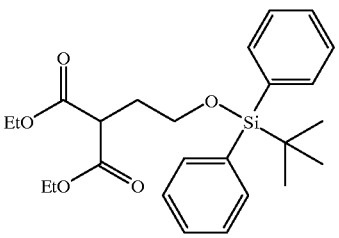

To a stirred solution diethyl malonate (32 mL, 210 mmol) in dry DMF (200 mL) at 0C under argon was added sodium hydride (60% mineral oil dispersion, 5.6 g, 140 mmol) in portions, maintaining the solution temperature at or below 10° C. When addition was complete, the reaction was warmed to room temperature. After stirring an additional 1 h, a solution of 147B (57.4 g, 140 mmol) in DMF (200 mL) was added at room temperature over 15 min. After 16 h, the solution was diluted with water (1 L) and extracted twice with Et$_2$O (300 mL portions). The organic extracts were combined, washed with saturated sodium bicarbonate solution, water and brine, dried (MgSO$_4$) and evaporated. Purification by flash chromatography on silica gel (hexane/CH$_2$Cl$_2$ step gradient) provided 147C as a white solid, 49.5 g (80% yield). LC/MS gave the correct molecular ion [(M+H)$^+$=443] for the desired compound.

D.

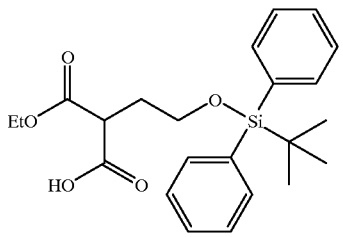

By the method of 59B, but using 147C product (17.50 g, 39.5 mmol), 147D was prepared as a white solid, 15.77 g, (93% yield). LC/MS gave the correct molecular ion [(M+H)$^+$=415] for the desired compound.

E.

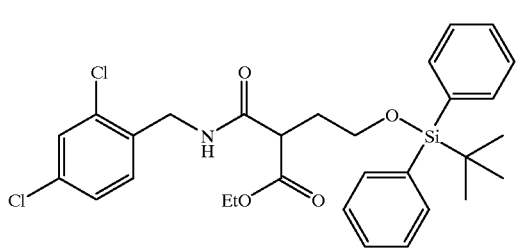

To a stirred mixture of 147D (46.34 g, 112 mmol) and 2,4-dichlorobenzylamine (15.3 mL, 117 mmol) in CH$_2$Cl$_2$ (300 mL) at 5° C. under argon was added N-ethyl-N-(N', N-dimethylaminoethyl) carbodiimide hydrochloride (EDAC, 22.5 g, 117 mmol) over 20 min. After 30 min, the reaction mixture was warmed to room temperature and stirred for 60 h. The resulting slurry was diluted with water (500 mL) and extracted three times with CH$_2$Cl$_2$ (200 mL portions). The combined organic extracts were washed with 10% citric acid solution (400 mL), saturated sodium bicarbonate solution (400 mL), water and brine and then filtered through a Celite pad. The filtrate was dried (MgSO$_4$) and evaporated. Purification by flash chromatography on silica gel (5:1 hexanes/EtOAc) gave 147E as a white solid, 43.5 g, (68% yield) mp 78–80° C. LC/MS gave the correct molecular ion [(M+H)$^+$=572] for the desired compound.

F.

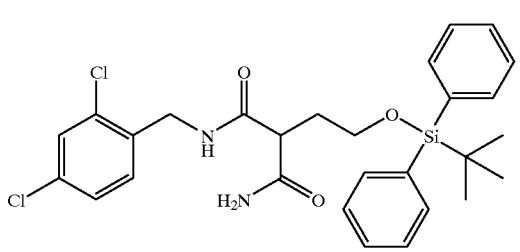

To a stirred solution of 147E (43.5 g, 76 mmol) in methanol (1500 mL) at 0° C. under argon was added ammonia gas until a saturated solution was obtained. The reaction mixture was allowed to warm to room temperature and stirred under an ammonia atmosphere for 16 h. The reaction mixture was again cooled to 0° C., re-saturated with ammonia gas, warmed to room temperature and stirred an additional 20 h. Cooling, resaturation and stirring at room temperature was repeated once more. The resulting slurry was evaporated to give 147F as a white solid, 40.0 g (97% yield) mp 146–147° C. LC/MS gave the correct molecular ion [(M+H)$^+$=542] for the desired compound.

G.

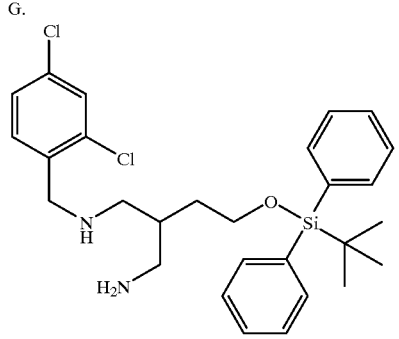

To a solution 147F (14.0 g, 25.8 mmol) in THF (100 mL) at room temperature under argon was added a solution of borane-THF complex (1 M in THF, 200 mL, 0.2 mol) dropwise, and the solution was then refluxed. After 18 h, the solution was cooled to 5° C. and quenched by dropwise addition of sodium hydroxide solution (1 M, 220 mL, 0.22 mol) and then stirred overnight. The resulting mixture was diluted with water (200 mL) and extracted twice with Et$_2$O (200 mL portions). The combined extracts were washed with water and brine, dried (Na$_2$SO$_4$) and evaporated to give 147G as a colorless oil, 13.0 g, (~100% yield). The material was used without purification for the preparation of 147H.

H.

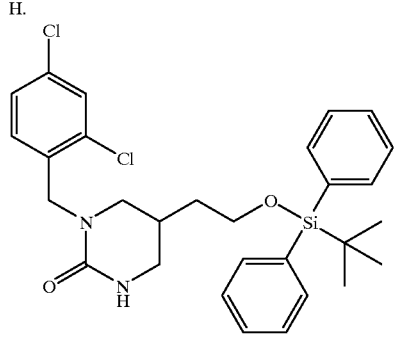

To a stirred solution of 147G (23.72 g, 46.0 mmol) and triethylamine (70 mL, 51 mmol) in CH$_3$CN (230 mL) at 5° C. under nitrogen was added a solution of carbonyl diimidazole (CDI, 3.73 g, 23 mmol) in CH$_3$CN (230 mL) over 30 min. After 1 h, solid CDI (1.24 g, 7.8 mmol) was added and, at 1 h intervals, additional CDI was added (1.24 g, 1.24 g and 1.24 g). After the last addition, the reaction mixture was warmed to room temperature and stirred for 16 h. After evaporation, the residue was partitioned between 5% potassium hydrogen sulfate solution and EtOAc (500 mL). The organic extract was dried (MgSO$_4$) and evaporated. Purification by flash chromatography on silica gel (EtOAc) gave 147H as a colorless glass, 14.9 g, (60% yield). LC/MS gave the correct molecular ion [(M+H)$^+$=541] for the desired compound.

I.

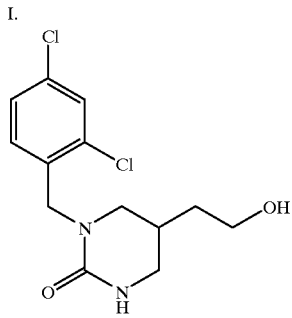

To a stirred solution of 147H (5.36 g, 9.90 mmol) in THF (40 mL) at room temperature under argon was added a solution of tetrabutylammonium fluoride (1 $\underline{M}$ in THF, 12 mL, 12 mmol). After 2 h, the reaction mixture was evaporated and then partitioned between water and EtOAc. The resulting white solids were collected and dried in vacuo to give 147I, 2.70 g, (90% yield) mp 152–153° C. LC/MS gave the correct molecular ion [(M+H)$^+$=303] for the desired compound.

J.

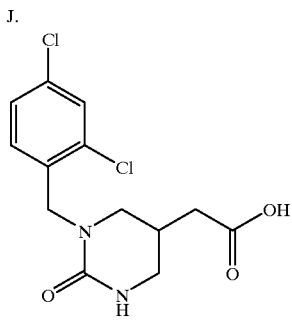

To a stirred suspension of 147I (5.0 g, 16.5 mmol) in acetone (120 mL) at room temperature under argon was added a saturated sodium bicarbonate solution (44 mL). The mixture was cooled to 0° C. and treated sequentially with potassium bromide (196 mg, 1.65 mmol) and TEMPO (2.71 g, 17.3 mmol). To the resulting mixture was added a solution of sodium hypochlorite (~4%, 40.5 mL) over 15 min. After 1 h, additional sodium hypochlorite solution (15.6 mL) was added and the reaction stirred for 1 h. The reaction mixture was quenched with saturated sodium bicarbonate solution (100 mL) and extrated three times with ether (100 mL portions). The aqueous phase was separated and brought to pH 2 with solid citric acid. The resulting white solids were collected, washed with water and dried in vacuo to give 147J, 4.40 g, (84% yield) mp 206–207° C. LC/MS gave the correct molecular ion [(M+H)$^+$=317] for the desired compound.

K.

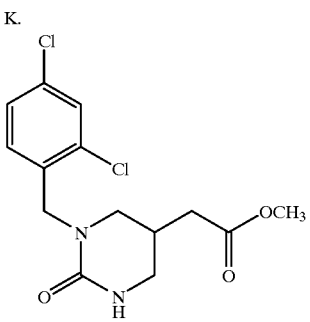

A stirred suspension of 147J (4.65 g, 14.7 mmol) in methanol (150 mL) at 0° C. was saturated with hydrogen chloride gas. The resulting solution was warmed to room temperature, stirred for 2 h and then evaporated. The residue was dissolved in CH$_2$Cl$_2$ (150 mL), washed with saturated sodium bicarbonate solution (100 mL), water and brine. The organic extract was dried (Na$_2$SO$_4$) and evaporated to give 147K as a light yellow glass, 4.61 g, (95% yield). LC/MS gave the correct molecular ion [(M+H)$^+$=331] for the desired compound.

EXAMPLES 148–185

The title compounds were prepared as part of a solution phase library run using the following procedure.

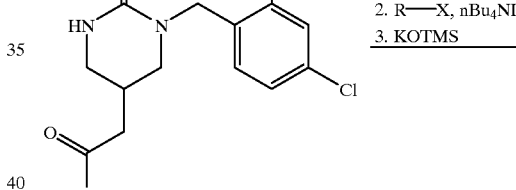

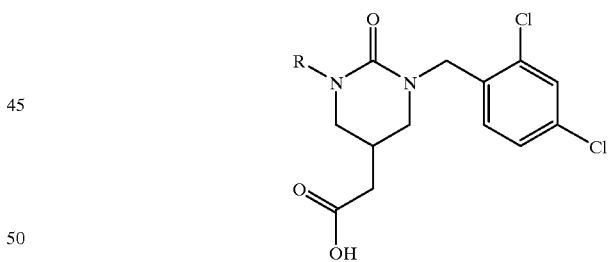

To a solution of 147K (33.1 mg, 0.1 mmol) and tetrabutylammonium iodide (37 mg, 0.1 mmol) in THF (0.4 mL) under argon at room temperature was added a solution of potassium hexamethyl disilazide (0.5 $\underline{M}$ in toluene, 210 μL, 0.105 mmol) and the mixture was shaken for 50 min. To this mixture was added a solution of R—X (0.16 mmol) in THF (0.4 mL). The reaction mixtures were shaken in a nitrogen atmosphere at room temperature for 18 h. The reactions were then each treated with a solution of potassium trimethylsilyloxide (51 mg, 0.33 mmol) in THF (0.5 mL) for 5 h at 40° C. Each reaction was then filtered and the filtrates evaporated. Each reaction was purified by reverse-phase HPLC (water/CH$_3$CN-0.2% TFA gradient). Mass spectrometric and HPLC data were collected for all compounds.

Following the above procedure, the following compounds of the invention were prepared:

| Ex. | X—R | Structure | Name | (M + H) positive ions |
|---|---|---|---|---|
| 148 | Br-(hexyl) | 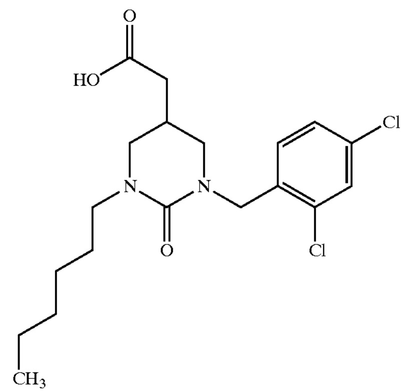 | 1-[(2,4-Dichloro-phenyl)methyl]hexa-hydro-3-hexyl-2-oxo-5-pyrimidineacetic acid | 401 |
| 149 | Br-(CH2)3-F | 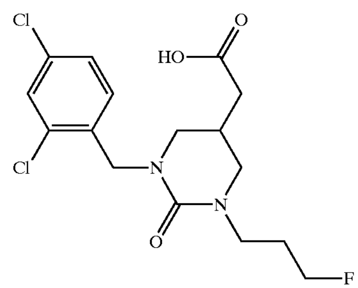 | 1-[(2,4-Dichloro-phenyl)methyl]-3-(3-fluoropropyl)hexa-hydro-2-oxo-5-pyrimidineacetic acid | 377 |

-continued

| Ex. | X—R | Structure | Name | (M + H) positive ions |
|---|---|---|---|---|
| 150 | (3,5,5-trimethylhexyl bromide) | (structure) | 1-[(2,4-Dichloro-phenyl)methyl]hexa-hydro-2-oxo-3-(3,5,5-trimethylhexyl)-5-pyrimidineacetic acid | 443 |
| 151 | (geranyl chloride) | (structure) | 1-[(2,4-Dichloro-phenyl)methyl]-3-(3,7-dimethyl-2,6-octadienyl)hexa-hydro-2-oxo-5-pyrimidineacetic acid | 453 |

| Ex. | X—R | Structure | Name | (M + H) positive ions |
|---|---|---|---|---|
| 152 | ethoxyethyl chloride | (structure) | 1-[(2,4-Dichlorophenyl)methyl]-3-(2-ethoxyethyl)hexahydro-2-oxo-5-pyrimidineacetic acid | 389 |
| 153 | 2-chloropentane | (structure) | 1-[(2,4-Dichlorophenyl)methyl]hexahydro-3-(1-methylbutyl)-2-oxo-5-pyrimidineacetic acid | 387 |
| 154 | (chloromethyl)cyclopropane | (structure) | 1-(Cyclopropylmethyl)-3-[(2,4-dichlorophenyl)methyl]hexahydro-2-oxo-5-pyrimidineacetic acid | 371 |

| Ex. | X—R | Structure | Name | (M + H) positive ions |
|---|---|---|---|---|
| 155 | | 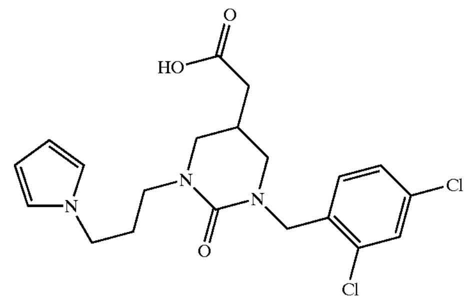 | 1-[(2,4-Dichloro-phenyl)methyl]hexa-hydro-2-oxo-3-[3-(1H-pyrrol-1-yl)-propyl]-5-pyrimidine-acetic acid | 424 |
| 156 | | 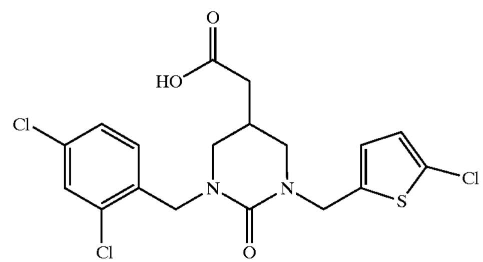 | 1-[(5-Chloro-2-thienyl)methyl]-3-[(2,4-dichloro-phenyl)methyl]hexa-hydro-2-oxo-5-pyrimidineacetic acid | 448 |
| 157 | | 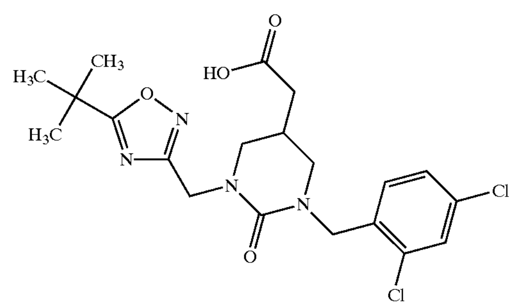 | 1-[(2,4-Dichloro-phenyl)methyl]-3-[[5-(1,1-dimethylethyl)-1,2,4-oxadiazol-3-yl]methyl]hexahydro-2-oxo-5-pyrimidine-acetic acid | 455 |

| Ex. | X—R | Structure | Name | (M + H) positive ions |
|---|---|---|---|---|
| 158 | 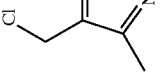 | 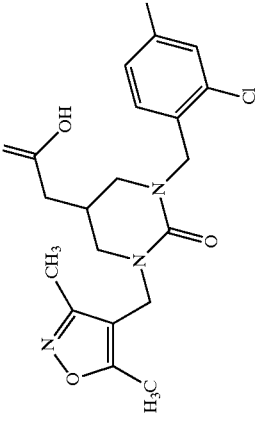 | 1-[(2,4-Dichloro-phenyl)methyl]-3-[(3,5-dimethyl-4-isoxazolyl)methyl]-hexahydro-2-oxo-5-pyrimidineacetic acid | 426 |
| 159 | 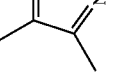 | 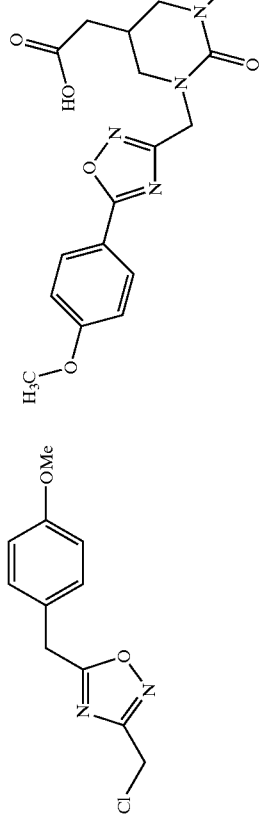 | 1-[(2,4-Dichloro-phenyl)methyl]hexa-hydro-3-[[5-(4-methoxyphenyl)-1,2,4-oxadiazol-3-yl]methyl]-2-oxo-5-pyrimidineacetic acid | 505 |
| 160 | 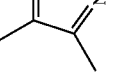 | 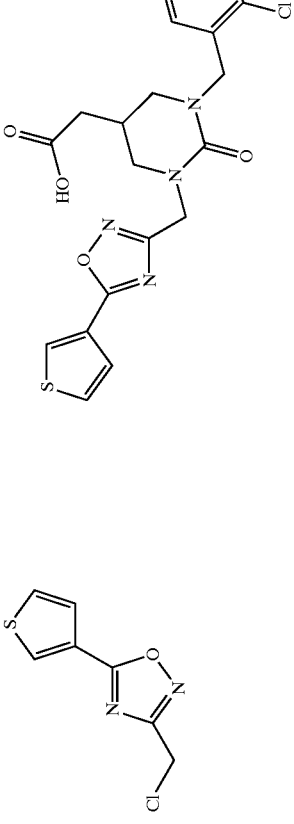 | 1-[(2,4-Dichloro-phenyl)methyl]hexa-hydro-2-oxo-3-[[5-(3-thienyl)-1,2,4-oxadi-azol-3-yl]methyl]-5-pyrimidineacetic acid | 481 |

| Ex. | X—R | Structure | Name | (M + H) positive ions |
|---|---|---|---|---|
| 161 | 3-phenoxypropyl bromide | 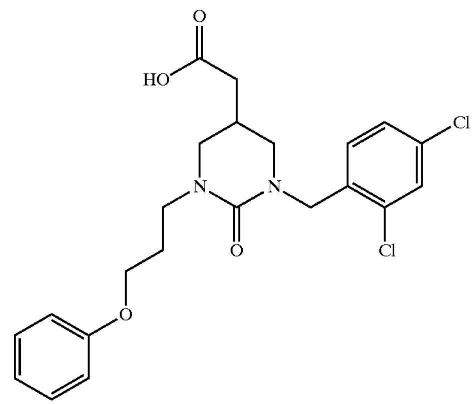 | 1-[(2,4-Dichloro-phenyl)methyl]hexa-hydro-2-oxo-3-(3-phenoxypropyl)-5-pyrimidineacetic acid | 451 |
| 162 | 1-methoxy-1-(4-methylphenyl)propyl bromide | 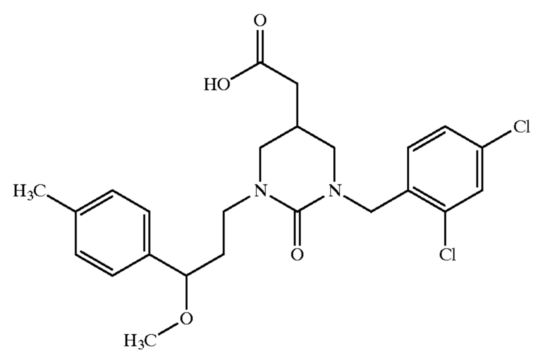 | 1-[(2,4-Dichloro-phenyl)methyl]hexa-hydro-3-[3-methoxy-3-(4-methylphenyl)-propyl]-2-oxo-5-pyrimidineacetic acid | 479 |

| Ex. | X—R | Structure | Name | (M + H) positive ions |
|---|---|---|---|---|
| 163 | 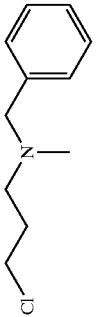 | 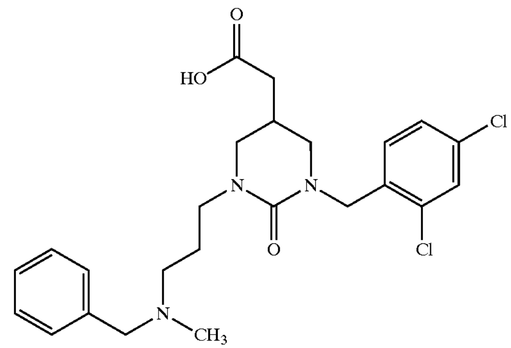 | 1-[(2,4-Dichloro-phenyl)methyl]hexa-hydro-3-[3-[methyl-(phenylmethyl)amino]propyl]-2-oxo-5-pyrimidineacetic acid | 478 |
| 164 | 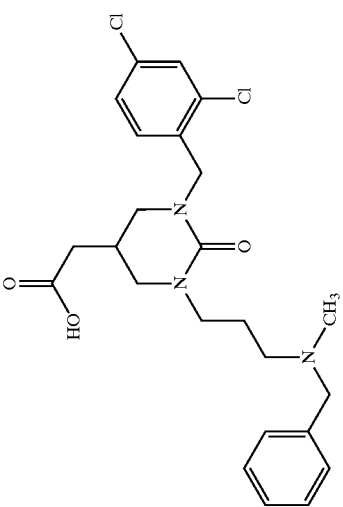 | 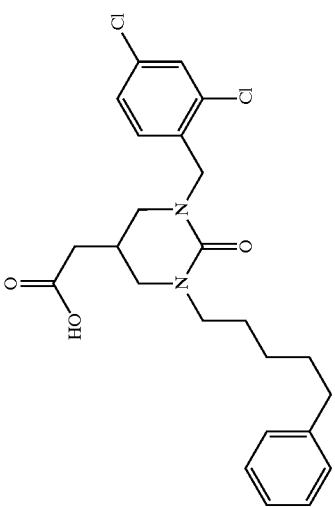 | 1-[(2,4-Dichloro-phenyl)methyl]hexa-hydro-2-oxo-3-(5-phenylpentyl)-5-pyrimidineacetic acid | 463 |

| Ex. | X—R | Structure | Name | (M + H) positive ions |
|---|---|---|---|---|
| 165 | (CH with 2-methylphenyl group and propyl-Cl chain) | (structure shown) | 1-[4-Cyano-4-(2-methylphenyl)butyl]-3-[(2,4-dichlorophenyl)methyl]hexahydro-2-oxo-5-pyrimidineacetic acid | 488 |
| 166 | (CH$_2$ with 4-benzyloxyphenyl group) | (structure shown) | 1-[(2,4-Dichlorophenyl)methyl]hexahydro-2-oxo-3-[[4-(phenylmethoxy)phenyl]methyl]-5-pyrimidineacetic acid | 513 |

| Ex. | X—R | Structure | Name | (M + H) positive ions |
|---|---|---|---|---|
| 167 | [3-methylphenylthio-propyl bromide] | [structure] | 1-[(2,4-Dichlorophenyl)methyl]hexahydro-3-[3-[(3-methylphenyl)thio]propyl]-2-oxo-5-pyrimidineacetic acid | 481 |
| 168 | [cinnamyl chloride] | [structure] | 1-[(2,4-Dichlorophenyl)methyl]hexahydro-2-oxo-3-(3-phenyl-2-propenyl)-5-pyrimidineacetic acid | 433 |
| 169 | [4-(methylsulfonyl)benzyl bromide] | [structure] | 1-[(2,4-Dichlorophenyl)methyl]hexahydro-3-[[4-(methylsulfonyl)phenyl]methyl]-2-oxo-5-pyrimidineacetic acid | 485 |

-continued

| Ex. | X—R | Structure | Name | (M + H) positive ions |
|---|---|---|---|---|
| 170 | 3-(bromomethyl)benzonitrile | 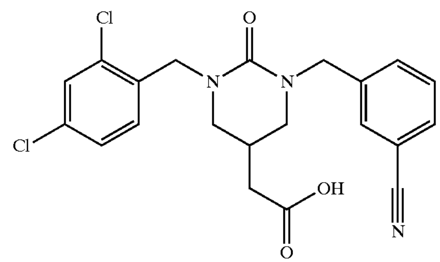 | 1-[(3-Cyanophenyl)methyl]-3-[(2,4-dichlorophenyl)methyl]hexahydro-2-oxo-5-pyrimidine-acetic acid | 432 |
| 171 | 2-(bromomethyl)-1-methoxy-4-nitrobenzene | 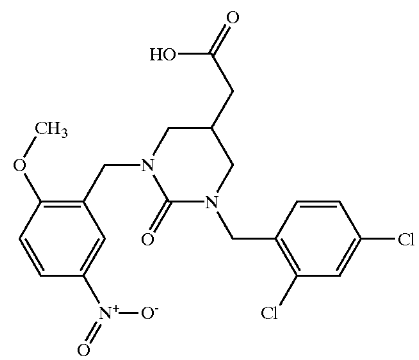 | 1-[(2,4-Dichlorophenyl)methyl]hexahydro-3-[(2-methoxy-5-nitrophenyl)methyl]-2-oxo-5-pyrimidineacetic acid | 482 |
| 172 | 1-(chloromethyl)naphthalene | 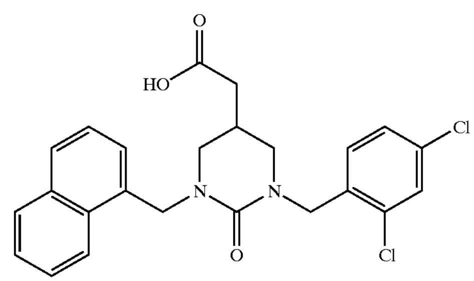 | 1-[(2,4-Dichlorophenyl)methyl]hexahydro-3-(1-naphthalenylmethyl)-2-oxo-5-pyrimidineacetic acid | 457 |

| Ex. | X—R | Structure | Name | (M + H) positive ions |
|---|---|---|---|---|
| 173 | 1,3-benzodioxol-5-ylmethyl chloride | 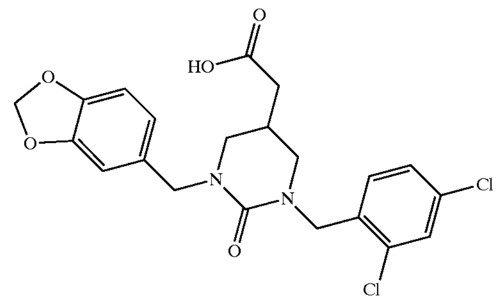 | 1-(1,3-Benzodioxol-5-ylmethyl)-3-[(2,4-dichlorophenyl)methyl]hexahydro-2-oxo-5-pyrimidineacetic acid | 451 |
| 174 | 2,4-difluorobenzyl bromide | 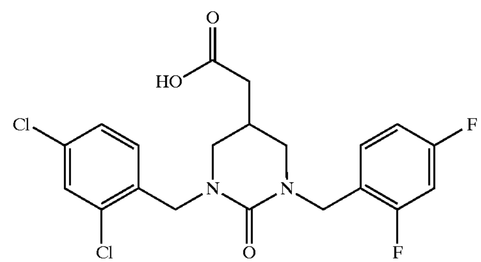 | 1-[(2,4-Dichlorophenyl)methyl]-3-[(2,4-difluorophenyl)methyl]hexahydro-2-oxo-5-pyrimidineacetic acid | 443 |
| 175 | 2-cyclohexylethyl bromide | 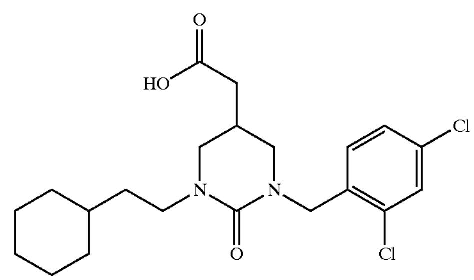 | 1-(2-Cyclohexylethyl)-3-[(2,4-dichlorophenyl)methyl]hexahydro-2-oxo-5-pyrimidineacetic acid | 427 |

-continued

| Ex. | X—R | Structure | Name | (M + H) positive ions |
|---|---|---|---|---|
| 176 | (4-SCH₃-phenyl)CH₂Cl | 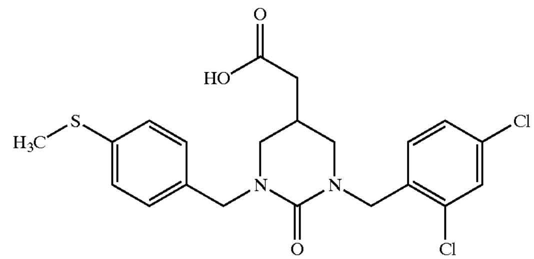 | 1-[(2,4-Dichlorophenyl)methyl]hexahydro-3-[[4-(methylthio)phenyl]methyl]-2-oxo-5-pyrimidineacetic acid | 453 |
| 177 | Br(CH₂)₄CN | 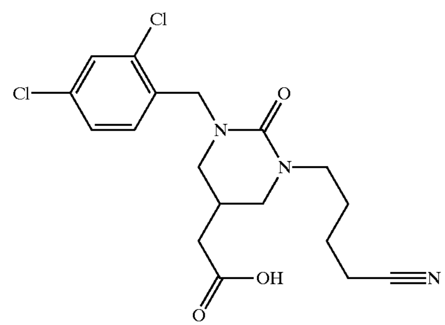 | 1-(4-Cyanobutyl)-3-[(2,4-dichlorophenyl)methyl]hexahydro-2-oxo-5-pyrimidineacetic acid | 398 |
| 178 | Br(CH₂)₃OCH₂Ph | 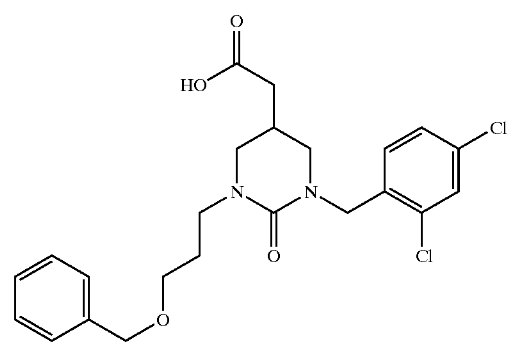 | 1-[(2,4-Dichlorophenyl)methyl]hexahydro-2-oxo-3-[3-(phenylmethoxy)propyl]-5-pyrimidineacetic acid | 465 |

| Ex. | X—R | Structure | Name | (M + H) positive ions |
|---|---|---|---|---|
| 179 | Br-CH2CH2-O-CH2CH2-O-CH3 | 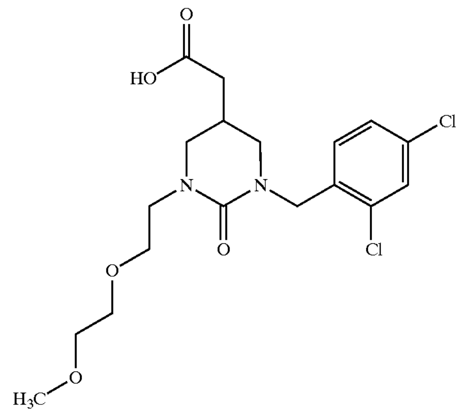 | 1-[(2,4-Dichloro-phenyl)methyl]hexa-hydro-3-[2-(2-methoxyethoxy)ethyl]-2-oxo-5-pyrimidine-acetic acid | 419 |
| 180 | Br-(CH2)3-CF3 | 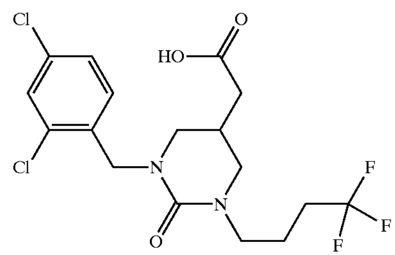 | 1-[(2,4-Dichloro-phenyl)methyl]hexa-hydro-2-oxo-3-(4,4,4-trifluorobutyl)-5-pyrimidineacetic acid | 427 |
| 181 | Br-CH2-CH=C(CH3)2 | 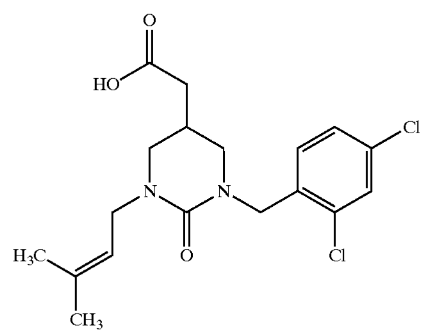 | 1-[(2,4-Dichloro-phenyl)methyl]hexa-hydro-3-(3-methyl-2-butenyl)-2-oxo-5-pyrimidineacetic acid | 385 |

| Ex. | X—R | Structure | Name | (M + H) positive ions |
|---|---|---|---|---|
| 182 | 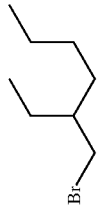 | 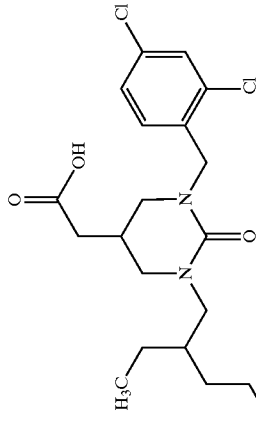 | 1-[(2,4-Dichloro-phenyl)methyl]-3-(2-ethylhexyl)hexahydro-2-oxo-5-pyrimidine-acetic acid | 429 |
| 183 |  | 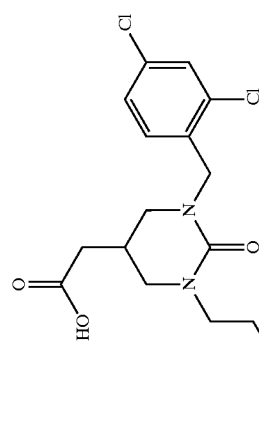 | 1-[(2,4-Dichloro-phenyl)methyl]hexa-hydro-2-oxo-3-(4-pentenyl)-5-pyrimidineacetic acid | 385 |
| 184 |  | 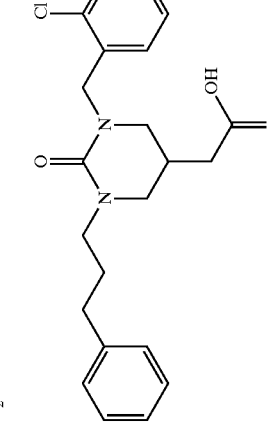 | 1-[(2,4-Dichloro-phenyl)methyl]hexa-hydro-2-oxo-3-(3-phenylpropyl)-5-pyrimidineacetic acid | 435 |

-continued
| Ex. | X—R | Structure | Name | (M + H) positive ions |
|---|---|---|---|---|
| 185 | 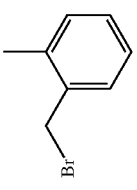 | 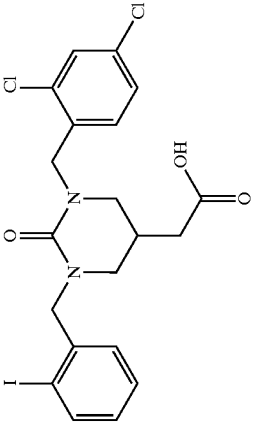 | 1-[(2,4-Dichloro-phenyl)methyl]hexa-hydro-3-(2-iodo-phenyl)methyl]-2-oxo-5-pyrimidine-acetic acid | 533 |

EXAMPLE 186

Methyl 1-[(2-Carboxyphenyl)methyl]-3-[(2,4-dichlorophenyl)methyl]hexahydro-2-oxo-5-pyrimidineacetate

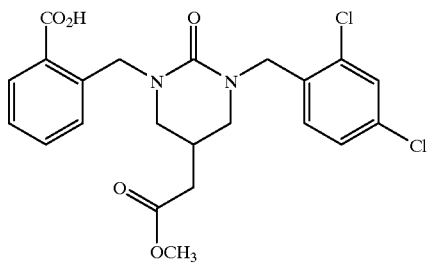

A.

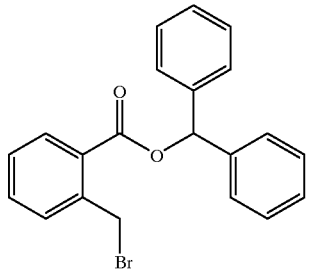

A mixture of phthalide (5.36 g, 40 mmol) and triphenylphosphonium dibromide (6.90 g, 40.0 mmol) was heated to 170° C. under argon for 3 h and then to 180° C. for 1 h. After cooling to room temperature, the reaction mixture was dissolved in CH$_2$Cl$_2$ (40 mL) to give a dark brown solution. This was added to a solution of diphenylmethanol (7.37 g, 40 mmol) and N-ethyl-N,N-diisopropylamine (14 mL, 80 mmol) in CH$_2$Cl$_2$ (40 mL) at 0° C. over 30 min. After an additional 30 min, the reaction was warmed to room temperature and stirred overnight and then evaporated. The residual material was dissolved in Et$_2$O (400 mL) and the remaining solids filtered. The filtrate was washed with 10% citric acid solution (100 mL) and half-saturated sodium bicarbonate solution (100 mL). The organic extract was dried (Na$_2$SO$_4$) and evaporated. Purification by flash chromatography on silica gel (1:2 CH$_2$Cl$_2$/hexanes as elutant) provided 186A as a colorless oil, 7.18 g (47%).

B.

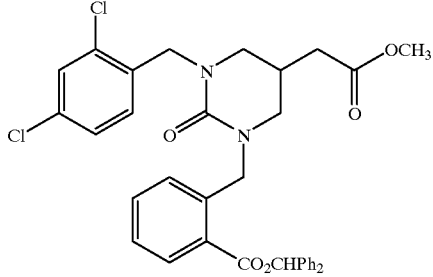

To a stirred solution of 147K (1.98 g, 6.00 mmol) in THF (40 mL) at room temperature under argon was added potassium hexamethyldisilazide solution (0.5 M in toluene, 12.6 mL, 6.3 mmol). After 5 min, a solution of 186A (3.43 g, 9.00 mmol) in THF (10 mL) was added in one portion, followed by tetrabutylammonium iodide (2.21 g, 6.0 mmol). After 16 h, the reaction mixture was partitioned between saturated sodium bicarbonate solution and Et$_2$O. The organic phase was dried (Na$_2$SO$_4$) and evaporated. Purification by flash chromatography (1:2 EtOAC/hexanes as elutant). Evaporation gave 186B as a white solid, 2.20 g (58%).

C.

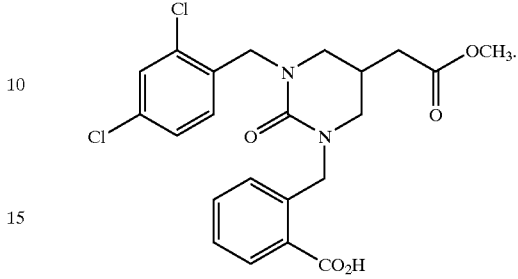

To a stirred solution of 186B (2.68 g, 4.24 mmol) and anisole (1.85 mL, 17.0 mmol) in CH$_2$Cl$_2$ (20 mL) at 0° C. under argon was added trifluoroacetic acid (10 mL). After 2 h, the reaction mixture was poured into saturated sodium bicarbonate solution (200 mL) and then solid sodium bicarbonate was added with stirring to bring the mixture to pH 8. The mixture was extracted with hexane and then Et$_2$O. The aqueous phase was cooled to 5° C. and acidified to pH 3 with 10% phosphoric acid solution. The resulting mixture was extracted twice with CH$_2$Cl$_2$. The CH$_2$Cl$_2$ extracts were combined, dried (MgSO$_4$) and evaporated to give 186C as a white amorphous solid, 1.76 g (89% yield). LC/MS gave the correct molecular ion [(M+H)$^+$=465] for the desired compound.

EXAMPLE 187

Methyl 1-[(2–Chlorocarbonylphenyl)methyl]-3-[(2,4-dichlorophenyl)methyl]hexahydro-2-oxo-5-pyrimidineacetate

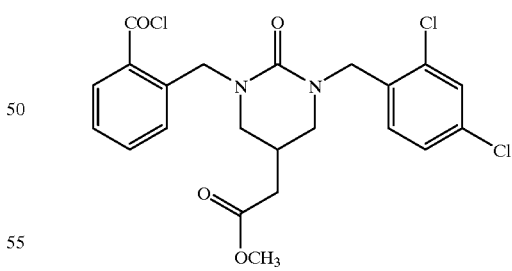

To a stirred solution of 186C (1.21 g, 2.6 mmol) in CH$_2$Cl$_2$ (20 mL) at room temperature under argon was added oxalyl chloride solution (2 M in CH$_2$Cl$_2$, 6.5 mL, 13 mmol) and DMF (2 drops). After 3 h, the reaction mixture was evaporated, dissolved in toluene and re-evaporated. The yellow oil was dissolved in CH$_2$Cl$_2$ (26.0 mL) to provide 187 as a light yellow solution, 0.1 M.

EXAMPLES 188–235

The title compounds were prepared as part of a solution phase library run using the following procedure.

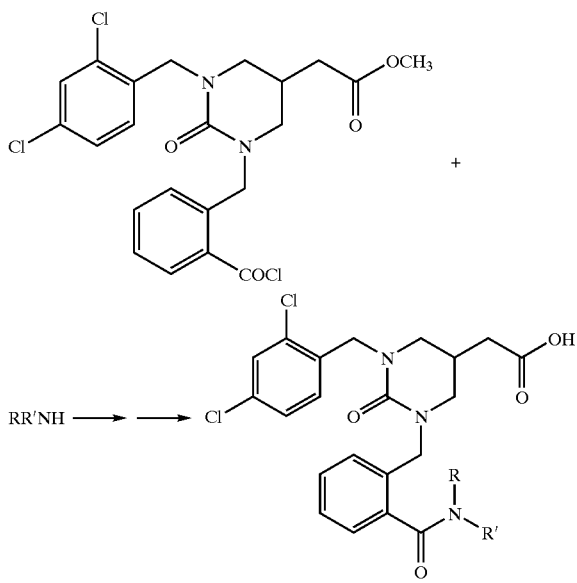

To RR'NH or RR'NH.HCl or RR'NH.2HCl (0.075 mmol) pre-weighed in a 2 dram vial was added a solution of triethylamine (0.375 $\underline{M}$ in $CH_2Cl_2$, 0.4 mL, 0.15 mmol). For amine hydrochloride salts, additional triethylamine was added (21 $\mu$L, 0.15 mmol for monohydrochlorides; 42 $\mu$L for dihydrochlorides). To this solution was added Example 187 solution (0.5 mL, 0.05 mmol) and the reaction vessels were sealed and agitated for 24 h. The reaction mixtures were evaporated and treated with a solution of potassium trimethylsilyloxide (38 mg, 0.3 mmol) in THF (0.5 mL) at room temperature for 18 h. The reaction mixtures were diluted with methanol (1 mL), filtered and the filtrates evaporated. Each reaction was purified by reverse-phase HPLC (water/$CH_3CN$-0.2% TFA gradient).

Mass spectrometric and HPLC data were collected for all compounds. Following the above procedure, the following compounds of the invention were prepared:

| Ex. | Structure | Name | (M + H) positive ions |
|---|---|---|---|
| 188 | 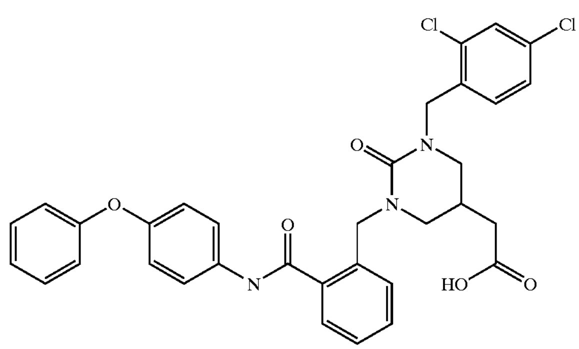 | 1-[(2,4-Dichlorophenyl)-methyl]hexahydro-2-oxo-3-[[2-[[(4-phenoxyphenyl)-amino]carbonyl]phenyl]methyl]-5-pyrimidineacetic acid | 618 |
| 189 | 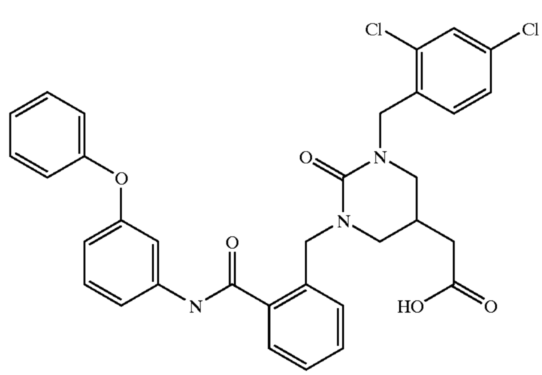 | 1-[(2,4-Dichlorophenyl)-methyl]hexahydro-2-oxo-3-[[2-[[(3-phenoxyphenyl)-amino]carbonyl]phenyl]methyl]-5-pyrimidineacetic acid | 618 |

| Ex. | Structure | Name | (M + H) positive ions |
|---|---|---|---|
| 190 | 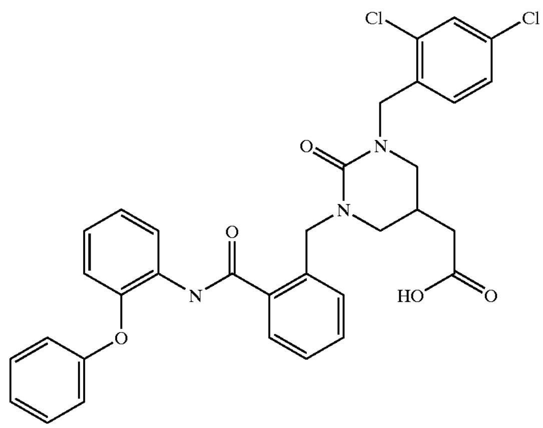 | 1-[(2,4-Dichlorophenyl)-methyl]hexahydro-2-oxo-3-[[2-[[(2-phenoxyphenyl)-amino]carbonyl]phenyl]methyl]-5-pyrimidineacetic acid | 618 |
| 191 | 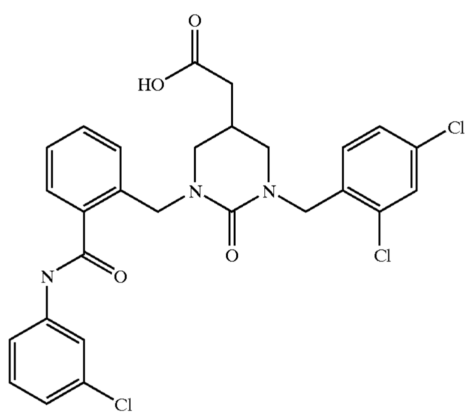 | 1-[[2-[[(3-Chlorophenyl)-amino]carbonyl]phenyl]methyl]-3-[(2,4-dichlorophenyl)-methyl]hexahydro-2-oxo-5-pyrimidineacetic acid | 560 |
| 192 | 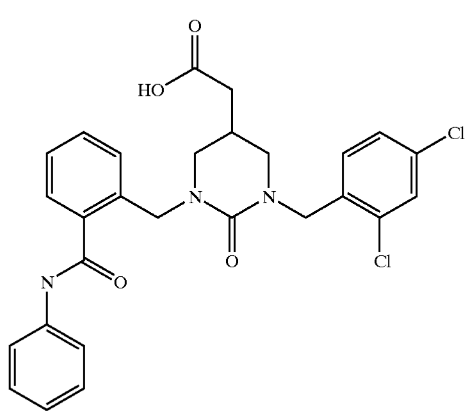 | 1-[(2,4-Dichlorophenyl)-methyl]hexahydro-2-oxo-3-[[2-[(phenylamino)-carbonyl]phenyl]methyl]-5-pyrimidineacetic acid | 526 |

-continued

| Ex. | Structure | Name | (M + H) positive ions |
|---|---|---|---|
| 193 | 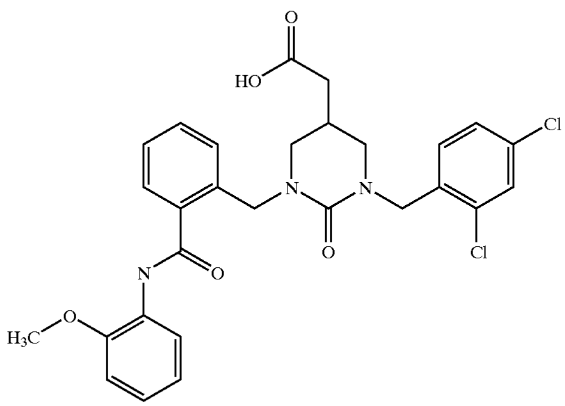 | 1-[(2,4-Dichlorophenyl)-methyl]hexahydro-3-[[2-[[[(2-methoxyphenyl)-amino]carbonyl]phenyl]-methyl]-2-oxo-5-pyrimi-dineacetic acid | 556 |
| 194 | 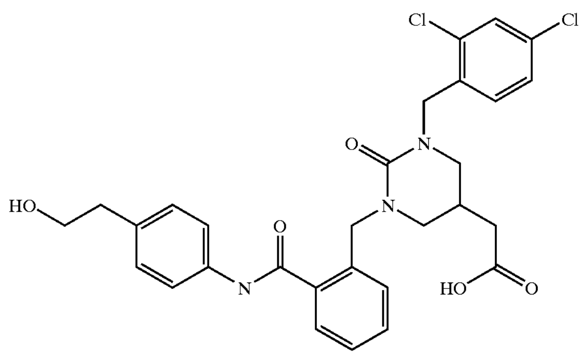 | 1-[(2,4-Dichlorophenyl)-methyl]hexahydro-3-[[2-[[[4-(2-hydroxyethyl)phenyl]-amino]carbonyl]-phenyl]-methyl]-2-oxo-5-pyrimi-dineacetic acid | 570 |
| 195 | 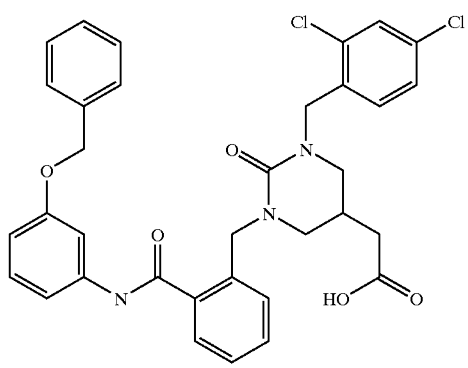 | 1-[(2,4-Dichlorophenyl)-methyl]hexahydro-2-oxo-3-[[2-[[[3-(phenyl-methoxy)-phenyl]amino]-carbonyl]phenyl]methyl]-5-pyrimidineacetic acid | 632 |
| 196 | 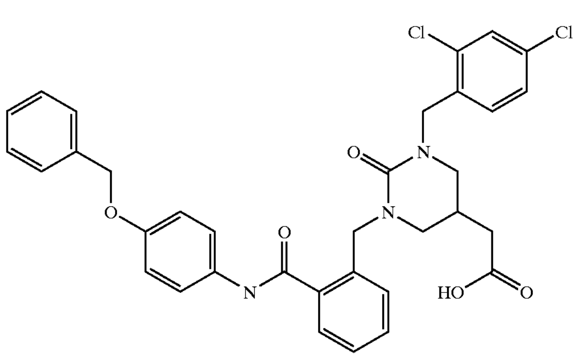 | 1-[(2,4-Dichlorophenyl)-methyl]hexahydro-2-oxo-3-[[2-[[[4-(phenyl-methoxy)-phenyl]amino]-carbonyl]phenyl]methyl]-5-pyrimidineacetic acid | 632 |

-continued

| Ex. | Structure | Name | (M + H) positive ions |
|---|---|---|---|
| 197 | 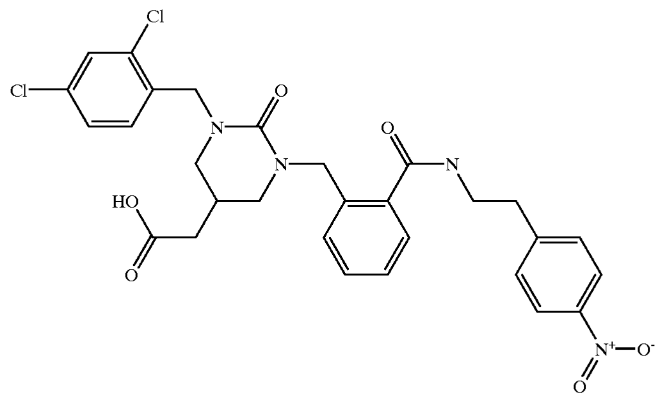 | 1-[(2,4-Dichlorophenyl)-methyl]hexahydro-3-[[2-[[[2-(4-nitrophenyl)-ethyl]amino]carbonyl]-phenyl]methyl]-2-oxo-5-pyrimidineacetic acid | 599 |
| 198 | 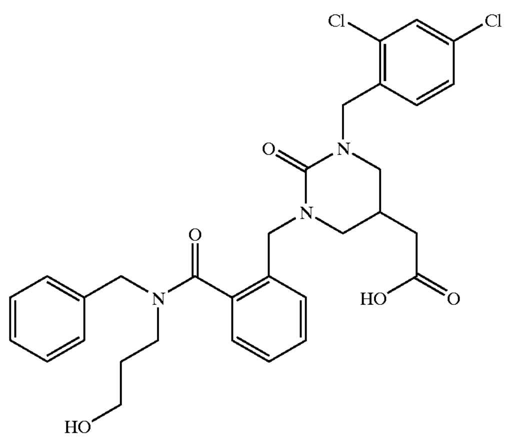 | 1-[(2,4-Dichlorophenyl)-methyl]hexahydro-3-[[2-[[[(3-hydroxypropyl)-(phenylmethyl)amino]-carbonyl]phenyl]methyl]-2-oxo-5-pyrimidineacetic acid | 598 |
| 199 | 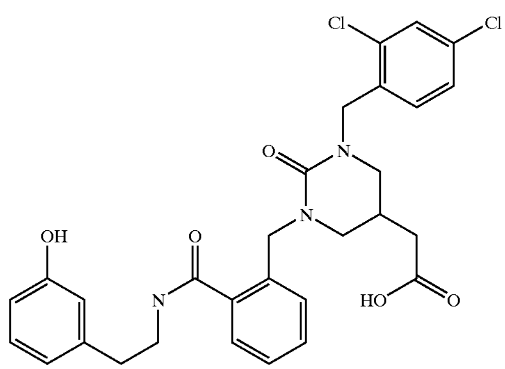 | 1-[(2,4-Dichlorophenyl)-methyl]hexahydro-3-[[2-[[[2-(3-hydroxyphenyl)-ethyl]amino]carbonyl]-phenyl]methyl]-2-oxo-5-pyrimidineacetic acid | 570 |
| 200 | 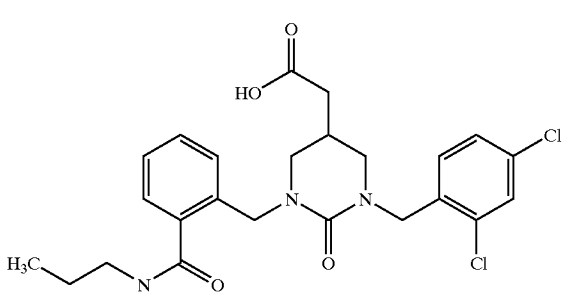 | 1-[(2,4-Dichlorophenyl)-methyl]hexahydro-2-oxo-3-[[2-[(propylamino)-carbonyl]phenyl]methyl]-5-pyrimidineacetic acid | 492 |

-continued

| Ex. | Structure | Name | (M + H) positive ions |
|---|---|---|---|
| 201 | 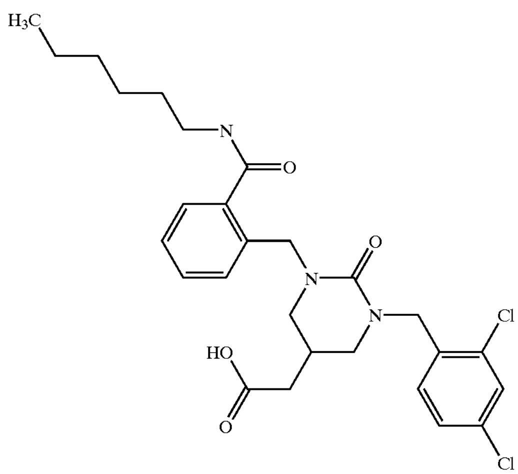 | 1-[(2,4-Dichlorophenyl)-methyl]-3-[[2-[(hexyl-amino)-carbonyl]phenyl]-methyl]hexahydro-2-oxo-5-pyrimidineacetic acid | 534 |
| 202 | 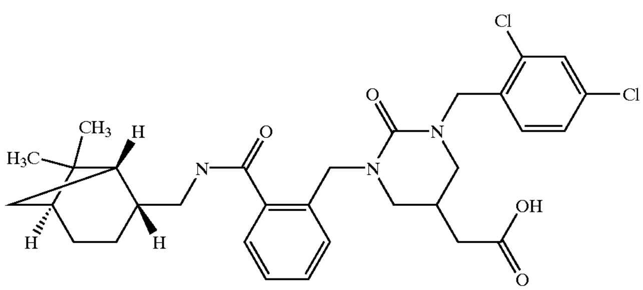 | 1-[(2,4-Dichlorophenyl)-methyl]-3-[[2-[[[[(1S,2R,5S)-6,6-dimethylbicyclo-[3.1.1]hept-2-yl]methyl]-amino]-carbonyl]-phenyl]-methyl]hexa-hydro-2-oxo-5-pyrimidineacetic acid | 586 |
| 203 | 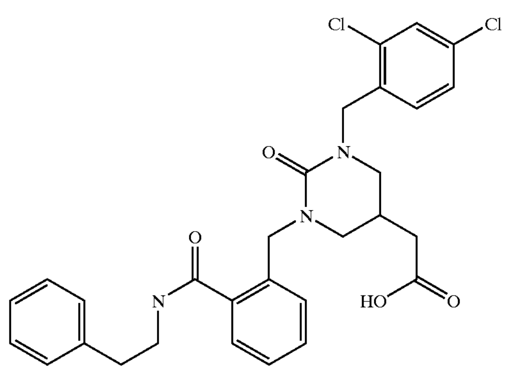 | 1-[(2,4-Dichlorophenyl)-methyl]hexahydro-2-oxo-3-[[2-[[(2-phenylethyl)-amino]-carbonyl]phenyl]methyl]-5-pyrimidineacetic acid | 554 |

| Ex. | Structure | Name | (M + H) positive ions |
|---|---|---|---|
| 204 | 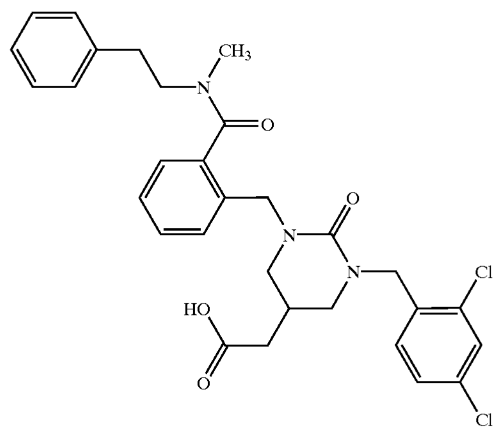 | 1-[(2,4-Dichlorophenyl)-methyl]hexahydro-3-[[2-[[methyl(2-phenylethyl)-amino]carbonyl]phenyl]-methyl]-2-oxo-5-pyrimidineacetic acid | 568 |
| 205 | 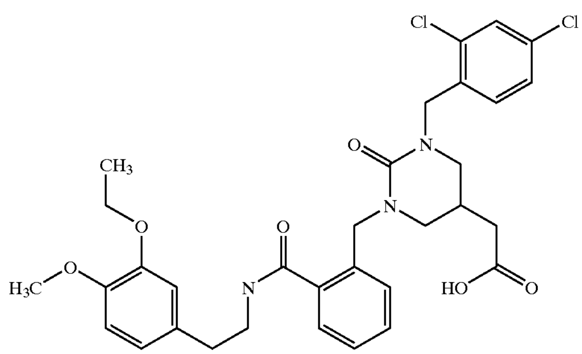 | 1-[(2,4-Dichlorophenyl)-methyl]hexahydro-3-[[2-[[[2-(3-ethoxy-4-methoxy-phenyl)-ethyl]amino]-carbonyl]phenyl]methyl]-2-oxo-5-pyrimidineacetic acid | 628 |
| 206 | 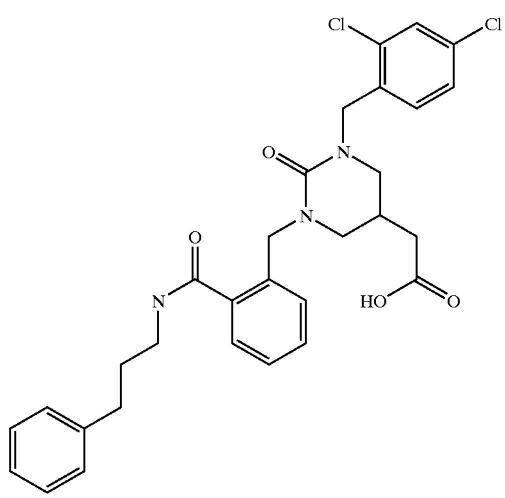 | 1-[(2,4-Dichlorophenyl)-methyl]hexahydro-2-oxo-3-[[2-[[(3-phenylpropyl)-amino]-carbonyl]-phenyl]methyl]-5-pyrimidineacetic acid | 568 |
| 207 | 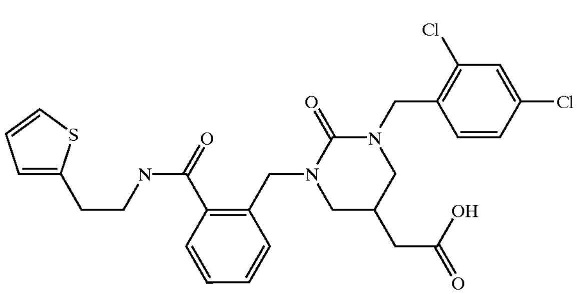 | 1-[(2,4-Dichlorophenyl)-methyl]hexahydro-2-oxo-3-[[2-[[[2-(2-thienyl)ethyl]-amino]-carbonyl]-phenyl]methyl]-5-pyrimidineacetic acid | 560 |

-continued

| Ex. | Structure | Name | (M + H) positive ions |
|---|---|---|---|
| 208 | 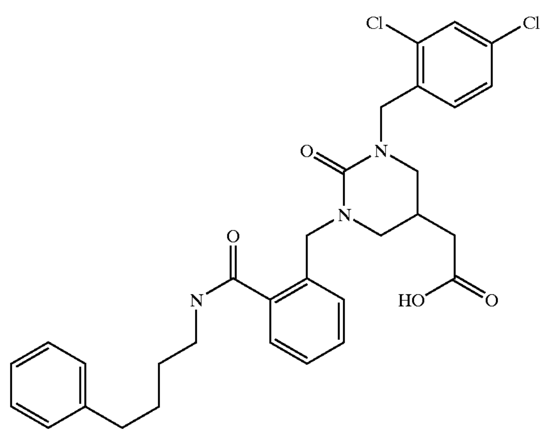 | 1-[(2,4-Dichlorophenyl)-methyl]hexahydro-2-oxo-3-[[2-[[(4-phenylbutyl)-amino]-carbonyl]-phenyl]methyl]-5-pyrimidineacetic acid | 582 |
| 209 | 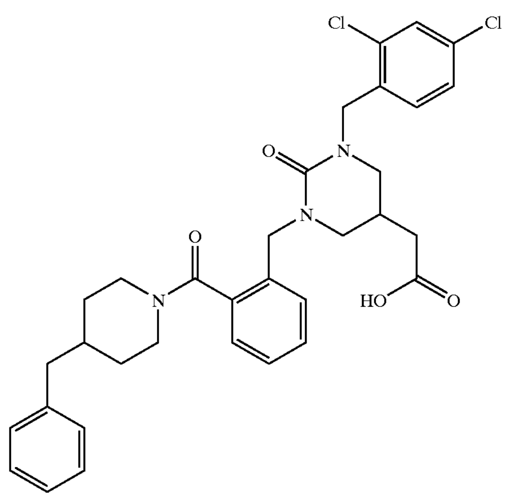 | 1-[(2,4-Dichlorophenyl)-methyl]hexahydro-2-oxo-3-[[2-[[4-(phenylmethyl)-1-piperi-dinyl]carbonyl]-phenyl]methyl]-5-pyrimidineacetic acid | 608 |
| 210 | 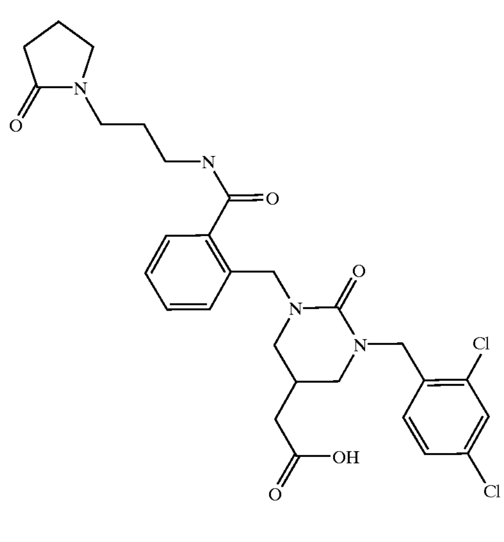 | 1-[(2,4-Dichlorophenyl)-methyl]hexahydro-2-oxo-3-[[2-[[[3-(2-oxo-1-pyrrolidinyl)-propyl]-amino]carbonyl]phenyl]-methyl]-5-pyrimidine-acetic acid | 575 |

-continued

| Ex. | Structure | Name | (M + H) positive ions |
|---|---|---|---|
| 211 | 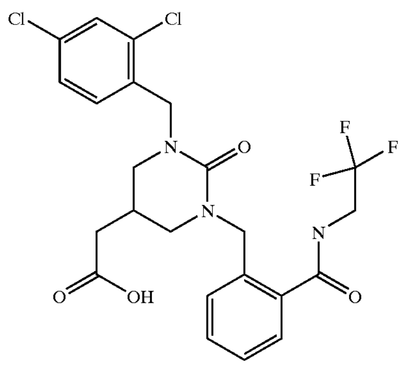 | 1-[(2,4-Dichlorophenyl)-methyl]hexahydro-2-oxo-3-[[2-[[(2,2,2-trifluoro-ethyl)-amino]carbonyl]-phenyl]methyl]-5-pyrimidineacetic acid | 532 |
| 212 | 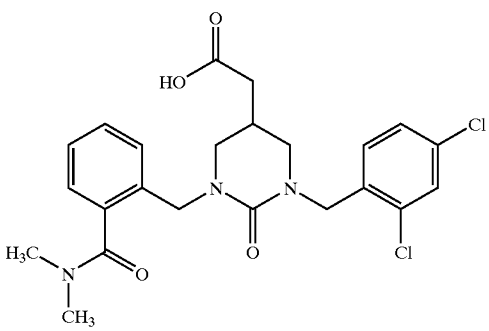 | 1-[(2,4-Dichlorophenyl)-methyl]-3-[[2-[(dimethyl-amino)-carbonyl]phenyl]-methyl]hexa-hydro-2-oxo-5-pyrimidineacetic acid | 478 |
| 213 | 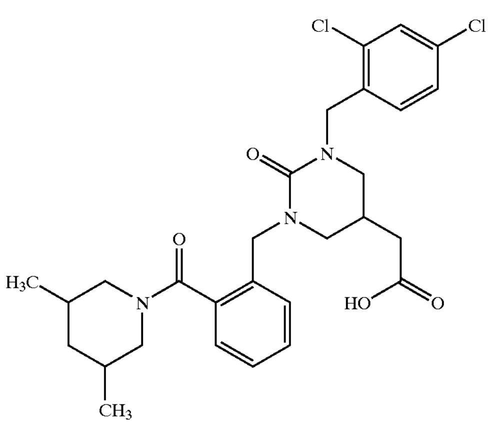 | 1-[(2,4-Dichlorophenyl)-methyl]-3-[[2-[(3,5-dimethyl-1-piperidinyl)-carbonyl]phenyl]methyl]-hexahydro-2-oxo-5-pyrimidineacetic acid | 546 |
| 214 | 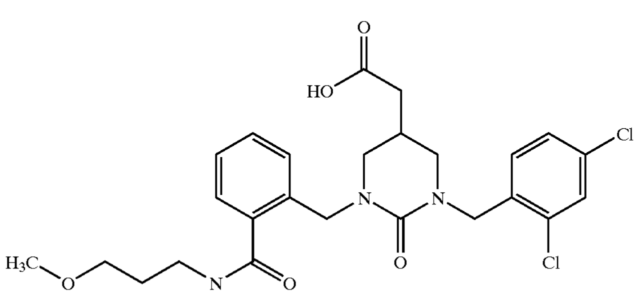 | 1-[(2,4-Dichloro-phenyl)methyl]hexa-hydro-3-[[2-[[(3-methoxy-propyl)amino]carbonyl]-phenyl]methyl]-2-oxo-5-pyrimidineacetic acid | 522 |

| Ex. | Structure | Name | (M + H) positive ions |
|---|---|---|---|
| 215 | 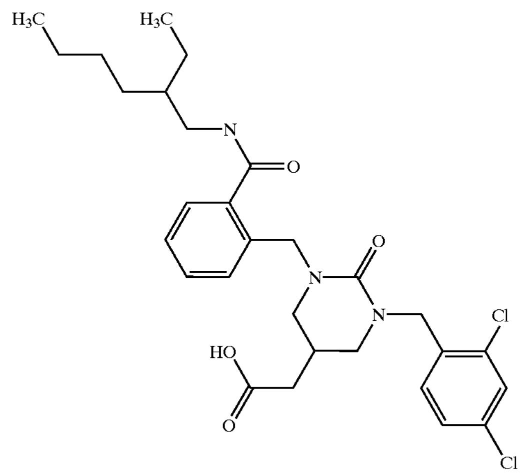 | 1-[(2,4-Dichlorophenyl)-methyl]-3-[[2-[[(2-ethyl-hexyl)amino]carbonyl]phenyl]-methyl]hexahydro-2-oxo-5-pyrimidineacetic acid | 562 |
| 216 | 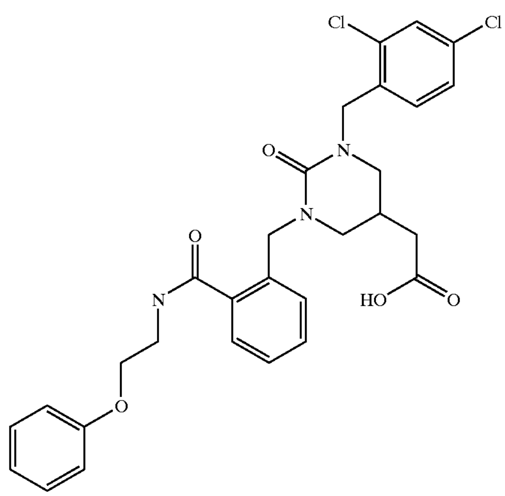 | 1-[(2,4-Dichlorophenyl)-methyl]hexahydro-2-oxo-3-[2-[[(2-phenoxyethyl)-amino]carbonyl]phenyl]-methyl]-5-pyrimidine-acetic acid | 570 |
| 217 | 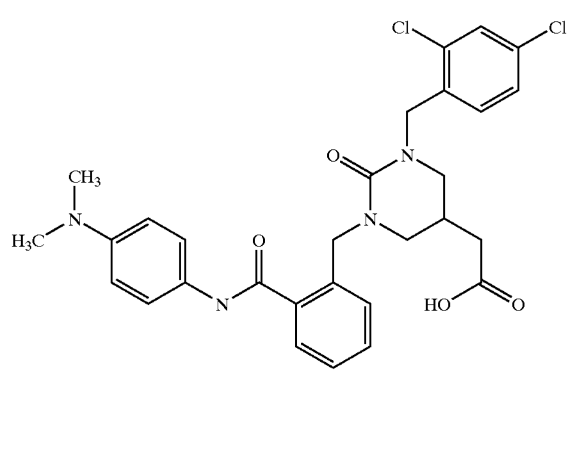 | 1-[(2,4-Dichlorophenyl)-methyl]-3-[[2-[[[4-(dimethyl-amino)phenyl]-amino]carbonyl]phenyl]-methyl]hexahydro-2-oxo-5-pyrimidineacetic acid | 569 |

| Ex. | Structure | Name | (M + H) positive ions |
|---|---|---|---|
| 218 | 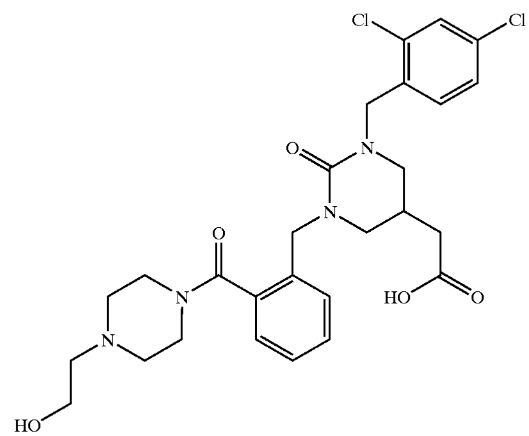 | 1-[(2,4-Dichlorophenyl)-methyl]hexahydro-3-[[2-[[4-(2-hydroxyethyl)-1-piperazinyl]-carbonyl]-phenyl]methyl]-2-oxo-5-pyrimidineacetic acid | 563 |
| 219 | 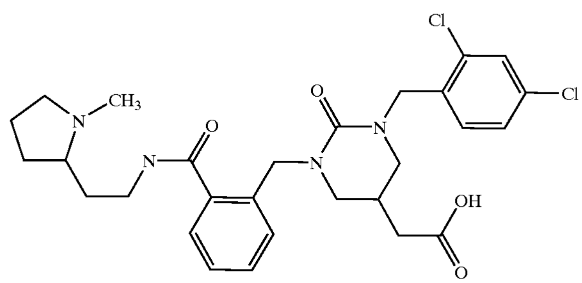 | 1-[(2,4-Dichlorophenyl)-methyl]hexahydro-3-[[2-[[[2-(1-methyl-2-pyrrolidinyl)-ethyl]amino]-carbonyl]phenyl]methyl]-2-oxo-5-pyrimidineacetic acid | 561 |
| 220 | 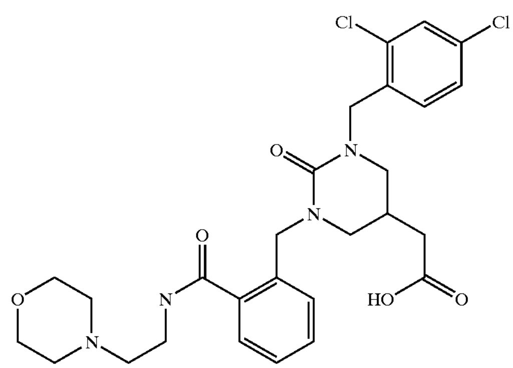 | 1-[(2,4-Dichlorophenyl)-methyl]hexahydro-3-[[2-[[[2-(4-morpholinyl)-ethyl]amino]carbonyl]-phenyl]methyl]-2-oxo-5-pyrimidineacetic acid | 563 |
| 221 | 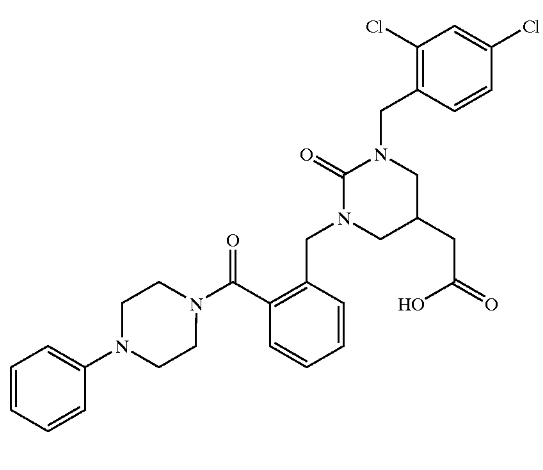 | 1-[(2,4-Dichlorophenyl)-methyl]hexahydro-2-oxo-3-[[2-[(4-phenyl-1-piperazinyl)car-bonyl]-phenyl]methyl]-5-pyrimidineacetic acid | 595 |

-continued

| Ex. | Structure | Name | (M + H) positive ions |
|---|---|---|---|
| 222 | 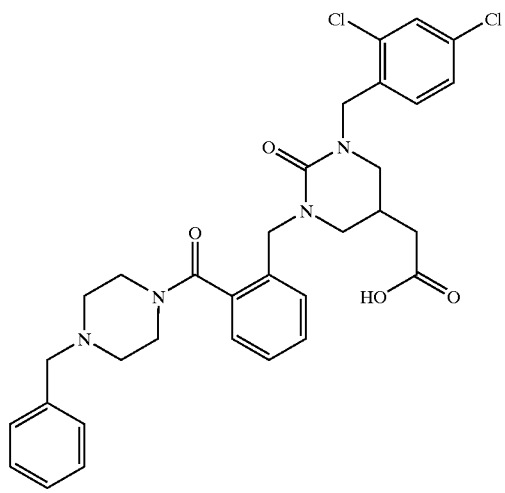 | 1-[(2,4-Dichlorophenyl)-methyl]hexahydro-2-oxo-3-[[2-[[4-(phenylmethyl)-1-piperazinyl]carbonyl]-phenyl]methyl]-5-pyrimidineacetic acid | 609 |
| 223 | 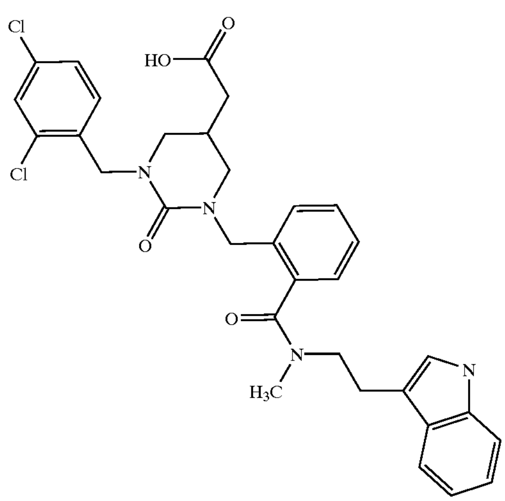 | 1-[(2,4-Dichlorophenyl)-methyl]hexahydro-3-[[2-[[[2-(1H-indol-3-yl)ethyl]-methyl-amino]carbonyl]-phenyl]methyl]-2-oxo-5-pyrimidineacetic acid | 607 |
| 224 | 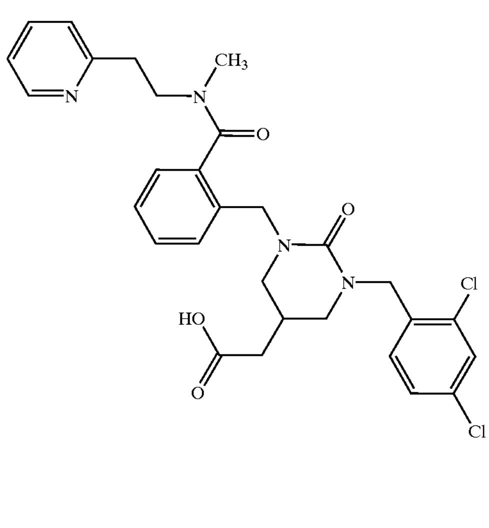 | 1-[(2,4-Dichlorophenyl)-methyl]hexahydro-3-[[2-[[methyl[2-(2-pyridinyl)-ethyl]-amino]carbonyl]-phenyl]methyl]-2-oxo-5-pyrimidineacetic acid | 569 |

-continued

| Ex. | Structure | Name | (M + H) positive ions |
|---|---|---|---|
| 225 | 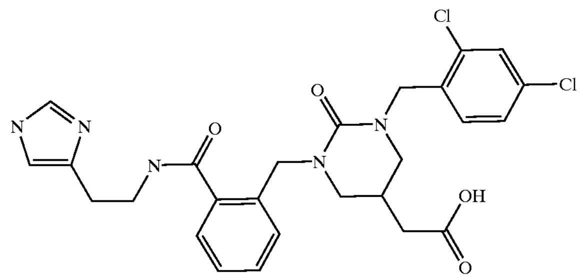 | 1-[(2,4-Dichlorophenyl)-methyl]hexahydro-3-[[2-[[[2-(1H-imidazol-4-yl)ethyl]amino]-carbonyl]-phenyl]methyl-2-oxo-5-pyrimidineacetic acid | 544 |
| 226 | 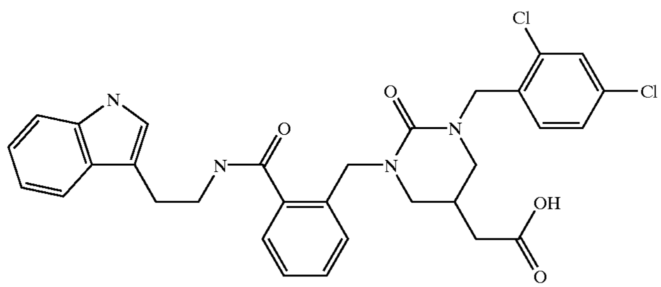 | 1-[(2,4-Dichlorophenyl)-methyl]hexahydro-3-[[2-[[[2-(1H-indol-3-yl)ethyl]-amino]-carbonyl]-phenyl]methyl]-2-oxo-5-pyrimidineacetic acid | 593 |
| 227 | 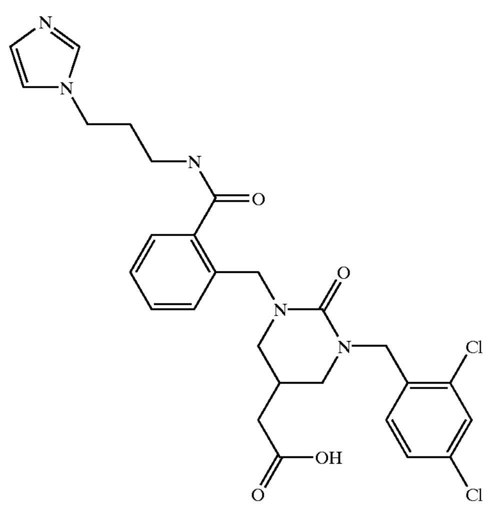 | 1-[(2,4-Dichlorophenyl)-methyl]hexahydro-3-[[2-[[[3-(1H-imidazol-1-yl)propyl]-amino]-carbonyl]phenyl]methyl]-2-oxo-5-pyrimidineacetic acid | 558 |
| 228 | 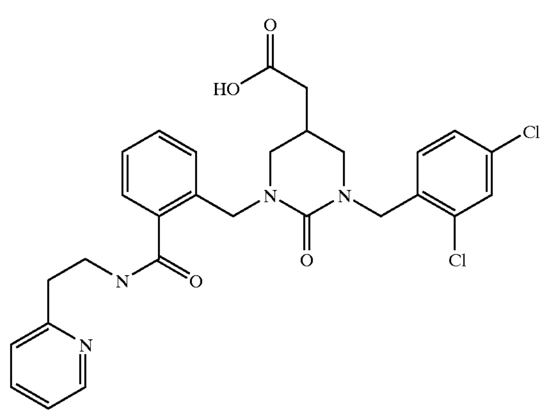 | 1-[(2,4-Dichlorophenyl)-methyl]hexahydro-2-oxo-3-[2-[[[2-(2-pyridinyl)-ethyl]-amino]carbonyl]-phenyl]methyl]-5-pyrimidineacetic acid | 555 |

-continued

| Ex. | Structure | Name | (M + H) positive ions |
|---|---|---|---|
| 229 | 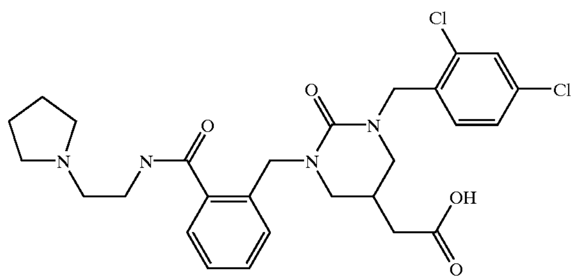 | 1-[(2,4-Dichlorophenyl)-methyl]hexahydro-2-oxo-3-[[2-[[[2-(1H-pyrrol-1-yl)ethyl]-amino]carbonyl]phenyl]methyl]-5-pyrimidineacetic acid | 547 |
| 230 | 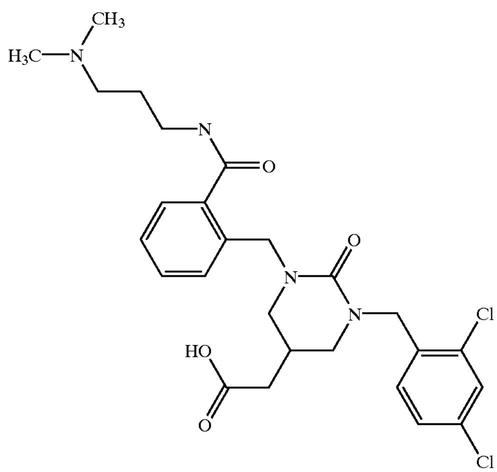 | 1-[(2,4-Dichlorophenyl)-methyl]-3-[[2-[[[3-(dimethyl-amino)propyl]-amino]carbonyl]-phenyl]-methyl]hexahydro-2-oxo-5-pyrimidineacetic acid | 535 |
| 231 | 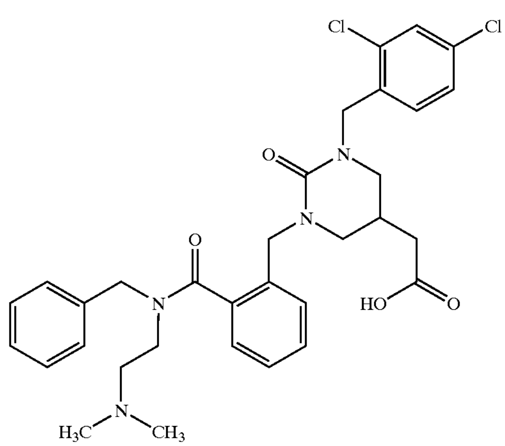 | 1-[(2,4-Dichlorophenyl)-methyl]-3-[[2-[[[2-(dimethyl-amino)ethyl]-(phenylmethyl)-amino]-carbonyl]phenyl]methyl]-hexahydro-2-oxo-5-pyrimidine-acetic acid | 611 |

-continued

| Ex. | Structure | Name | (M + H) positive ions |
|---|---|---|---|
| 232 | 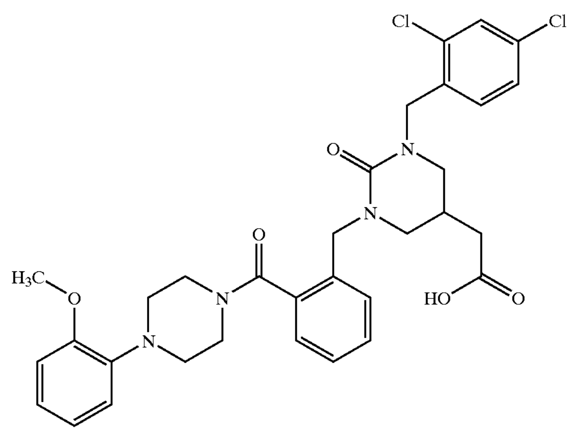 | 1-[(2,4-Dichlorophenyl)-methyl]hexahydro-3-[[2-[[4-(2-methoxyphenyl)-1-pipera-zinyl]carbonyl]-phenyl]methyl]-2-oxo-5-pyrimidineacetic acid | 625 |
| 233 | 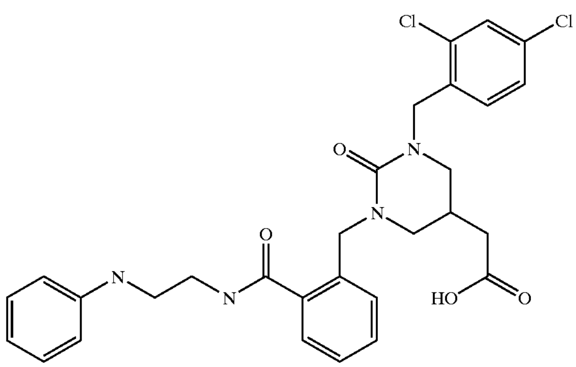 | 1-[(2,4-Dichlorophenyl)-methyl]hexahydro-2-oxo-3-[[2-[[[2-(phenylamino)-ethyl]-amino]carbonyl]-phenyl]methyl]-5-pyrimidineacetic acid | 569 |
| 234 | 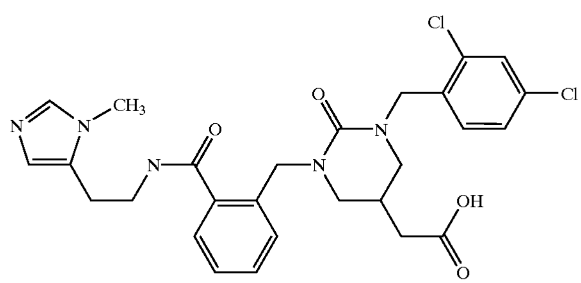 | 1-[(2,4-Dichlorophenyl)-methyl]hexahydro-3-[[2-[[[2-(1-methyl-1H-imi-dazol-5-yl)ethyl]-amino]carbonyl]-phenyl]methyl]-2-oxo-5-pyrimidineacetic acid | 558 |
| 235 | 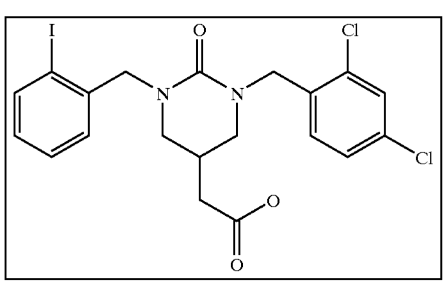 | 1-[(2,4-Dichlorophenyl)-methyl]hexahydro-3-(2-iodophenyl)methyl]-2-oxo-5-pyrimidineacetic acid | 533 |

EXAMPLE 236

1-[(2–Carboxyphenyl)methyl]-3-[(2,4-dichlorophenyl)methyl]hexahydro-2-oxo-5-pyrimidineacetic acid

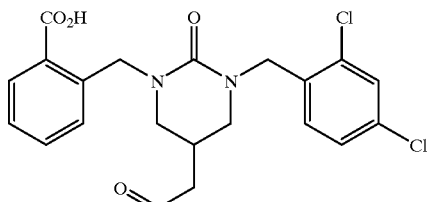

A.

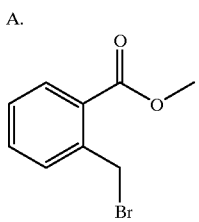

A mixture of phthalide (3.35 g, 25 mmol) and triphenylphosphonium dibromide (10.6 g, 25.1 mmol) was heated to 170° C. under argon for 3 h and then to 180° C. for 1 h. After cooling to room temperature, the reaction mixture was dissolved in $CH_2Cl_2$ (30 mL). This was added to methanol (20 mL) at 0° C. over 30 min. After an additional 1 h, the reaction was warmed to room temperature and then evaporated. The residual material was evaporated onto silica gel (21 g). Purification by flash chromatography on silica gel (1:3 $CH_2Cl_2$/hexanes as elutant) provided 236A as a colorless oil, 3.90 g (68%).

B.

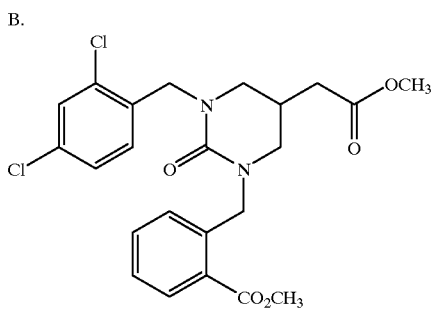

To a stirred solution of 147K (50 mg, 0.15 mmol) in THF (0.5 mL) at room temperature under argon was added potassium hexamethyldisilazide solution (0.5 M in toluene, 310 µL, 0.155 mmol). After 5 min, 235A (38.0 mg, 0.165 mmol) was added in one portion, followed by tetrabutylammonium iodide (55.4 mg, 0.15 mmol). After 1 h, the reaction mixture was partitioned between saturated sodium bicarbonate solution and $Et_2O$. The organic phase was dried ($Na_2SO_4$) and evaporated. Purification by flash chromatography (1:1 EtOAC/hexanes as elutant). Evaporation gave 236B, 42 mg (58%).

C.

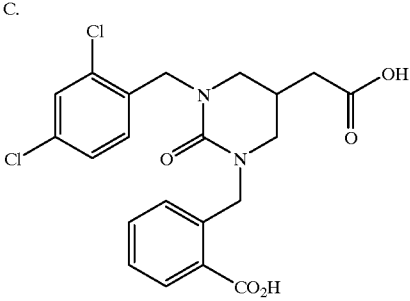

To a stirred solution of 236B (42 mg, 0.088 mmol) in THF (1 mL) at room temperature under argon was added sodium hydroxide (1 M, 1 mL, 1 mmol). After 17 h, the reaction mixture was extracted twice with $Et_2O$. The aqueous phase was cooled to 0° C. and acidified to pH 3 with 1 M hydrochloric acid. The resulting precipitate was collected, washed with water and dried in vacuo to give 236C as a white solid, 40 mg (100% yield), mp 212–213° C. LC/MS gave the correct molecular ion [(M+H)$^+$=451] for the desired compound.

EXAMPLE 237 t-Butyl 1-(4-Bromophenyl)-hexahydro-2-oxo-5-pyrimidineacetate

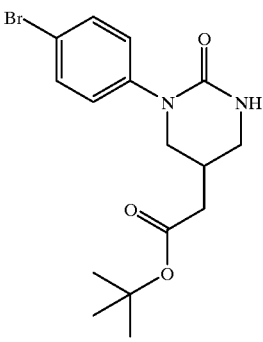

A.

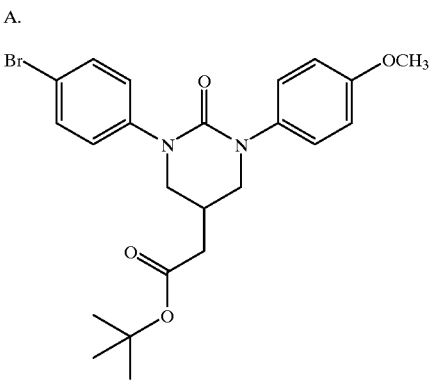

To a stirred solution of chromium trioxide (6.05 g, 60.5 mmol) in $CH_2Cl_2$ (40 mL) and DMF (10 mL) at room temperature was added pyridine (9.8 mL, 121 mmol). The mixture was stirred for 15 min and then a solution of 8E (6.1 g, 15 mmol) in $CH_2Cl_2$ (20 mL) and DMF (5 mL) was added, followed immediately by acetic anhydride (11.6 mL, 121 mmol) and t-butanol (28 mL, 302 mmol). After 16 h, the reaction mixture was diluted with ethanol (10 mL) and stirred for 15 min. Ether (200 mL) was then added and the slurry was filtered through Celite. The filtrate was washed with water and brine, dried (Na₂SO₄) and evaporated. Purification by flash chromatography on silica gel (2:1 hexanes/EtOAc as elutant) provided 237A as a colorless glass, 3.80 g (53%). LC/MS gave the correct molecular ion [(M+H)⁺= 475] for the desired compound.

B.

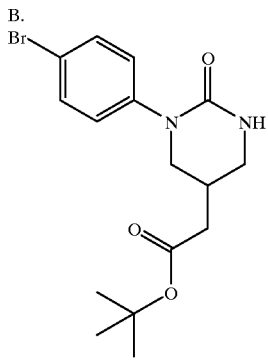

To a stirred solution of ceric ammonium nitrate (13.0 g, 24 mmol) in water (40 mL) at −10° C. was added a solution of 237A (3.80 g, 7.99 mmol) in CH₃CN (60 mL) over 30 min. After an additional 15 min, the reaction mixture was quenched with 10% sodium acetate solution to pH 7. The mixture was extracted three times with EtOAc (150 mL portions) and the combined organic extracts were washed with 10% sodium sulfite solution (buffered to pH 7 with sodium bisulfite), water and brine. The organic phase was dried (Na₂SO₄) and evaporated. Purification by flash chromatography on silica gel (EtOAc as elutant) gave 237B as a colorless oil, 1.18 g (40% yield). LC/MS gave the correct molecular ion [(M+H)⁺=369] for the desired compound.

C.

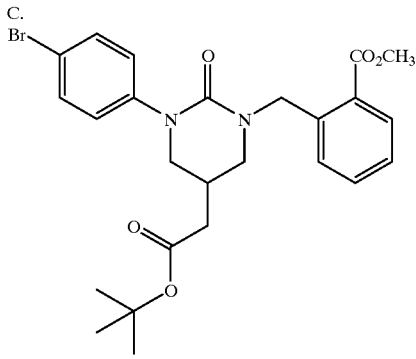

To a stirred solution of 237B (1.11 g, 3.00 mmol) in THF (20 mL) at room temperature under nitrogen was added potassium hexamethyldisilazide solution ( 0.5 M in toluene, 6.3 mL, 3.2 mmol). After 5 min, a solution of 236A (756 mg, 3.3 mmol) in THF (10 mL) was added, followed by tetrabutylammonium iodide (1.11 g, 3.0 mmol). After 3 h, the reaction mixture was quenched with saturated ammonium chloride solution and extracted three times with Et₂O (100 mL portions). The combined organic extracts were washed with water and brine. The organic phase was dried (Na₂SO₄) and evaporated. Purification by flash chromatography on silica gel (1:2 EtOAc/hexanes as elutant) gave 237C as a colorless amorphous solid, 1.41 g (91% yield). LC/MS gave the correct molecular ion [(M+H)⁺=517] for the desired compound.

D.

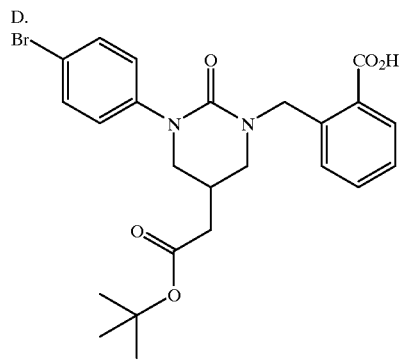

To a stirred solution of 237C (1.40 g, 2.71 mmol) in THF (5 mL) at room temperature under nitrogen was added potassium trimethylsilyloxide (0.381 g, 3.0 mmol). The reaction was monitored to minimize loss of the t-butyl ester. After 3 h, the reaction mixture was evaporated, diluted with water (5 mL), cooled to 5° C. and treated with 0.3 N potassium hydrogen sulfate solution to pH 4. The reaction mixture was then extracted three times with CH₂Cl₂ (40 mL portions). The combined organic extracts were washed with water and brine. The organic phase was dried (Na₂SO₄) and evaporated. Purification by flash chromatography on silica gel (190:10:1 CH₂Cl₂/CH₃OH/HOAc as elutant) gave 237D as a colorless amorphous solid, 620 mg (45% yield). LC/MS gave the correct molecular ion [(M+H)⁺=503] for the desired compound.

EXAMPLES 238–257

The title compounds were prepared as part of a solution phase library run using the following procedure.

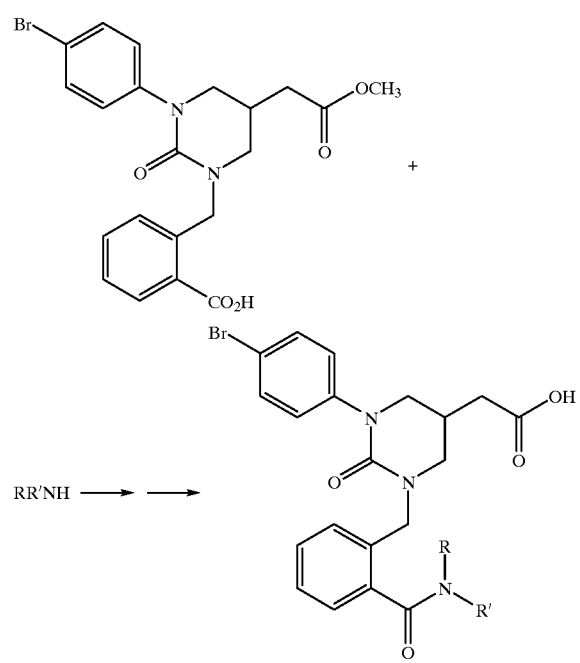

To 237D (35 mg, 0.07 mol), RR'NH (0.139 mmol), and HOAt (19 mg, 0.14 mol) in CH₂Cl₂ (1 mL) at room temperature was added EDAC (27 mg, 0.14 mmol) and the reaction vessels were sealed and agitated for 24 h. The reaction mixtures were evaporated and treated with a solution of potassium trimethylsilyloxide (38 mg, 0.3 mmol) in THF (0.5 mL) at room temperature for 18 h. The reaction mixtures were diluted with methanol (1 mL), filtered and the filtrates evaporated. Each reaction was purified by reverse-phase HPLC (water/CH₃OH—0.2% TFA gradient).

Mass spectrometric and HPLC data were collected for all compounds. Following the above procedure, the following compounds of the invention were prepared:

| Ex. | Structure | Name | (M + H) positive ion |
|---|---|---|---|
| 238 | 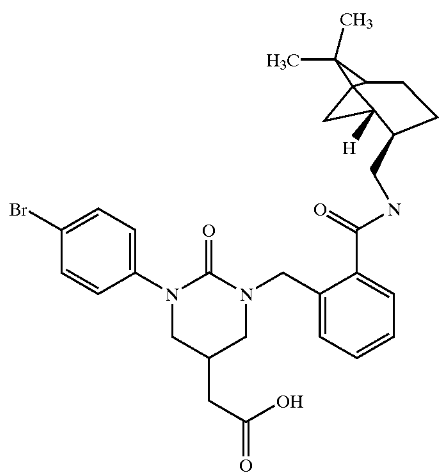 | 1-(4-Bromophenyl)-3-[[2-[[[[(1a,2b,5a)-6,6-dimethyl-bicyclo[3.1.1]hept-2-yl]methyl]amino]carbonyl]-phenyl]methyl]hexahydro-2-oxo-5-pyrimidineacetic acid | 582 |
| 239 | 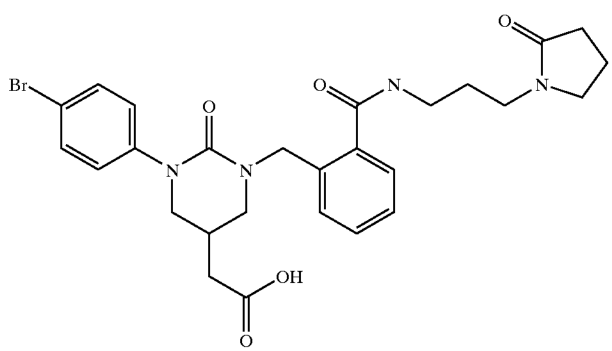 | 1-(4-Bromophenyl)-hexahydro-2-oxo-3-[[2-[[[3-(2-oxo-1-pyrroli-dinyl)propyl]amino]car-bonyl]phenyl]methyl]-5-pyrimidineacetic acid | 571 |
| 240 | 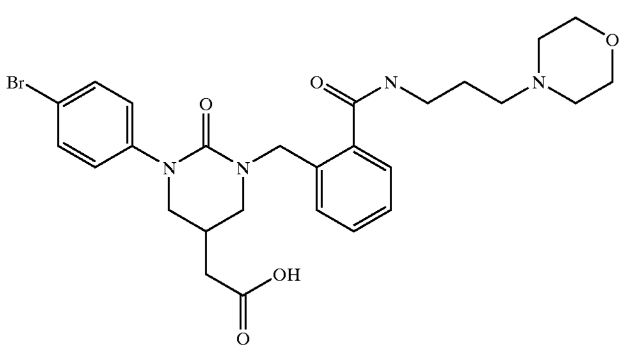 | 1-(4-Bromophenyl)-hexahydro-3-[[2-[[[3-(4-morpholinyl)propyl]amino]carbonyl]phenyl]methyl]-2-oxo-5-pyrimidineacetic acid | 573 |

| Ex. | Structure | Name | (M + H) positive ion |
|---|---|---|---|
| 241 | 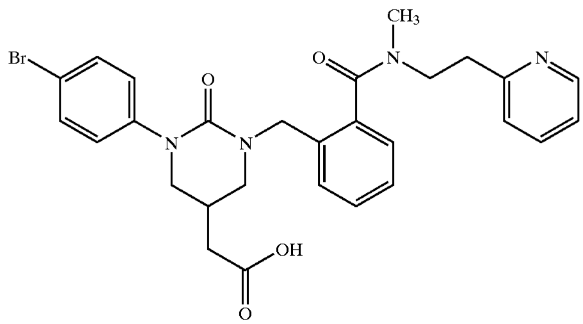 | 1-(4-Bromophenyl)-hexahydro-3-[[2-[[methyl[2-(2-pyridinyl)-ethyl]amino]carbonyl]-phenyl]methyl]-2-oxo-5-pyrimidineacetic acid | 565 |
| 242 | 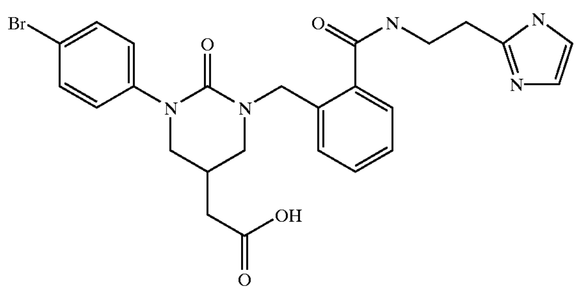 | 1-(4-Bromophenyl)-hexahydro-3-[[2-[[[2-(1H-imidazol-2-yl)ethyl]amino]-carbonyl]phenyl]methyl]-2-oxo-5-pyrimidineacetic acid | 540 |
| 243 | 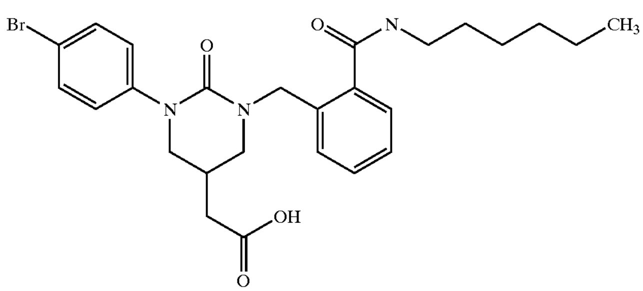 | 1-(4-Bromophenyl)-3-[[2-[(hexylamino)carbonyl]phenyl]methyl]hexahydro-2-oxo-5-pyrimidineacetic acid | 530 |
| 244 | 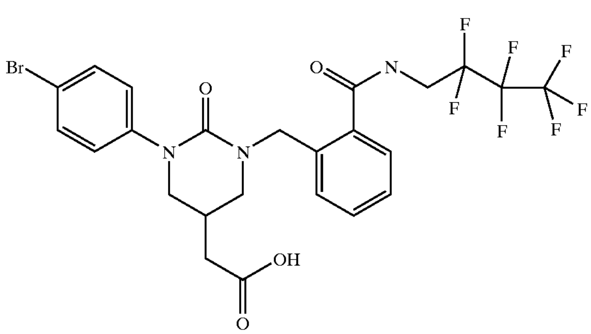 | 1-(4-Bromophenyl)-3-[[2-[[(2,2,3,3,4,4,4-hepta-fluorobutyl)amino]carbonyl]phenyl]methyl]hexahydro-2-oxo-5-pyrimidineacetic acid | 628 |

| Ex. | Structure | Name | (M + H) positive ion |
|---|---|---|---|
| 245 | 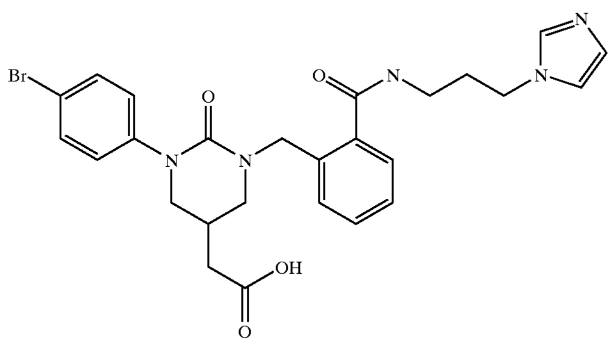 | 1-(4-Bromophenyl)-hexahydro-3-[[2-[[[3-(1H-imidazol-1-yl)propyl]-amino]carbonyl]phenyl]-methyl]-2-oxo-5-pyrimidineacetic acid | 554 |
| 246 | 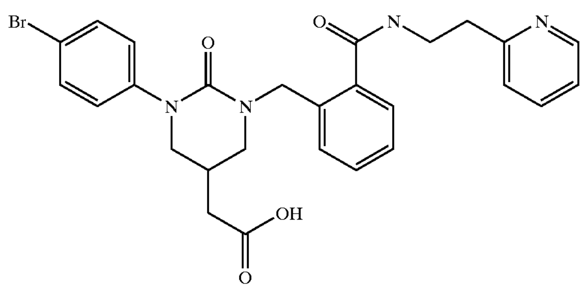 | 1-(4-Bromophenyl)-hexahydro-2-oxo-3-[[2-[[[2-(2-pyridinyl)ethyl]-amino]carbonyl]phenyl]-methyl]-5-pyrimidineacetic acid | 551 |
| 247 | 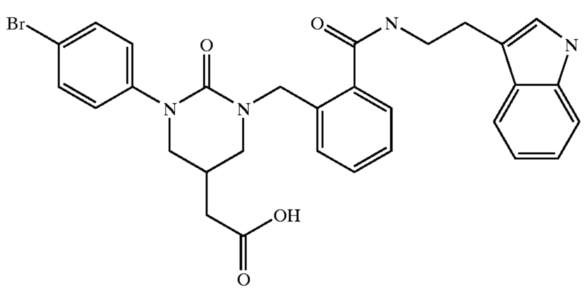 | 1-(4-Bromophenyl)-hexahydro-3-[[2-[[[2-(1H-indol-3-yl)ethyl]amino]-carbonyl]phenyl]methyl]-2-oxo-5-pyrimidineacetic acid | 589 |
| 248 | 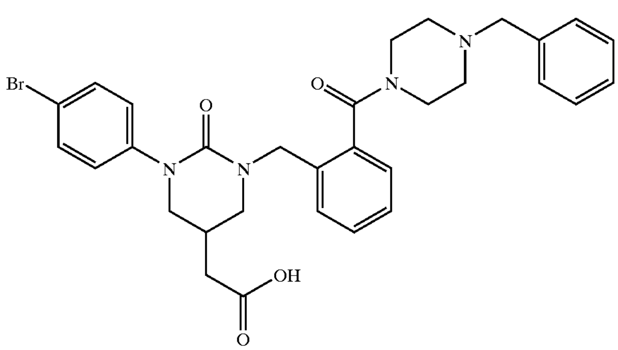 | 1-(4-Bromophenyl)-hexahydro-2-oxo-3-[[2-[[4-(phenylmethyl)-1-pipera-zinyl]carbonyl]-phenyl]-methyl]-5-pyrimidineacetic acid | 605 |

-continued

| Ex. | Structure | Name | (M + H) positive ion |
|---|---|---|---|
| 249 | 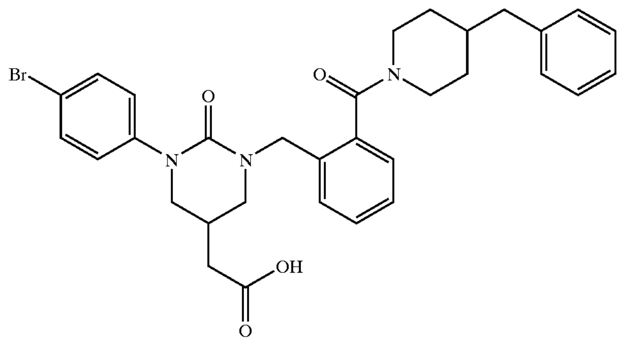 | 1-(4-Bromophenyl)-hexahydro-2-oxo-3-[[2-[[4-(phenylmethyl)-1-piperidinyl]carbonyl]-phenyl]-methyl]-5-pyrimidineacetic acid | 604 |
| 250 | 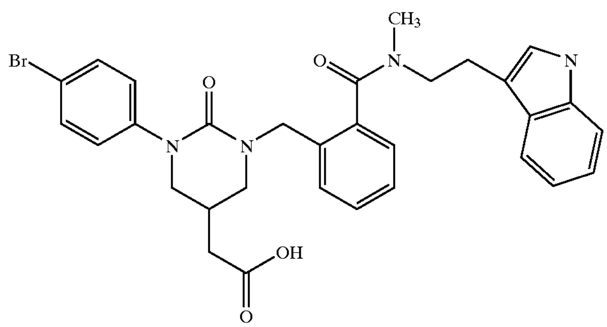 | 1-(4-Bromophenyl)-hexahydro-3-[[2-[[[2-(1H-indol-3-yl)ethyl]methyl-amino]carbonyl]phenyl]-methyl]-2-oxo-5-pyrimidineacetic acid | 603 |
| 251 | 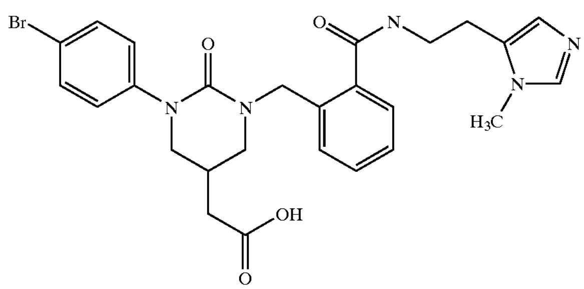 | 1-(4-Bromophenyl)-hexahydro-3-[[2-[[[2-(1-methyl-1H-imidazol-5-yl)ethyl]amino]-carbonyl]-phenyl]methyl]-2-oxo-5-pyrimidineacetic acid | 554 |
| 252 | 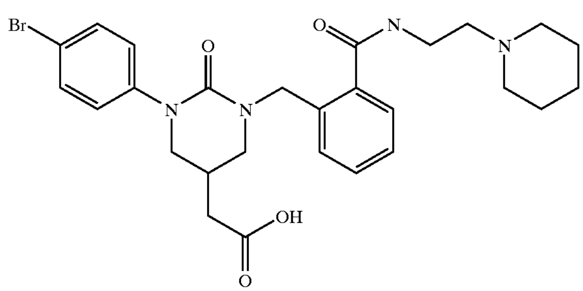 | 1-(4-Bromophenyl)-hexahydro-2-oxo-3-[[2-[[[2-(1-piperidinyl)-ethyl]-amino]carbonyl]phenyl]-methyl]-5-pyrimidineacetic acid | 557 |
| 253 | 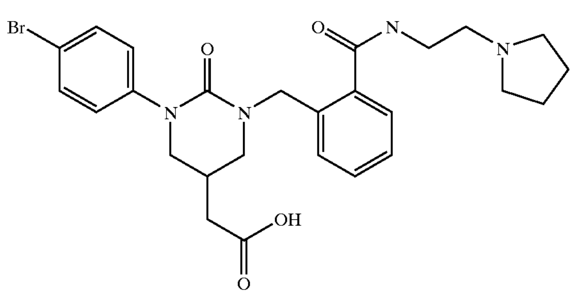 | 1-(4-Bromophenyl)-hexahydro-2-oxo-3-[[2-[[[2-(1-pyrrolidinyl)-ethyl]amino]carbonyl]-phenyl]methyl]-5-pyrimidineacetic acid | 543 |

-continued

| Ex. | Structure | Name | (M + H) positive ion |
|---|---|---|---|
| 254 | 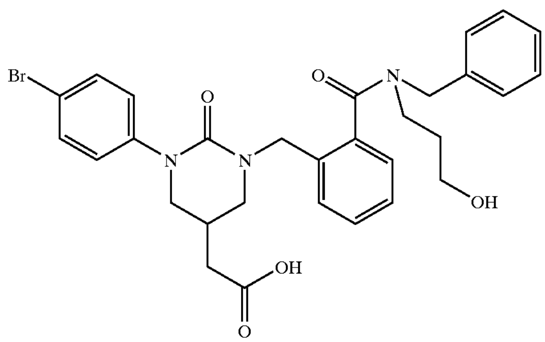 | 1-(4-Bromophenyl)-hexahydro-3-[[2-[[(3-hydroxypropyl)-(phenylmethyl)amino]carbonyl]-phenyl]methyl]-2-oxo-5-pyrimidineacetic acid | 594 |
| 255 | 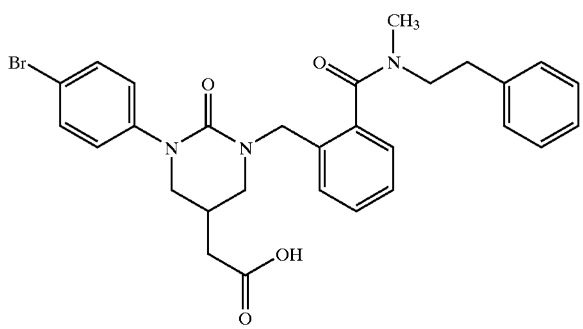 | 1-(4-Bromophenyl)-hexahydro-3-[[2-[[methyl(2-phenylethyl)-amino]carbonyl]phenyl]-methyl]-2-oxo-5-pyrimidineacetic acid | 564 |
| 256 | 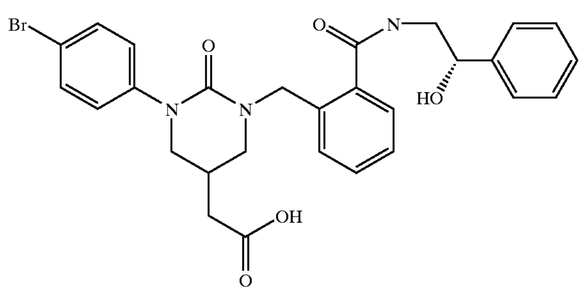 | 1-(4-Bromophenyl)-hexahydro-3-[[2-[[[(2S)-2-hydroxy-2-phenylethyl]-amino]carbonyl]-phenyl]-methyl]-2-oxo-5-pyrimidineacetic acid | 566 |
| 257 | 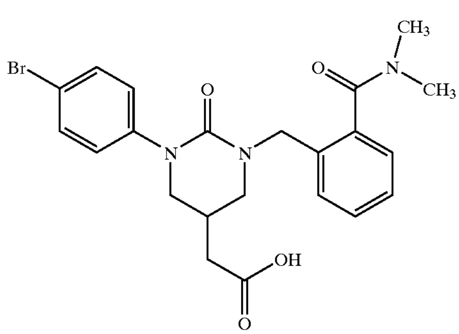 | 1-(4-Bromophenyl)-3-[[2-[(dimethylamino)carbonyl]phenyl]methyl]hexahydro-2-oxo-5-pyrimidineacetic acid | 474 |

EXAMPLE 258

1-[(2,4-Dichlorophenyl)methyl]hexahydro-2-oxo-3-(phenylmethyl)-5-pyrimidineacetic acid

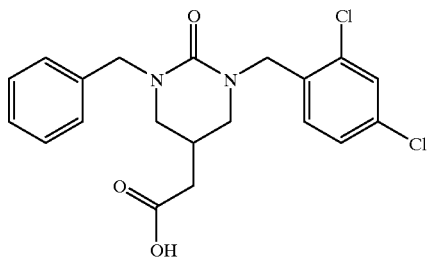

By the method of examples 148–185, using 147K and benzyl bromide as the alkylating agent, the title compound was prepared. LC/MS gave the correct molecular ion [(M+H)$^+$=407].

We claim:
1. A compound of formula I

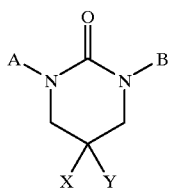

I enantiomers, diastereomers, or pharmaceutically acceptable salts thereof wherein A is
—$R^1$,
—$(CR^3R^4)_n$—$R^1$,
—$R^5(CR^3R^4)_p$—$R^1$,
—$(CR^3R^4)_m R^5(CR^6R^7)_p$—$R^1$,
—$(CR^3R^4)_n R^5(CR^6R^7)_p$—$R^1$,
—S(O)$R^1$,
—S(O$_2$)$R^1$, or
—NH(CR$^3$R$^4$)$_n$—$R^1$;

$R^1$ is substituted alkyl, aryl, substituted aryl, heteroaryl, substituted heteroaryl, alkyl or cycloalkyl;

B is
—$R^2$,
—$(CR^3R^4)_n$—$R^2$,
—$R^5(CR^3R^4)_p$—$R^2$,
—$(CR^3R^4)_m R^5(CR^6R^7)_p$—$R^2$,
—$(CR^3R^4)_n(CR^6R^7)_p$—$R^2$,
—S(O)$R^2$,
—S(O$_2$)$R^2$, or
—NH(CR$^3$R$^4$)$_n R^2$;

$R^2$ is aryl, substituted aryl, cycloalkylalkyl, heteroaryl or substituted heteroaryl;

$R^3$ and $R^4$ are the same or different and are independently H, alkyl, cycloalkyl, alkenyl, cycloalkenyl, alkynyl, alkoxycarbonyl, alkylcarbonyl, aminocarbonyl, alkylaminocarbonyl, arylaminocarbonyl, arylcarbonyl, aryl and heteroaryl, halo, hydroxy, alkoxy and aryloxy;

$R^5$ is a bond, O, NR$^8$, S, SO, SO$_2$, CO or CONH;

$R^6$ and $R^7$ are the same or different and are independently H, alkyl, cycloalkyl, aryl, hydroxy, amino, halo, alkoxy, aryloxy, alkylthio, arylthio, alkylamino, dialkylamino, arylamino, diarylamino, alkoxycarbonyl, alkylaminocarbonyl or alkylcarbonylamino;

$R^8$ is H, aryl, arylcarbonyl, alkylaminocarbonyl, arylaminocarbonyl, alkoxycarbonyl, aryloxycarbonyl, alkyl or alkylcarbonyl;

$R^9$ is H, alkyl, substituted alkyl, cycloalkyl, substituted cycloalkyl, cycloheteroalkyl, substituted cycloheteroalkyl, aryl, substituted aryl, aralkyl, substituted aralkyl, heteroaryl, substituted heteroaryl, heteroarylalkyl, or substituted heteroarylalkyl;

$R^{11}$ is hydrogen, alkyl, substituted alkyl, cycloalkyl, substituted cycloalkyl, alkenyl, substituted alkenyl, cycloalkenyl, substituted cycloalkenyl, aryl, substituted aryl, heteroaryl, substituted heteroaryl, aralkyl, substituted aralkyl, heteroaralkyl, substituted heteroaralkyl, cycloheteroalkyl and substituted cycloheteroalkyl;

$R^{12}$ and $R^{13}$ are the same or different and are independently H, alkyl, substituted alkyl, cycloalkyl, substituted cycloalkyl, cycloheteroalkyl, substituted cycloheteroalkyl, aryl, substituted aryl, aralkyl, substituted aralkyl, heteroaryl, substituted heteroaryl, heteroarylalkyl, or substituted heteroarylalkyl;

or $R^{12}$ and $R^{13}$ together with the nitrogen atom to which they are bonded together form an optionally substituted cycloheteroalkyl ring;

X is selected from —Z, —(CR$^3$R$^4$)$_n$—Z, —O—(CR$^3$R$^4$)$_p$—Z, —S—(CR$^3$R$^4$)$_p$—Z, —NHC(=O)Z, —CH=CHZ, -(cycloalkylene)-Z, or —N(R$^8$)(CR$^3$R$^4$)$_n$—Z;

Y is hydrogen, OH, or —(CR$^3$R$^4$)$_n$—CO2R$^9$, or X and Y taken together with the atom to which they are joined provide a group of the formula

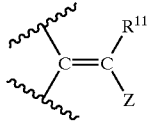

Z is CO$_2$R$^9$, CONR$^{12}$R$^{13}$, PO$_3$H$_2$, CONHOH, or tetrazole of the formula

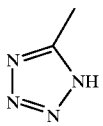

or its tautomer;
n is an integer selected from 0 to 5;
m is an integer selected from 1 to 5; and
p is an integer selected from 0 to 4.

2. The compound of claim 1 wherein

A is $R^1$;

B is (CR$^3$R$^4$)$_n$—R$^2$ where n is 1 and R$^3$ and R$^4$ are the same or different and are selected from hydrogen, alkyl and substituted alkyl;

X is (CR$^3$R$^4$)$_n$—Z where n is 0 or 1 and R$^3$ and R$^4$ are the same or different and are selected from hydrogen, hydroxy, alkyl and substituted alkyl;

or X and Y, taken together with the atom to which they are joined, provide a group of the formula

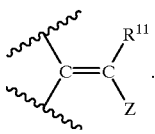

3. The compound as defined in claim 2 wherein
$R^1$ is
  (a) alkyl substituted with one or more groups selected from aryl, aryloxy and alkoxy, or
  (b) optionally substituted phenyl;
B is $(CR^3R^4)_n$—$R^2$ where n is 1 and $R^3$ and $R^4$ are each hydrogen;
$R^2$ is phenyl, napthyl, substituted phenyl or substituted napthyl;
X is $(CR^3R^4)_n$—Z where n is 0 or 1 and $R^3$ and $R^4$ are hydrogen; and
Z is $CO_2H$, $CONR^{12}R^{13}$ or tetrazole.

4. The compound as defined in claim 3 wherein
$R^1$ is (aryl)alkyl, (aryloxy)alkyl, or phenyl independently substituted with one or more halogen, alkoxy, or aryloxy;
$R^2$ is phenyl or napthyl independently substituted with one or more halogen, alkyl, substituted alkyl, alkoxy; arylalkoxy, aryloxy or cyano;
Y is hydrogen or —$CH_2CO_2H$;
X is $(CR^3R^4)_n$—Z where n is 1 and $R^3$ and $R^4$ are hydrogen; and
Z is $CO_2H$ or $CONR^{12}R^{13}$.

5. The compound of claim 4 wherein one $R^{12}$ and $R^{13}$ is hydrogen and the other is optionally substituted aryl, optionally substituted cycloheteroalkyl or optionally substituted cycloalkyl.

6. A compound of formula II

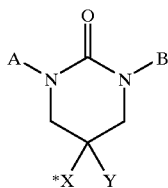

II enantiomers, diastereomers, or salts thereof wherein
A is
  —$R^1$,
  —$(CR^3R^4)_n$—$R^1$,
  —$R^5(CR^3R^4)_p$—$R^1$,
  —$(CR^3R^4)_m R^5(CR^6R^7)_p$—$R^1$,
  —$(CR^3R^4)_n(CR^6R^7)_p$—$R^1$,
  —$S(O)R^1$,
  —$S(O_2)R^1$, or
  —$NH(CR^3R^4)_n$—$R^1$;
$R^1$ is substituted alkyl, aryl, substituted aryl, heteroaryl, substituted heteroaryl, alkyl or cycloalkyl;
B is
  —$R^2$,
  —$(CR^3R^4)_n$—$R^2$,
  —$R^5(CR^3R^4)_p$—$R^2$,
  —$(CR^3R^4)_m R^5(CR^6R^7)_p$—$R^2$,
  —$(CR^3R^4)_n R^5(CR^6R^7)_p$—$R^2$,
  —$S(O)R^2$,
  —$S(O_2)R^2$, or
  —$NH(CR^3R^4)_n$—$R^2$;
$R^2$ is aryl, substituted aryl, cycloalkylalkyl, heteroaryl or substituted heteroaryl;
$R^3$ and $R^4$ are the same or different and are independently H, alkyl, cycloalkyl, alkenyl, cycloalkenyl, alkynyl, alkoxycarbonyl, alkylcarbonyl, aminocarbonyl, alkylaminocarbonyl, arylaminocarbonyl, arylcarbonyl, aryl and heteroaryl, halo, hydroxy, alkoxy and aryloxy;
$R^5$ is a bond, O, $NR^8$, S, SO, $SO_2$, CO or CONH;
$R^6$ and $R^7$ are the same or different and are independently H, alkyl, cycloalkyl, aryl, hydroxy, amino, halo, alkoxy, aryloxy, alkylthio, arylthio, alkylamino, dialkylamino, arylamino, diarylamino, alkoxycarbonyl, alkylaminocarbonyl or alkylcarbonylamino;
$R^8$ is H, aryl, arylcarbonyl, alkylaminocarbonyl, arylaminocarbonyl, alkoxycarbonyl, aryloxycarbonyl, alkyl or alkylcarbonyl;
X* is —W, —$(CR^3R^4)_n$—W, —$O(CR^3R^4)_n$—W, —$S(CR^3R^4)_n$—W, —NHC(=O)W, —CH=CHW, -(cycloalkylene)-W, or —$N(R^8)(CR^3R^4)_n$—W;
Y is hydrogen, OH or alkenyl,
or X* and Y taken together with the atom to which they are joined provide a group of the formula

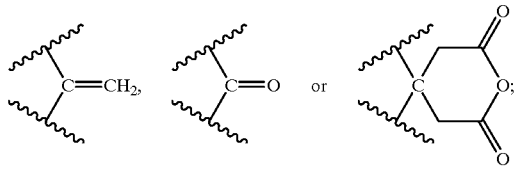

W is cyano, halogen, hydroxy, alkenyl, C(O)Cl, or C(O)H;
n is an integer selected from 0 to 5;
m is an integer selected from 1 to 5; and
p is an integer selected from 0 to 4.

7. The compound of claim 6 wherein
A is $R^1$;
B is $(CR^3R^4)_n$—$R^2$ where n is 1 and $R^3$ and $R^4$ are the same or different and are selected from hydrogen, alkyl and substituted alkyl;
X* is $(CR^3R^4)_n$—W where n is 0 or 1 and $R^3$ and $R^4$ are the same or different and are selected from hydrogen, hydroxy, alkyl and substituted alkyl;
or X* and Y, taken together with the atom to which they are joined, provide a group of the formula

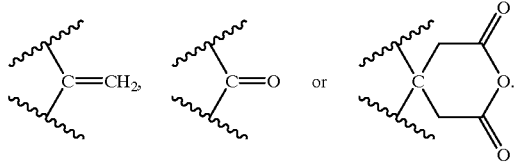

8. The compound as defined in claim 2 wherein
$R^1$ is
  (a) alkyl substituted with one or more groups selected from aryl, aryloxy and alkoxy, or
  (b) optionally substituted phenyl;
B is $(CR^3R^4)_n$—$R^2$ where n is 1 and $R^3$ and $R^4$ are each hydrogen $R^2$ is phenyl, napthyl, substituted phenyl or substituted napthyl.

9. The compound as defined in claim 8 wherein
$R^1$ is (aryl)alkyl, (aryloxy)alkyl, or phenyl independently substituted with one or more halogen, alkoxy, or aryloxy;
$R^2$ is phenyl or napthyl independently substituted with one or more halogen, alkyl, substituted alkyl, alkoxy; arylalkoxy, aryloxy or cyano; and
Y is hydrogen.

10. A pharmaceutical composition comprising at least one compound of claim 1 and a pharmaceutically acceptable carrier therefor.

11. A method for treating insulin resistance, hyperglycemia, hyperinsulinemia, or elevated blood levels of free fatty acids or glycerol, obesity, hypertriglyceridemia, atherosclerosis, diabetic retinopathy, diabetic neuropathy or diabetic nephropathy which comprises administering to a mammalian species in need thereof an effective amount of of a compound of the following formula I

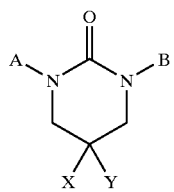

I enantiomers, diastereomers, or pharmaceutically acceptable salts thereof wherein A and B are the same or different and are independently
—J,
—(CR³RR⁴)ₙ—J,
—R⁵(CR³R⁴)ₚ—J,
—(CR³R⁴)ₘR⁵(CR⁶R⁷)ₚ—J,
—(CR³R⁴)ₙ(CR⁶R⁷)ₚ—J,
—S(O)J where J is other than hydrogen,
—S(O₂)J where J is other than hydrogen, and
—NH(CR³R⁴)ₙ—J;

J is independently $R^1$ or $R^2$;

$R^1$ and $R^2$ are independently hydrogen, alkyl, substituted alkyl, cycloalkyl, substituted cycloalkyl, alkenyl, substituted alkenyl, cycloalkenyl, substituted cycloalkenyl, aryl, substituted aryl, heteroaryl, substituted heteroaryl, aralkyl, substituted aralkyl, heteroaralkyl, substituted heteroaralkyl, cycloheteroalkyl and substituted cycloheteroalkyl;

$R^3$ and $R^4$ are the same or different and are independently H, alkyl, cycloalkyl, alkenyl, cycloalkenyl, alkynyl, alkoxycarbonyl, alkylcarbonyl, aminocarbonyl, alkylaminocarbonyl, arylaminocarbonyl, arylcarbonyl, aryl and heteroaryl, halo, hydroxy, alkoxy and aryloxy;

$R^5$ is a bond, O, $NR^8$, S, SO, $SO_2$, CO or CONH;

$R^6$ and $R^7$ are the same or different and are independently H, alkyl, cycloalkyl, aryl, hydroxy, amino, halo, alkoxy, aryloxy, alkylthio, arylthio, alkylamino, dialkylamino, arylamino, diarylamino, alkoxycarbonyl, alkylaminocarbonyl or alkylcarbonylamino;

$R^8$ is H, aryl, arylcarbonyl, alkylaminocarbonyl, arylaminocarbonyl, alkoxycarbonyl, aryloxycarbonyl, alkyl or alkylcarbonyl;

$R^9$ is H, alkyl, substituted alkyl, cycloalkyl, substituted cycloalkyl, cycloheteroalkyl, substituted cycloheteroalkyl, aryl, substituted aryl, aralkyl, substituted aralkyl, heteroaryl, substituted heteroaryl, heteroarylalkyl, or substituted heteroarylalkyl;

$R^{10}$ is H, alkyl, substituted alkyl, cycloalkyl, substituted cycloalkyl, cycloheteroalkyl, substituted cycloheteroalkyl, aryl, substituted aryl, aralkyl, substituted aralkyl, heteroaryl, substituted heteroaryl, heteroarylalkyl, or substituted heteroarylalkyl;

$R^{11}$ is hydrogen, alkyl, substituted alkyl, cycloalkyl, substituted cycloalkyl, alkenyl, substituted alkenyl, cycloalkenyl, substituted cycloalkenyl, aryl, substituted aryl, heteroaryl, substituted heteroaryl, aralkyl, substituted aralkyl, heteroaralkyl, substituted heteroaralkyl, cycloheteroalkyl and substituted cycloheteroalkyl;

$R^{12}$ and $R^{13}$ are the same or different and are independently H, alkyl, substituted alkyl, cycloalkyl, substituted cycloalkyl, cycloheteroalkyl, substituted cycloheteroalkyl, aryl, substituted aryl, aralkyl, substituted aralkyl, heteroaryl, substituted heteroaryl, heteroarylalkyl, or substituted heteroarylalkyl;

or $R^{12}$ and $R^{13}$ together with the nitrogen atom to which they are bonded together form an optionally substituted cycloheteroalkyl ring;

X is selected from —Z, —(CR³R⁴)ₙ—Z, —O—(CR³R⁴)ₚ—Z, —S—(CR³R⁴)ₚ—Z, —NHC(=O)Z, —CH=CHZ, -(cycloalkylene)-Z, or —N(R⁸)(CR³R⁴)ₙ—Z;

Y is H, alkyl, aryl, aralkyl, alkoxy, aryloxy, alkylthio, arylthio, hydroxy, —(CR³R⁴)ₙ—CO₂R⁹, —(CR³R⁴)ₙ—CONR¹²R¹³, —NR³R⁴, aralkoxy, or heteroarylalkyl, provided that Y is other than hydroxy or NH₂ when X is —O(CR³R⁴)ₚ—Z, —S(CR³R⁴)ₚ—Z, —NHC(=O)Z, or —N(R⁸)(CR³R⁴)ₙ—Z;

or X and Y, taken together with the atom to which they are joined, provide a group of the formula

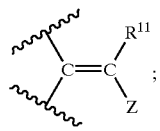

Z is $CO_2R^9$, $SO_3H$, $PO_3R^9R^{10}$, CONHOH, $CONR^{12}R^{13}$, $(CR^3R^4)_mOH$, or tetrazole of the formula

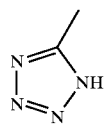

or its tautomer;
n is an integer selected from 0 to 5;
m is an integer selected from 1 to 5; and
p is an integer selected from 0 to 4.

* * * * *